US012576240B2

(12) United States Patent
Zhao et al.

(10) Patent No.: US 12,576,240 B2
(45) Date of Patent: Mar. 17, 2026

(54) MICROROBOTS WITH DISTRIBUTED ACTUATION

(71) Applicant: OHIO STATE INNOVATION FOUNDATION, Columbus, OH (US)

(72) Inventors: Renee Zhao, Columbus, OH (US); Shuai Wu, Columbus, OH (US); Qiji Ze, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 1083 days.

(21) Appl. No.: 17/589,609

(22) Filed: Jan. 31, 2022

(65) Prior Publication Data

US 2022/0249817 A1 Aug. 11, 2022

Related U.S. Application Data

(60) Provisional application No. 63/144,219, filed on Feb. 1, 2021, provisional application No. 63/143,715, filed on Jan. 29, 2021.

(51) Int. Cl.
| | |
|---|---|
| *A61M 25/01* | (2006.01) |
| *A61K 9/00* | (2006.01) |
| *A61M 37/00* | (2006.01) |

(52) U.S. Cl.
CPC ....... *A61M 25/0116* (2013.01); *A61K 9/0009* (2013.01); *A61K 9/0097* (2013.01); *A61M 37/00* (2013.01); *A61M 2205/0288* (2013.01)

(58) Field of Classification Search
CPC .............. A61M 37/00; A61M 25/0116; A61M 25/0158; A61M 25/0127; A61M 2205/0272; A61M 2205/8287; A61K 9/0002; A61K 9/0009; A61K 9/0097; A61B 2017/00345; A61B 2562/162
See application file for complete search history.

(56) References Cited

U.S. PATENT DOCUMENTS

2016/0317796 A1* 11/2016 Zhang ................... A61L 31/128
2017/0303965 A1* 10/2017 Rus ........................ A61B 34/72

FOREIGN PATENT DOCUMENTS

KR 20130005631 A * 1/2013 ............. A61B 1/041
WO WO-2016176509 A1 * 11/2016 ....... A61B 17/00234
(Continued)

OTHER PUBLICATIONS

C.-Y. Yeh, C.Y. Chen and J.-Y. Juang, Soft hopping and crawling robot for in-pipe travelling, Extreme Mechanics Letters (2020), doi: https://doi.org/10.1016/j.eml.2020.100854. (Year: 2020).*
(Continued)

*Primary Examiner* — Michael J Tsai
*Assistant Examiner* — Katerina A. Wittliff
(74) *Attorney, Agent, or Firm* — Meunier Carlin & Curfman LLC

(57) ABSTRACT

Described herein are unit cells including a base plate; a top plate; and a lumen extending longitudinally from the base plate to the top plate, the lumen defined by a side wall formed from a plurality of cojoined panels extending between a bottom surface of the top plate and a top surface of the base plate. The unit cell can be magnetically actuatable, such that the unit cell can be reversibly transitioned between a contracted configuration, an extended configuration, or a combination thereof using an applied magnetic field.

19 Claims, 93 Drawing Sheets

(56) References Cited

FOREIGN PATENT DOCUMENTS

WO WO-2018111327 A1 * 6/2018 ........... A61B 5/4887
WO WO-2020188484 A1 * 9/2020 ........ A61M 37/0015

OTHER PUBLICATIONS

A Healthy Diet Is Costly for People and the Planet. Nature Food 2021. https://doi.org/gtdp He, P., Feng, K., Baiocchi, G., Sun, L., & Hubacek, K. (2021). Shifts towards healthy diets in the US can reduce environmental impacts but would be unaffordable for poorer minorities. Nature Food. doi:10.1038/s43016-021-00350-5.

Ahmed AR, Gauntlett OC, & Camci-Unal G (2020) Origami-Inspired Approaches for Biomedical Applications. ACS Omega 6(1):46-54.

Banerjee, N. Pusalkar, H. Ren, Single-motor controlled tendon-driven peristaltic soft origami robot. Journal of Mechanisms and Robotics 10, (2018).

Bernth, A. Arezzo, H. Liu, A novel robotic meshworm with segment-bending anchoring for colonoscopy. IEEE Robotics and Automation Letters 2, 1718-1724 (2017).

Bhovad, J. Kaufmann, S. Li, Peristaltic locomotion without digital controllers: Exploiting multi-stability in origami to coordinate robotic motion. Extreme Mechanics Letters 32, 100552 (2019).

Biomimetic origami robot arm. Engineering. Sep. 7, 2021, 3 pages.

Boyvat M, Koh J-S, & Wood RJ (2017) Addressable wireless actuation for multijoint folding robots and devices. Science Robotics 2(8).

Calisti, G. Picardi, C. Laschi, Fundamentals of soft robot locomotion. Journal of The Royal Society Interface 14, Jan. 1, 2017 (2017).

Chen, O. R. Bilal, R. Lang, C. Daraio, K. Shea, Autonomous deployment of a solar panel using elastic origami and distributed shape-memory-polymer actuators. Phys. Rev. Applied 11, 064069 (2019).

Chen, Y. Cao, M. Sarparast, H. Yuan, L. Dong, X. Tan, C. Cao, Soft crawling robots: design, actuation, and locomotion. Advanced Materials Technologies 5, 1900837 (2020).

Cheng Q, et al. (2013) Folding paper-based lithium-ion batteries for higher areal energy densities. Nano letters 13(10):4969-4974.

Coad, L. H. Blumenschein, S. Cutler, J. A. R. Zepeda, N. D. Naclerio, H. El-Hussieny, U. Mehmood, J.-H. Ryu, E. W. Hawkes, A. M. Okamura, Vine robots: Design, teleoperation, and deployment for navigation and exploration. IEEE Robotics & Automation Magazine 27, 120-132 (2019).

Cui et al., Nanomagnetic encoding of shape-morphing micromachines. Nature 575, 164-168 (2019).

Faber JA, Arrieta AF, & Studart AR (2018) Bioinspired spring origami. Science 359(6382):1386-1391.

Fang, Y. Zhang, K. Wang, Origami-based earthworm-like locomotion robots. Bioinspiration & Biomimetics 12, 065003 (2017).

Filipov, K Liu, T Tachi, M Schenk, G Paulino, Bar and hinge models for scalable analysis of origami. Int. J. Solids Struct. 124, 26-45 (2017).

Filipov, T. Tachi, G. H. Paulino, Origami tubes assembled into stiff, yet reconfig-urable structures and metamaterials. Proc. Natl. Acad. Sci. U.S.A. 112, 12321-12326 (2015).

Forsberg, A., & Engström, Å. (2018). Critical care nurses' experiences of performing successful peripheral intravenous catheterization in difficult situations. Journal of Vascular Nursing, 36(2), 64-70.

Grubich J (2011) Octopus Arm and Sucker Kinematics. video recording, 2011). https://www.youtube.com/watch?v=AfTiHudkmc4. Accessed Feb. 4, 2021.

Gu, J. Zou, R. Zhao, X. Zhao, X. Zhu, Soft wall-climbing robots. Science Robotics 3, (2018).

Gustafson, O. Angatkina, A. Wissa, Model-based design of a multistable origami-enabled crawling robot. Smart Materials and Structures 29, 015013 (2019).

Hawkes, L. H. Blumenschein, J. D. Greer, A. M. Okamura, A soft robot that navigates its environment through growth. Science Robotics 2, (2017).

Hu F, Wang W, Cheng J, & Bao Y (2020) Origami spring-inspired metamaterials and robots: An attempt at fully programmable robotics. Science Progress 103(3):0036850420946162.

Hu, Wenqi, et al. "Small-scale soft-bodied robot with multimodal locomotion." Nature 554.7690 (2018): 81-85.

Ingestible origami robot. Robot unfolds from ingestible capsule, removes button battery stuck to wall of simulated stomach. Larry Hardesty | MIT News Office Publication Date: May 12, 2016. On-line at: https://news.mit.edu/2016/ingestible-origami-robot-0512.

Jape S, et al. (2020) Self-foldable origami reflector antenna enabled by shape memory polymer actuation. Smart Materials and Structures 29(11):115011.

Joey, A. A. Calderón, L. Chang, N. O. Pérez-Arancibia, An earthworm-inspired friction-controlled soft robot capable of bidirectional locomotion. Bioinspiration & Biomimetics 14, 036004 (2019).

Joyee, Y. Pan, A fully three-dimensional printed inchworm-inspired soft robot with magnetic actuation. Soft Robotics 6, 333-345 (2019).

Kamata, S. Yamazaki, Y. Tanise, Y. Yamada, T. Nakamura, Morphological change in peristaltic crawling motion of a narrow pipe inspection robot inspired by earthworm's locomotion. Advanced Robotics 32, 386-397 (2018).

Kandhari, Y. Wang, H. J. Chiel, R. D. Quinn, K. A. Daltorio, An analysis of peristaltic locomotion for maximizing velocity or minimizing cost of transport of earthworm-like robots. Soft Robotics, (2020).

Kaufmann J, Bhovad P, & Li S (2021) Harnessing the Multistability of Kresling Origami for Reconfigurable Articulation in Soft Robotic Arms. Soft Robotics.

Kidambi N & Wang K (2020) Dynamics of Kresling origami deployment. Physical Review E 101(6):063003.

Kim S-J, Lee D-Y, Jung G-P, & Cho K-J (2018) An origami-inspired, self-locking robotic arm that can be folded flat. Science Robotics 3(16):eaar2915.

Kim, J. Byun, J.-K. Kim, W.-Y. Choi, K. Jakobsen, J. Jakobsen, D.-Y. Lee, K.-J. Cho, Bioinspired dual-morphing stretchable origami. Science Robotics 4, (2019).

Koh, K.-J. Cho, Omega-shaped inchworm-inspired crawling robot with large-index-and-pitch (LIP) SMA spring actuators. IEEE/ASME Transactions On Mechatronics 18, 419-429 (2012).

Kotikian A, et al. (2019) Untethered soft robotic matter with passive control of shape morphing and propulsion. Science Robotics 4(33).

Kresling, "Folded tubes as compared to kikko ("Tortoise-Shell") bamboo" in Origami3 : Proceedings of the Third International Meeting of Origami Science, Mathematics, and Education, T. C. Hull, Ed. (A.K. Peters, 2002), p. 197.

Kresling, Natural twist buckling in shells: from the hawkmoth's bellows to the deployable kresling-pattern and cylindrical Miura-ori in Proceedings of the 6th International Conference on Computation of Shell and Spatial Structures, eds. JF Abel, JR Cooke. pp. 1-4 (2008).

Kuang, S. Wu, Q. Ze, L. Yue, Y. Jin, S. M. Montgomery, F. Yang, H. J. Qi, R. Zhao, Magnetic Dynamic Polymers for Modular Assembling and Reconfigurable Morphing Architectures. Advanced Materials 33, 2102113 (2021).

Leon, et al., On the effect of constraint parameters on the generalized displacement control method. Mech. Res. Commun. 56, 123-129 (2014).

Leong TG, et al. (2009) Tetherless thermobiochemically actuated microgrippers. Proceedings of the National Academy of Sciences 106(3):703-708.

Li S, et al. (2019) A vacuum-driven origami "magic-ball" soft gripper. 2019 International Conference on Robotics and Automation (ICRA), (IEEE), pp. 7401-7408.

Li, D. M. Vogt, D. Rus, R. J. Wood, Fluid-driven origami-inspired artificial muscles. Proc. Natl. Acad. Sci. U.S.A. 114, 13132-13137 (2017).

Li, N. Kidambi, L. Wang, K.-W. Wang, Uncovering rotational multifunctionalities of coupled Kresling modular structures. Extreme Mechanics Letters 39, 100795 (2020).

(56) References Cited

OTHER PUBLICATIONS

Li, Z. Zou, G. Mao, X. Yang, Y. Liang, C. Li, S. Qu, Z. Suo, W. Yang, Agile and resilient insect-scale robot. Soft Robotics 6, 133-141 (2019).

Lin, L. S. Novelino, H. Wei, N. A. Alderete, G. H. Paulino, H. D. Espinosa, S. Krishnaswamy, Folding at the Microscale: Enabling Multifunctional 3D Origami-Architected Metamaterials. Small 16, 2002229 (2020).

Liu T, Wang Y, & Lee K (2017) Three-dimensional printable origami twisted tower: Design, fabrication, and robot embodiment. IEEE Robotics and Automation Letters 3(1):116-123.

Liu, B., Breuer, K. S. & Powers, T. R. Propulsion by a helical flagellum in a capillary tube. Physics of Fluids 26, 011701 (2014).

Liu, et al., Big influence of small random imperfections in origami-based metamaterials. Proc. Royal Soc. A: Math. Phys. Eng. Sci. (2020).

Liu, G. H. Paulino, Nonlinear mechanics of non-rigid origami: An efficient computational approach. Proc. Math. Phys. Eng. Sci. 473, 20170348 (2017).

Liu, J. Wu, G. H. Paulino, H. J. Qi, Programmable deployment of tensegrity structures by stimulus-responsive polymers. Sci. Rep. 7, 1-8 (2017).

Lu, M. Zhang, Y. Yang, Q. Huang, T. Fukuda, Z. Wang, Y. Shen, A bioinspired multilegged soft millirobot that functions in both dry and wet conditions. Nature Communications 9, 1-7 (2018).

Lum et al., Shape-programmable magnetic soft matter. Proc. Natl. Acad. Sci. U.S.A. 113, E6007-E6015 (2016).

Martinez RV, Fish CR, Chen X, & Whitesides GM (2012) Elastomeric origami: programmable paper-elastomer composites as pneumatic actuators. Advanced functional materials 22(7):1376-1384.

Melancon D, Gorissen B, García-Mora CJ, Hoberman C, & Bertoldi K (2021) Multistable inflatable origami structures at the metre scale. Nature 592(7855):545-550.

Miskin et al., Graphene-based bimorphs for micron-sized, autonomous origami machines. Proc. Natl. Acad. Sci. U.S.A. 115, 466-470 (2018).

Miyashita S, Guitron S, Ludersdorfer M, Sung CR, & Rus D (2015) An untethered miniature origami robot that self-folds, walks, swims, and degrades. 2015 IEEE International Conference on Robotics and Automation (ICRA), (IEEE), pp. 1490-1496.

Na et al., Programming reversibly self-folding origami with micropatterned photo-crosslinkable polymer trilayers. Adv. Mater. 27, 79-85 (2015).

Nakamura, Y. Hidaka, M. Yokojima, K. Adachi, Development of peristaltic crawling robot with artificial rubber muscles attached to large intestine endoscope. Advanced Robotics 26, 1161-1182 (2012).

Nauroze, L. S. Novelino, M. M. Tentzeris, G. H. Paulino, Continuous-range tun-able multilayer frequency-selective surfaces using origami and inkjet printing. Proc. Natl. Acad. Sci. U.S.A. 115, 13210-13215 (2018).

Nayakanti, S. H. Tawfick, A. J. Hart, Twist-coupled kirigami cells and mechanisms. Extreme Mech. Lett. 21, 17-24 (2018).

Novelino, Larissa S., et al. "Untethered control of functional origami microrobots with distributed actuation." Proceedings of the National Academy of Sciences 117.39 (2020): 24096-24101.

Ochiai, Y., Kato, M., Kiguchi, Y., Akimoto, T., Nakayama, A., Sasaki, M., . . . & Yahagi, N. (2019). Current status and challenges of endoscopic treatments for duodenal tumors. Digestion, 99(1), 21-26.

Omori, T. Murakami, H. Nagai, T. Nakamura, T. Kubota, Development of a novel bio-inspired planetary subsurface explorer: initial experimental study by prototype excavator with propulsion and excavation units. IEEE/ASME Transactions on Mechatronics 18, 459-470 (2012).

Onal, R. J. Wood, D. Rus, An origami-inspired approach to worm robots. IEEE/ASME Transactions on Mechatronics 18, 430-438 (2012).

Overvelde et al., A three-dimensional actuated origami-inspired transformable metamaterial with multiple degrees of freedom. Nat. Commun. 7, 10929 (2016).

Paez L, Agarwal G, & Paik J (2016) Design and analysis of a soft pneumatic actuator with origami shell reinforcement. Soft Robotics 3(3):109-119.

Pagano A, Yan T, Chien B, Wissa A, & Tawfick S (2017) A crawling robot driven by multi-stable origami. Smart Materials and Structures 26(9):094007.

Qian, Q. Chen, Y. Yang, Y. Xu, Z. Li, Z. Wang, Y. Wu, Y. Wei, Y. Ji, Untethered recyclable tubular actuators with versatile locomotion for soft continuum robots. Advanced Materials 30, 1801103 (2018).

Qin, X. Liang, H. Huang, C. K. Chui, R. C.-H. Yeow, J. Zhu, A versatile soft crawling robot with rapid locomotion. Soft Robotics 6, 455-467 (2019).

Rafsanjani, Y. Zhang, B. Liu, S. M. Rubinstein, K. Bertoldi, Kirigami skins make a simple soft actuator crawl. Sci. Robotics 3, eaar7555 (2018).

Reis, A perspective on the revival of structural (In)stability with novel oppor-tunities for function: From buckliphobia to buckliphilia. J. Appl. Mech. 82, 111001 (2015).

Rogóż, H. Zeng, C. Xuan, D. S. Wiersma, P. Wasylczyk, Light-driven soft robot mimics caterpillar locomotion in natural scale. Advanced Optical Materials 4, 1689-1694 (2016).

Rothemund, A. Ainla, L. Belding, D. J. Preston, S. Kurihara, Z. Suo, G. M. Whitesides, A soft, bistable valve for autonomous control of soft actuators. Science Robotics 3, (2018).

Runciman, A. Darzi, G. P. Mylonas, Soft robotics in minimally invasive surgery. Soft Robotics 6, 423-443 (2019).

Rus, D. & Tolley, M. T. Design, fabrication and control of origami robots. Nature Reviews Materials 3, 101-112 (2018).

Saga, T. Nakamura, Development of a peristaltic crawling robot using magnetic fluid on the basis of the locomotion mechanism of the earthworm. Smart Materials and Structures 13, 566 (2004).

Salerno M, Zhang K, Menciassi A, & Dai JS (2016) A novel 4-DOF origami grasper with an SMA-actuation system for minimally invasive surgery. IEEE Transactions on Robotics 32(3):484-498.

Santoso J & Onal CD (2020) An Origami Continuum Robot Capable of Precise Motion Through Torsionally Stiff Body and Smooth Inverse Kinematics. Soft Robotics. 16 pages.

Schenk, S. D. Guest, Geometry of Miura-folded metamaterials. Proc. Natl. Acad. Sci. U.S.A. 110, 3276-3281 (2013).

Seok, C. D. Onal, K.-J. Cho, R. J. Wood, D. Rus, S. Kim, Meshworm: a peristaltic soft robot with antagonistic nickel titanium coil actuators. IEEE/ASME Transactions on mechatronics 18, 1485-1497 (2012).

Shepherd, F. Ilievski, W. Choi, S. A. Morin, A. A. Stokes, A. D. Mazzeo, X. Chen, M. Wang, G. M. Whitesides, Multigait soft robot. Proceedings of the national academy of sciences 108, 20400-20403 (2011).

Silverberg et al., Using origami design principles to fold reprogrammable mechanical metamaterials. Science 345, 647-650 (2014).

Sitti, H. Ceylan, W. Hu, J. Giltinan, M. Turan, S. Yim, E. Diller, Biomedical applications of untethered mobile milli/microrobots. Proceedings of the IEEE 103, 205-224 (2015).

Soncin, Silvia, et al. "High-resolution dietary reconstruction of victims of the 79 CE Vesuvius eruption at Herculaneum by compound-specific isotope analysis." Science Advances 7.35 (2021): eabg5791.

Spagnolie, S. E., Liu, B. & Powers, T. R. Locomotion of helical bodies in viscoelastic fluids: enhanced swimming at large helical amplitudes. Physical review letters 111, 068101 (2013).

Sumbre G, Gutfreund Y, Fiorito G, Flash T, & Hochner B (2001) Control of octopus arm extension by a peripheral motor program. Science 293(5536):1845-1848.

Tang et al., Leveraging elastic instabilities for amplified performance: Spine-inspired high-speed and high-force soft robots. Sci. Adv. 6, eaaz6912 (2020).

Treml, A. Gillman, P. Buskohl, R. Vaia, Origami mechanologic. Proc. Natl. Acad. Sci. U.S.A. 115, 6916-6921 (2018).

Verma, A. Ainla, D. Yang, D. Harburg, G. M. Whitesides, A soft tube-climbing robot. Soft Robotics 5, 133-137 (2018).

Walrath, B. D., Harper, S., Barnard, E., Tobin, J. M., Drew, B., Cunningham, C., . . . & Martin, M. (2018). Airway management for trauma patients. Military medicine, 183(suppl_2), 29-31.

(56)          References Cited

OTHER PUBLICATIONS

Wu et al., Symmetry-breaking actuation mechanism for soft robotics and active metamaterials. ACS Appl. Mater. Interfaces 11, 41649-41658 (2019).

Wu, C. M. Hamel, Q. Ze, F. Yang, H. J. Qi, R. Zhao, Evolutionary Algorithm-Guided Voxel-Encoding Printing of Functional Hard-Magnetic Soft Active Materials. Advanced Intelligent Systems 2, 2000060 (2020).

Wu, J. K. Yim, J. Liang, Z. Shao, M. Qi, J. Zhong, Z. Luo, X. Yan, M. Zhang, X. Wang, Insect-scale fast moving and ultrarobust soft robot. Science Robotics 4, (2019).

Wu, Shuai, et al. "Stretchable origami robotic arm with omnidirectional bending and twisting." Proceedings of the National Academy of Sciences 118.36 (2021):e2110023118.

Xiao, Z. C. Jiang, X. Tong, Y. Zhao, Biomimetic locomotion of electrically powered "Janus" soft robots using a liquid crystal polymer. Advanced Materials 31, 1903452 (2019).

Xu T, Zhang J, Salehizadeh M, Onaizah O, & Diller E (2019) Millimeter-scale flexible robots with programmable three-dimensional magnetization and motions. Science Robotics 4(29).

Xu, Z. Yan, K.-I. Jang, W. Huang, H. Fu, J. Kim, Z. Wei, M. Flavin, J. McCracken, R. Wang, Assembly of micro/nanomaterials into complex, three-dimensional architectures by compressive buckling. Science 347, 154-159 (2015).

Yan Z, et al. (2016) Controlled mechanical buckling for origami-inspired construction of 3D microstructures in advanced materials. Advanced functional materials 26(16):2629-2639.

Yasuda et al., Origami-based impact mitigation via rarefaction solitary wave creation. Sci. Adv. 5, eaau2835 (2019).

Yasuda H, Tachi T, Lee M, & Yang J (2017) Origami-based tunable truss structures for non-volatile mechanical memory operation. Nature communications 8(1):1-7.

Yeh, C.-Y. Chen, J.-Y. Juang, Soft hopping and crawling robot for in-pipe traveling. Extreme Mechanics Letters 39, 100854 (2020).

Yekutieli Y, Sumbre G, Flash T, & Hochner B (2002) How to move with no rigid skeleton? Biologist 49(6):250-254.

Yim S, Gultepe E, Gracias DH, & Sitti M (2013) Biopsy using a magnetic capsule endoscope carrying, releasing, and retrieving untethered microgrippers. IEEE Transactions on Biomedical Engineering 61(2):513-521.

Ze et al., Magnetic shape memory polymers with integrated multifunctional shape manipulation. Adv. Mater. 32, 1906657 (2020).

Zhai, Y. Wang, H. Jiang, Origami-inspired, on-demand deployable and collapsible mechanical metamaterials with tunable stiffness. Proc. Natl. Acad. Sci. U.S.A. 115, 2032-2037 (2018).

Zhang et al., A mechanically driven form of kirigami as a route to 3D mesostruc-tures in micro/nanomembranes. Proc. Natl. Acad. Sci. U.S.A. 112, 11757-11764 (2015).

Zhang, E. Diller, Untethered miniature soft robots: Modeling and design of a millimeter-scale swimming magnetic sheet. Soft Robotics 5, 761-776 (2018).

Zhao Z, et al. (2017) Origami by frontal photopolymerization. Science advances 3(4):e1602326.

Zhao Z, et al. (2018) 3D printing of complex origami assemblages for reconfigurable structures. Soft Matter 14(39):8051-8059.

Zirbel et al., Accommodating thickness in origami-based deployable arrays. J. Mech. Des. 135, 111005 (2013).

Zou, Y. Lin, C. Ji, H. Yang, A reconfigurable omnidirectional soft robot based on caterpillar locomotion. Soft Robotics 5, 164-174 (2018).

* cited by examiner

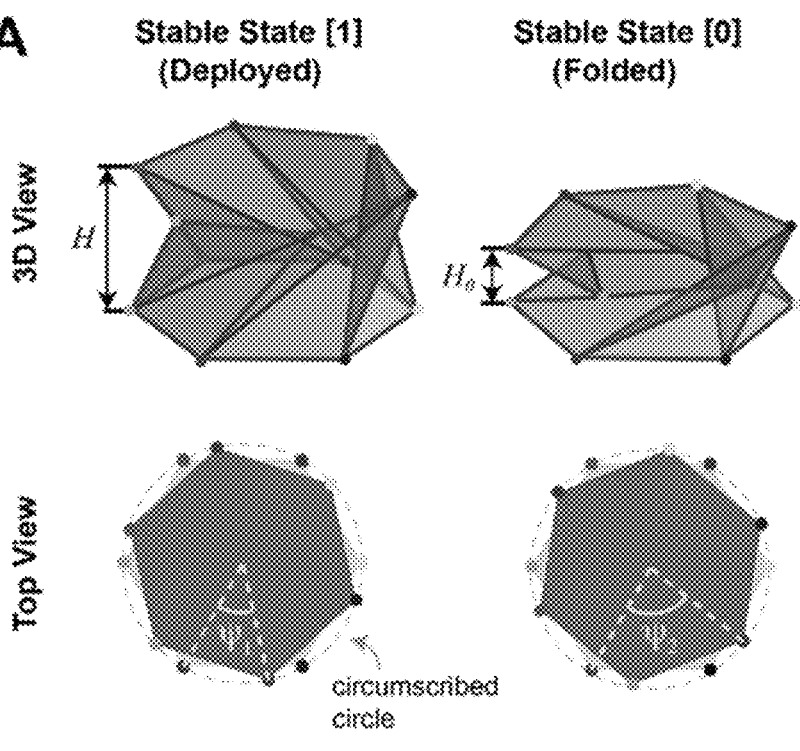
FIG. 5A
Crease Pattern
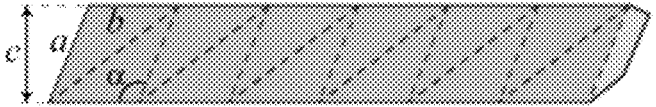
Modified Crease Pattern
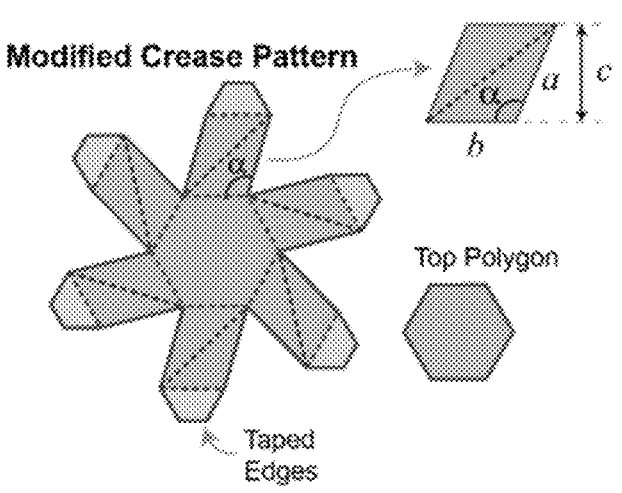
FIG. 5B

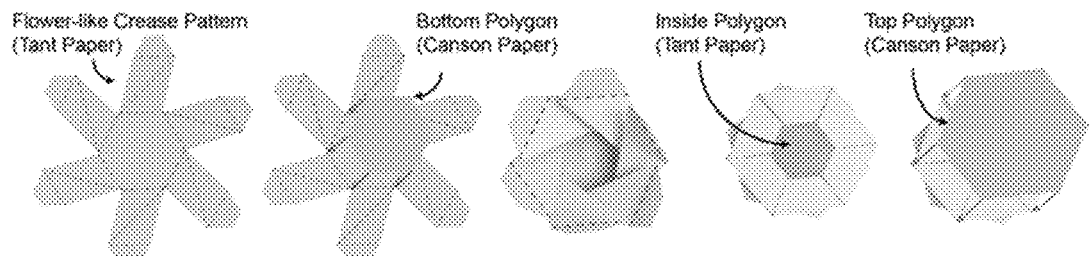
FIG. 5C
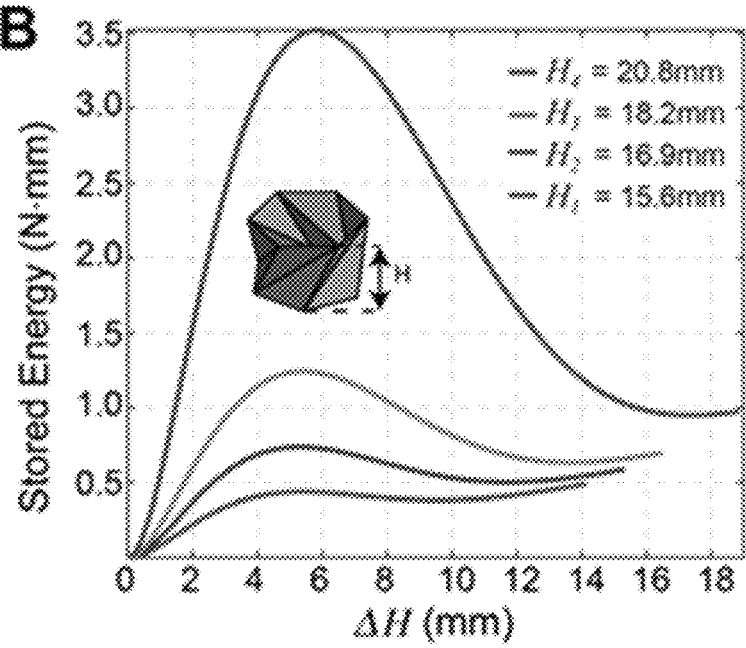
FIG. 6A
FIG. 6B

Omnidirectional bending

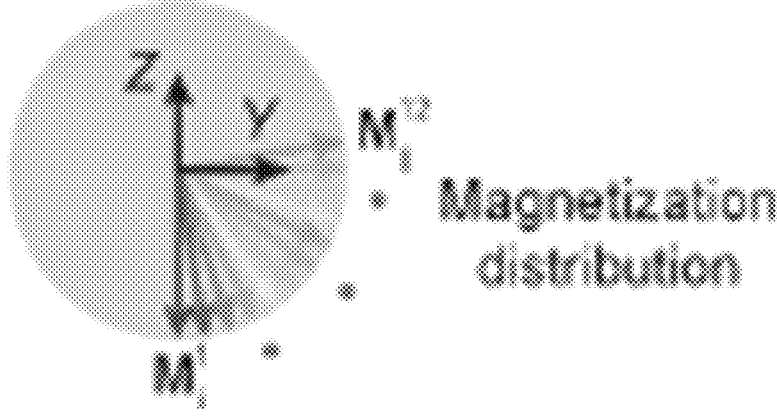
FIG. 30C
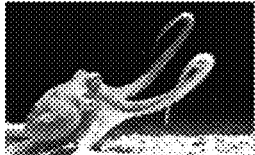
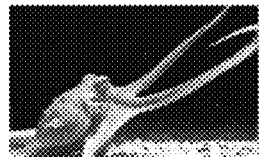
FIG. 30D

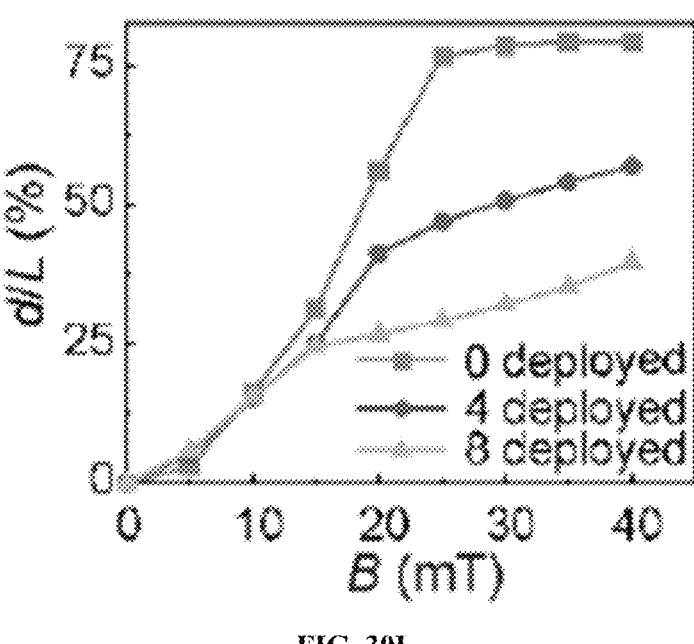
FIG. 30I
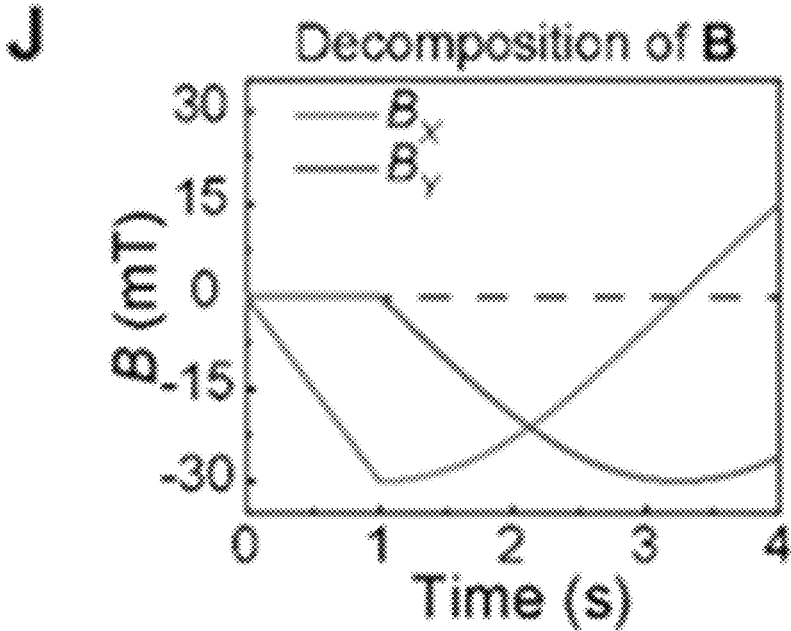
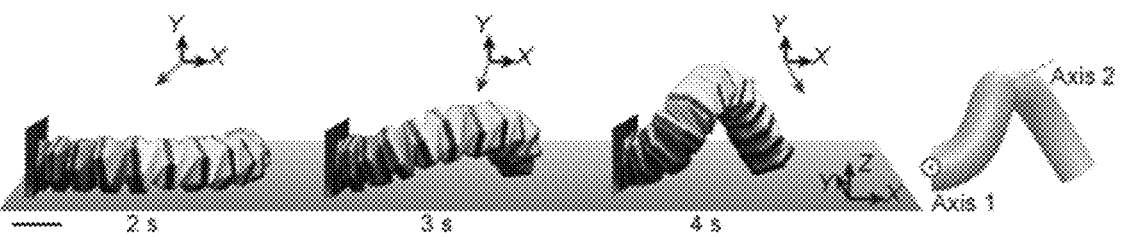
FIG. 30J

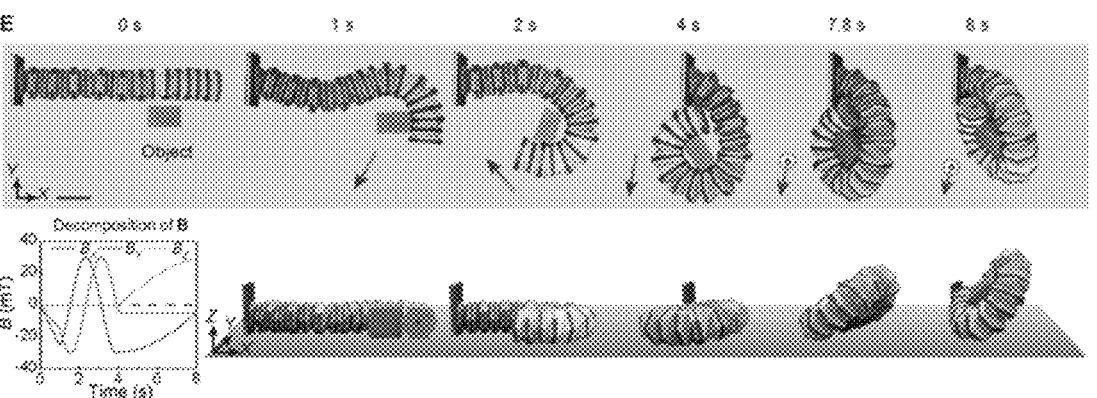
FIG. 31E
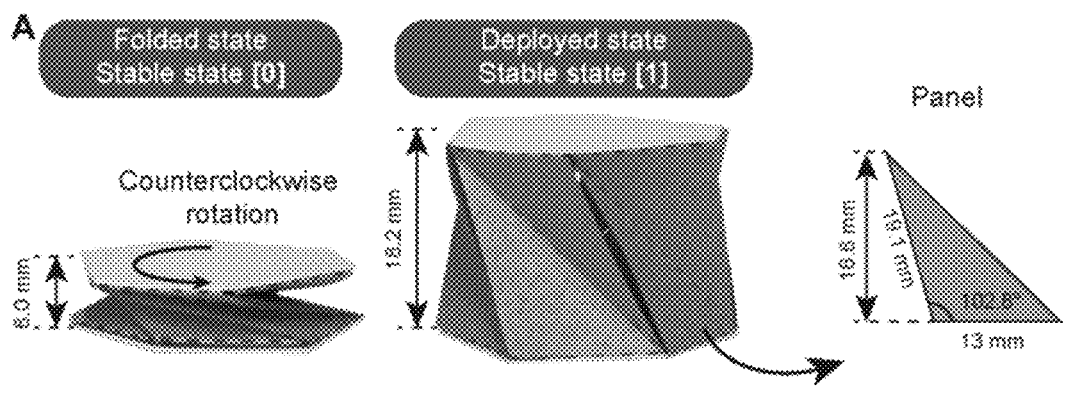
FIG. 32A
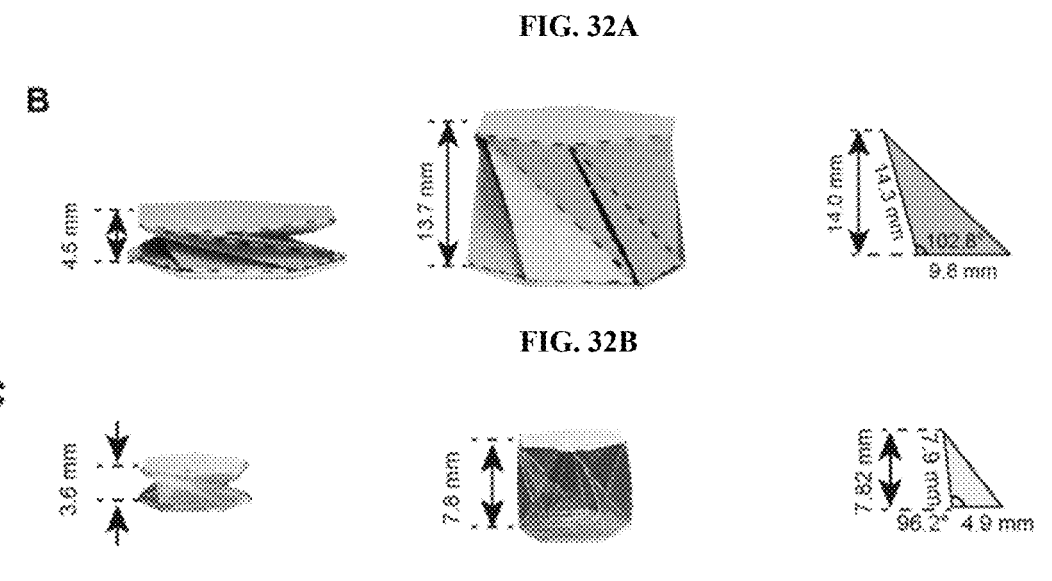
FIG. 32B
FIG. 32C

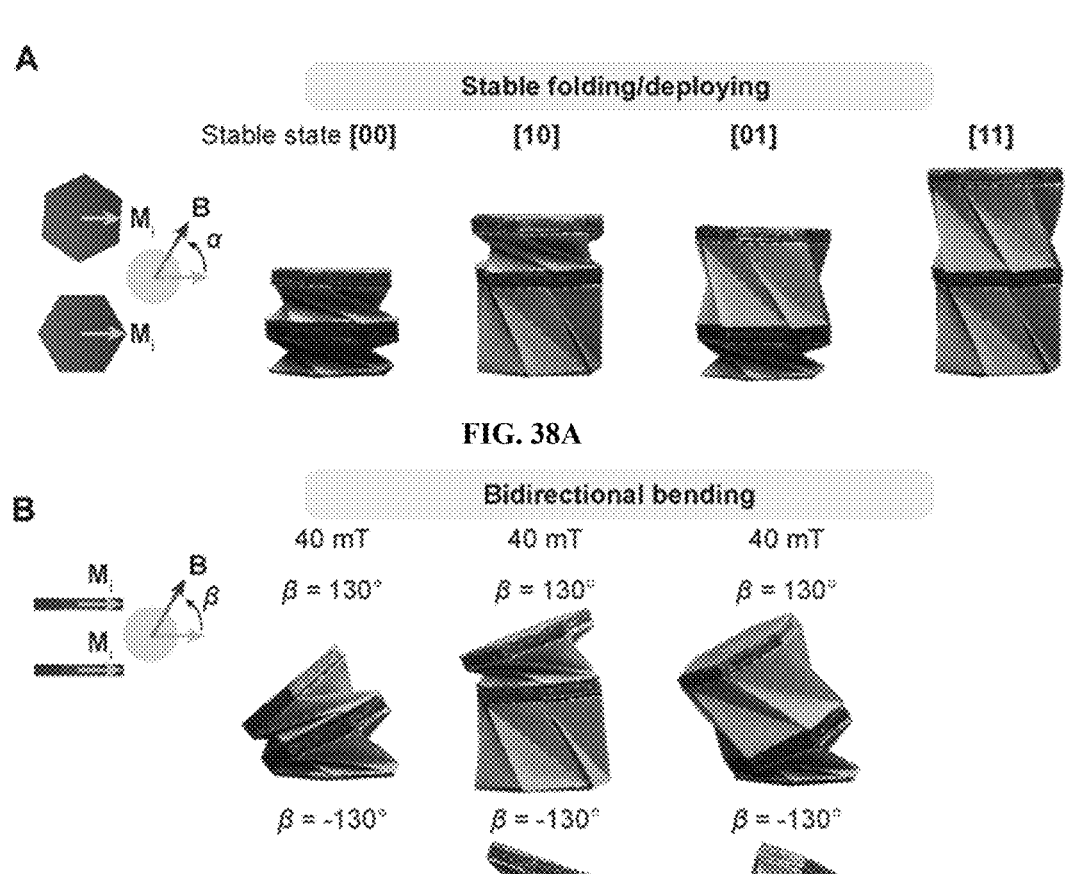
FIG. 38A
FIG. 38B
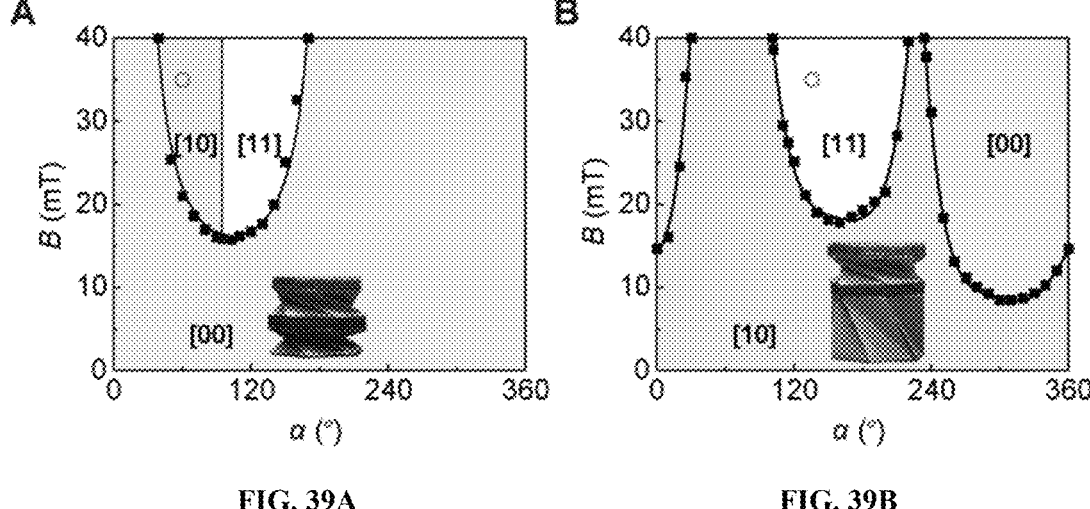
FIG. 39A                          FIG. 39B

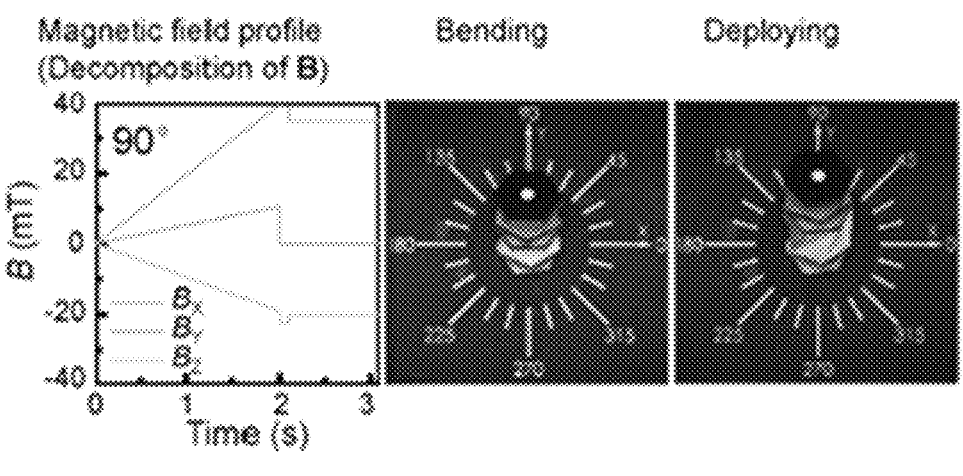
FIG. 42C
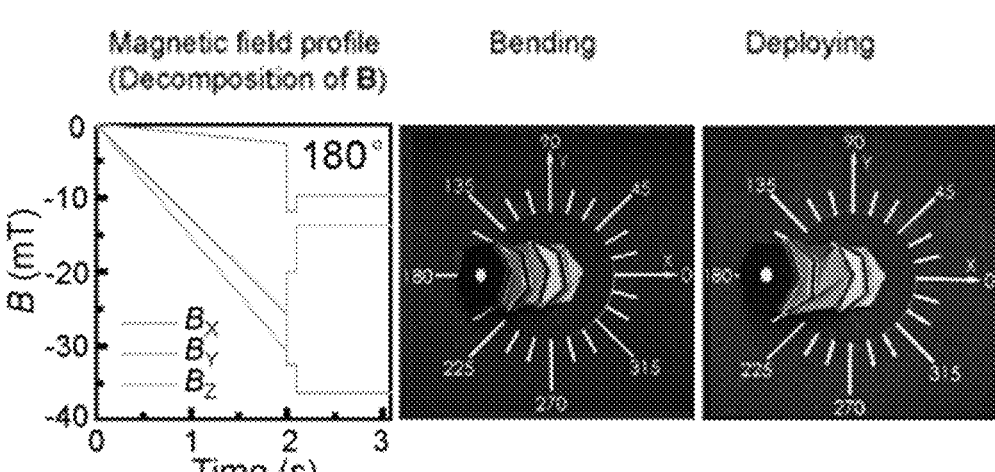
FIG. 42D
FIG. 42E

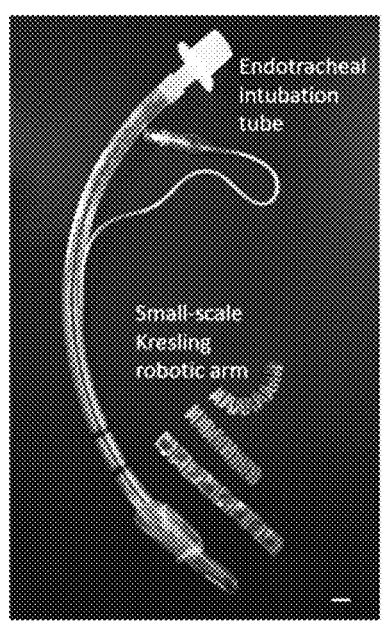
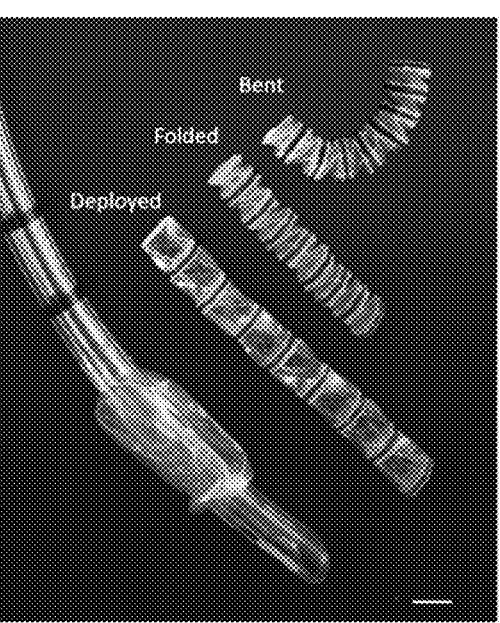
FIG. 47
A
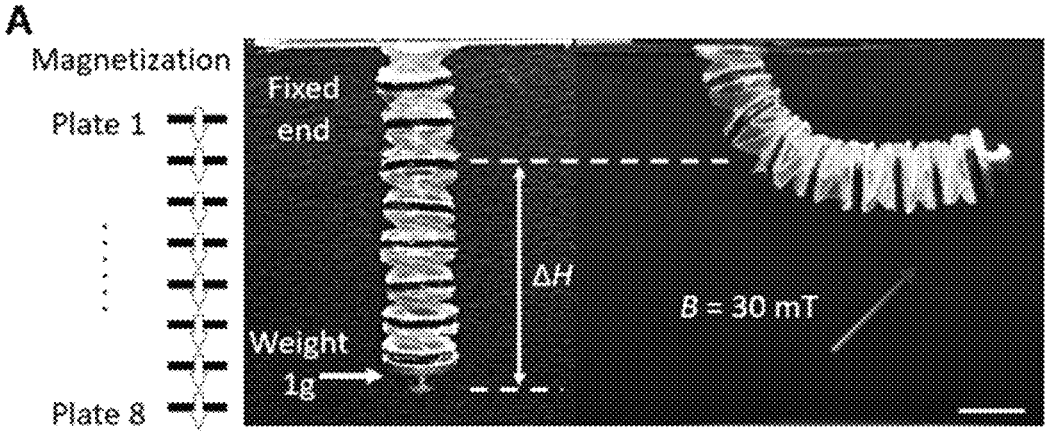
FIG. 48A
B
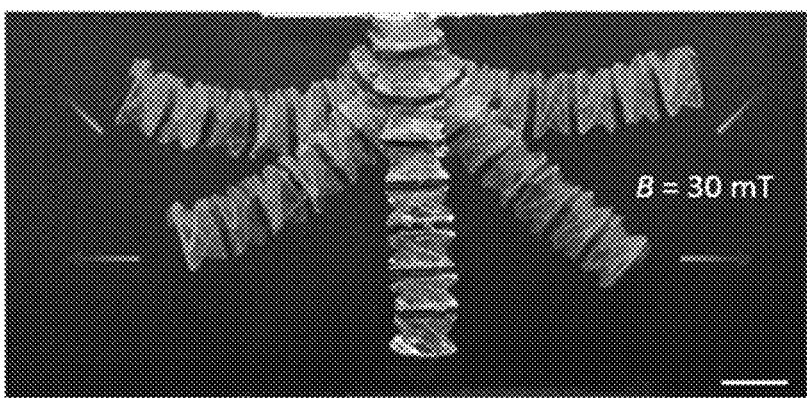
FIG. 48B

Magnetization

FIG. 50A    FIG. 50B

Central & Mirror symmetries
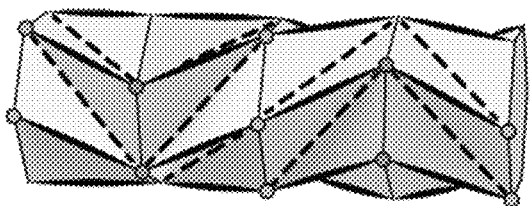
No rotation at center plane & two ends
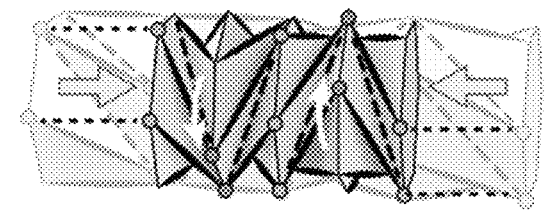
FIG. 50D
Torque distribution
$T_1$          $T_2$          $T_3$          $T_4$
U1          U2          U3          U4
FIG. 50E
Simulation (FEA)
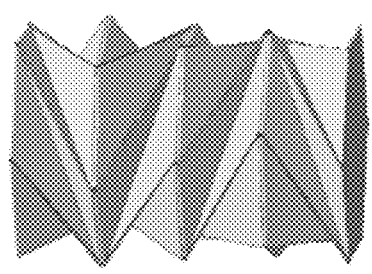
- - - - - Valley fold     ——— Cut (Mountain fold)     ⇨ Contraction     ⟶ Torque
FIG. 50F

A

Net magnetization M$_{net}$ ⟶

B

Initial

Contracted

Torque $T_{U1}^m$ $T_{U2}^m$ $T_{U3}^m$ $T_{U4}^m$ $B_y$ ⟶

$T_{U1}^m = T_{U4}^m$ $T_{U2}^m = T_{U3}^m$

90° − 16°
(74°)    $\theta_r = 32°$    90° + 16°
(106°)

$\theta_2$ or $\theta_3$

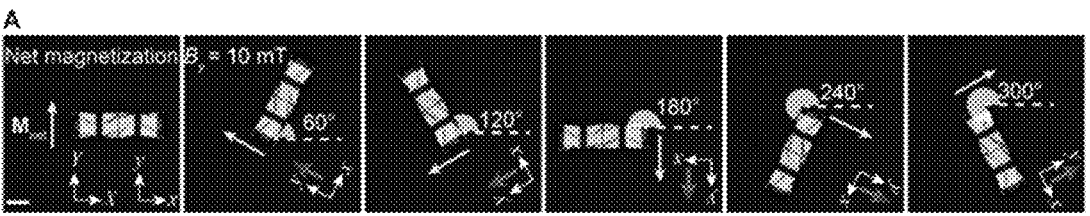
FIG. 53A
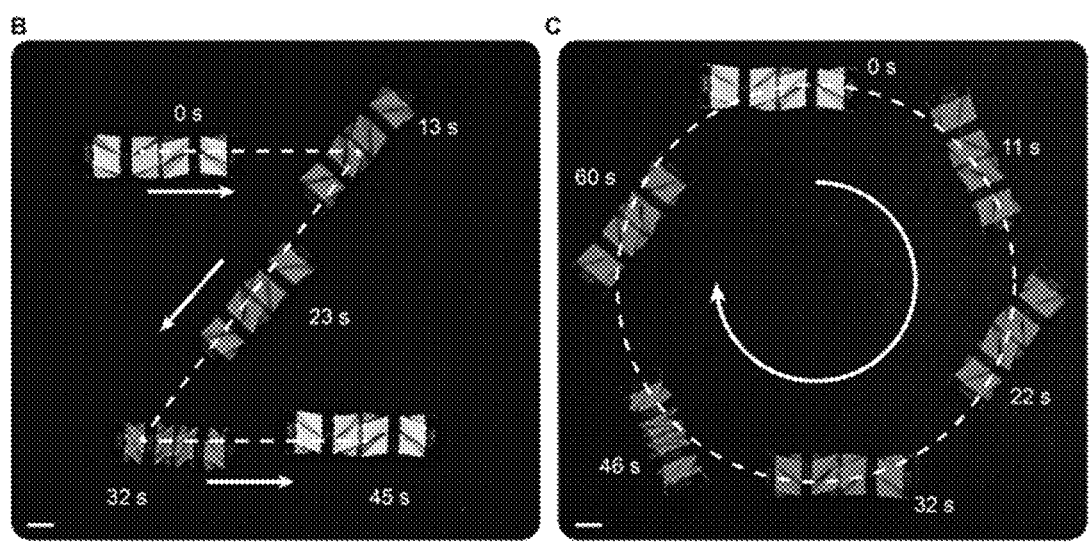
FIG. 53B                    FIG. 53C
Axial compression
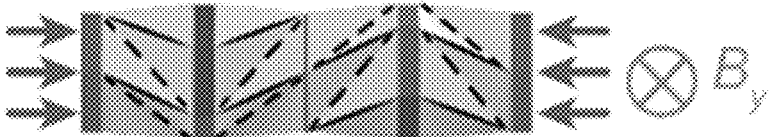
Lateral compression
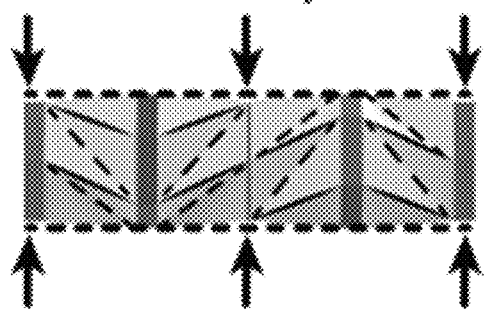
FIG. 54A

Crawling in a confined space

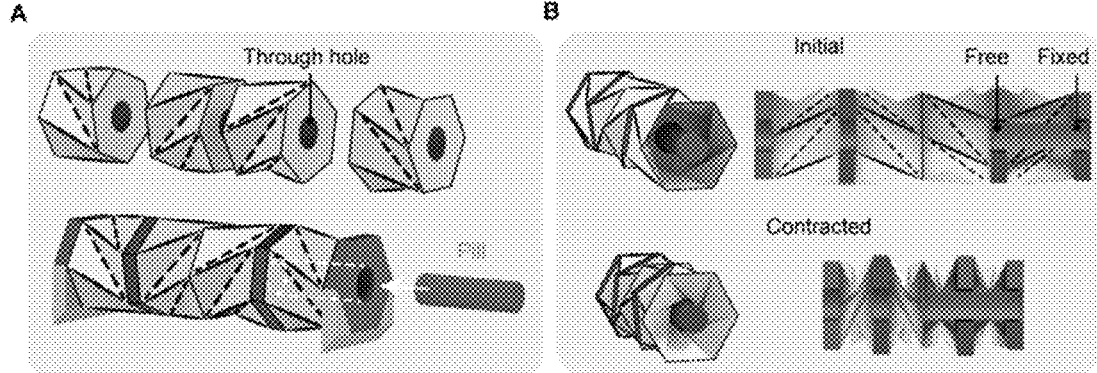
FIG. 55A                        FIG. 55B
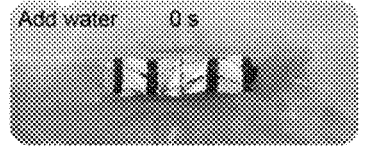 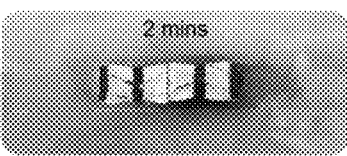 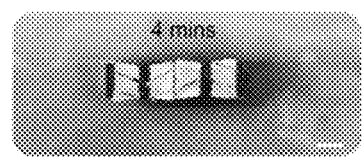
FIG. 55C

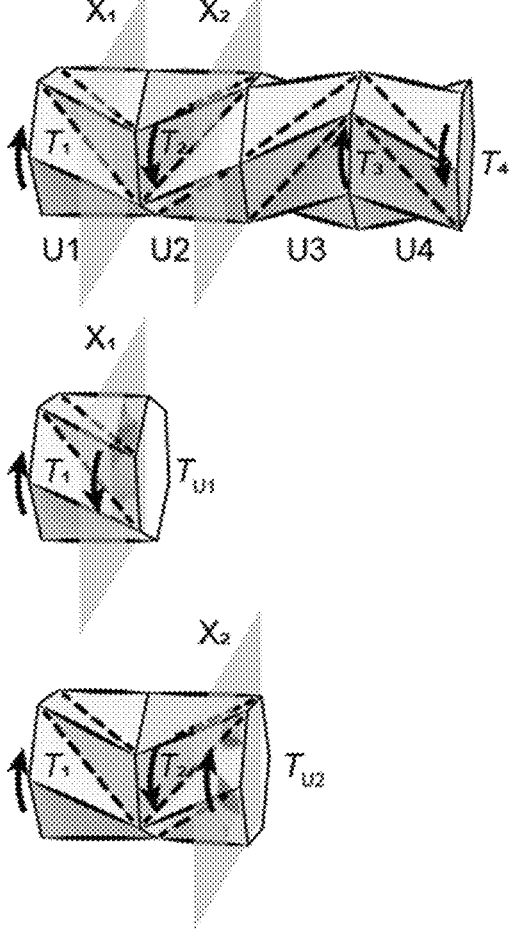
FIG. 60
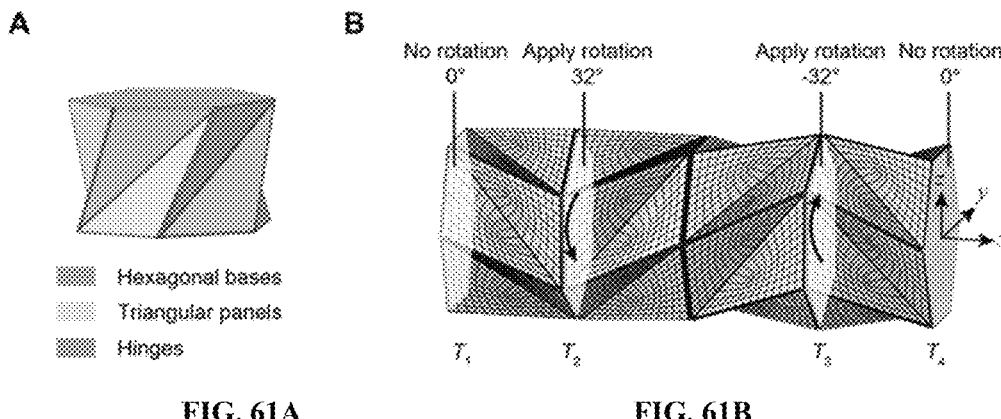
FIG. 61A                    FIG. 61B

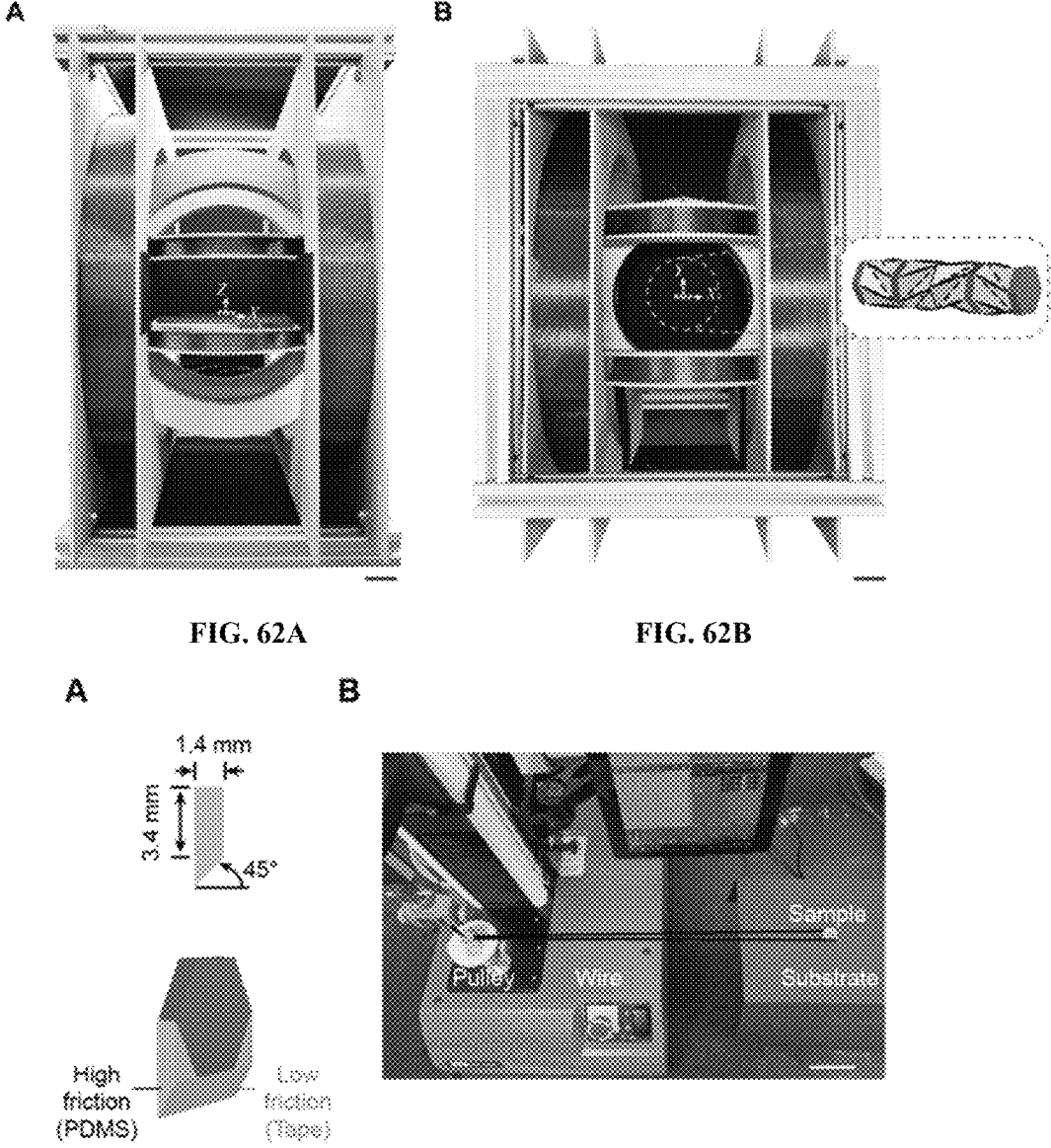
FIG. 62A                    FIG. 62B
FIG. 63A                    FIG. 63B

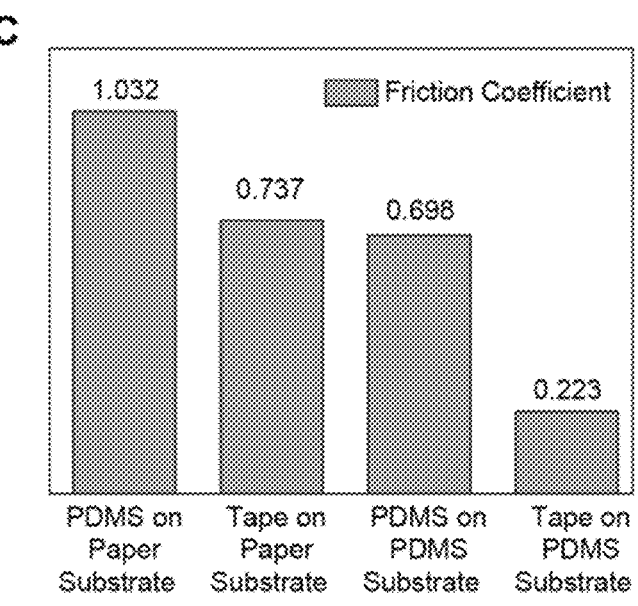
FIG. 63C
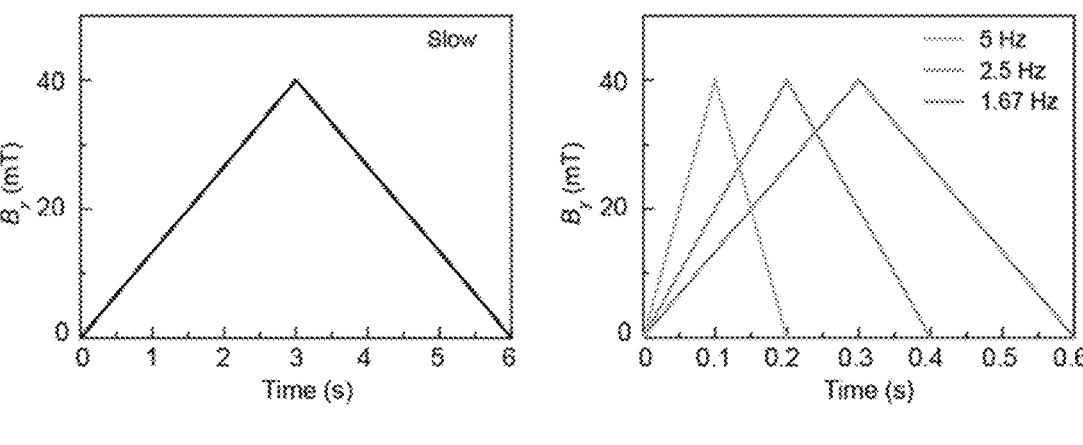
FIG. 64A                FIG. 64B
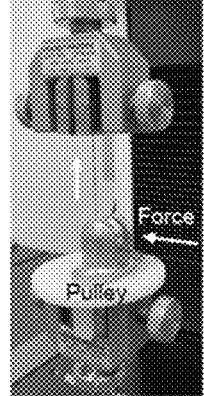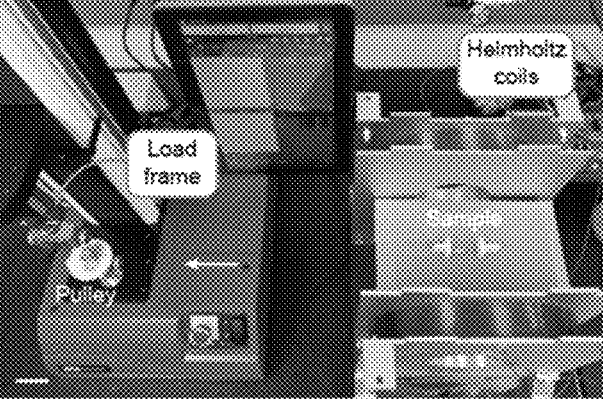
FIG. 65A

B

C

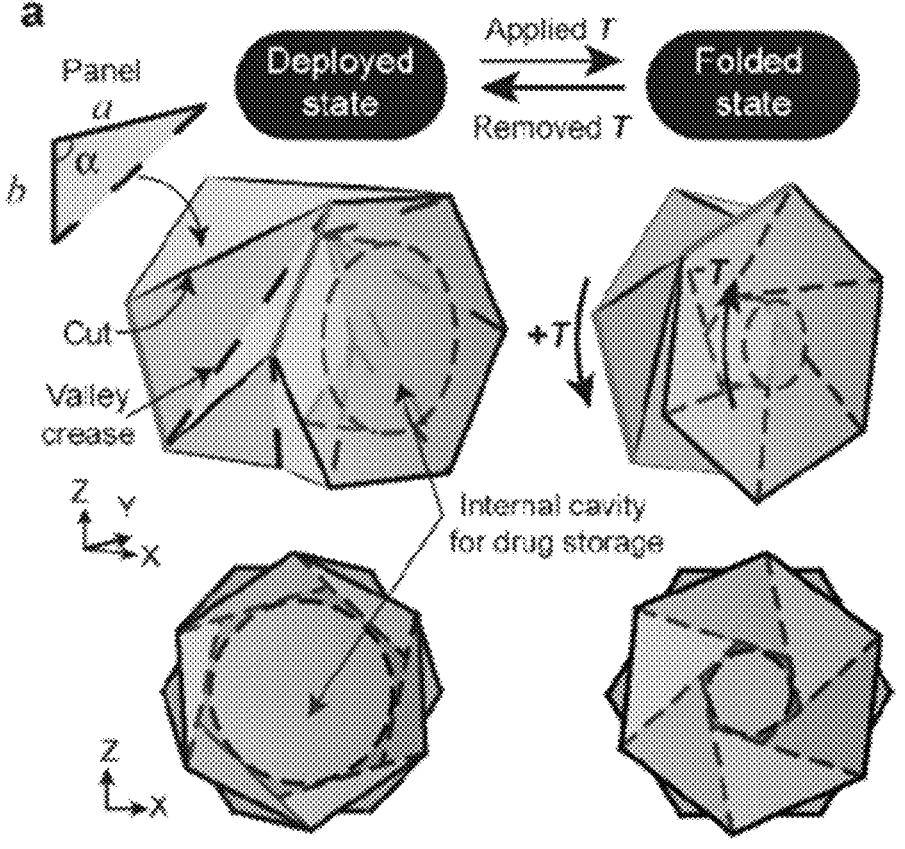
FIG. 67A
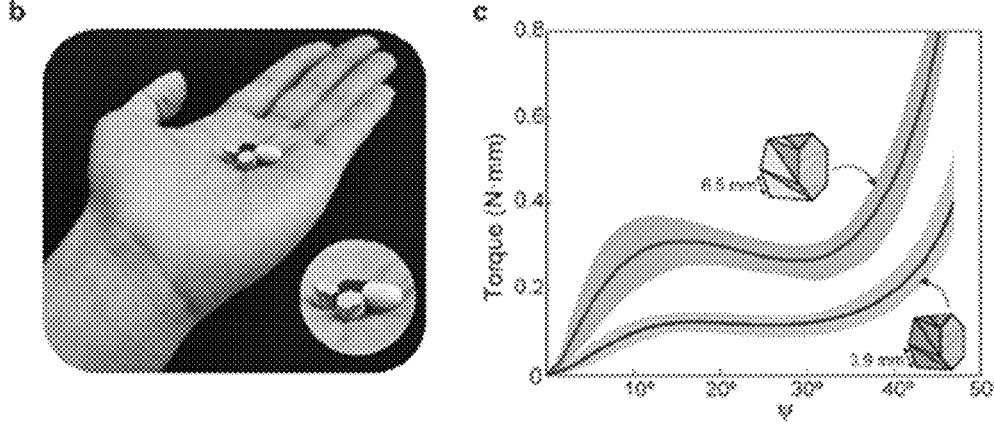
FIG. 67B                    FIG. 67C

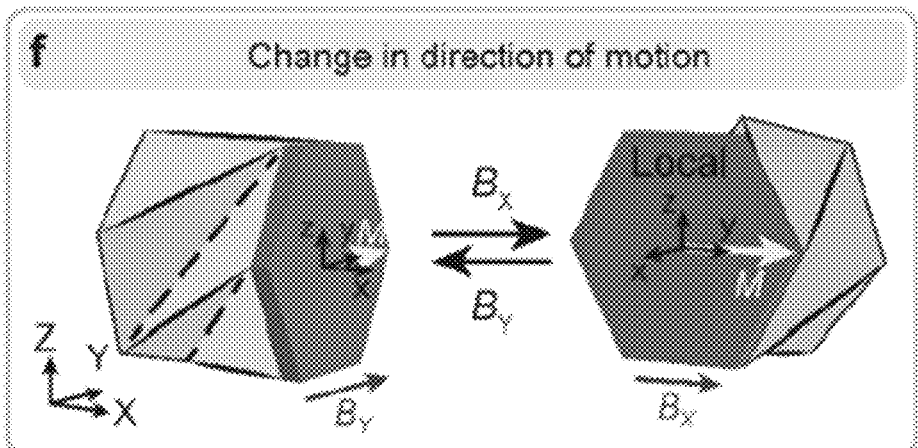
FIG. 67F
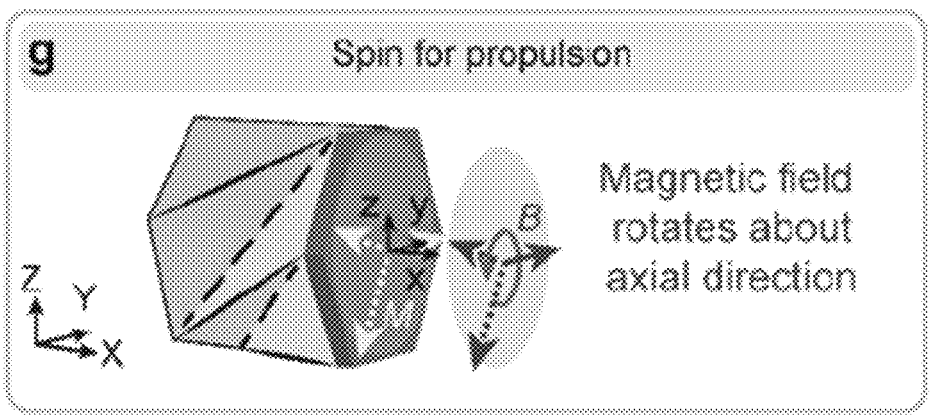
FIG. 67G
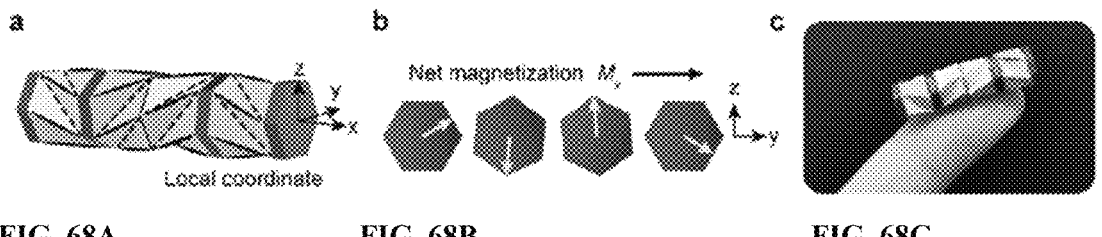
FIG. 68A                    FIG. 68B                    FIG. 68C

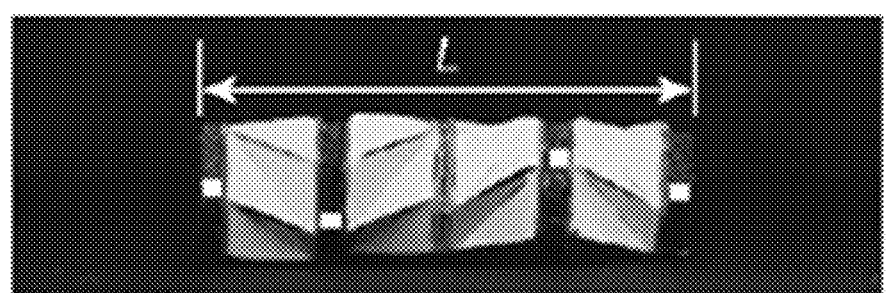
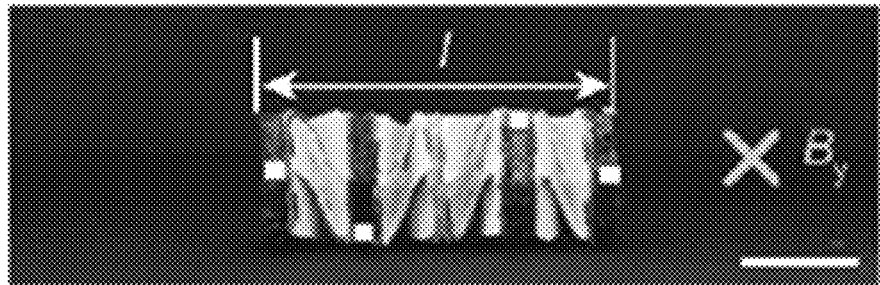
FIG. 68D
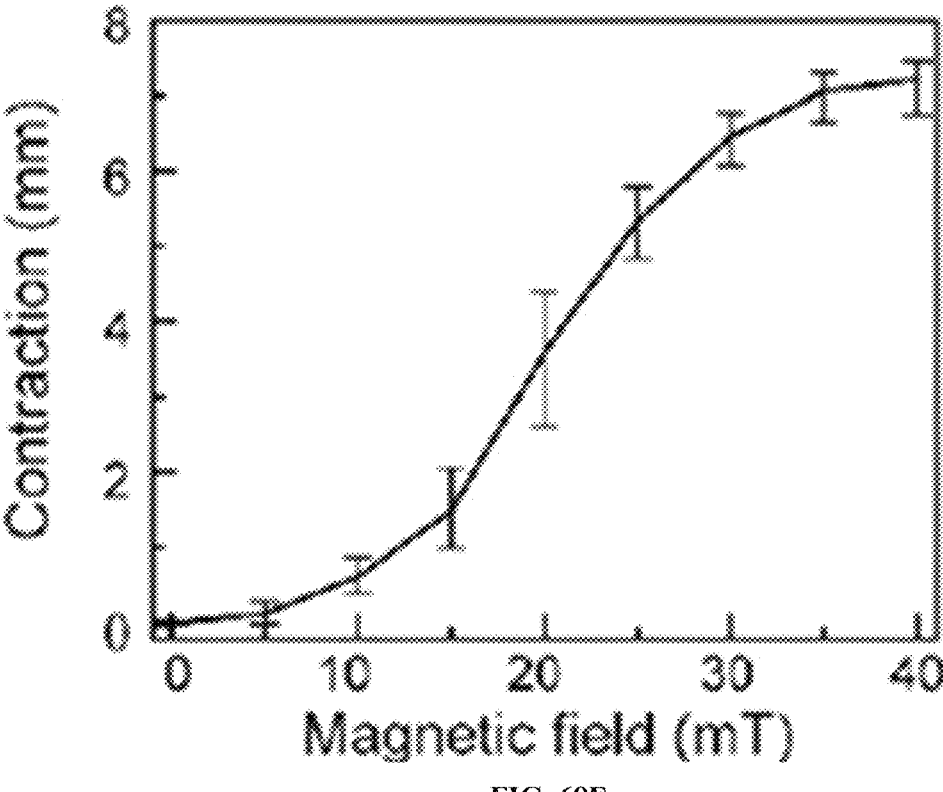
FIG. 68E

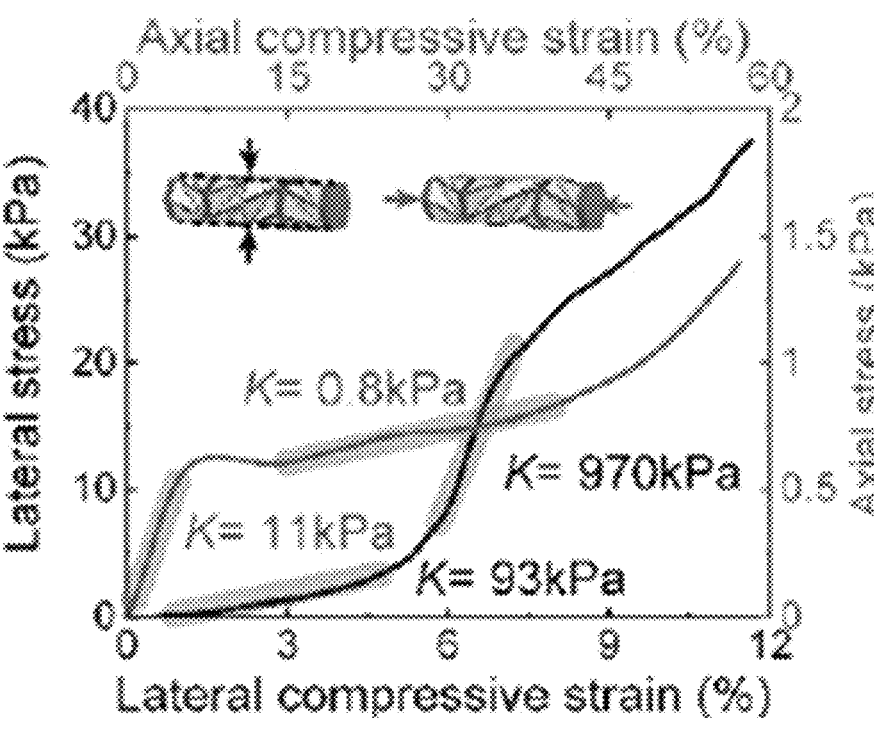
FIG. 68F
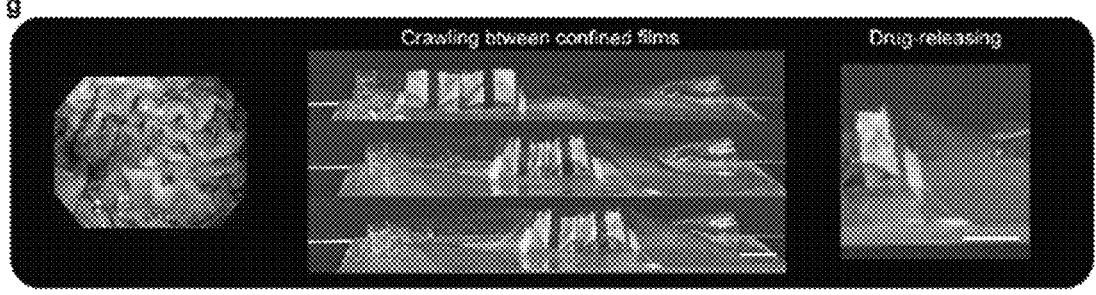
FIG. 68G
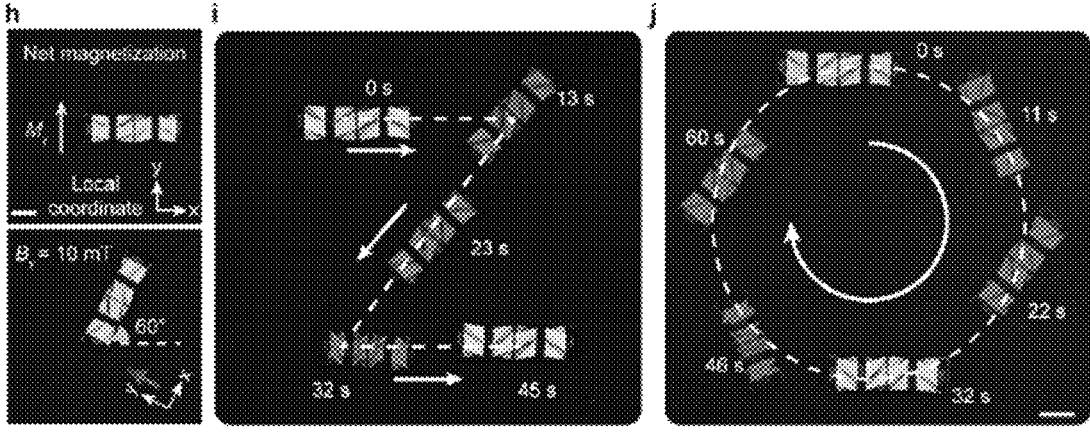
FIG. 68H        FIG. 68I        FIG. 68J a b

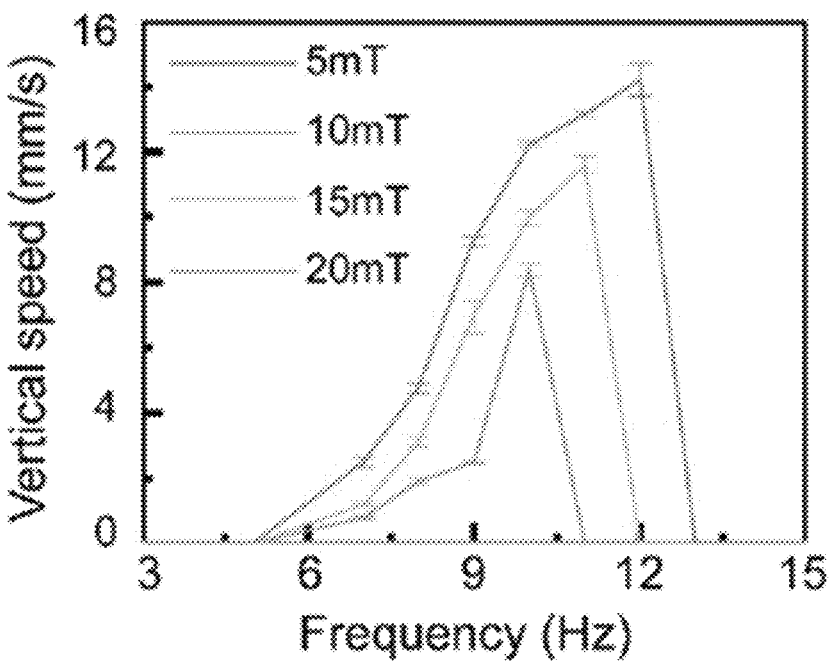
FIG. 69E
a
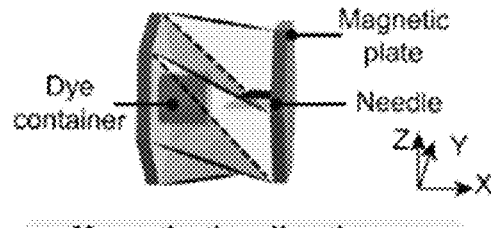
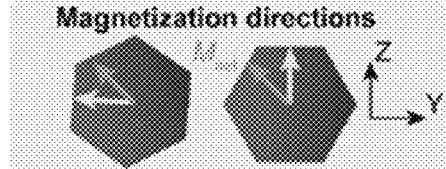
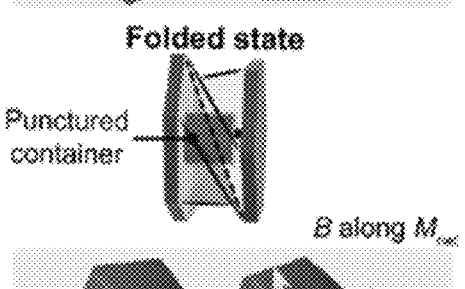
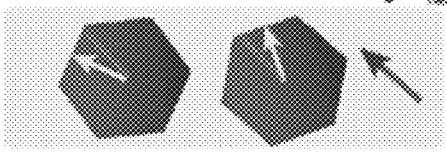
FIG. 70A

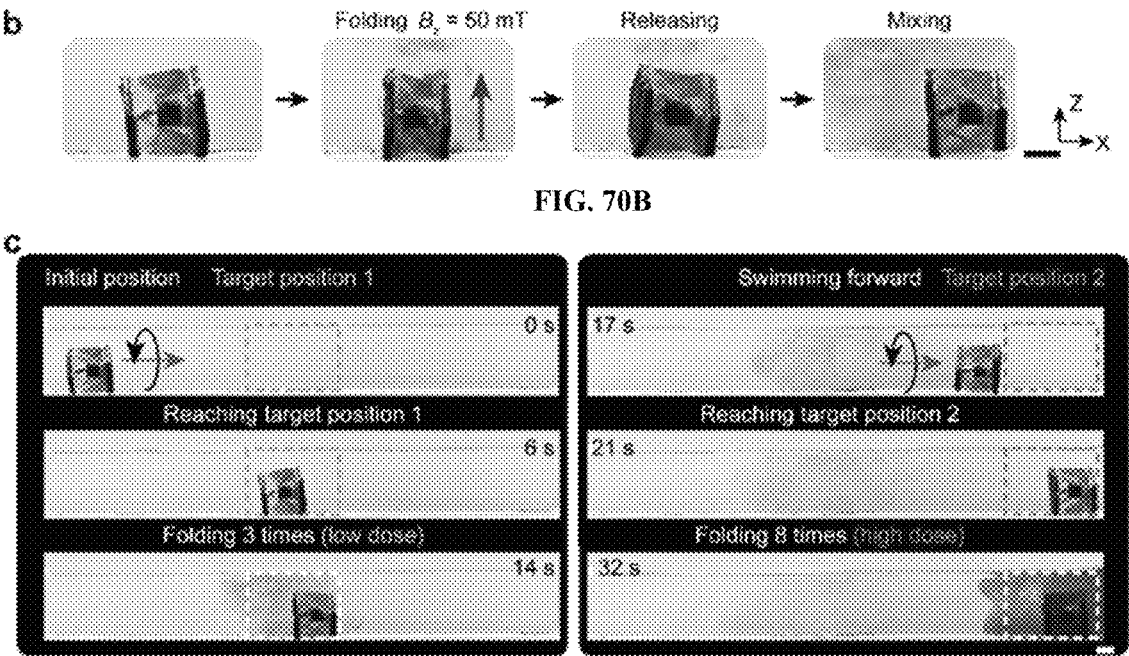
FIG. 70B
FIG. 70C
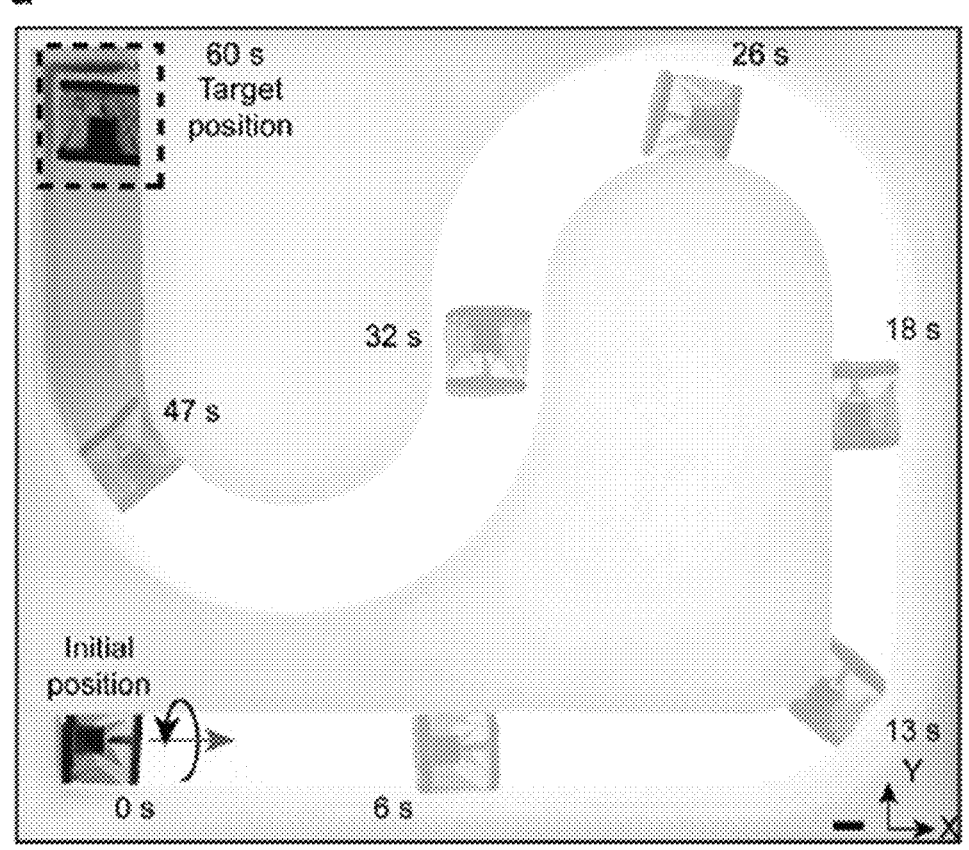
FIG. 70D

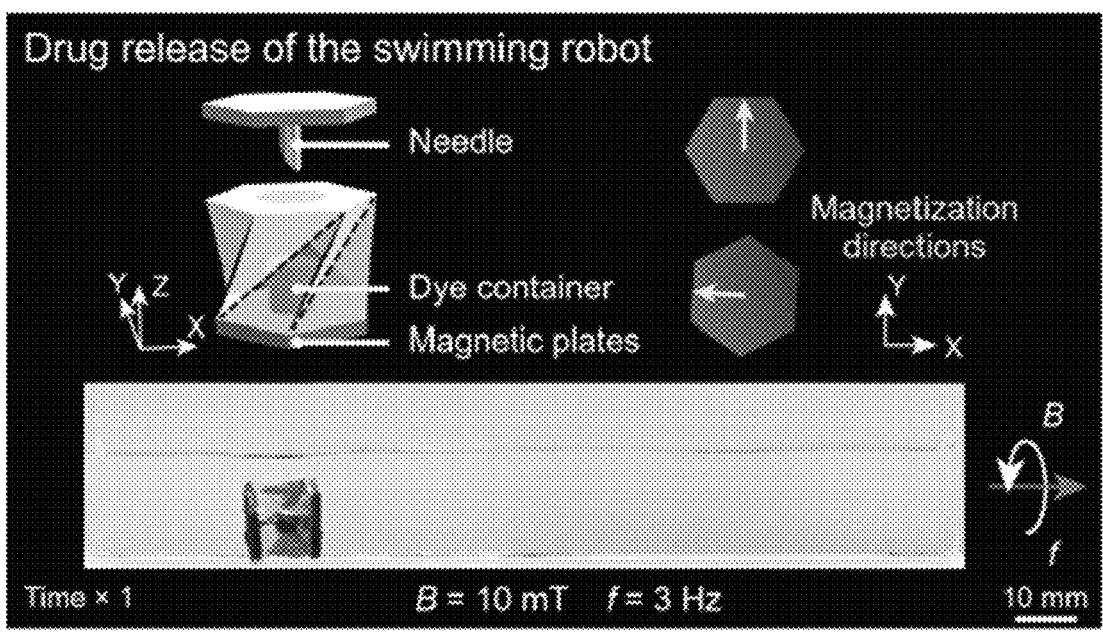
FIG. 75
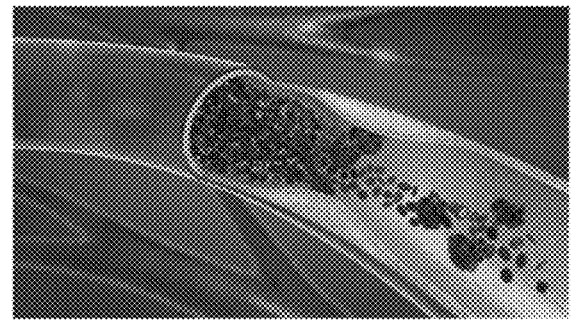
FIG. 76
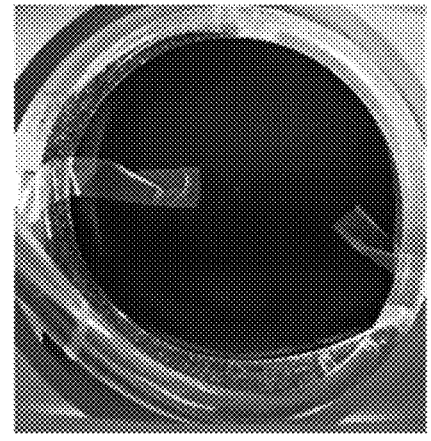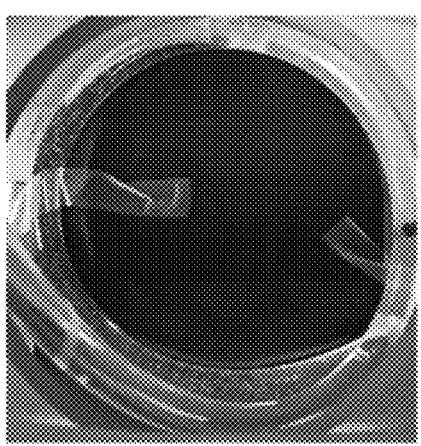
FIG. 77

MICROROBOTS WITH DISTRIBUTED ACTUATION

CROSS-REFERENCE TO RELATED APPLICATIONS

The application claims the benefit of U.S. Provisional Application No. 63/143,715, filed Jan. 29, 2021 and U.S. Provisional Application No. 63/144,219, filed Feb. 1, 2021, which are hereby incorporated herein by reference in their entirety.

STATEMENT REGARDING FEDERALLY SPONSORED RESEARCH OR DEVELOPMENT

This invention was made with government support under CNMI1943070, CNMI1939543, and CNMI1538830 awarded by the National Science Foundation. The government has certain rights in the invention.

BACKGROUND

Small-scale (millimeter scale) magnetically controlled robots have been demonstrated to have great potentials in developing the next-generation biomedical devices for minimally invasive techniques. Although existing works can achieve locomotion through the morphing of the soft body, these robots have two major limitations. First, these robots lose function in confined spaces as their intrinsic stiffness is too low and they cannot deform under the resistance between tissues and organs. Second, the existing soft magnetic robots mainly focus their capability of realizing locomotion, they are not designed for functional biomedical tasks such as effective drug delivery, as carrying objects significantly hinders their moving capability. The critical questions are: is it always smaller the better? Is always the softer the better?How to achieve effective targeted drug delivery?

There is a need for devices that can be remotely actuated for complex motions to achieve shape-changing capabilities and functionalities.

The devices and methods disclosed herein address these and other needs.

SUMMARY

Provided herein are unit cells including a base plate; a top plate; and a lumen extending longitudinally from the base plate to the top plate, the lumen defined by a side wall formed from a plurality of cojoined panels extending between a bottom surface of the top plate and a top surface of the base plate. The unit cell can be magnetically actuatable, such that the unit cell can be reversibly transitioned between a contracted configuration, an extended configuration, or a combination thereof using an applied magnetic field. In some embodiments, the transition between a contracted configuration, an extended configuration, or a combination thereof can include reorientation of the plurality of conjoined panels forming the side wall. In some embodiments, the transition between a contracted configuration and an extended configuration can include reorientation of the plurality of conjoined panels forming the side wall. In some embodiments, reorientation can include folding of one or more of the conjoined panels, unfolding of one or more of the conjoined panels, or any combination thereof. In some embodiments, the side wall can have an extended configuration height and a contracted configuration height, wherein the extended configuration height can be at least 2 times the contracted configuration height. In some embodiments, the unit cell can have a cross sectional dimension of from 2 mm to 10 mm. In some embodiments, the extended configuration height of the side wall can be of from 2 mm to 30 mm. In some embodiments, the contracted configuration height of the side wall can be of from 1 mm to 10 mm. In some embodiments, the extended configuration height and contracted configuration height can have the same cross-sectional dimension. In some embodiments, the base plate, the top plate, or any combination thereof comprises a magnetic responsive plate. In some embodiments, the applied magnetic field generates a magnetic torque on the unit cell. In some embodiments, the unit cell can further include an active agent in the lumen of the unit cell. In some embodiments, the unit cell can be actuated the active agent releases from the unit cell. Described herein are also devices including a plurality of unit cells described herein joint in series.

Described herein are also methods of actuating the unit cell described herein including providing the unit cell, wherein the unit cell is capable of being programmed to transition between a contracted configuration, an extended configuration, or a combination thereof; and actuating the unit cell under an applied magnetic field. Described herein are also methods of actuating a device to perform an activity on a subject including positioning a unit cell described herein in a first position with regard to the subject, wherein the unit cell can be capable of being programmed to transition between a contracted configuration, an extended configuration, or a combination thereof; and actuating the device under an applied magnetic field.

Described herein are also methods of drug delivery including administering to a subject in need thereof a unit cell described herein, wherein the unit cell can be capable of being programmed to transition between a contracted configuration, an extended configuration, or a combination thereof; and actuating the device using an applied magnetic field.

The details of one or more embodiments of the disclosure are set forth in the accompanying drawings and the description below. Other features, objects, and advantages of the disclosure will be apparent from the description and drawings, and from the claims.

DESCRIPTION OF DRAWINGS

FIG. 5A-5C show Kresling pattern (5A) geometry, (5B) crease pattern, and (5C) fabrication steps.

FIG. 6A-6F show simulation of the Kresling unit cell used to guide the geometric design. (6A) Bar-and-hinge model representing the unit cell. Valley folds (blue lines) are modeled by bars with area A t b, where the paper thickness t=0.1 mm and b=13 mm, and rotational springs with stiffness $k_f$=2.4 $10^{-3}$ N mm (rad mm)−1. Mountain folds with slit cuts (dashed lines) are modeled as bars with area $A_{slit}$ 0.5 A and rotational springs with stiffness $k_{slit}$ 0.01$k_f$. Arrows represent the direction of applied displacement 0.9Hi (i=1.4). (6B) Stored energy vs. displacement curve. Force-displacement curves for (6C) Design 1 (H1=15.6 mm), (6D) Design 2 (H2=16.9 mm), (6E) Design 3 (H3=18.2 mm), and (6F) Design 4 (H4=20.8 mm)

FIGS. 30A-30K show octopus-like robotic arm with stretching, bending, and twisting motions. (30A) An octopus with its configurable arms. (30B) Schematic design of a twelve-unit robotic arm for biomimetic motions. (30C) Magnetization distribution of the robotic arm. (30D) Photos of stretching and bending behaviors of octopus arms during preying, adapted from reference (41) (30E) Experimental results of controlled stretching and contracting of the robotic arm under rotating magnetic fields. (30F) Stretching ratio ΔL/L with respect to the direction of the applied rotating magnetic field α in YZ-plane. (30G) Controlled bending behavior with various deployed units. (30H) Bending angle θ of the robotic arm with respect to the intensity of the applied magnetic field B with 0, 4, and 8 deployed units. (30I) Normalized deflection d/L of the robotic arm with respect to the intensity of the applied magnetic field B with 0, 4, and 8 deployed units. (30J) A rotating magnetic field in XY-plane, a twisting motion of the octopus-like robotic arm, and corresponding two bending axes along the arm. (30K) A rotating magnetic field in YZ-plane, a twisting motion of the octopus arm-like robot, and corresponding three bending axes along the arm. Scale bars: 20 mm.

FIGS. 31A-31E show octopus-like robotic arm with omnidirectional bending and functionality illustrated by object grasping. (31A) Schematic design and out-of-plane magnetization distribution of an eighteen-unit robotic arm for biomimetic motions. (31B-31C) An octopus wiggles its arms to different curled shapes, adapted from reference (42). (31D) Magnetic profile and experimental results of the robotic arm omnidirectional bending motion from top view and front view. (31E) Magnetic profile and experimental results of the robotic arm object grasping and lifting motions from top view and front view. Scale bars: 20 mm.

FIG. 32A-32C show images and dimensions of the Kresling units used in this work. Unit pictured in (32A) is designed for demonstrations of the single-unit (FIG. 27), two-unit assemblies (FIG. 28), and four-unit robotic arm (FIG. 29). Unit pictured in (32B) is designed for arms including the 12-unit (FIG. 30) and 18-unit (FIG. 31)

Figure 49:
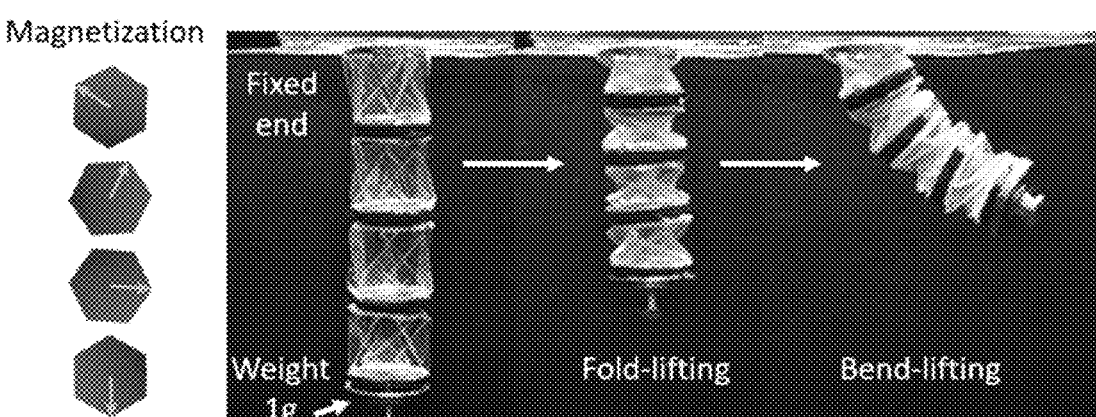

octopus-like robotic arms. Unit pictured in (32C) is designed for the small-scale arms (FIG. 47-FIG. 49).

Figure 33C:
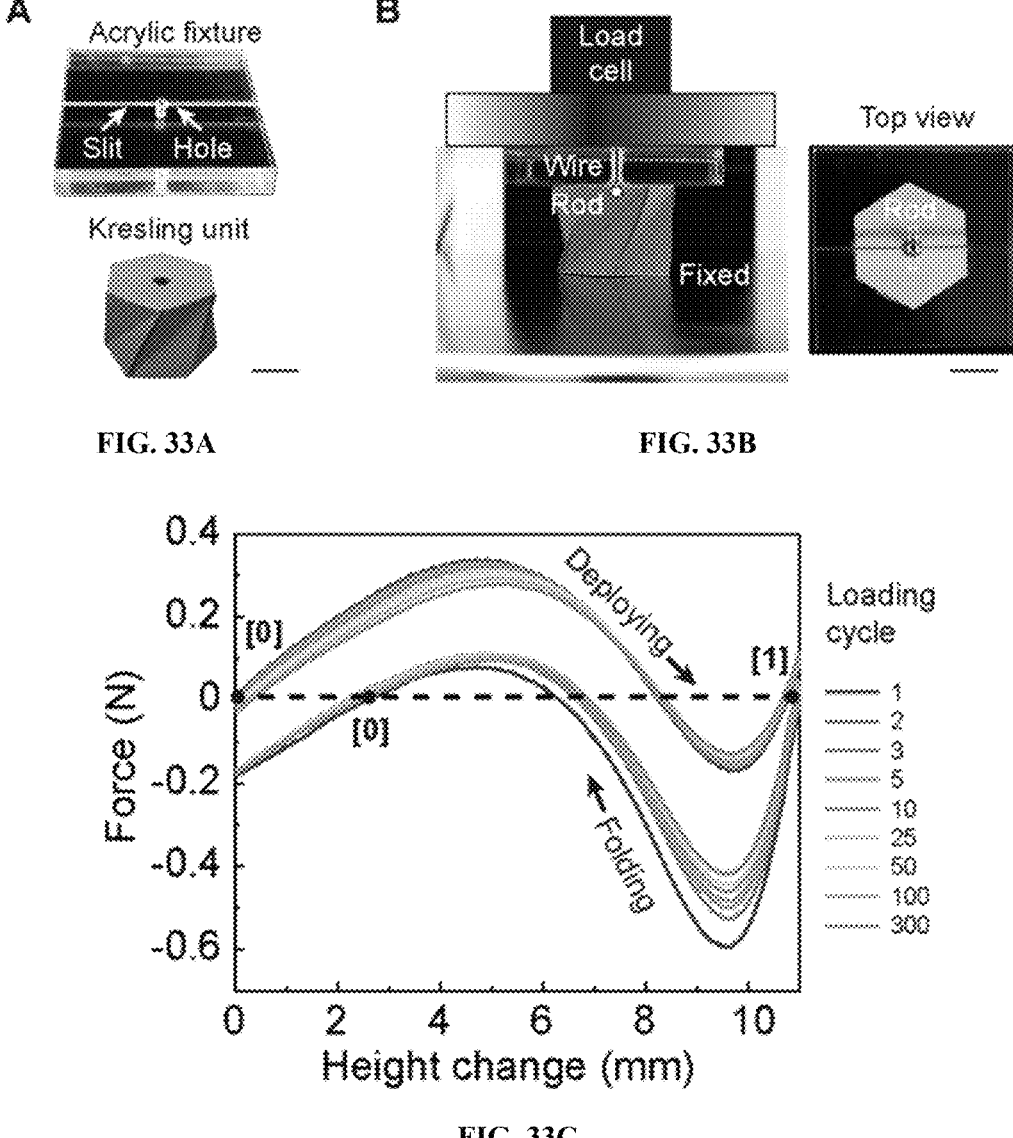

FIG. 33A-33C show mechanical characterization of a Kresling unit. (33A) Acrylic fixture and Kresling unit for deploying-folding test. (33B) Experimental setup of the tension and compression tests. A wire is used to connect the unit and the rod in the unit to constrain displacement without influencing rotation. (33C) The mechanical response of fabricated Kresling unit under cyclic deploying-folding tests. Scale bars: 10 mm.

Figures 34A, 34B:
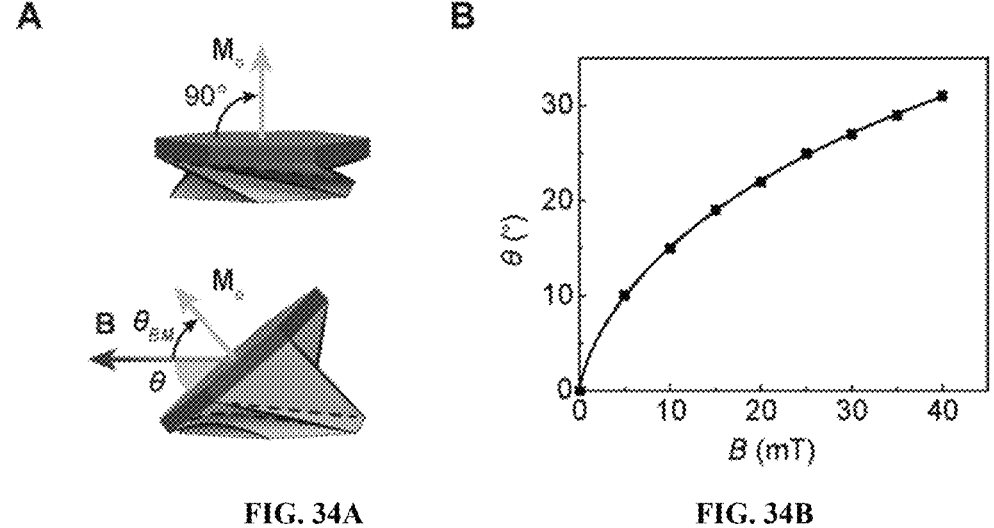

FIG. 34A-34B show (34A) Experimental measurement of the magnetically actuated bending behavior of the Kresling unit. An out-of-plane magnetized plate is attached to the unit. (34B) Bending angle versus magnetic field. Dots are from experimental measurement, fitted by a polynomial function.

Figure 35:
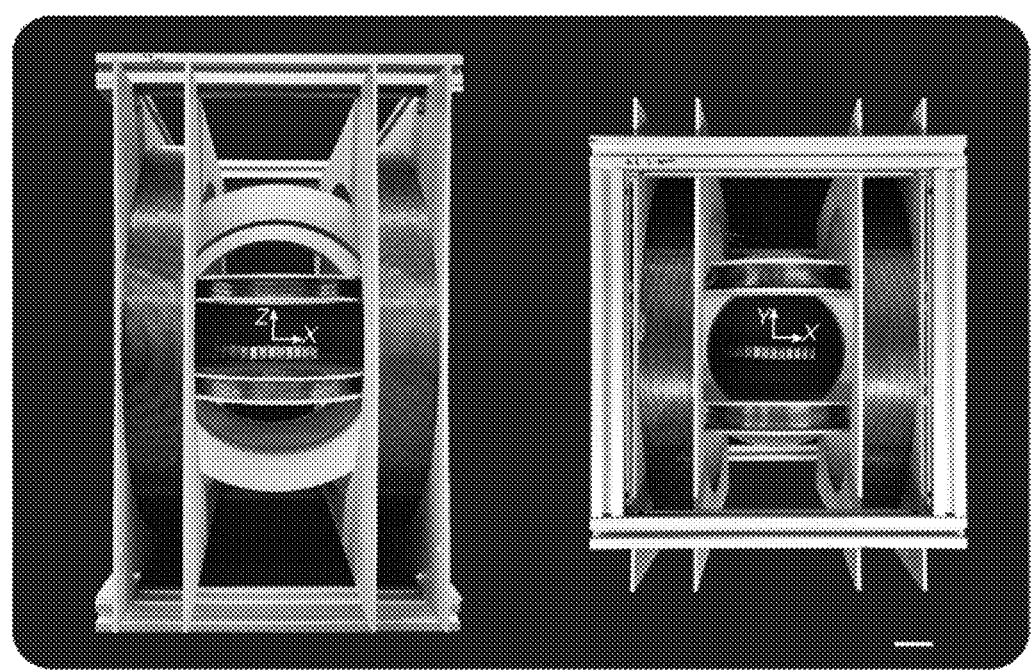

FIG. 35 show front view and top view of the 3D Helmholtz coils with a 12-unit octopus-like robotic arm inside the magnetic apparatus. Scale bar: 5 cm FIG. 36. Experimental measurement of the contour plot shows the magnetic field conditions for the magnetic Kresling to switch from the stable state [1] to the stable state [0]. The dashed orange line represents the in-plane magnetization component direction at the state [0] while the solid orange arrow rotated by 520 corresponds to the magnetization direction at state [1]. Dots are from experiment measurements, fitted by a polynomial function.

Figure 37A:
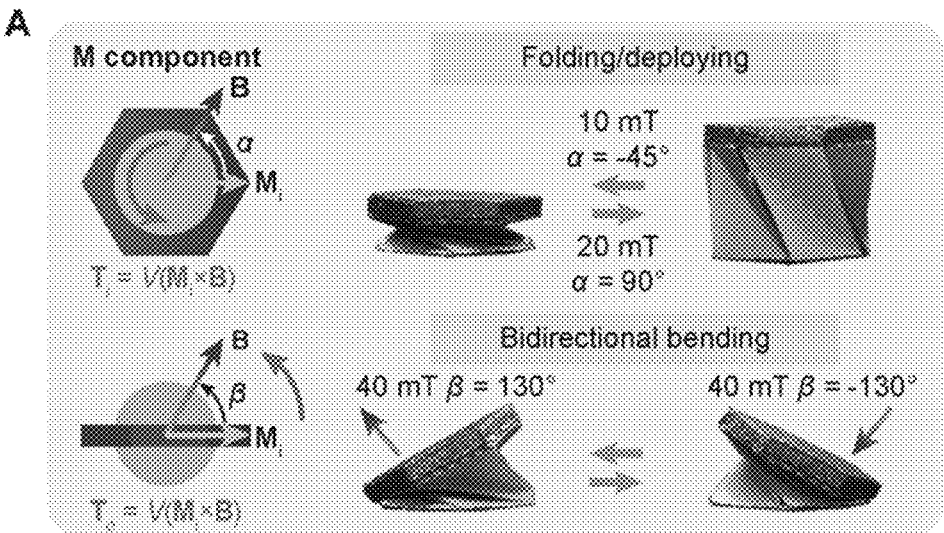
Figure 37B:
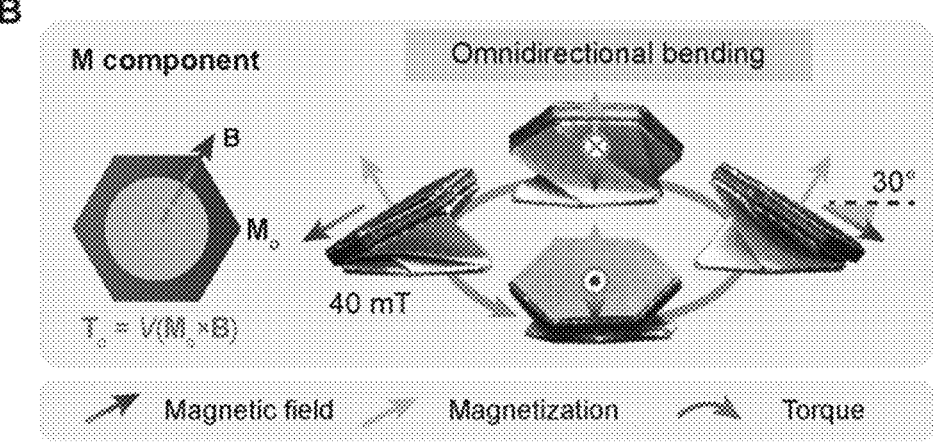

FIG. 37A-37B Experimental results of folding/deploying and bending of Kresling units (37A) Folding/deploying and bidirectional bending induced by an in-plane magnetization component $M_i$. (37B) Omnidirectional bending induced by an out-of-plane magnetization component $M_o$. A Magnetic field inclined by 30° can help achieve a larger omnidirectional bending angle in (37B).

FIG. 38A-38B Experimental results of folding/deploying and bidirectional bending of two-unit magnetic Kresling assembly with in-plane magnetizations. (38A) State shifting of the two-unit Kresling assembly with in-plane magnetic fields. (38B) Bidirectional bending of the two-unit Kresling assembly under the applied out-of-plane magnetic fields.

FIG. 39A-39D Experimental results of state shifting phase diagram of the two-unit Kresling assembly with in-plane magnetizations. Actuation results from (39A) state [00], (39B) state [10], (39C) state [11], and (39D) state [01]. Dots are from experimental measurements, fitted by a polynomial function. Hollow circles in (39A-39D) correspond to the conditions used in FIG. 38A for a sequential state shifting ([00] to [10] to [11] to [01] to [00]).

Figures 39C, 39D, 40A, 40B, 41A, 41C:
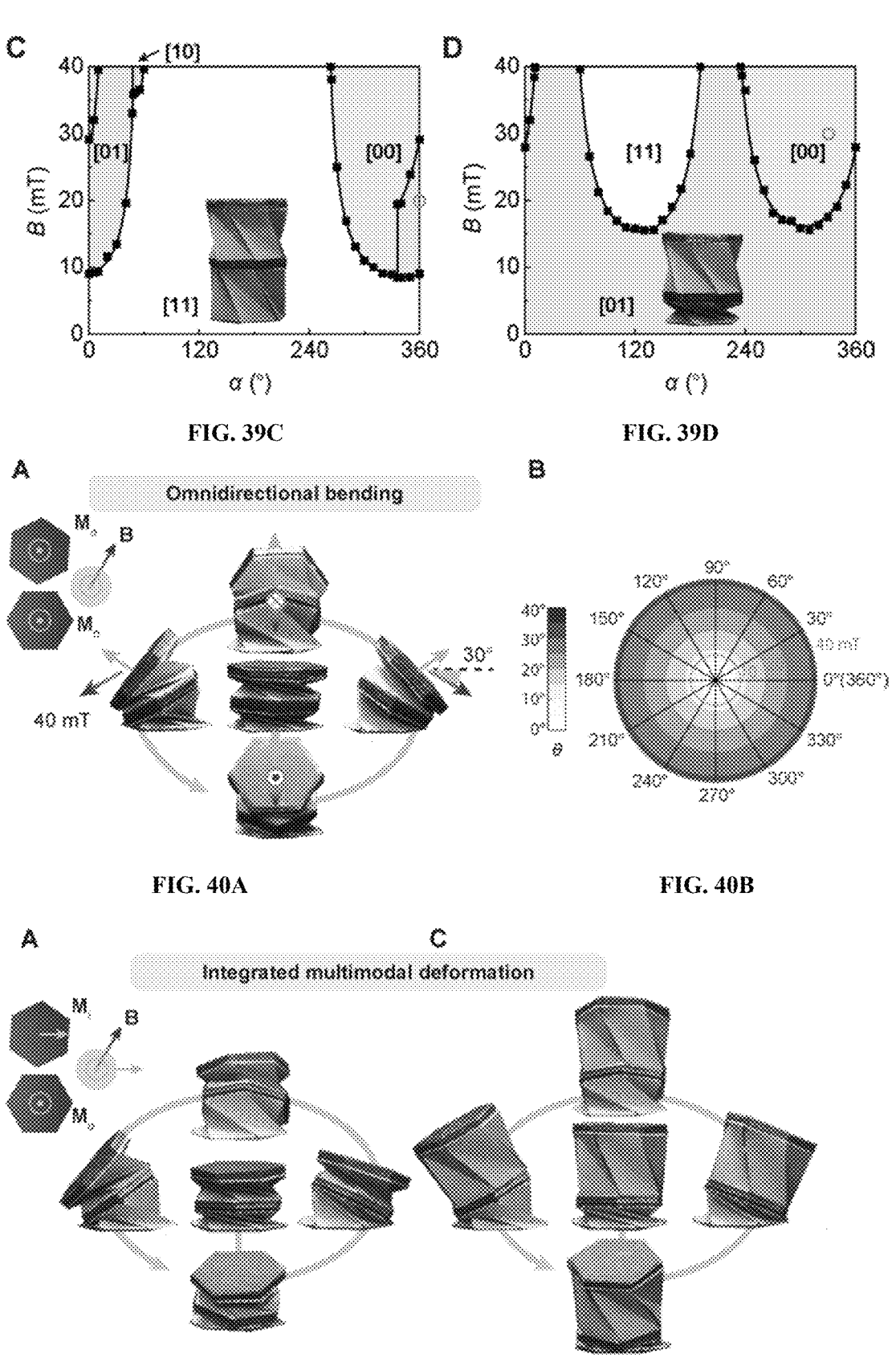

FIG. 40A-40B Experimental results of omnidirectional bending (40A) and the resulting bending angle polar plot of the two-unit magnetic Kresling assembly with out-of-plane magnetizations. A Magnetic field inclined by 300 can help achieve a larger omnidirectional bending angle in (40A). A magnetic field in the plane of the fixed end is used for characterizations in (40B).

FIG. 41A-41D Experimental results of multimodal actuation of the two-unit magnetic Kresling assembly with both in-plane and out-of-plane magnetizations. (41A-41B) Experimental results of omnidirectional bending (A) and the resulting bending angle polar plot (41B) at state [00]. (41C-41D) Experimental results of omnidirectional bending (41C) and the resulting bending angle polar plot (41D) at state [01]. The grey area in (41D) denotes the conditions when the top unit folds. Magnetic fields in the plane of the fixed end are used for characterizations in (41B) and (41D). The dashed lines in (41B) and (41D) correspond to conditions used in (41A) and (41C).

FIG. 42A-42H Magnetic field profiles of four-unit robotic arm bending and deploying at (42A) 0°, (42B) 45°, (42C) 90°, (42D) 135°, (42E) 180°, (42F) 225°, (42G) 270°, and (42H) 315° directions.

Figures 43A, 43B, 44, 45A, 45B:
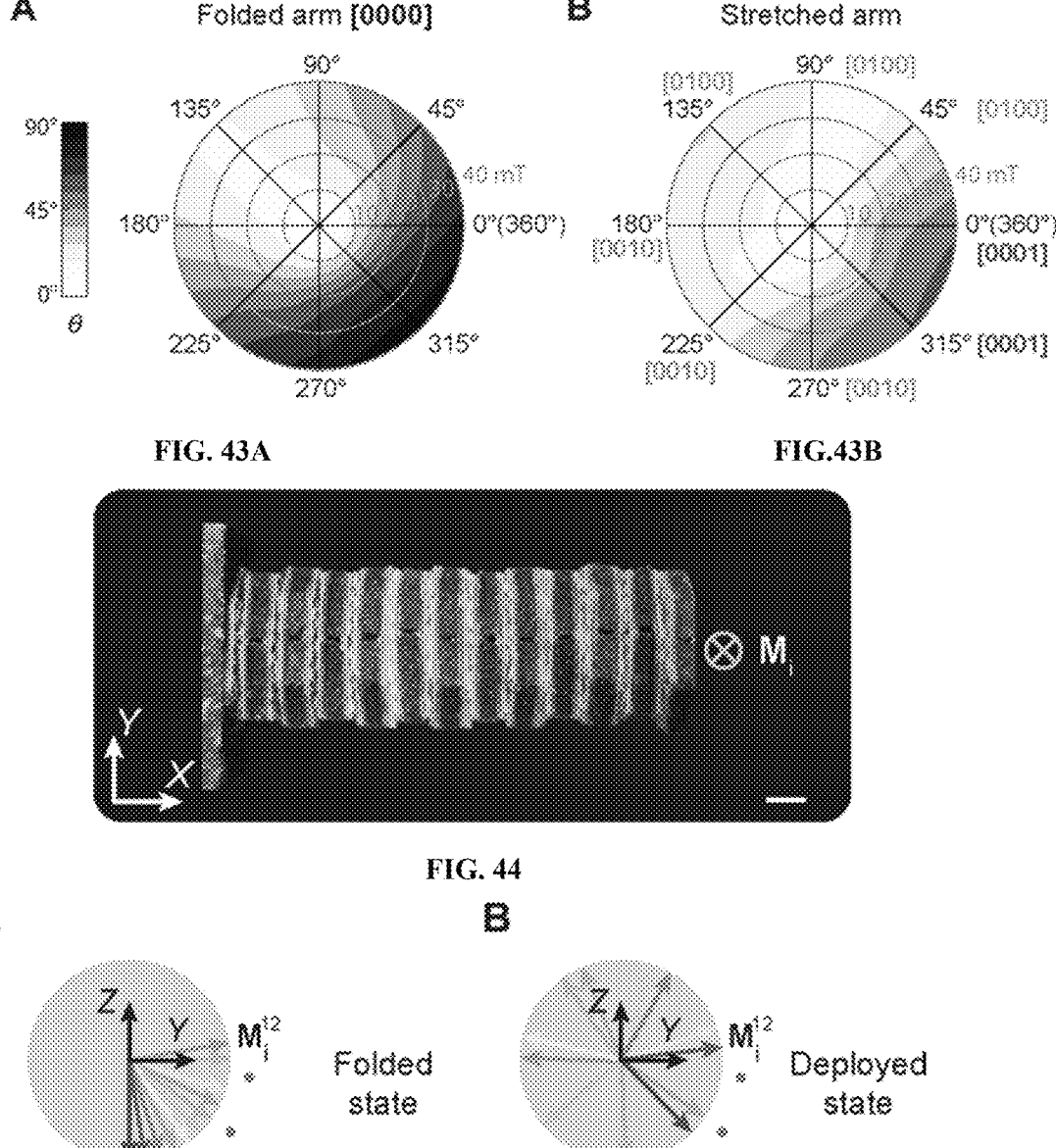

FIG. 43A-43B Bending angle polar plots of the (43A) folded arm and (43B) stretched arm of the four-unit robotic arm.

FIG. 44 The magnetizations of the 12-unit robotic arm are programmed to be in the same negative Z-direction at the all-folded state under compression.

FIG. 45A-45B Magnetization distributions of the 12-unit robotic arm at (45A) folded state and (45B) deployed state.

FIG. 46A-46D Control of Kresling robotic arm's stretching and contracting motions. (46A) Magnetic profile for stretching motion. (46B) Magnetic profile for contracting motion. (46C) Length change of the robotic arm during stretching and contracting with respect to time. (46D) Length change of the robotic arm during stretching and contracting with respect to the magnetic field direction.

FIG. 47 Prototype of a small-scale eight-unit robotic arm with a comparable cross-section dimension to an endotracheal intubation tube. The aim of this design is to provide well-controlled motion at the tip of medical tubes and catheters to guide the difficult navigation and positioning process during intubation (3), upper endoscopy (4), or catheterization (5) and to achieve object manipulation capability. Scale bars: 10 mm.

FIGS. 48A-48B show (48A) Bend-lifting and weight motion of the small-scale eight-unit Kresling robotic arm. (48B) Versatile motion of the robotic arm under programmable magnetic fields. Scale bars: 10 mm.

FIG. 49 shows fold-lifting and bend-lifting of the small-scale four-unit Kresling robotic arm. Scale bar: 10 mm.

FIGS. 50A-50F show mechanism of the four-unit Kresling crawler based on the Kresling dipole. (50A) Schematic of a Kresling unit, showing contraction coupled with a twist deformation. (50B) Schematic of a Kresling dipole made of two standard Kresling units with reverse crease directions, showing no rotation at the two ends (green circles) but rotation at the center plane (blue circles) during contraction. (50C) The experimentally measured torque-contraction curve of the Kresling unit. Contraction is defined as $\Delta H/H$, where H is the initial height of the unit and $\Delta H$ is the difference between the initial and contracted heights. Parameter $T_e$ is defined as the corresponding torque at 35% contraction of the unit for effective crawling motion. The solid line is the averaged responses of three Kresling unit samples, and the shaded region represents the range of responses. (50D) Schematic of the Kresling crawler made of two Kresling dipoles, showing no rotation at the center plane and two ends. (50E) The required torque distribution to actuate the Kresling crawler for simultaneous contraction of all units. (50F) Finite element analysis (FEA) verification of the derived torque distribution for simultaneous contraction of all units.

FIGS. 51A-51E show magnetic actuation mechanism of the Kresling crawler. (51A) Image of a fingertip holding the fabricated Kresling crawler and designed magnetization directions of attached four magnetic plates for distributed torques. (51B) Crawler configurations and magnetization directions at the initial state and contracted state. $B_y$ is the magnetic field applied to the crawler along its net magnetization direction. Angle $\theta_r$ is the total rotation angle of $\theta_2$ or $\theta_3$ during contraction. $T_{U1}{}^m$, $T_{U2}{}^m$, $T_{U3}{}^m$, and $T_{U4}{}^m$ are torque magnitudes on units U1, U2, U3, and U4 under magnetic actuation, respectively. Green marks on the vertices of the magnetic plates indicate no rotation at the two ends of the Kresling crawler. (51C) Torque ratio between units U1 and U2 (U4 and U3) during contraction. Contraction of the unit of 35% (rotation angle $\theta_r$ of 32°) is defined as an effective crawling motion under a reasonably small torque. Note that angles $\theta_1$ and $\theta_4$ stay unchanged during contraction. Angles $\theta_2$ and $\theta_3$ are designed to swing between 106° and 74° to minimize the dynamic fluctuation of magnetic torques during contraction. (51D) The magnetically actuated contraction under a magnetic field of 40 mT. (51E) Characterization of the Kresling crawler contraction at different magnetic field magnitudes. Contraction is defined as 1−l/L, where L and l are lengths of the crawler at the initial state and after contraction, respectively. The solid line is the averaged responses of three Kresling crawler samples, and the shaded region represents the range of responses. Scale bars: 5 mm.

Figures 51A, 51B, 51C, 51D:
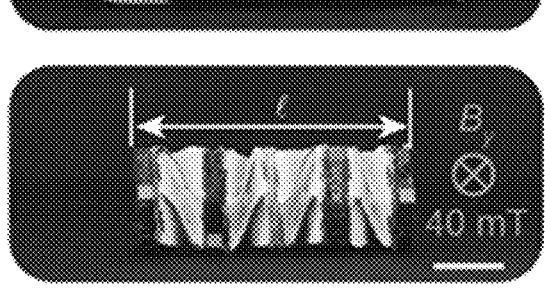
Figures 51E, 52A:
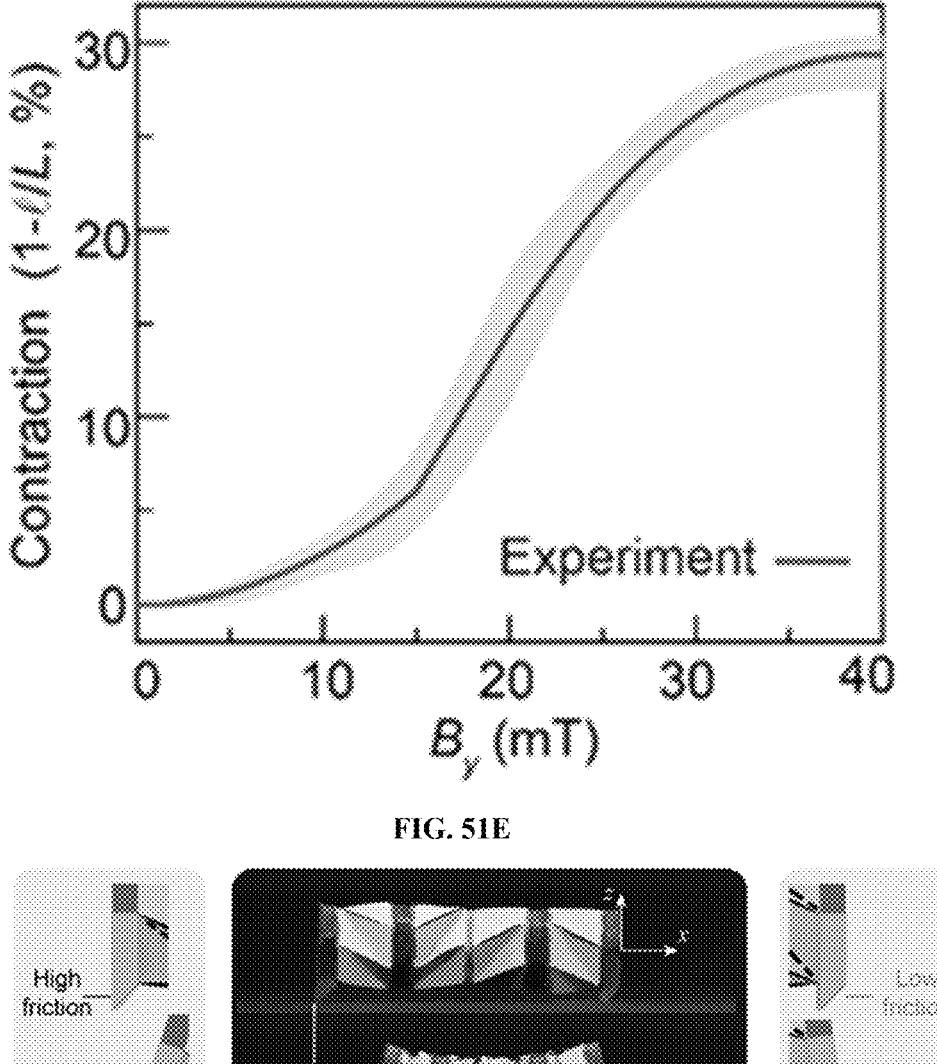
Figures 52B, 52C:
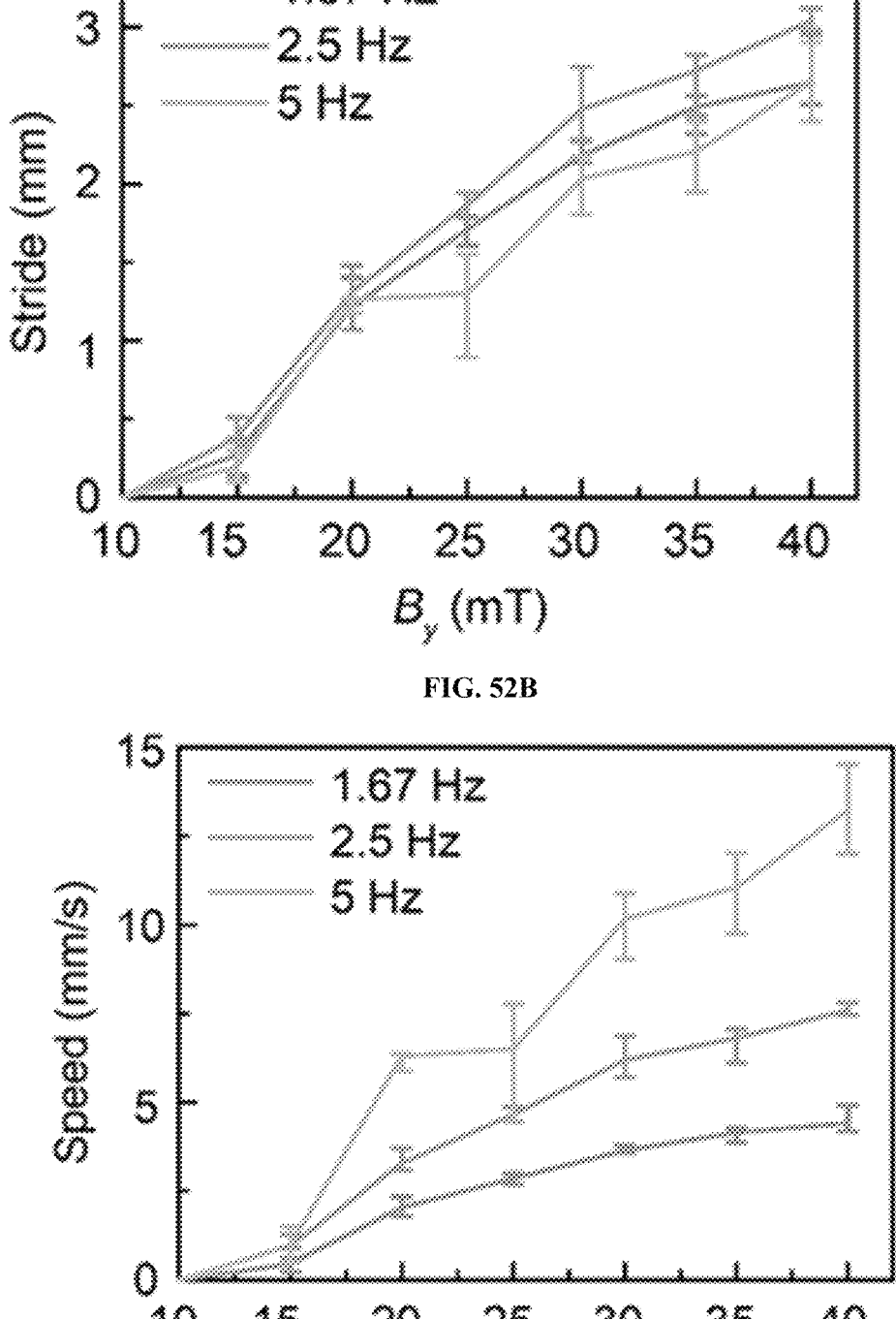

FIGS. 52A-52C show crawling mechanism of the Kresling robot. (52A) Single stride of the Kresling crawler under a magnetic field of 40 mT. Scale bar: 5 mm. (52B) Stride and (52C) speed characterization of crawling motion at various magnetic field magnitudes and frequencies.

FIGS. 53A-53C show steering and navigation of the Kresling crawler. (53A) The steering mechanism. (X, Y) and (x, y) refer to the global and local (deformed) configurations, respectively. The crawler always tends to align its net magnetization $M_{net}$ with the applied magnetic field direction. (53B) The "Z" crawling path (three straight segments) at selected times. (53C) The "O" crawling path (continuous angular changes) at selected times. Scale bars: 5 mm.

FIG. 54A-54E Anisotropic and magnetically reinforced structure stiffness of the Kresling crawler. (54A) Schematic of the compression tests along axial and lateral directions of the crawler. Compressive stress-strain curves for the crawler (54B) along the axial direction under different magnetic fields and (54C) along the lateral direction. The negative value of the magnetic field indicates that the magnetic field has the opposite direction with the net magnetization of the Kresling crawler, tending to stretch the crawler. (54D) Schematic of crawling in a confined space and corresponding magnetic field profile. (54E) The crawler gradually cracks the open front space and moves forward in a timely fashion. Scale bar: 5 mm.

FIGS. 55A-55C show conceptual scheme for drug storage and release using the Kresling crawler. (55A) Exploded view and assembly of the modified Kresling crawler with a through hole. The internal cavity of the front Kresling unit is used for pill storage. (55B) Pill positions at initial and contracted states of the Kresling crawler. The crawler contracts without interfering with the cylindrical pill. (55C) Pill gradually dissolves in water as indicated by the intensity of the blue dye for four minutes. Scale bar: 5 mm.

Figure 56:
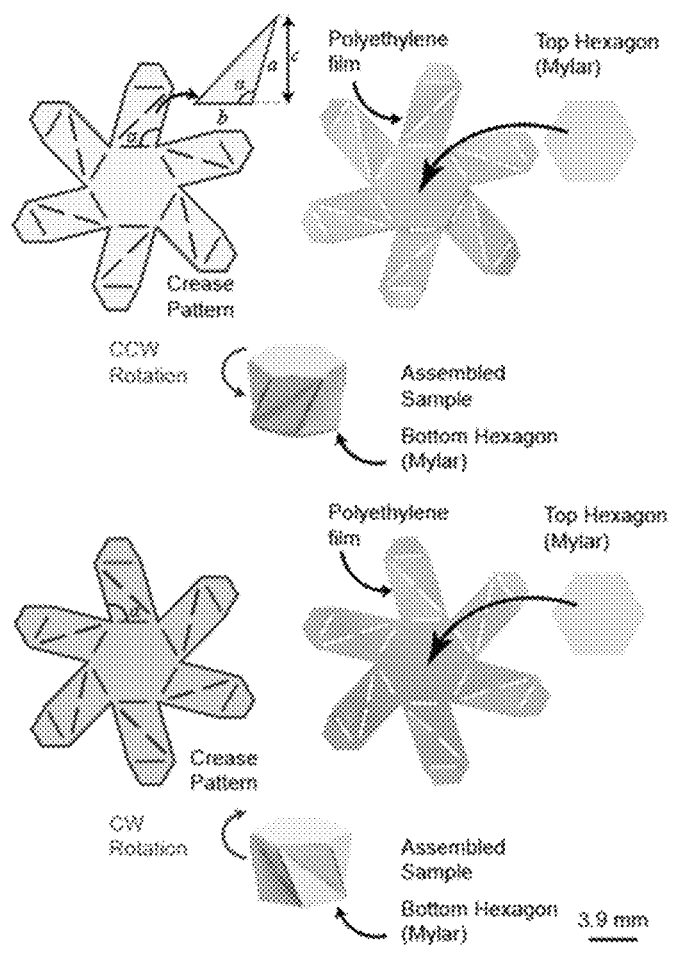

FIG. 56 shoes geometry, materials, and fabrication processes of Kresling units. Abbreviations CCW and CW represent counterclockwise and clockwise, respectively.

Figure 57:
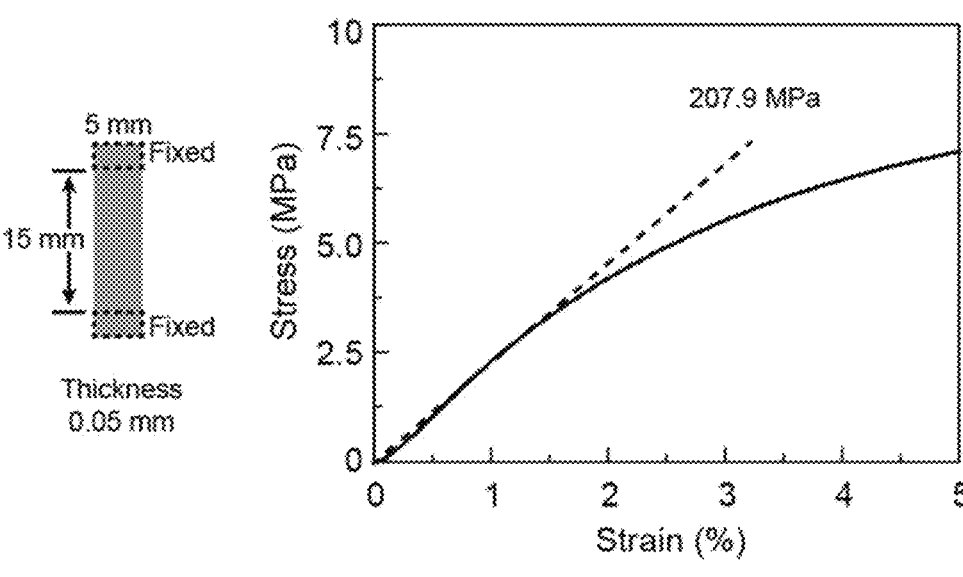

FIG. 57 shows uniaxial tensile test of the polyethylene film. The polyethylene film is stretched to 5% strain at a strain rate of 0.01 s$^{-1}$. Its Young's modulus is calculated to be 207.9 MPa using the secant modulus at 0.5% strain.

Figure 58A:
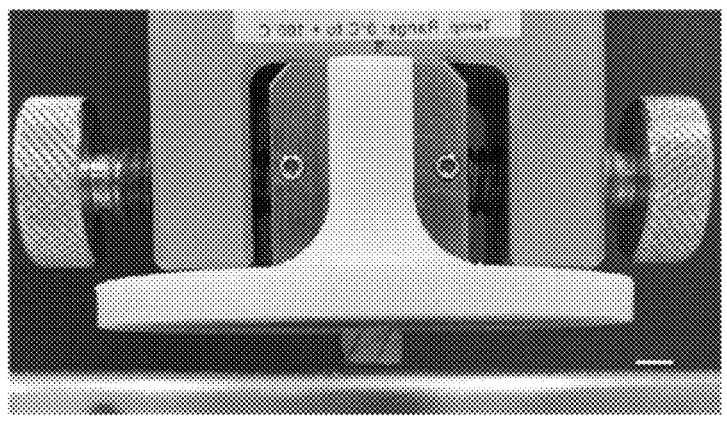
Figure 58B:
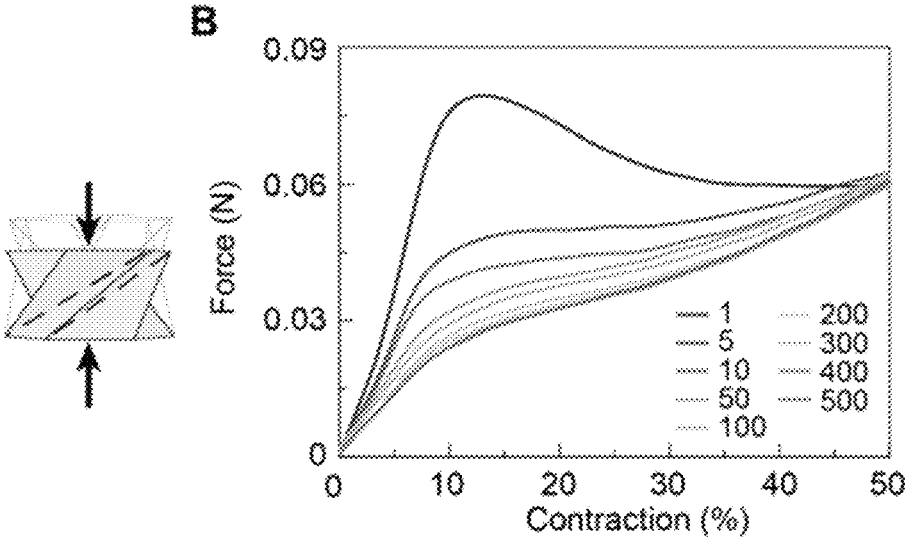

FIGS. 58A-58B show experimental setup and the measured mechanical behavior of Kresling unit under cyclic axial compression. (58A) Compression test setup of the Kresling unit. Scale bar: 5 mm. (58B) Force-contraction curves of Kresling unit up to 500 compression cycles. Notice that the mechanical response stabilizes after 400 cycles approximately.

FIGS. 59A-59D show mechanical characterization of Kresling units under axial compression. (59A) Experimental force-contraction (ΔH/H) curve of fabricated Kresling units. The results are measured after manually compressing the Kresling units for 400 cycles for a stable mechanical behavior. (59B) Stored energy-contraction curve by integrating measured force-displacement results. (59C) Relationship between relative rotation angle ψ and contraction obtained via FEA. (59D) Calculated torque-contraction curve. Parameter $T_e$ is defined as the corresponding torque at 35% contraction of the unit for effective crawling motion. Solid lines are the averaged responses of three Kresling unit samples, and shaded regions represent the range of responses.

FIG. 60 shows free body diagrams and torque distribution of the Kresling crawler. $T_1$, $T_2$, $T_3$, and T4 are magnitudes of applied torques at the $1^{st}$, $2^{nd}$, $4^{th}$, and $5^{th}$ hexagonal planes of the crawler from left to right. $X_1$ and $X_2$ are two cut-off planes on units U1 and U2, respectively. $T_{U1}$, $T_{U2}$, $T_{U3}$, and $T_{U4}$ are the torque magnitudes on units U1, U2, U3, and U4, respectively.

FIGS. 61A-61D Verification of torque distribution via finite element analysis (FEA). (61A) FEA model of Kresling unit consists of three sections: hexagonal bases, triangular panels, and hinges connecting the panels and bases. (61B) Mesh and boundary conditions of the Kresling crawler. Parameters $T_1$, $T_2$, $T_3$, and $T_4$ are magnitudes of corresponding reaction torques. (61C) Exported normalized torque-rotation angle curves. (61D) Comparison of torque distribution for simultaneous contraction of four units from theory and finite element simulation.

FIGS. 62A-62B show 3D Helmholtz coils for magnetic actuation with the Kresling crawler inside the magnetic apparatus. (62A) Front view. (62B) Top view. Scale bars: 4 cm.

FIGS. 63A-63C show crawler feet design and friction coefficient measurement. (63A) Dimensions of the feet and anisotropic friction design. (63B) Experimental setup for friction coefficient measurement. Scale bar: 7 cm. (63C) Measured friction coefficients between two materials (PDMS and tape) for feet design and two different substrates (paper and PDMS).

FIGS. 64A-64B show magnetic field profiles applied to the Kresling crawler. Magnetic field profiles for (64A) relatively slow single stride to demonstrate the crawling mechanism and (64B) relatively fast single stride with different frequencies for crawling motion characterization.

Figure 65B:
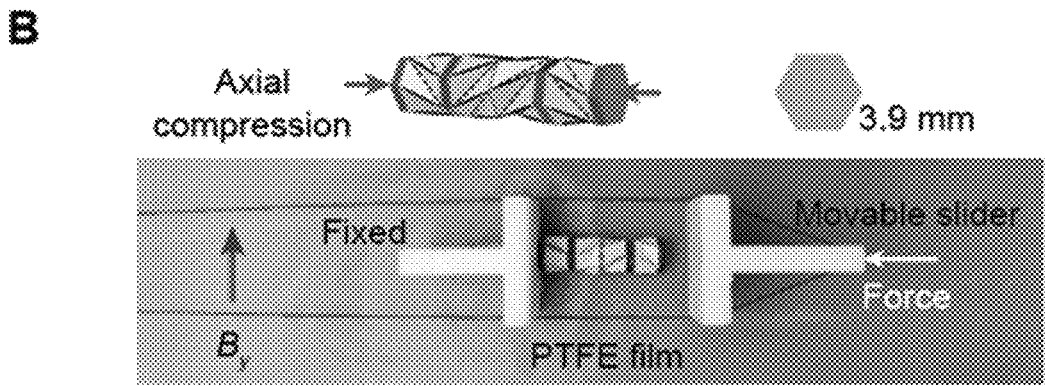
Figure 65C:
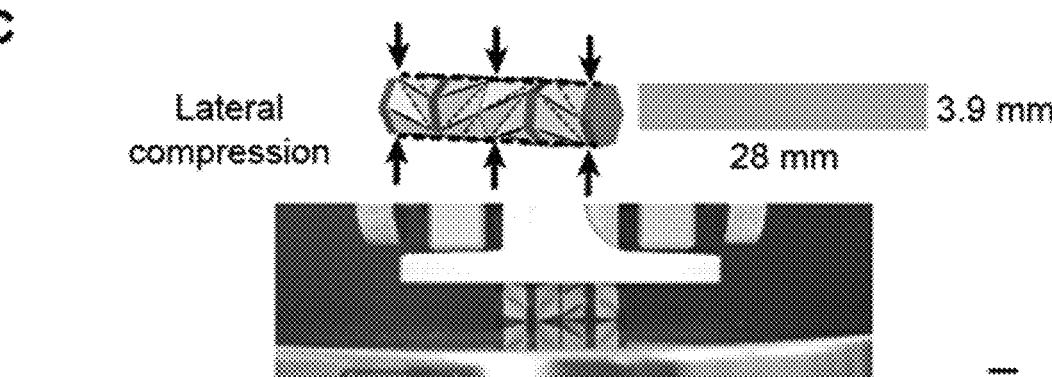

FIGS. 65A-65C show measurement of the anisotropic structure stiffness of the crawler body. (65A) Experimental setup. To measure the axial stiffness of the crawler under magnetic fields, pulley and wire are used to transmit the force from the machine to a slider in the electromagnetic coils. The coils can provide a uniform magnetic field. Scale bar: 7 cm. (65B) Schematics and experimental images of the compression tests along the axial direction. The positive magnetic field direction is identical to the net magnetization direction of the crawler. (65C) Schematics and experimental images of the compression tests along the lateral direction. Scale bar: 5 mm.

Figure 66A:
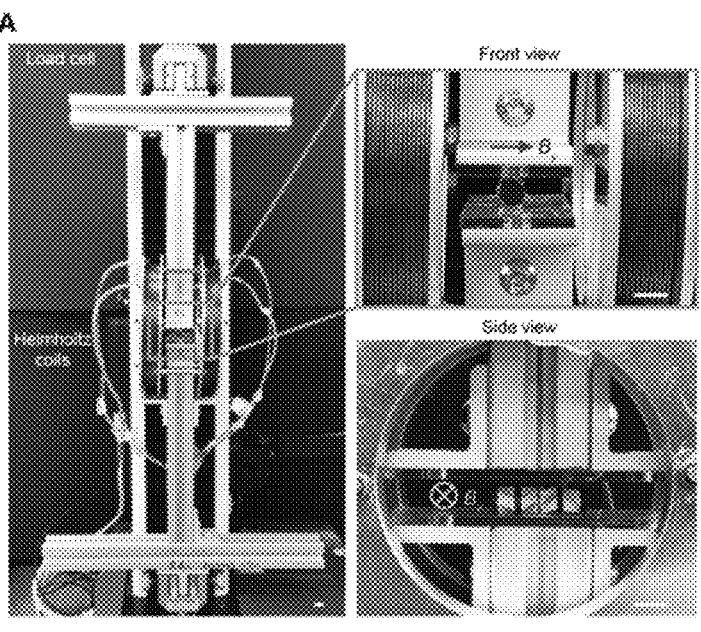
Figure 66B:
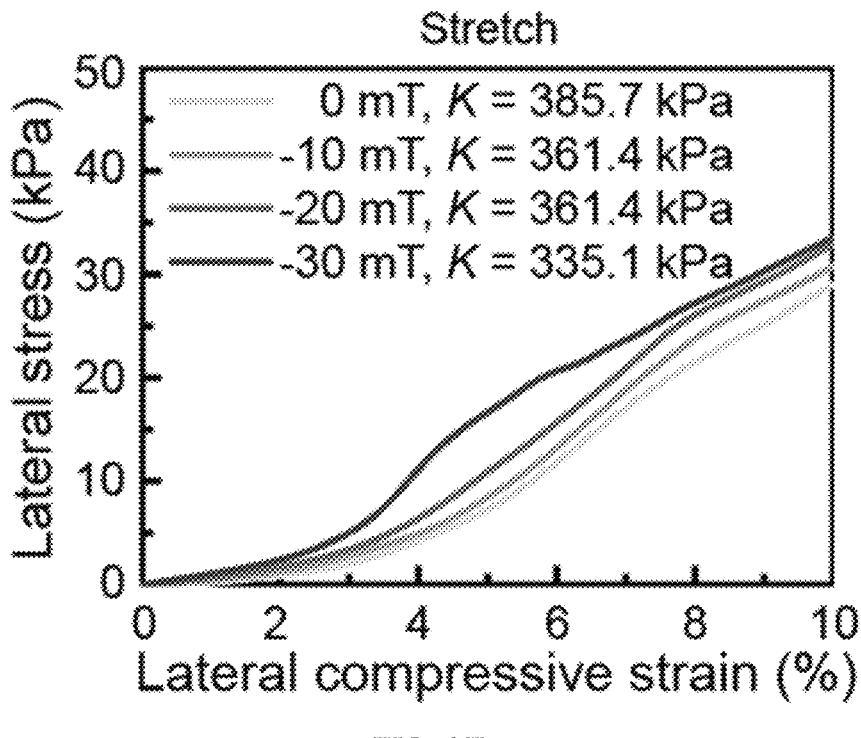
Figure 66C:
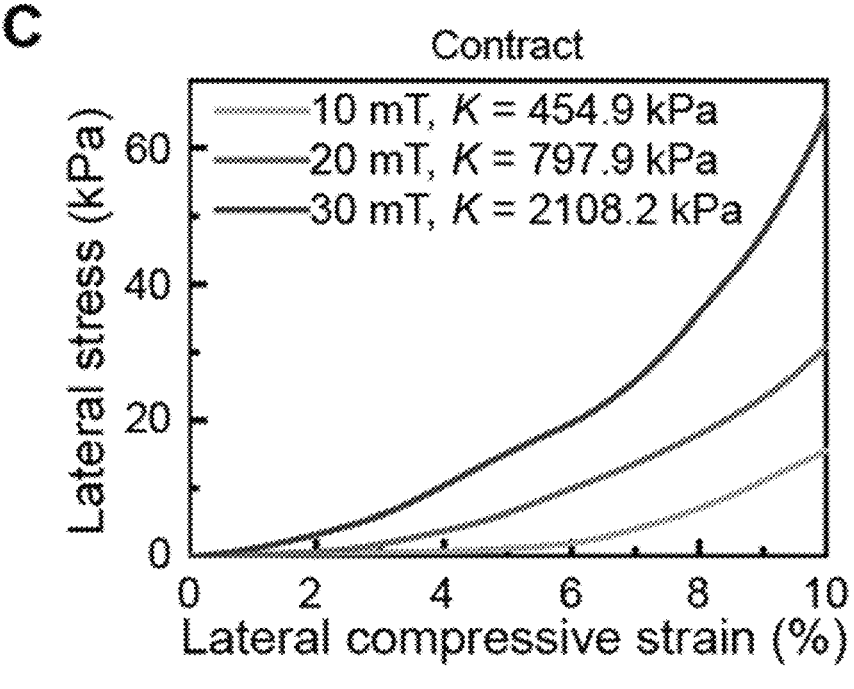

FIGS. 66A-66C show measurement of the lateral stiffness of the crawler body under different magnetic fields. (66A) Experimental setup. The positive magnetic field direction is identical to the net magnetization direction of the crawler. Scale bars: 10 mm. Compressive stress-strain curves for the crawler along lateral direction under (66B) negative magnetic fields and (66C) positive magnetic fields. The crawler stretches under negative magnetic field (−10 mT, −20 mT, and −30 mT) and contracts under positive magnetic field (10 mT, 20 mT, and 30 mT). The stiffnesses are measured at the strain of 10%.

FIGS. 67A-67G show mechanism: deploy, folding, crawling, swimming, steering, and combination. (67A) Deformation of the Kresling unit and the internal cavity for drug storage. (67B) Real size of the Kresling units. Scale bar: 8 mm. (67C) Mechanical properties of the units. (67D) Mechanism of Kresling unit's folding and unfolding behaviors for crawling or drug release. (67E) Magnetic actuation performance of Kresling units. (67F) Steering mechanism to change the direction of motion. (67G) Spinning mechanism to generate propulsion to swim.

FIGS. 68A-68J show walking robot mechanism. (68A) Schematic of a four-unit assembly. (68B) The magnetization directions of the four magnetic plates. (68C) Image of a finger holding the fabricated four-unit assembly. (68D) The contraction mechanism. (68E) Evaluation of contraction under the magnetic field. (68F) Anisotropic structural stiffnesses of the four-unit assembly. (68G) Crawling in confined space. (68H) The steering mechanism. (68I) The "Z" crawling path. (68J), The "O" crawling path. Scale bars: 5 mm.

FIGS. 69A-69E show swimming motions and characterizations of the One-plate Kresling robot. 69A, Schematic of the swimming robot and a resembled right-handed propeller. 69B, Horizontal swimming motion of the robot. 69C, Vertical swimming motion of the robot. 69D, Characterization of the horizontal swimming. 69E, Characterization of the vertical swimming. Scale bars: 13 mm.

FIGS. 70A-70D Controlled navigation and drug release of the swimming robot. (70A) Schematic. (70B) Images of on-demand drug release and mixing process by folding and spinning motion of the swimming robot, respectively. (70C) Targeted drug delivery with controllable releasing position and dose. (70D) Navigation and targeted drug release of the swimming robot in the maze (restricted and tortuous space). Scale bars: 8 mm.

Figure 71:
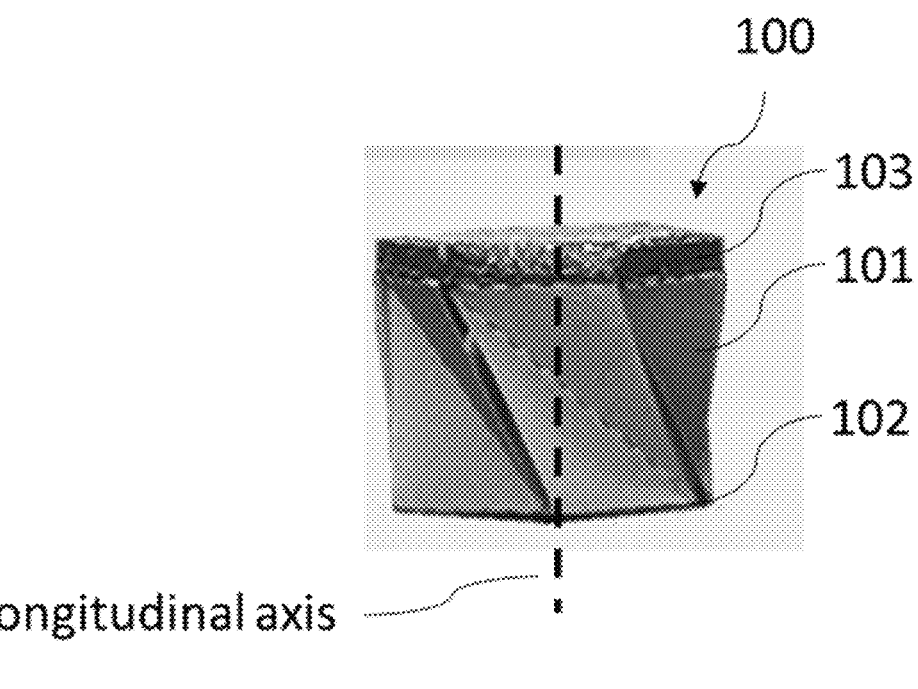

FIG. 71 shows a diagram of a unit cell 100 including a base plate 102, a top plate 103 (such as a magnetic responsive plate), and a plurality of panels 101.

Figure 72:
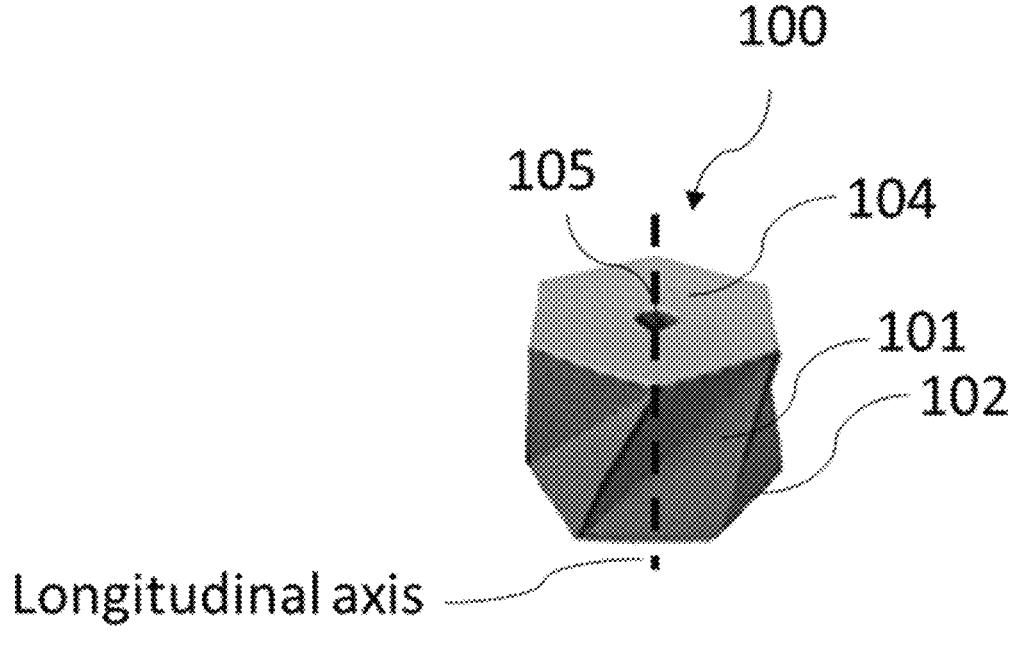

FIG. 72 shows a diagram of a unit cell 100 including a base plate 102, a cap 104, and a lumen 105, and a plurality of panels 101.

Figure 73:
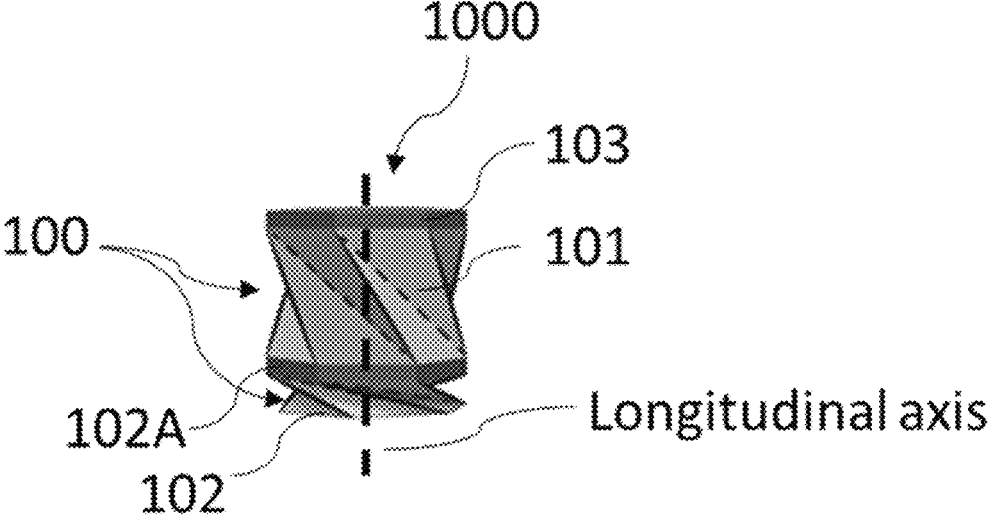

FIG. 73 shows a diagram of device 1000 including two unit cells 100, a base plate 102A (magnetic responsive plate), a base plate 102 (non-magnetic plate), a top plate 103 (a magnetic responsive plate), and a plurality of panels 101.

Figure 74:
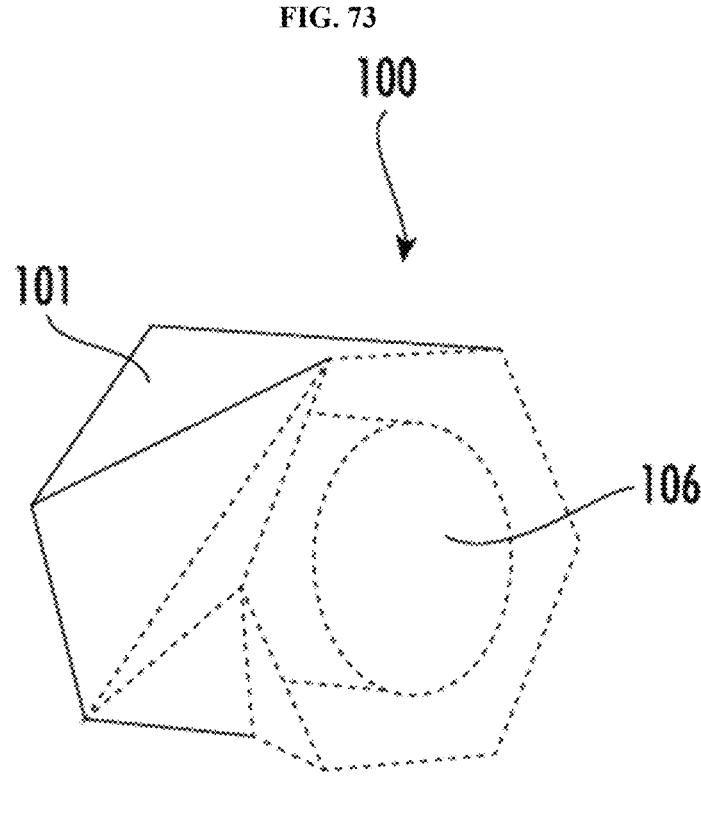

FIG. 74 shows a diagram of a unit cell 100, a lumen comprising an active agent containing compartment 106, and a plurality of panels 101.

FIG. 75 shows a diagram of drug release of a swimming robot.

FIG. 76 shows origami robot rolls in the tube with two different modes for in-vein drug delivery.

FIG. 77 shows origami robot swims in the circular tube.

Like reference symbols in the various drawings indicate like elements.

DETAILED DESCRIPTION

A number of embodiments of the disclosure have been described. Nevertheless, it will be understood that various modifications may be made without departing from the spirit and scope of the invention. Accordingly, other embodiments are within the scope of the following claims.

Definitions

To facilitate understanding of the disclosure set forth herein, a number of terms are defined below. Unless defined otherwise, all technical and scientific terms used herein generally have the same meaning as commonly understood by one of ordinary skill in the art to which this disclosure belongs. Publications cited herein and the materials for which they are cited are specifically incorporated by reference.

General Definitions

As used in this specification and the following claims, the terms "comprise" (as well as forms, derivatives, or variations thereof, such as "comprising" and "comprises") and "include" (as well as forms, derivatives, or variations thereof, such as "including" and "includes") are inclusive (i.e., open-ended) and do not exclude additional elements or steps. For example, the terms "comprise" and/or "comprising," when used in this specification, specify the presence of stated features, integers, steps, operations, elements, and/or components, but do not preclude the presence or addition of one or more other features, integers, steps, operations, elements, components, and/or groups thereof. Other than where noted, all numbers expressing quantities of ingredients, reaction conditions, geometries, dimensions, and so forth used in the specification and claims are to be understood at the very least, and not as an attempt to limit the application of the doctrine of equivalents to the scope of the claims, to be construed in light of the number of significant digits and ordinary rounding approaches.

Accordingly, these terms are intended to not only cover the recited element(s) or step(s), but may also include other elements or steps not expressly recited. Furthermore, as used herein, the use of the terms "a", "an", and "the" when used in conjunction with an element may mean "one," but it is also consistent with the meaning of "one or more," "at least one," and "one or more than one." Therefore, an element preceded by "a" or "an" does not, without more constraints, preclude the existence of additional identical elements.

Ranges can be expressed herein as from "about" one particular value, and/or to "about" another particular value. By "about" is meant within 5% of the value, e.g., within 4, 3, 2, or 1% of the value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. A range may be construed to include the start and the end of the range. For example, a range of 10% to 20% (i.e., range of 10%-20%) can includes 10% and also includes 20%, and includes percentages in between 10% and 20%, unless explicitly stated otherwise herein.

As used herein, the terms "may," "optionally," and "may optionally" are used interchangeably and are meant to include cases in which the condition occurs as well as cases in which the condition does not occur. Thus, for example, the statement that a formulation "may include an excipient" is meant-to include cases in which the formulation includes an excipient as well as cases in which the formulation does not include an excipient.

It is understood that when combinations, subsets, groups, etc. of elements are disclosed (e.g., combinations of components in a composition, or combinations of steps in a method), that while specific reference of each of the various individual and collective combinations and permutations of these elements may not be explicitly disclosed, each is specifically contemplated and described herein.

"Administration" to a subject includes any route of introducing or delivering to a subject an agent. Administration can be carried out by any suitable route, including oral, topical, transcutaneous, transdermal, intra-joint, intra-arteriole, intradermal, intraventricular, intralesional, intranasal, rectal, vaginal, by inhalation, via an implanted reservoir, parenteral (e.g., subcutaneous, intravenous, intramuscular, intra-articular, intra-synovial, intrasternal, intrathecal, intra-peritoneal, intrahepatic, intralesional, and intracranial injections or infusion techniques), and the like. "Concurrent administration", "administration in combination", "simultaneous administration" or "administered simultaneously" as used herein, means that the compounds are administered at the same point in time or essentially immediately following one another. In the latter case, the two compounds are administered at times sufficiently close that the results observed are indistinguishable from those achieved when the compounds are administered at the same point in time. "Systemic administration" refers to the introducing or delivering to a subject an agent via a route which introduces or delivers the agent to extensive areas of the subject's body (e.g. greater than 50% of the body), for example through entrance into the circulatory or lymph systems. By contrast, "local administration" refers to the introducing or delivery to a subject an agent via a route which introduces or delivers the agent to the area or area immediately adjacent to the point of administration and does not introduce the agent systemically in a therapeutically significant amount. For example, locally administered agents are easily detectable in the local vicinity of the point of administration but are undetectable or detectable at negligible amounts in distal parts of the subject's body. Administration includes self-administration and the administration by another.

As used here, the terms "beneficial agent" and "active agent" are used interchangeably herein to refer to a chemical compound or composition that has a beneficial biological effect. Beneficial biological effects include both therapeutic effects, i.e., treatment of a disorder or other undesirable physiological condition, and prophylactic effects, i.e., prevention of a disorder or other undesirable physiological condition. The terms also encompass pharmaceutically acceptable, pharmacologically active derivatives of beneficial agents specifically mentioned herein, including, but not limited to, salts, esters, amides, prodrugs, active metabolites, isomers, fragments, analogs, and the like. When the terms "beneficial agent" or "active agent" are used, then, or when a particular agent is specifically identified, it is to be understood that the term includes the agent per se as well as pharmaceutically acceptable, pharmacologically active salts, esters, amides, prodrugs, conjugates, active metabolites, isomers, fragments, analogs, etc.

As used herein, the terms "treating" or "treatment" of a subject includes the administration of a drug to a subject with the purpose of preventing, curing, healing, alleviating, relieving, altering, remedying, ameliorating, improving, stabilizing or affecting a disease or disorder, or a symptom of a disease or disorder. The terms "treating" and "treatment" can also refer to reduction in severity and/or frequency of symptoms, elimination of symptoms and/or underlying cause, prevention of the occurrence of symptoms and/or their underlying cause, and improvement or remediation of damage.

By the term "effective amount" of a therapeutic agent is meant a nontoxic but sufficient amount of a beneficial agent to provide the desired effect. The amount of beneficial agent that is "effective" will vary from subject to subject, depending on the age and general condition of the subject, the particular beneficial agent or agents, and the like. Thus, it is not always possible to specify an exact "effective amount". However, an appropriate "effective' amount in any subject case may be determined by one of ordinary skill in the art using routine experimentation. Also, as used herein, and unless specifically stated otherwise, an "effective amount" of a beneficial can also refer to an amount covering both therapeutically effective amounts and prophylactically effective amounts.

An "effective amount" of a drug necessary to achieve a therapeutic effect may vary according to factors such as the age, sex, and weight of the subject. Dosage regimens can be adjusted to provide the optimum therapeutic response. For example, several divided doses may be administered daily or the dose may be proportionally reduced as indicated by the exigencies of the therapeutic situation.

As used herein, a "therapeutically effective amount" of a therapeutic agent refers to an amount that is effective to achieve a desired therapeutic result, and a "prophylactically effective amount" of a therapeutic agent refers to an amount that is effective to prevent an unwanted physiological condition. Therapeutically effective and prophylactically effective amounts of a given therapeutic agent will typically vary with respect to factors such as the type and severity of the disorder or disease being treated and the age, gender, and weight of the subject. The term "therapeutically effective amount" can also refer to an amount of a therapeutic agent, or a rate of delivery of a therapeutic agent (e.g., amount over time), effective to facilitate a desired therapeutic effect. The precise desired therapeutic effect will vary according to the condition to be treated, the tolerance of the subject, the drug and/or drug formulation to be administered (e.g., the potency of the therapeutic agent (drug), the concentration of drug in the formulation, and the like), and a variety of other factors that are appreciated by those of ordinary skill in the art.

A "control" is an alternative subject or sample used in an experiment for comparison purposes. A control can be "positive" or "negative."

As used herein, by a "subject" is meant an individual. Thus, the "subject" can include domesticated animals (e.g., cats, dogs, etc.), livestock (e.g., cattle, horses, pigs, sheep, goats, etc.), laboratory animals (e.g., mouse, rabbit, rat, guinea pig, etc.), and birds. "Subject" can also include a mammal, such as a primate or a human. Thus, the subject can be a human or veterinary patient. The term "patient" refers to a subject under the treatment of a clinician, e.g., physician. Administration of the therapeutic agents can be carried out at dosages and for periods of time effective for treatment of a subject. In some embodiments, the subject is a human.

Reference will now be made in detail to specific aspects of the disclosed materials, compounds, compositions, articles, and methods, examples of which are illustrated in the accompanying Examples and Figures.

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods and in the steps or in the sequence of steps of the methods described herein without departing from the concept, spirit and scope of the disclosure. More specifically, it will be apparent that certain agents which are both chemically related may be substituted for the agents described herein while the same or similar results would be achieved. All such similar substitutes and modifications apparent to those skilled in the art are deemed to be within the spirit, scope and concept of the disclosure as defined by the appended claims.

Unit Cell

Described herein is a unit cell including a base plate; a top plate; and a lumen extending longitudinally from the base plate to the top plate. The lumen can be defined by a side wall formed from a plurality of cojoined panels extending between a bottom surface of the top plate and a top surface of the base plate. In some embodiments, the unit cell can be magnetically actuatable, such that the unit cell can be reversibly transitioned between a contracted configuration, an extended configuration, or a combination thereof using an applied magnetic field. In some embodiments, the transition between a contracted configuration, an extended configuration, or a combination thereof can include reorientation of the plurality of conjoined panels forming the side wall. In some embodiments; the transition between a contracted configuration and an extended configuration can include reorientation of the plurality of conjoined panels forming the side wall. In some embodiments, reorientation can include folding of one or more of the conjoined panels, unfolding of one or more of the conjoined panels, or any combination thereof. In some embodiments, the unit cell can bend, fold, unfold, twist, or a combination thereof. In some embodiments, the unit cell can bend, fold, unfold, and twist. In some embodiments, the unit cell can bend. In some embodiments, the unit cell can twist. In some embodiments, the unit cell can fold. In some embodiments, the unit cell can unfold. In some embodiments, the unit cell can bend and twist. In some embodiments, the unit cell can fold and unfold. In some embodiments, the lumen extends from the base plate through the top plate.

In some embodiments, the side wall has an extended configuration height and a contracted configuration height, wherein the extended configuration height can be at least 2 times the contracted configuration height (e.g., at least 3 times, or at least 4 times). In some embodiments, the side wall has an extended configuration height and a contracted configuration height, wherein the extended configuration height can be 5 times or less the contracted configuration height (e.g., 4 times or less, or 3 times or less).

The side wall can have an extended configuration height and a contracted configuration height ranging of from any of the minimum values described above to any of the maximum values described above. For example, in some embodiments, the extended configuration height can be from 2 times to 5 times the contracted configuration height, (e.g., from 2 times to 4 times, or from 2 times to 3 times).

In some embodiments, the unit cell can have a cross sectional dimension of at least 2 mm (e.g, at least 3 mm, at least 4 mm, at least 5 mm, at least 6 mm, at least 7 mm, at least 8 mm, or at least 9 mm). In some embodiments, the unit cell can have a cross sectional dimension of 10 mm or less (e.g, 9 mm or less, 8 mm or less, 7 mm or less, 6 mm or less, 5 mm or less, 4 mm or less, or 3 mm or less).

The unit cell can have a cross sectional dimension ranging of from any of the minimum values described above to any of the maximum values described above. For example, in some embodiments, the unit cell can have a cross sectional dimension of from 2 mm to 10 mm, (e.g., from 2 mm to 4 mm, from 2 mm to 6 mm, from 2 mm to 8 mm, from 4 mm to 10 mm, from 4 mm to 8 mm, from 4 mm to 6 mm, from 6 mm to 10 mm, from 6 mm to 8 mm, or from 8 mm to 10 mm).

In some embodiments, the extended configuration height of the side wall can be of at least 2 mm, (e.g., at least 4 mm, at least 6 mm, at least 8 mm, at least 10 mm, at least 12 mm, at least 14 mm, at least 16 mm, at least 18 mm, at least 20 mm, at least 22-mm, or at least 24 mm). In some embodiments, the extended configuration height of the side wall can be of 30 mm or less, (e.g., 25 mm or less, 22 mm or less, 20 mm or less, 18 mm or less, 16 mm or less, 14 mm or less, 12 mm or less, 10 mm or less, 8 mm or less, 6 mm or less, or 4 mm or less).

The extended configuration height of the side wall can be ranging of from any of the minimum values described above to any of the maximum values described above. For example, in some embodiments, the extended configuration height of the side wall can be of from 2 mm to 30 mm, (e.g., from 2 to 25 mm, from 6 to 25 mm, from 6 to 30 mm, from 7 mm to 21 mm, from 8 mm to 20 mm, from 12 mm to 18 mm, or from 15 mm to 20 mm).

In some embodiments, the contracted configuration height of the side wall can be of at least 1 mm, (e.g., at least 2 mm, at least 3 mm, at least 4 mm, at least 5 mm, at least 6 mm, at least 7 mm, at least 8 mm, or at least 9 mm). In some embodiments, the contracted configuration height of the side wall can be of 10 mm or less, (e.g., 9 mm or less, 8 mm or less, 7 mm or less, 6 mm or less, 5 mm or less, 4 mm or less, or 3 mm or less). The contracted configuration height of the side wall can be of ranging of from any of the minimum values described above to any of the maximum values described above. For example, in some embodiments, the contracted configuration height of the side wall can be of from 1 mm to 10 mm, (e.g., from 2 mm to 10 mm, from 1 mm to 8 mm, from 1 mm to 6 mm, from 1 mm to 4 mm, from 1 mm to 2 mm, from 2 mm to 8 mm, from 2 mm to 6 mm, from 2 mm to 4 mm, from 4 mm to 6 mm, from 4 mm to 8 mm, from 4 mm to 10 mm, from 6 mm to 8 mm, from 6 mm to 10 mm, or from 8 mm to 10 mm).

In some embodiments, the extended configuration and contracted configuration can have the same cross-sectional dimension. In some embodiments, the base plate, the top plate, or any combination thereof can include a magnetic responsive plate. In some embodiments, the base plate, the top plate, or any combination thereof can include a fixed non-magnetic plate. In some embodiments, at least one of the base plate or the top plate includes a magnetic responsive plate. In some embodiments, the magnetic responsive plate can have a programed magnetization direction. In some embodiments, the magnetic responsive plate can have a programed magnetization direction in a plane perpendicular to the longitudinal axis of the unit cell. In some embodiments, the applied magnetic field generates a magnetic torque on the unit cell. In some embodiments, the applied magnetic field generates a magnetic torque sufficient to allow the unit cell to transition between a contracted configuration, an extended configuration, or a combination thereof (such that some portions of the unit cell are extended and others are contracted so as to access a variety of bended/twisted conformations). In some embodiments, the applied magnetic field generates a magnetic torque sufficient to allow the unit cell to transition between a contracted configuration, an extended configuration, or a combination thereof can include reorientation of the plurality of conjoined panels forming the side wall. In some embodiments, the unit cell exhibits an actuation speed of from 1 millisecond to 10 minutes (e.g., 1 millisecond to 8 minutes, 1 millisecond to 5 minutes, 1 millisecond to 1 minutes, 1 millisecond to 30 seconds, 1 millisecond to 15 seconds, 1 millisecond to 10 seconds, 1 millisecond to 5 seconds, 1 millisecond to 1 second, or 1 millisecond to 30 milliseconds).

In some embodiments, the magnetic field can have a magnetic field strength of from 0 mT to 300 mT (e.g., from 0 mT to 250 mT, from 0 mT to 200 mT, from 0 mT to 150 mT, from 0 mT to 100 mT, from 0 mT to 50 mT, from 0 mT to 40 mT, form 0 mT to 35 mT, from 0 mT to 30 mT, from 0 mT to 25 mT, from 0 mT to 20 mT, from 0 mT to 15 mT, from 0 mT to 10 mT, from 0 mT to 5 mT, from 5 mT to 250 mT, from 5 mT to 200 mT, from 5 mT to 150 mT, from 5 mT to 100 mT, from 5 mT to 50 mT, from 5 mT to 40 mT, form 5 mT to 35 mT, from 5 mT to 30 mT, from 5 mT to 25 mT, from 5 mT to 20 mT, from 5 mT to 15 mT, from 5 mT to 10 mT, from 10 mT to 250 mT, from 10 mT to 200 mT, from 10 mT to 150 mT, from 10 mT to 100 mT, from 10 mT to 50 mT, from 10 mT to 40 mT, form 10 mT to 35 mT, from 10 mT to 30 mT, from 10 mT to 25 mT, from 10 mT to 20 mT, from 10 mT to 15 mT, from 20 mT to 250 mT, from 20 mT to 200 mT, from 20 mT to 150 mT, from 20 mT to 100 mT, from 20 mT to 50 mT, from 20 mT to 40 mT, form 20 mT to 35 mT, from 20 mT to 30 mT, from 20 mT to 25 mT, from 30 mT to 250 mT, from 30 mT to 200 mT, from 30 mT to 150 mT, from 30 mT to 100 mT, from 30 mT to 50 mT, from 30 mT to 40 mT, form 30 mT to 35 mT, from 40 mT to 250 mT, from 40 mT to 200 mT, from 40 mT to 150 mT, from 40 mT to 100 mT, from 40 mT to 50 mT, from 50 mT to 250 mT, from 50 mT to 200 mT, from 50 mT to 150 mT, from 50 mT to 100 mT, from 100 mT to 250 mT, from 100 mT to 200 mT, from 100 mT to 150 mT, from 150 mT to 250 mT, from 150 mT to 200 mT, from 150 mT to 300 mT, from 200 mT to 250 mT, from 200 mT to 300 mT, or from 250 mT to 300 mT).

In some embodiments, the magnetic field can have a magnetic field direction angle of from 0° to 3600 relative to the longitudinal axis of the unit cell, (e.g., from 0° to 45°, from 0° to 90°, from 0° to 135°, from 0° to 180°, from 0° to 225°, from 0° to 270°, from 0° to 315°, from 45° to 90°, from 450 to 135°, from 450 to 180°, from 450 to 225°, from 450 to 270°, from 450 to 315°, from 450 to 360°, from 900 to 135°, from 900 to 180°, from 900 to 225°, from 900 to 270°, from 900 to 315°, from 900 to 360°, from 1350 to 1800, from 1350 to 225°, from 1350 to 270°, from 1350 to 315°, from 1350 to 360°, from 180° to 225°, from 1800 to 270°, from 1800 to 315°, from 1800 to 360°, from 225° to 270°, from 225° to 315°, from 225° to 360°, from 2700 to 315°, from 2700 to 360°, or from 315° to 360°).

In some embodiments, the unit cell can further include a cap positioned between the side wall and the top surface of the base plate, the bottom surface of the top plate or any combination thereof. In some embodiments, the cap can be formed from a polymeric material, a paper material, or any combination thereof. In some embodiments, the cap can have a hexagonal shape, round shape, or any combination thereof. In some embodiments, the cap can have a hexagonal shape.

In some embodiments, the panels can be formed from a polymeric material, a paper, or any combination thereof. In some embodiments, the panels can be formed from a paper. In some embodiments, the panels can be formed from a polymeric material. Suitable polymeric materials for forming the panels can include but are not limited to, polyepoxides (epoxy resins), polyphosphazenes, poly(vinyl alcohols), polyamides, polyester amides, poly(amino acid)s, polyanhydrides, polycarbonates, polyacrylates, polyalkylenes (e.g, polyethylene), polyacrylamides, polyalkylene glycols, polyalkylene oxides, polyalkylene terephthalates, polyortho esters, polyvinyl ethers, polyvinyl esters, polyvinyl halides, polyesters, polylactides, polyglycolides, polysiloxanes, polyurethanes, polyethers, polyether amides, polyether esters, and copolymers thereof, polystyrene, polypropylene, polyvinyl phenol, polyvinylpyrrolidone, chlorinated polybutylene, poly(octadecyl vinyl ether), ethylene vinyl acetate, polyethylene, poly(ethylene oxide)-poly(ethylene terephthalate), polyethylene/nylon (graft copolymer), polycaprolactones-polyamide (block copolymer), poly(caprolactone) dimethacrylate-n-butyl acrylate, poly(norbornyl-polyhedral oligomeric silsequioxane), polyvinylchloride, urethane/butadiene copolymers, polyurethane block copolymers, styrene-butadiene-styrene block copolymers, and the like. In some embodiments, the panels can include polyethylene.

In some embodiments, the polymeric material suitable to form the panels can exhibit a Young's modulus of from 1 MPa to 2000 MPa (e.g., from 1 MPa to 1500 MPa, from 1 MPa to 1000 MPa, from 1 MPa to 800 MPa, from 1 MPa to 600 MPa, from 1 MPa to 300 MPa, from 1 MPa to 100 MPa, from 1 MPa to 50 MPa, from 1 MPa to 20 MPa, from 1 MPa to 10 MPa, from 50 MPa to 2000 MPa, from 50 MPa to 1500 MPa, from 50 MPa to 1000 MPa, from 50 MPa to 800 MPa, from 50 MPa to 600 MPa, from 50 MPa to 300 MPa, from 50 MPa to 100 MPa, from 100 MPa to 2000 MPa, from 100 MPa to 1500 MPa, from 100 MPa to 1000 MPa, from 100 MPa to 800 MPa, from 100 MPa to 600 MPa, from 100 MPa to 300 MPa, from 200 MPa to 2000 MPa, from 200 MPa to 1500 MPa, from 200 MPa to 1000 MPa, from 200 MPa to 800 MPa, from 200 MPa to 600 MPa, from 200 MPa to 300 MPa, from 100 MPa to 200 MPa, from 500 MPa to 2000 MPa, from 500 MPa to 1500 MPa, from 500 MPa to 1000 MPa, from 500 MPa to 800 MPa, from 500 MPa to 600 MPa, from 1000 MPa to 2000 MPa, from 1000 MPa to 1500 MPa, or from 1500 MPa to 2000 MPa)

In some embodiments, the cap can be formed from a polymeric material, a paper, or any combination thereof. In some embodiments, the cap can be formed from a paper. In some embodiments, the cap can be formed from a polymeric material. Suitable polymeric materials for forming the panels can include but are not limited to, polyepoxides (epoxy resins), polyphosphazenes, poly(vinyl alcohols), polyamides, polyester amides, poly(amino acid)s, polyanhydrides, polycarbonates, polyacrylates, polyalkylenes (e.g, polyethylene), polyacrylamides, polyalkylene glycols, polyalkylene oxides, polyalkylene terephthalates, polyortho esters, polyvinyl ethers, polyvinyl esters, polyvinyl halides, polyesters, polylactides, polyglycolides, polysiloxanes, polyurethanes, polyethers, polyether amides, polyether esters, and copolymers thereof, polystyrene, polypropylene, polyvinyl phenol, polyvinylpyrrolidone, chlorinated polybutylene, poly(octadecyl vinyl ether), ethylene vinyl acetate, polyethylene, poly(ethylene oxide)-poly(ethylene terephthalate), polyethylene/nylon (graft copolymer), polycaprolactones-polyamide (block copolymer), poly(caprolactone) dimethacrylate-n-butyl acrylate, poly(norbornyl-polyhedral oligomeric silsequioxane), polyvinylchloride, urethane/butadiene copolymers, polyurethane block copolymers, styrene-butadiene-styrene block copolymers, and the like. In some embodiments, the cap can include polyethylene terephthalate.

In some embodiments, the polymer suitable to form the cap can exhibit a Young's modulus of from 1 MPa to 1000 MPa (e.g., from 1 MPa to 800 MPa, from 1 MPa to 600 MPa, from 1 MPa to 300 MPa, from 1 MPa to 100 MPa, from 1 MPa to 50 MPa, from 1 MPa to 20 MPa, from 1 MPa to 10 MPa, from 50 MPa to 800 MPa, from 50 MPa to 600 MPa, from 50 MPa to 300 MPa, from 50 MPa to 100 MPa, from 100 MPa to 800 MPa, from 100 MPa to 600 MPa, or from 100 MPa to 300 MPa).

In some embodiments, the unit cell can further include an active agent present in the lumen of the unit cell. In some embodiments, when the unit cell can be actuated the active agent releases from the unit cell. In some embodiments, the unit cell can further include an active agent containing compartment positioned in the lumen of the unit cell. In some embodiments, the active agent containing compartment can include an active agent. In some embodiments, the unit cell can further include an active agent release mechanism. In some embodiments, the unit cell can further include a puncturing component positioned at an opposite end to the active agent containing compartment inside the lumen of the unit cell.

In some embodiments, the magnetic responsive plates can include a population of hard-magnetic particles dispersed within the polymer matrix.

In some embodiments, the polymer matrix can include any suitable polymer or blend of polymers. Examples of suitable materials include thermoplastics (e.g., thermoplastic elastomers), thermosets, single-single crosslinked network, interpenetrating networks, semi-interpenetrating networks, or mixed networks. The polymers can be a single polymer or a blend of polymers. The polymers can be linear or branched thermoplastic elastomers or thermosets with side chains or dendritic structural elements.

Suitable polymers for the magnetic responsive plate include, but are not limited to, polyepoxides (epoxy resins), polyphosphazenes, poly(vinyl alcohols), polyamides, polyester amides, poly(amino acid)s, polyanhydrides, polycarbonates, polyacrylates, polyalkylenes, polyacrylamides, polyalkylene glycols, polyalkylene oxides, polyalkylene terephthalates, polyortho esters, polyvinyl ethers, polyvinyl esters, polyvinyl halides, polyesters, polylactides, polyglycolides, polysiloxanes, polyurethanes, polyethers, polyether amides, polyether esters, and copolymers thereof. Examples of suitable polyacrylates include poly(methyl methacrylate), poly(ethyl methacrylate), poly(butyl methacrylate), poly(isobutyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate) and poly(octadecyl acrylate). Examples of other suitable polymers include polystyrene, polypropylene, polyvinyl phenol, polyvinylpyrrolidone, chlorinated polybutylene, poly(octadecyl vinyl ether), ethylene vinyl acetate, polyethylene, poly(ethylene oxide)-poly(ethylene terephthalate), polyethylene/nylon (graft copolymer), polycaprolactones-polyamide (block copolymer), poly(caprolactone) dimethacrylate-n-butyl acrylate, poly(norbornyl-polyhedral oligomeric silsequioxane), polyvinylchloride, urethane/butadiene copolymers, polyurethane block copolymers, styrene-butadiene-styrene block copolymers, and the like.

In some embodiments, the polymer matrix can include a shape memory polymer (SMPs). SMPs are known in the art and generally refer to polymeric materials that demonstrate the ability to return to some previously defined shape when subjected to an appropriate thermal stimulus. Shape memory polymers are capable of undergoing phase transitions in which their shape is altered as a function of temperature. Generally, SMPs have two main segments, a hard segment and a soft segment. The previously defined or permanent shape can be set by melting or processing the polymer at a temperature higher than the highest thermal transition followed by cooling below that thermal transition temperature. The highest thermal transition is usually the glass transition temperature (Tg) or melting point of the hard segment. A temporary shape can be set by heating the material to a temperature higher than the Tg or the transition temperature of the soft segment, but lower than the Tg or melting point of the hard segment. The temporary shape is set while processing the material at the transition temperature of the soft segment followed by cooling to fix the shape. The material can be reverted back to the permanent shape by heating the material above the transition temperature of the soft segment.

In some embodiments, the polymer matrix can include a biocompatible polymer or blend of biocompatible polymers. In certain embodiments, the polymer matrix can comprise a polyester (e.g., polycaprolactone, polylactic acid, polyglycolic acid, a polyhydroxyalkanoate, and copolymers thereof), a polyether (e.g., a polyalkylene oxides such as polyethylene glycol, polypropylene oxide, polybutylene oxide, and copolymers thereof), blends thereof, and copolymers thereof.

In some embodiments, the polymer or blend of polymers forming the polymer matrix can have a Tg of at least −40° C. (e.g., at least −20° C., at least 0° C., at least 25° C., at least 30° C., at least 35° C., at least 40° C., at least 45° C., at least 50° C., at least 55° C., at least 60° C., at least 65° C., at least 70° C., at least 75° C., at least 80° C., at least 85° C., at least 90° C., at least 95° C., at least 100° C., at least 105° C., at least 110° C., at least 115° C., at least 120° C., at least 150° C., at least 200° C. or more). In some embodiments, the polymer or blend of polymers forming the polymer matrix can have a Tg above room temperature (23° C.). In some embodiments, the polymer or blend of polymers forming the polymer matrix can have a Tg above physiological temperature (37° C.). In some embodiments, the polymer or blend of polymers forming the polymer matrix can have a Tg of 250° C. or less (e.g., 200° C. or less, 150° C. or less, 120° C. or less, 115° C. or less, 110° C. or less, 105° C. or less, 100° C. or less, 95° C. or less, 90° C. or less, 85° C. or less, 80° C. or less, 75° C. or less, 70° C. or less, 65° C. or less, 60° C. or less, 55° C. or less, 50° C. or less, 45° C. or less, 40° C. or less, 35° C. or less, 30° C. or less, or 25° C. or less).

The polymer or blend of polymers forming the polymer matrix can have a Tg ranging from any of the minimum values described above to any of the maximum values described above. In some embodiments, the polymer or blend of polymers forming the polymer matrix can have a Tg of from 0° C. to 100° C., a Tg of from 150° C. to 250° C., a Tg of from 25° C. to 100° C., a Tg of from 30° C. to 100° C., a Tg of from 30° C. to 80° C., a Tg of from 38° C. to 100° C., a Tg of from 38° C. to 80° C., a Tg of from 40° C. to 100° C., a Tg of from 40° C. to 80° C., a Tg of from 50° C. to 100° C., or a Tg of from 50° C. to 80° C.

In some embodiments, the polymer matrix can exhibit a Young's modulus of from 10 kPa to 20 MPa (e.g., from 10 kPa to 10 MPa, from 10 kPa to 5 MPa, from 10 kPa to 1 MPa, from 1 MPa to 5 MPa, from 1 MPa to 10 MPa, from 1 MPa to 20 MPa, from 10 kPa to 800 kPa, from 10 kPa to 600 kPa, from 10 kPa to 500 kPa, from 50 kPa to 800 kPa, from 100 kPa to 800 kPa, from 200 kPa to 800 kPa, from 50 kPa to 600 kPa, from 100 kPa to 600 kPa, from 200 kPa to 600 kPa, from 50 kPa to 500 kPa, from 100 kPa to 500 kPa, or from 200 kPa to 500 kPa) when heated to a temperature at or above the Tg of the polymer or blend of polymers but below the melting point or decomposition point of the polymer or blend of polymers. In some embodiments, the polymer matrix can exhibit a Young's modulus of from 10 kPa to 20 MPa (e.g., from 10 kPa to 10 MPa, from 10 kPa to 5 MPa, from 10 kPa to 1 MPa, from 1 MPa to 5 MPa, from 1 MPa to 10 MPa, from 1 MPa to 20 MPa, from 10 kPa to 800 kPa, from 10 kPa to 600 kPa, from 10 kPa to 500 kPa, from 50 kPa to 800 kPa, from 100 kPa to 800 kPa, from 200 kPa to 800 kPa, from 50 kPa to 600 kPa, from 100 kPa to 600 kPa, from 200 kPa to 600 kPa, from 50 kPa to 500 kPa, from 100 kPa to 500 kPa, or from 200 kPa to 500 kPa) when heated to a temperature at or above the Tg of the polymer or blend of polymers (e.g., a temperature equal to the Tg of the polymer or blend of polymers, a temperature equal to 5° C. above the Tg of the polymer or blend of polymers, a temperature equal to 10° C. above the Tg of the polymer or blend of polymers, a temperature equal to 20° C. above the Tg of the polymer or blend of polymers, or a temperature equal to 30° C. above the Tg of the polymer or blend of polymers).

In some embodiments, the polymer matrix can exhibit a Young's modulus of at least 0.1 GPa (e.g., at least 0.5 GPa, at least 1.0 GPa, at least 1.5 GPa, at least 2.0 GPa, at least 2.5 GPa, at least 3 GPa, at least 3.5 GPa, or at least 4 GPa) at a temperature below the Tg (e.g., a temperature at 25° C., a temperature at 37° C., a temperature at 38° C., a temperature at 40° C., or a temperature at 45° C.).

In some embodiments, the polymer matrix can exhibit a Young's modulus of at least 0.1 GPa (e.g., at least 0.5 GPa, at least 1.0 GPa, at least 1.5 GPa, at least 2.0 GPa, at least 2.5 GPa, at least 3 GPa, at least 3.5 GPa, or at least 4 GPa) at 25° C.

In some embodiments, the polymer matrix can exhibit a Young's modulus of at least 0.1 GPa (e.g., at least 0.5 GPa, at least 1.0 GPa, at least 1.5 GPa, at least 2.0 GPa, at least 2.5 GPa, at least 3 GPa, at least 3.5 GPa, or at least 4 GPa) at 37° C.

In some embodiments, the polymer matrix can exhibit a Young's modulus of at least 0.1 GPa (e.g., at least 0.5 GPa, at least 1.0 GPa, at least 1.5 GPa, at least 2.0 GPa, at least 2.5 GPa, at least 3 GPa, at least 3.5 GPa, or at least 4 GPa) at 38° C.

In some embodiments, the polymer matrix can exhibit a Young's modulus of at least 0.1 GPa (e.g., at least 0.5 GPa, at least 1.0 GPa, at least 1.5 GPa, at least 2.0 GPa, at least 2.5 GPa, at least 3 GPa, at least 3.5 GPa, or at least 4 GPa) at 40° C.

In some embodiments, the polymer matrix can exhibit a Young's modulus of at least 0.1 GPa (e.g., at least 0.5 GPa, at least 1.0 GPa, at least 1.5 GPa, at least 2.0 GPa, at least 2.5 GPa, at least 3 GPa, at least 3.5 GPa, or at least 4 GPa) at 45° C.

In some embodiments, the polymer matrix can exhibit a Young's modulus of from 10 kPa to 20 MPa (e.g., from 10 kPa to 10 MPa, from 10 kPa to 5 MPa, from 10 kPa to 1 MPa, from 1 MPa to 5 MPa, from 1 MPa to 10 MPa, from 1 MPa to 20 MPa, from 10 kPa to 800 kPa, from 10 kPa to 600 kPa, from 10 kPa to 500 kPa, from 50 kPa to 800 kPa, from 100 kPa to 800 kPa, from 200 kPa to 800 kPa, from 50 kPa to 600 kPa, from 100 kPa to 600 kPa, from 200 kPa to 600 kPa, from 50 kPa to 500 kPa, from 100 kPa to 500 kPa, or from 200 kPa to 500 kPa) at 50° C.

In some embodiments, the polymer matrix can exhibit a Young's modulus of from 10 kPa to 20 MPa (e.g., from 10 kPa to 10 MPa, from 10 kPa to 5 MPa, from 10 kPa to 1 MPa, from 1 MPa to 5 MPa, from 1 MPa to 10 MPa, from 1 MPa to 20 MPa, from 10 kPa to 800 kPa, from 10 kPa to 600 kPa, from 10 kPa to 500 kPa, from 50 kPa to 800 kPa, from 100 kPa to 800 kPa, from 200 kPa to 800 kPa, from 50 kPa to 600 kPa, from 100 kPa to 600 kPa, from 200 kPa to 600 kPa, from 50 kPa to 500 kPa, from 100 kPa to 500 kPa, or from 200 kPa to 500 kPa) at 60° C.

In some embodiments, the polymer matrix can comprise a thermoplastic polymer or a thermoset. In certain embodiments, the polymer matrix can be elastomeric.

In certain examples, the polymer matrix can comprise a crosslinked epoxy resin (e.g., an epoxy resin derived from the reaction of bisphenol A and epichlorohydrin).

In some embodiments, the hard-magnetic particles can be present in varying amounts within the polymer matrix. In some examples, the hard-magnetic particles can be present in the polymer matrix at a concentration of from 0.1% v/v to 60% v/v hard-magnetic particles, such as from 0.1% v/v to 50% v/v hard-magnetic particles, from 1% v/v to 50% v/v hard-magnetic particles, from 5% v/v to 50% v/v hard-magnetic particles, from 5% v/v to 60% v/v hard-magnetic particles, from 1% v/v to 60% v/v hard-magnetic particles, from 10% v/v to 60% v/v hard-magnetic particles, from 10% v/v to 50% v/v hard-magnetic particles, from 5% v/v to 30% v/v hard-magnetic particles, from 10% v/v to 30% v/v hard-magnetic particles, from 5% v/v to 25% v/v hard-magnetic particles, or from 10% v/v to 25% v/v hard-magnetic particles.

The population of hard-magnetic particles can have any suitable average particle size. In some examples, the population of hard-magnetic particles can have an average particle size of from 1 nm to 1 mm (e.g., from 30 nm to 500 microns, from 1 nm to 100 microns, from 30 nm to 100 microns, from 0.1 microns to 100 microns, from 0.5 microns to 100 microns, from 1 micron to 100 microns, from 1 micron to 50 microns, from 1 micron to 500 microns, or from 50 microns to 500 microns). The "particle size" in the polymer matrix can be measured by a transmission electron microscope (TEM). The average particle size is defined as the average value of the particle sizes of 500 particles randomly extracted and measured in a photograph taken by a transmission electron microscope.

The hard-magnetic particles can be formed from any suitable hard-magnetic material (i.e., material which exhibits hard magnetism). Such materials can not exhibit changes in polarity under the designated working conditions.

In some embodiments, the term "hard magnetism" can refer to a coercive force of equal to or higher than 10 kA/m. That is, the hard-magnetic particles can have a coercive force of equal to or higher than 10 kA/m. A hard-magnetic particle with a coercive force of equal to or higher than 10 kA/m can exhibit a high crystal magnetic anisotropy, and can thus have good thermal stability.

The constant of crystal magnetic anisotropy of the hard-magnetic particle (also referred to as the "hard-magnetic phase" hereinafter) can be equal to or higher than $1 \times 10^{-1}$ J/cc ($1 \times 10^6$ erg/cc) (e.g., equal to or higher than $6 \times 10^{-1}$ J/cc ($6 \times 10^6$ erg/cc)).

The saturation magnetization of the hard-magnetic particles can be from $0.4 \times 10^{-1}$ to $2 \text{ A·m}^2/\text{g}$ (40 to 2,000 emu/g) (e.g., from $5 \times 10^{-1}$ to $1.8 \text{ A·m}^2/\text{g}$ (500 to 1,800 emu/g)). They can be of any shape, such as spherical or polyhedral.

Examples of the hard-magnetic phase are magnetic materials comprised of rare earth elements and transition metal elements; oxides of transition metals and alkaline earth metals; metal alloy; and magnetic materials comprised of rare earth elements, transition metal elements, and metalloids (also referred to as "rare earth-transition metal-metalloid magnetic materials" hereinafter). In certain embodiments, the hard-magnetic particles can comprise a rare earth-transition metal-metalloid magnetic materials and hexagonal ferrite. In certain embodiments, the hard-magnetic particles can comprise metal alloys (e.g., AlNiCo, FeCrCo). Depending on the type of hard-magnetic particle, there are times when oxides such as rare earth oxides can be present on the surface of the hard-magnetic particle. Such hard-magnetic particles are also included among the hard-magnetic particles.

More detailed descriptions of rare earth-transition metal-metalloid magnetic materials and hexagonal ferrite are given below.

Examples of rare earth elements are Y, Ce, Pr, Nd, Sm, Gd, Tb, Dy, Ho, Er, Tm, and Lu. Of these, Y, Ce, Pr, Nd, Gd, Tb, Dy, and Ho, which exhibit single-axis magnetic anisotropy, are preferred; Y, Ce, Gd, Ho, Nd, and Dy, which having constants of crystal magnetic anisotropy of $6 \times 10^{-1}$ J/cc to 6 J/cc ($6 \times 10^6$ erg/cc to $6 \times 10^7$ erg/cc), are of greater preference; and Y, Ce, Gd, and Nd are of even greater preference.

The transition metals Fe, Ni, and Co are desirably employed to form ferromagnetic materials. When employed singly, Fe, which has the greatest crystal magnetic anisotropy and saturation magnetization, is desirably employed.

Examples of metalloids are boron, carbon, phosphorus, silicon, and aluminum. Of these, boron and aluminum are desirably employed, with boron being optimal. That is, magnetic materials comprised of rare earth elements, transition metal elements, and boron (referred to as "rare earth-transition metal-boron magnetic materials", hereinafter) are desirably employed as the above hard-magnetic phase. Rare earth-transition metal-metalloid magnetic materials including rare earth-transition metal-boron magnetic materials are advantageous from a cost perspective in that they do not contain expensive noble metals such as Pt.

The composition of the rare earth-transition metal-metalloid magnetic material can be 10 atomic percent to 15 atomic percent rare earth, 70 atomic percent to 85 atomic percent transition metal, and 5 atomic percent to 10 atomic percent metalloid.

When employing a combination of different transition metals as the transition metal, for example, the combination of Fe, Co, and Ni, denoted as $Fe_{(1-x-y)}Co_xNi_y$, can have a composition in the ranges of x=0 atomic percent to 45 atomic percent and y=25 atomic percent to 30 atomic percent; or the ranges of x=45 atomic percent to 50 atomic percent and y=0 atomic percent to 25 atomic percent, from the perspective of ease of controlling the coercive force of the hard-magnetic material to the range of 240 kA/m to 638 kA/m (3,000 Oe to 8,000 Oe).

From the perspective of low corrosion, the ranges of x=0 atomic percent to 45 atomic percent and y=25 atomic percent to 30 atomic percent, or the ranges of x=45 atomic percent to 50 atomic percent and y=10 atomic percent to 25 atomic percent, are desirable.

In other cases, the ranges of x=20 atomic percent to 45 atomic percent and y=25 atomic percent to 30 atomic percent, or the ranges of x=45 atomic percent to 50 atomic percent and y=0 atomic percent to 25 atomic percent, can be desirable.

Accordingly, from the perspectives of coercive force, corrosion, and temperature characteristics, the ranges of x=20 atomic percent to 45 atomic percent and y=25 atomic percent to 30 atomic percent or the ranges of x=45 atomic percent to 50 atomic percent and y=10 atomic percent to 25 atomic percent are desirable, and the ranges of x=30 atomic percent to 45 atomic percent and y=28 atomic percent to 30 atomic percent are preferred.

In certain embodiments, the hard-magnetic particles can include NdFeB particles.

Examples of hexagonal ferrites include barium ferrite, strontium ferrite, lead ferrite, calcium ferrite, and various substitution products thereof such as Co substitution products. Specific examples are magnetoplumbite-type barium ferrite and strontium ferrite; magnetoplumbite-type ferrite in which the particle surfaces are covered with spinels; and magnetoplumbite-type barium ferrite, strontium ferrite, and the like partly comprising a spinel phase. The following may be incorporated into the hexagonal ferrite in addition to the prescribed atoms: Al, Si, S, Sc, Ti, V, Cr, Cu, Y, Mo, Rh, Pd, Ag, Sn, Sb, Te, Ba, Ta, W, Re, Au, Hg, Pb, Bi, La, Ce, Pr, Nd, P, Co, Mn, Zn, Ni, Sr, B, Ge, Nb and the like. Compounds to which elements such as Co—Zn, Co—Ti, Co—Ti—Zr, Co—Ti—Zn, Ni—Ti—Zn, Nb—Zn—Co, Sb—Zn—Co, and Nb—Zn have been added may generally also be employed. They may comprise specific impurities depending on the starting materials and manufacturing methods employed. There are cases where a substitution element which substitutes for Fe is added as a coercive force-adjusting component for reducing a coercive force of hexagonal ferrite. However, incorporation of the substitution element can reduce crystal magnetic anisotropy. To that end, in some cases, hexagonal ferrites containing no substitution elements can be selected for use as the hard-magnetic particle. Hexagonal ferrites containing no substitution elements can have a composition denoted by general formula: $AFe_{12}O_{19}$ [wherein A is at least one element selected from the group consisting of Ba, Sr, Pb, and Ca].

In some embodiments, the magnetic responsive plate can further include a population of auxiliary magnetic particles (e.g., soft magnetic particles) dispersed within the polymer matrix. The auxiliary magnetic particles can be used to inductively heat the polymer matrix (e.g., to above the Tg of the polymer or blend of polymers forming the polymer matrix) under application of a high frequency magnetic field.

The auxiliary magnetic particles can be present in varying amounts within the polymer matrix. In some examples, the auxiliary magnetic particles can be present in the polymer matrix at a concentration ranging from 0.1% v/v to 60% v/v auxiliary magnetic particles, such as from 0.1% v/v to 50% v/v auxiliary magnetic particles, from 1% v/v to 50% v/v auxiliary magnetic particles, from 5% v/v to 50% v/v auxiliary magnetic particles, from 5% v/v to 60% v/v auxiliary magnetic particles, from 1% v/v to 60% v/v auxiliary magnetic particles, from 10% v/v to 60% v/v auxiliary magnetic particles, from 10% v/v to 50% v/v auxiliary magnetic particles, from 5% v/v to 30% v/v auxiliary magnetic particles, from 10% v/v to 30% v/v auxiliary magnetic particles, from 5% v/v to 25% v/v auxiliary magnetic particles, or from 10% v/v to 25% v/v auxiliary magnetic particles.

The population of auxiliary magnetic particles can have any suitable average particle size. In some examples, the population of auxiliary magnetic particles can have an average particle size of from 1 nm to 1 mm (e.g., from 30 nm to 500 microns, from 1 nm to 100 microns, from 30 nm to 100 microns, from 0.1 microns to 100 microns, from 0.5 microns to 100 microns, from 1 micron to 100 microns, from 1 micron to 50 microns, from 1 micron to 500 microns, or from 50 microns to 500 microns). The "particle size" in the polymer matrix can be measured by a transmission electron microscope (TEM). The average particle size is defined as the average value of the particle sizes of 500 particles randomly extracted and measured in a photograph taken by a transmission electron microscope.

In certain embodiments, the auxiliary magnetic particles can comprise a second population of hard-magnetic particles, such as any of the hard-magnetic particles described above. In some embodiments, the hard-magnetic particles have a higher coercive force than the soft magnetic particles. In some embodiments, the auxiliary magnetic particles exhibit a coercive force of less than 40 kA/m, such as a coercive force ranging from 1 kA/m to less than 40 kA/m, from 5 kA/m to 10 kA/m, from 5 kA/m to less than 40 kA/m, from 5 kA/m to 20 kA/m, from 5 kA/m to 30 kA/m, from 5 kA/m to 40 kA/m.

In some embodiments, the auxiliary magnetic particles can include ferromagnetic hexagonal ferrite particles, wherein the particles have a specific Curie temperature (Tc) in the matrix material. In some embodiments, the ferromagnetic hexagonal ferrite particles can comprise $SrFe_{12}O_{19}$ (hereinafter referred to as "SrF"), $Me_a$-2W, $Me_a$-2Y, and $Me_a$-2Z, wherein 2W is $BaO:2Me_aO:8Fe_2O_3$, 2Y is $2(BaO:Me_aO:3Fe_2O_3)$, and 2Z is $3BaO:2Me_aO:12Fe_2O_3$, and wherein $Me_a$ is a divalent cation. The divalent cation can be selected from Mg, Co, Mn and Zn. In some cases, the ferromagnetic hexagonal ferrite particles can have the composition SrF, $Co_2Ba_2Fe_{12}O_{22}$ (hereinafter referred to as Co-2Y), $Mg_2Ba_2Fe_{12}O_{22}$ (hereinafter referred to as "Mg-2Y"), $Zn_1Mg_1Ba_2Fe_{12}O_{22}$ (hereinafter referred to as "Zn/Mg-2Y") and $Zn_1Co_1Ba_2Fe_{12}O_{22}$ (hereinafter referred to as "Zn/Co-2Y") or combinations thereof.

In some embodiments, the auxiliary magnetic particles can comprise a material with a low curie temperature (e.g., from 40-100 degrees Celsius). Such materials can include Ni—Si, Fe—Pt, and Ni—Pd alloys. A number of magnetic powders can be used including Ni—Zn—Fe—O, Ba—Co—Fe—O, and Fe—O. Another material is a substituted magnetite or ferric oxide crystalline lattice with a portion of the iron atoms substituted by one of the following, cobalt, nickel, manganese, zinc, magnesium, copper, chromium, cadmium, or gallium. A Palladium Cobalt alloy that also has a controllable curie temperature in the range of 40-100 degrees Celsius can also be used. Nickel Zinc Ferrite (a soft ferrite) can also be used. A very useful property of this material is that its curie temperature can be greatly influenced by the amount of Zinc present in the material. Curie temperatures ranging from 30-600 degrees Celsius are achievable [Strontium Ferrite (a hard ferrite) and Nickel (an elemental ferromagnetic material)] can be used.

In some embodiments, the auxiliary magnetic particles can comprise soft magnetic particles (e.g., the particles can be formed from a soft magnetic material). In some cases, the constant of crystal magnetic anisotropy of the soft magnetic material can be from 0 to $5\times10^{-2}$ J/cc (0 to $5\times10^5$ erg/cc) (e.g., from 0 to $1\times10^{-2}$ J/cc (0 to $1\times10^5$ erg/cc)). In some embodiments, the saturation magnetization of the soft magnetic material can range from $1\times10^{-1}$ to 2 A·m²/g (100 emu/g to 2,000 emu/g) (e.g., from $3\times10^{-1}$ to 1.8 A·m²/g (300 to 1,800 emu/g)).

In some examples, Fe, an Fe alloy, or an Fe compound, such as iron, permalloy, sendust, or soft ferrite, can be employed as the soft magnetic material. The soft magnetic material can be selected from the group consisting of transition metals and compounds of transition metals and oxygen. Examples of transition metals are Fe, Co, and Ni. Fe and Co are desirable.

In some examples, the constant of crystal magnetic anisotropy of the soft magnetic material can be from 0.01 to 0.3-fold that of the hard-magnetic particles.

In some embodiments, the auxiliary magnetic particles can include magnetically soft ferrite particles. In certain examples, the particles can have the composition $1Me_bO:1Fe_2O_3$, where $Me_bO$ is a transition metal oxide. Examples of $Me_b$ include Ni, Co, Mn, and Zn. Example particles include, but are not limited to: $(Mn, ZnO) Fe_2O_3$ and $(Ni, ZnO)Fe_2O_3$.

Devices

Described are also devices including a plurality of unit cells described herein that are joined in series. In some embodiments, the unit cells are joined in such a way that the top plate of a unit cell becomes the bottom plate of another unit cell. In some embodiments, a device can include 2-unit cells, 5-unit cells, 10-unit cells, 15-unit cells, 30-unit cells, 40-unit cells, 50-unit cells, 60-unit cell, 70-unit cells, 80-unit cells, 90-unit cells, or 100-unit cells or more. In some embodiments, each unit cell can be magnetically actuatable, such that each unit cell can reversibly transition between a contracted configuration, an extended configuration, or a combination thereof using an applied magnetic field. In some embodiments, a plurality of unit cells joined in series can be magnetically actuatable, such that each unit cell can reversibly transition between a contracted configuration, an extended configuration, or a combination thereof using an applied magnetic field. In some embodiments, a plurality of unit cells joined in series can each be independently magnetically actuatable, such that each unit cell can reversibly transition between a contracted configuration, an extended configuration, or a combination thereof using an applied magnetic field. For example, in some embodiments, two or more unit cells can be joined in series and each unit cell can be independently magnetically actuated as to reversibly transition between a contracted configuration, an extended configuration, or a combination thereof.

Methods of Use

Described herein are also methods of actuating the unit cells described herein. The method described herein can include providing the unit cell described herein, wherein the unit cell can be capable of being programmed to transition between a contracted configuration, an extended configuration, or a combination thereof; and actuating the unit cell described herein under an applied magnetic field.

Described herein are also methods of actuating a device to perform an activity on a subject. The method can include positioning a unit cell described herein in a first position with regard to the subject, wherein the unit cell is capable of being programmed to transition between a contracted configuration, an extended configuration, or a combination thereof; and actuating the device under an applied magnetic field.

Described herein are also methods of drug delivery. The method can include administering to a subject in need thereof a unit cell described herein, wherein the unit cell is capable of being programmed to transition between a contracted configuration, an extended configuration, or a combination thereof; and actuating the device using an applied magnetic field.

In some embodiments, the magnetic field can have a magnetic field strength of from 0 mT to 300 mT (e.g., from 0 mT to 250 mT, from 0 mT to 200 mT, from 0 mT to 150 mT, from 0 mT to 100 mT, from 0 mT to 50 mT, from 0 mT to 40 mT, form 0 mT to 35 mT, from 0 mT to 30 mT, from 0 mT to 25 mT, from 0 mT to 20 mT, from 0 mT to 15 mT, from 0 mT to 10 mT, from 0 mT to 5 mT, from 5 mT to 250 mT, from 5 mT to 200 mT, from 5 mT to 150 mT, from 5 mT to 100 mT, from 5 mT to 50 mT, from 5 mT to 40 mT, form 5 mT to 35 mT, from 5 mT to 30 mT, from 5 mT to 25 mT, from 5 mT to 20 mT, from 5 mT to 15 mT, from 5 mT to 10 mT, from 10 mT to 250 mT, from 10 mT to 200 mT, from 10 mT to 150 mT, from 10 mT to 100 mT, from 10 mT to 50 mT, from 10 mT to 40 mT, form 10 mT to 35 mT, from 10 mT to 30 mT, from 10 mT to 25 mT, from 10 mT to 20 mT, from 10 mT to 15 mT, from 20 mT to 250 mT, from 20 mT to 200 mT, from 20 mT to 150 mT, from 20 mT to 100 mT, from 20 mT to 50 mT, from 20 mT to 40 mT, form 20 mT to 35 mT, from 20 mT to 30 mT, from 20 mT to 25 mT, from 30 mT to 250 mT, from 30 mT to 200 mT, from 30 mT to 150 mT, from 30 mT to 100 mT, from 30 mT to 50 mT, from 30 mT to 40 mT, form 30 mT to 35 mT, from 40 mT to 250 mT, from 40 mT to 200 mT, from 40 mT to 150 mT, from 40 mT to 100 mT, from 40 mT to 50 mT, from 50 mT to 250 mT, from 50 mT to 200 mT, from 50 mT to 150 mT, from 50 mT to 100 mT, from 100 mT to 250 mT, from 100 mT to 200 mT, from 100 mT to 150 mT, from 150 mT to 250 mT, from 150 mT to 200 mT, from 150 mT to 300 mT, from 200 mT to 250 mT, from 200 mT to 300 mT, or from 250 mT to 300 mT).

The magnetic field has a frequency of from 0.01 Hz to 100 Hz, (e.g., from 1 Hz to 50 Hz, from 0.01 Hz to 50 Hz, from 50 Hz to 100 Hz, from 10 Hz to 50 Hz, from 10 Hz to 100 Hz, from 1 Hz to 15 Hz, from 1 Hz to 10 Hz, from 1 Hz to 5 Hz, from 1 Hz to 2.5 Hz, from 5 Hz to 15 Hz, from 5 Hz to 10 Hz, or from 10 Hz to 15 Hz).

In some embodiments, the magnetic field can have a magnetic field direction angle of from 0° to 360° from the longitudinal axis of the unit cell, (e.g., from 0° to 45°, from 0° to 90°, from 0° to 135°, from 0° to 180°, from 0° to 225°, from 0° to 270°, from 0° to 315°, from 45° to 90°, from 45° to 135°, from 45° to 180°, from 45° to 225°, from 45° to 270°, from 45° to 315°, from 45° to 360°, from 90° to 135°, from 90° to 180°, from 90° to 225°, from 90° to 270°, from 90° to 315°, from 90° to 360°, from 135° to 180°, from 135° to 225°, from 135° to 270°, from 135° to 315°, from 135° to 360°, from 180° to 225°, from 180° to 270°, from 180° to 315°, from 180° to 360°, from 225° to 270°, from 225° to 315°, from 225° to 360°, from 270° to 315°, from 270° to 360°, or from 315° to 360°).

In some embodiments, the unit cell or device including a plurality of unit cells described herein can be actuated to translocate from a first position to another position. In some embodiments, the unit cell or the device including a plurality of unit cells described herein can be actuated to release an active agent. In some embodiments, the device can be used as a medical device. In some embodiments, the medical device can be used as a tube or catheter used during medical procedures such as endoscopy, intubation, and catheterization. In some embodiments, the unit cell or the device can be actuated to clean up cloth in blood vessels. In some embodiments, the unit cell or the device can be actuated to diagnosing internal bleeding and targeted drug delivery.

By way of non-limiting illustration, examples of certain embodiments of the present disclosure are given below.

EXAMPLES

We report a magnetic origami robot that has a size less than a capsule. The multifunctional magnetic origami structure 1) serves as a moving mechanism for robotic locomotion; 2) serves as a carrier for safe drug storage; 3) provides intrinsic stiffness to overcome the resistance from the contact between tissues and organs during operation.

Our origami robot naturally provides anisotropic stiffness in the moving direction and lateral direction, effectively overcome the resistance from the in-contacted tissues and organs. It can squeeze between crowded tissues and organs without affecting its functionality. The high lateral stiffness can crack open space between the contacted tissues, guiding a way for the crawling robot. The tilted origami panels also serve as propeller blade-like structures to create propulsion when it spins with high frequency in the fluid. The internal cavity of the swimming origami serves as the space for drug storage. Once the robot swims to the targeted region, the stored drug can be released by controlling the folding motion of the origami robot. Additionally, the dose can be controlled by the folding intensity and folding cycles.

Example 1: Untethered Control of Functional Origami Microrobots with Distributed Actuation Abstract Deployability, multifunctionality, and tunability are features that can be explored in the design space of origami engineering solutions. These features arise from the shape-changing capabilities of origami assemblies, which require effective actuation for full functionality. Current actuation strategies rely on either slow or tethered or bulky actuators (or a combination). To broaden applications of origami designs, we introduce an origami system with magnetic control. We couple the geometrical and mechanical properties of the bistable Kresling pattern with a magnetically responsive material to achieve untethered and local/distributed actuation with controllable speed, which can be as fast as a tenth of a second with instantaneous shape locking. We show how this strategy facilitates multimodal actuation of the multicell assemblies, in which any unit cell can be independently folded and deployed, allowing for on-the-fly programmability. In addition, we demonstrate how the Kresling assembly can serve as a basis for tunable physical properties and for digital computing. The magnetic origami systems are applicable to origami-inspired robots, morphing structures and devices, metamaterials, and multifunctional devices with multiphysics responses.

Introduction

Origami, the art of paper folding, has unfolded engineering applications in various fields. We can find such applications in materials (1, 2), electrical (3), civil (4), aerospace (5, 6), and biomedical (7) engineering. Those applications take advantage of the origami shape-changing capabilities to create tunable, deployable, and multifunctional systems. Naturally, shape-changing systems require proper actuation. Unfortunately, the lack of a robust solution for shape actuation is one of the barriers to widespread use of origami-based engineering solutions. While many applications focus on mechanical (8) and pneumatic (9-12) actuations, those solutions result in bulky assemblages with excessive wiring. Although other solutions exist, where thermo- (6, 13, 14), humidity- (15), and pH-responsive (16) materials are adopted, the actuation speed of the shape transformation is significantly limited by the slow response rate of the materials and/or actuation sources.

By means of origami engineering, kinematic shape change can be synergistically integrated with mechanical instabilities to devise functional mechanisms (12, 17-19). Such instabilities may arise from nonrigid foldable patterns with an unstable deformation path leading to a stable state, representing multi-stability and instantaneous shape locking (2, 10). The Kresling pattern (20) is an example of a geometrically bistable pattern that can be spontaneously generated on a thin cylindrical shell under axial and torsional load, displaying a natural coupling between axial deformation and rotation. For a bistable Kresling, the bistability represents an instantaneous shape locking of the pattern in the two stable states, which are achieved either by axial forces or torques that are superior to the energy barrier between states. When composed of axially assembled N unit cells, the Kresling assembly can effectively accomplish tremendous height shrinkage, while possessing the capability of achieving $2^N$ independent stable states if each unit cell is actuated locally. Because of those properties, this pattern has been used in several applications, such as metamaterials (21, 22), robots (8), and wave propagation media (23). However, under currently available actuation methods (e.g., motors, pressure, shape memory polymers, and hydrogels), those Kresling structures are limited by slow actuation or bulky wiring systems. Further, local/distributed control requires multiple actuation sources as well as multiple controllers, leading to increased system complexity.

Figure 1A:
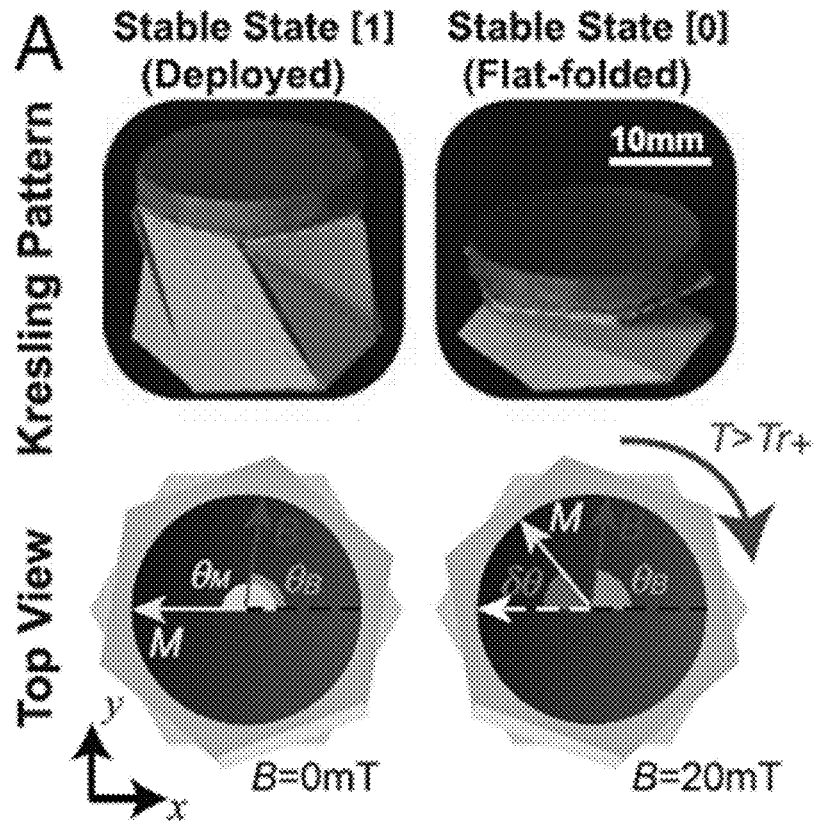
FIG. 1A-1E show magnetic actuation of the Kresling pattern and assembly. (1A) Kresling pattern with a magnetic plate at deployed and folded states, where BB is the direction of the applied magnetic field B, $\theta_M$ is the direction of the plate magnetization M, and 60 is the rotation angle controlled by B. (1B) Torque required to fold the unit cell and magnetic torque versus plate rotation angle $\delta\theta$ at given B. (1C) Contour plot of the analytical and measured results showing whether the unit cell will switch from stable state [1] to stable state [0], depending on the direction $\theta_B$ and intensity B. Dashed line represents the analytical prediction. (1D) Schematics of the magnetic actuation of a two-cell Kresling assembly. The first column represents the initial state of the unit cells, and the other three columns show the three different stable states of the assembly after the magnetic actuation. The parameters $\delta\theta_1$ and $\delta\theta_2$ denote the rotation angle of the bottom and top unit cells, respectively. In each column, the corner Insets represent the unit cell state after the magnetic field is removed. Tr+ and Tr represent the required torques to fold and deploy the unit cell, respectively. The red cross (on the third column) denotes that the rotation is constrained by the geometry. (1E) Contour plot of experimental measurements for the actuation from the [00] state to the other three states.

Recently, magnetic-responsive materials have emerged as a promising alternative for shape control (24, 25), as this allows for untethered ultrafast and controlled actuation speed, as well as distributed actuation (26, 27). The magnetic untethered control separates the power source and controller out of the actuator by using field-responsive materials, making applications possible at different scales (e.g., macro, micro, and nano). These features promote magnetic actuation as an ideal solution for origami shape transformation, as explored in this paper. Thus, we attach magnetic-responsive plates to the Kresling unit cells for the application of torsion to a level that triggers the bistable state transition (FIG. 1A). This torsional force is instantaneously generated in the presence of an external magnetic field B, which causes the plate to rotate while trying to align its programmed magnetization M with B. For a multicell Kresling assembly, with a magnetic plate attached on each unit cell, different magnetic torque intensities and directions can be exerted by distinguishing the magnetization directions of the magnetic plates. The unit cells can be actuated either simultaneously or independently by using different magnetic torques of the magnetic plates and distinct geometric-mechanical properties of each unit cell. Further, the magnetization directions change with the states of the multicell assembly, allowing multimodal distributed actuation by controlling just the magnetic field.

Results and Discussion

Figure 1B:
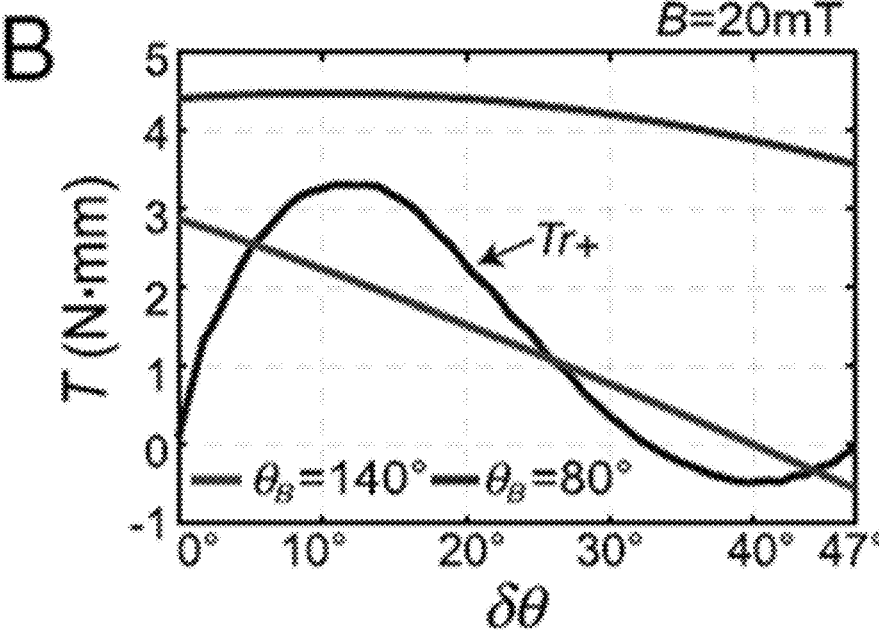
Figure 1C:
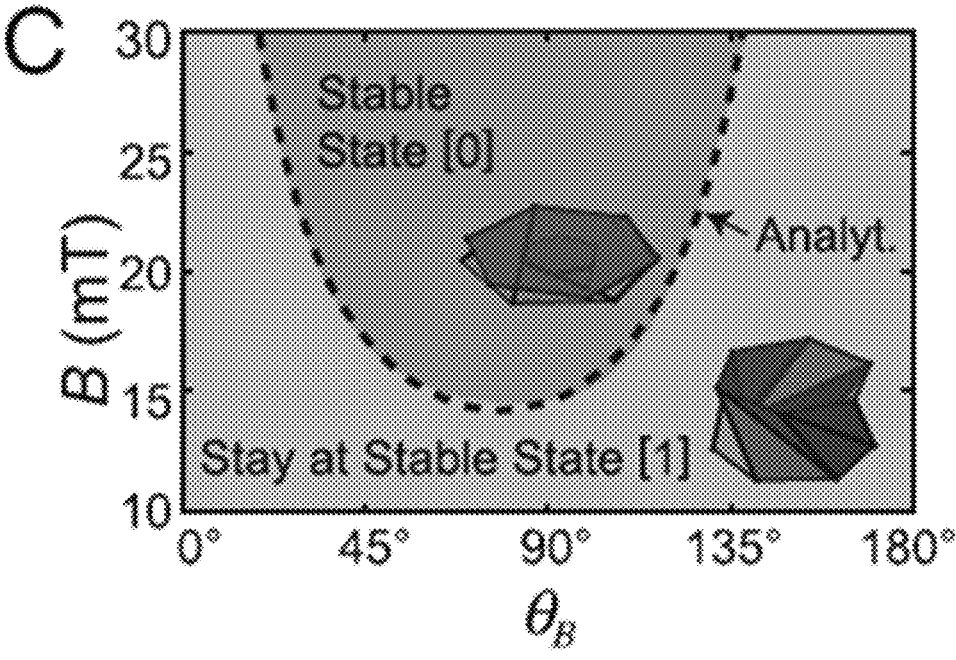
Figure 14A:
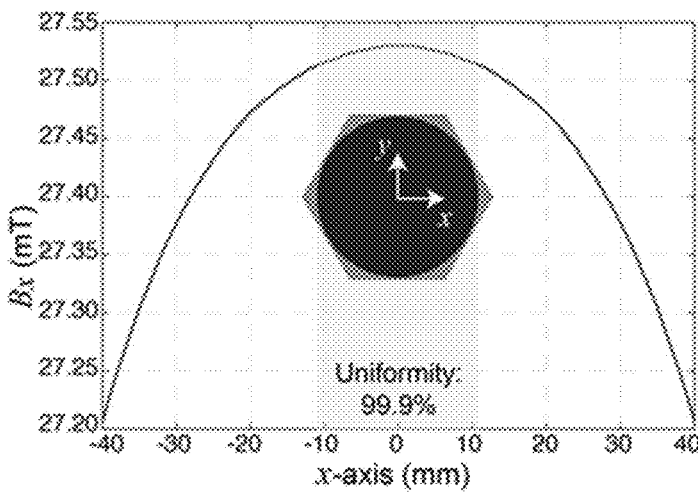
FIG. 14A-14D show the magnetic field distributions of 2D Helmholtz coils. (14A) Bx along x axis. (14B) Bx along z axis. (14C) By along y axis. (14D) By along z axis.
Figure 14B:
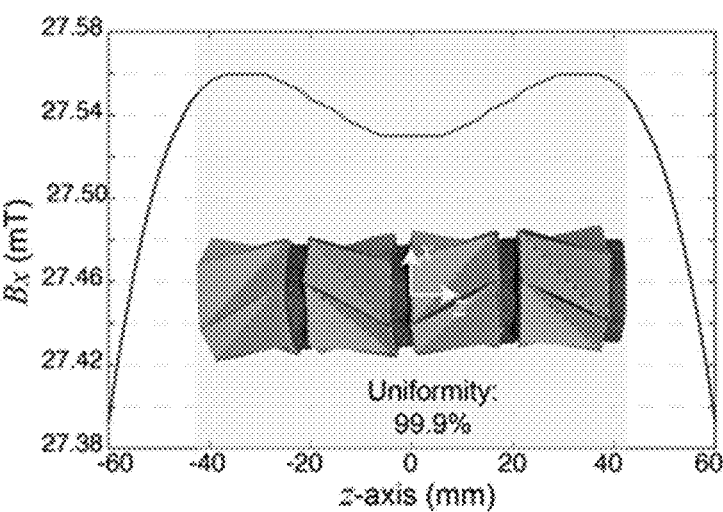
Figure 14C:
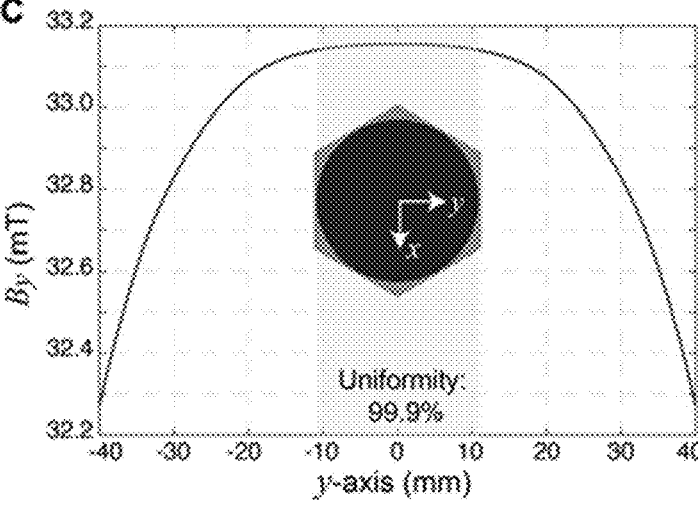
Figures 14D, 15A:
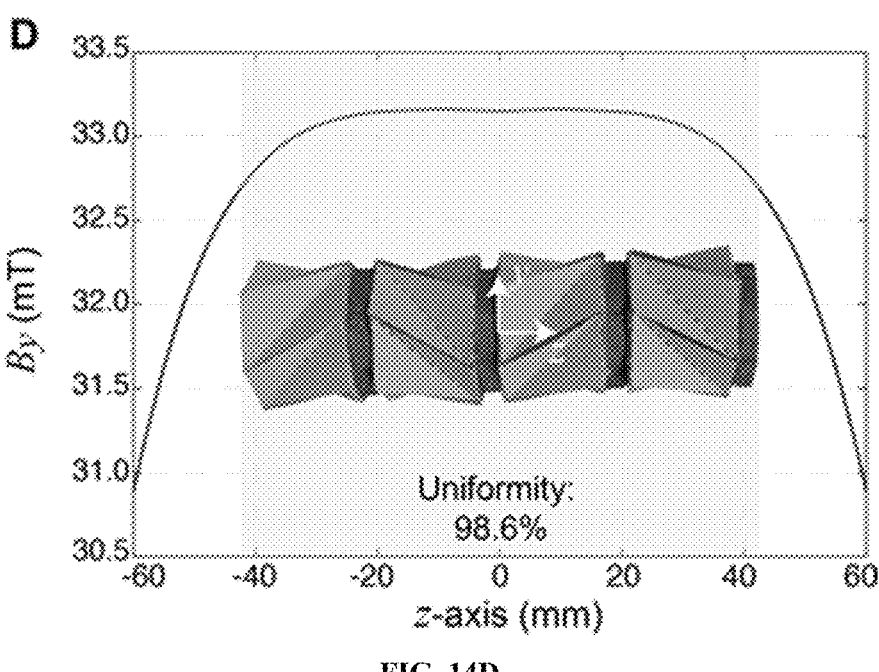
FIG. 15A-15C show magnetic actuation of the Kresling pattern (H=18.2 mm) from folded state [0] to deployed state [1] (15A) Schematic of the actuation process, where $\theta_B$=240° is the direction of the magnetic field B, and the magnetization M has direction $\theta_M$=129°. (15B) Torque Tr− is required to switch the unit cell stable state, and the torques produced by the magnetic actuation versus the rotation angle δθ (15C) Contour plot of the experimental and analytical (dashed lines) results for the deployment, showing if the unit cell will switch from stable state [0] to stable state [1], depending on the direction of the magnetic field $\theta_B$ and intensity of the magnetic field B.
Figure 15B:
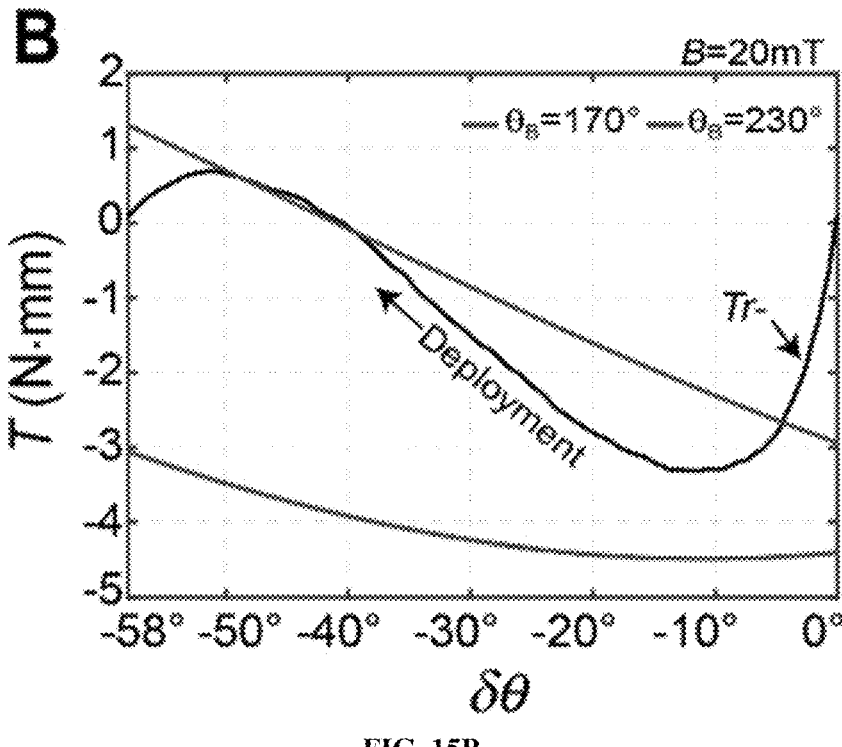
Figure 15C:
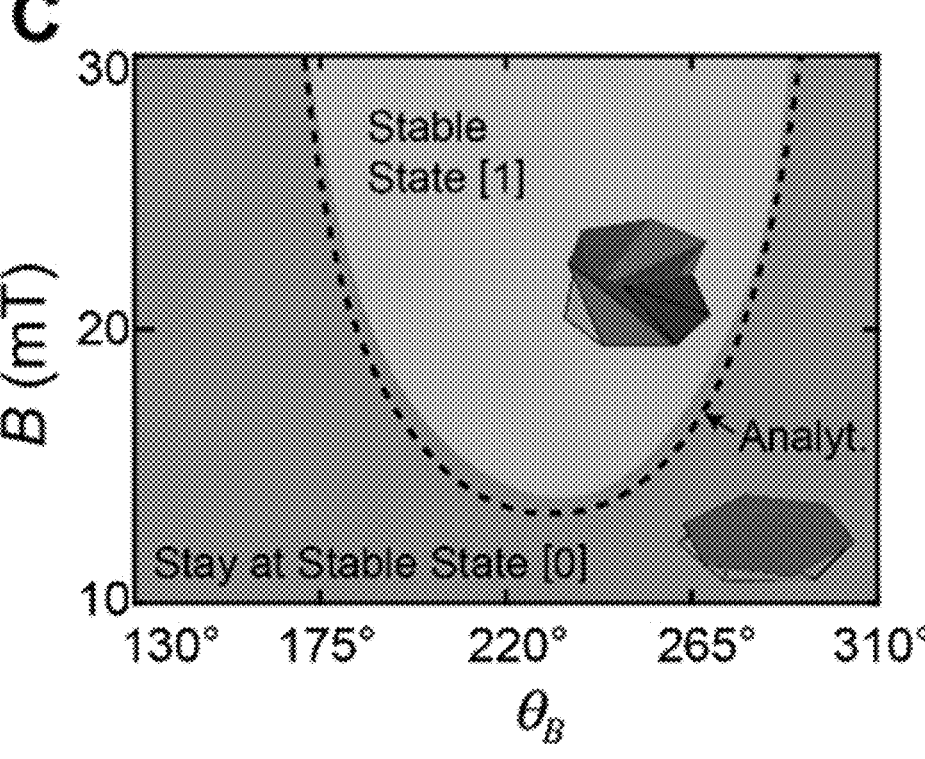
Figure 16A:
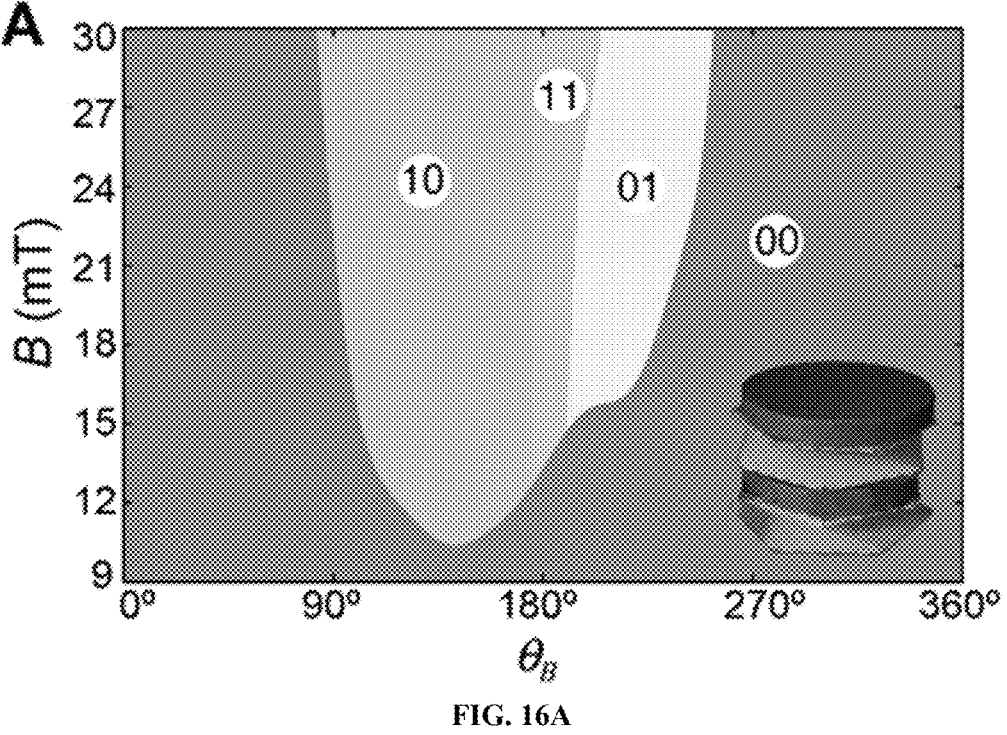
FIG. 16A-16D show contour plots for the experimental measurements of the magnetic actuation of the two-cell Kresling pattern with same crease direction (FIG. 1). Actuation results from global (16A) state [00], (16B) state [01], (16C) state [10], and (16D) state [11].
Figure 16B:
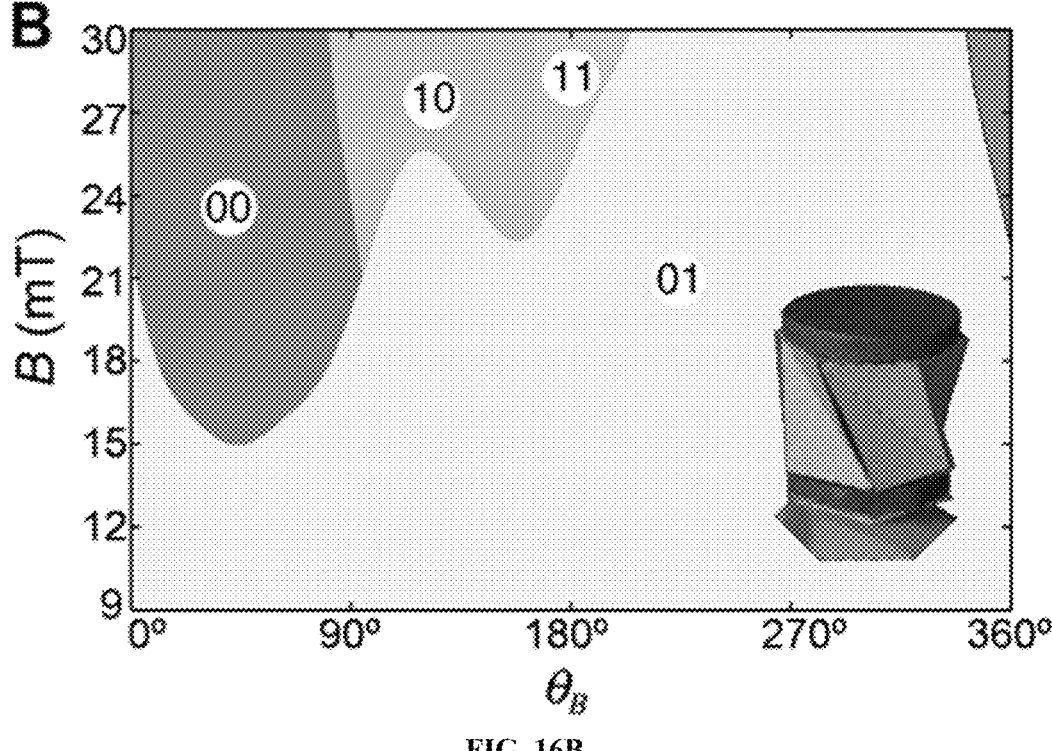
Figure 16C:
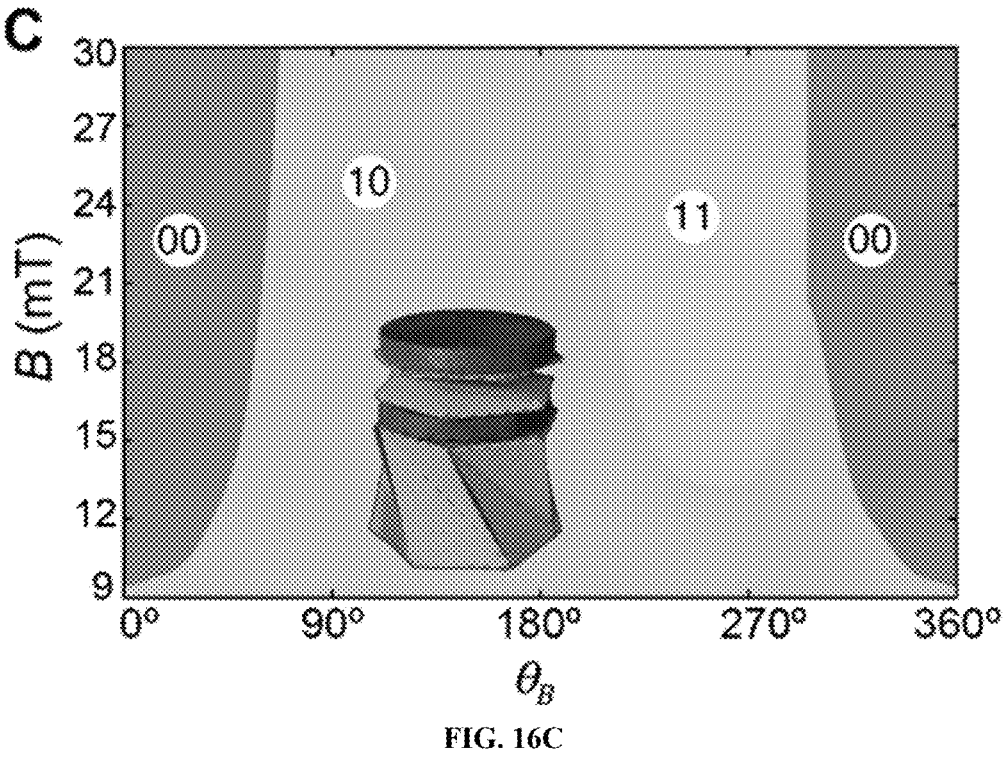
Figure 16D:
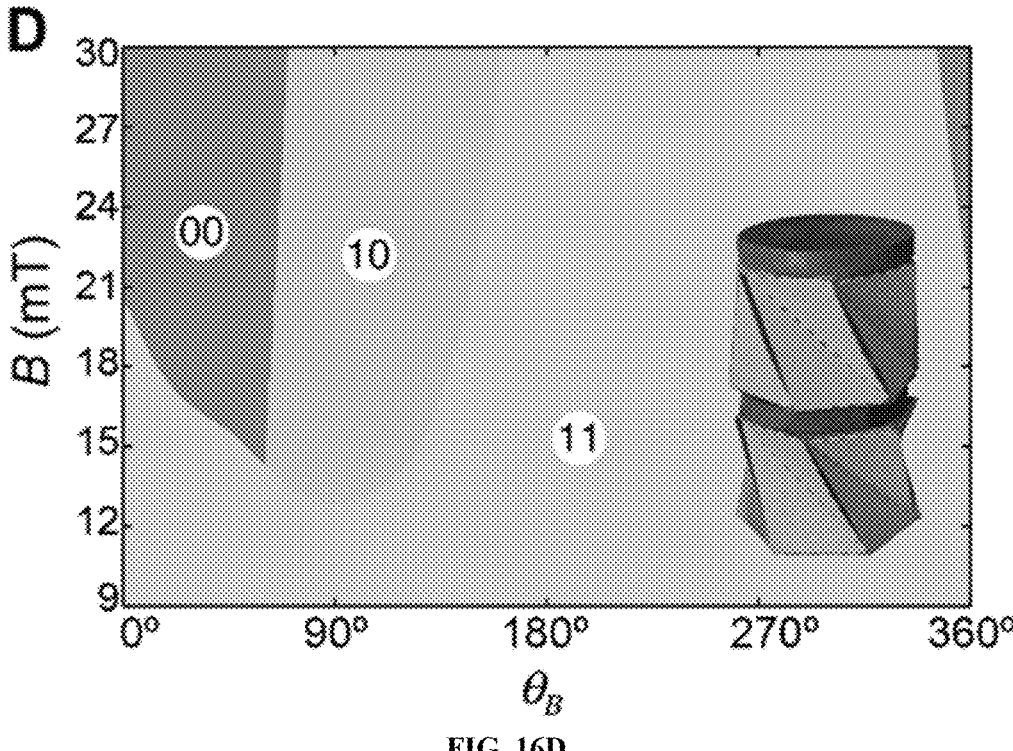
Figures 17A, 17B:
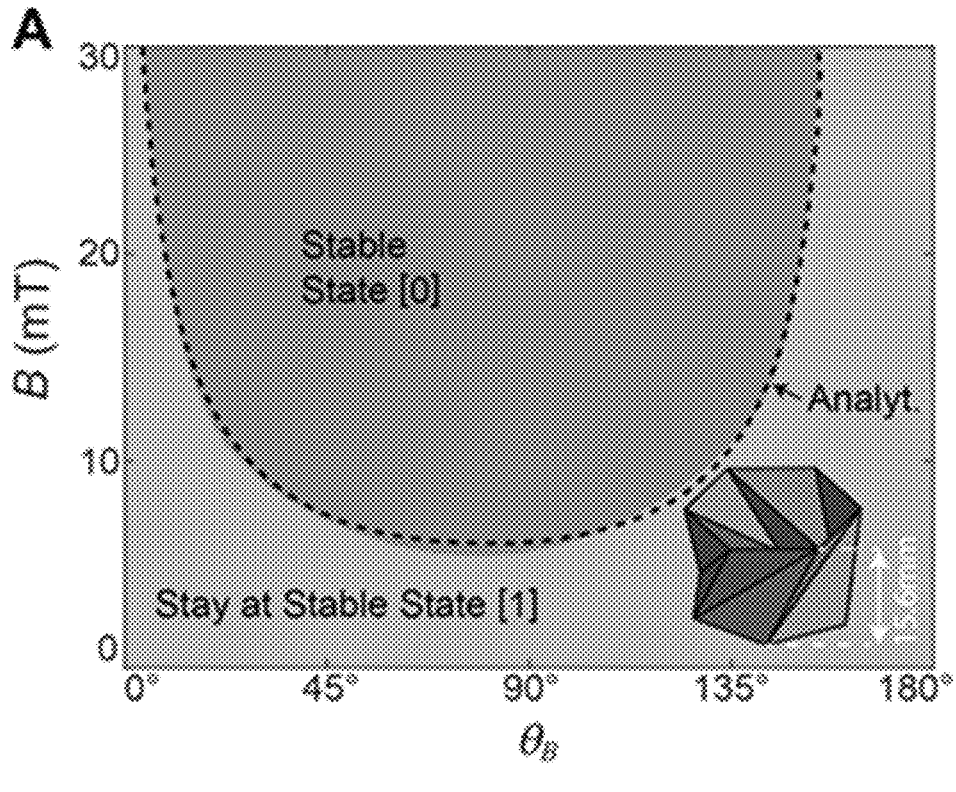
FIG. 17A-17D show magnetic actuation contours for unit cells with geometries in Table 1. (17A) Design 1 (H1=15.6 mm). (17B) Design 2 (H2=16.9 mm). (17C) Design 3 (H3=18.2 mm). (17D) Design 4 (H4=20.8 mm).
Figures 17C, 17D:
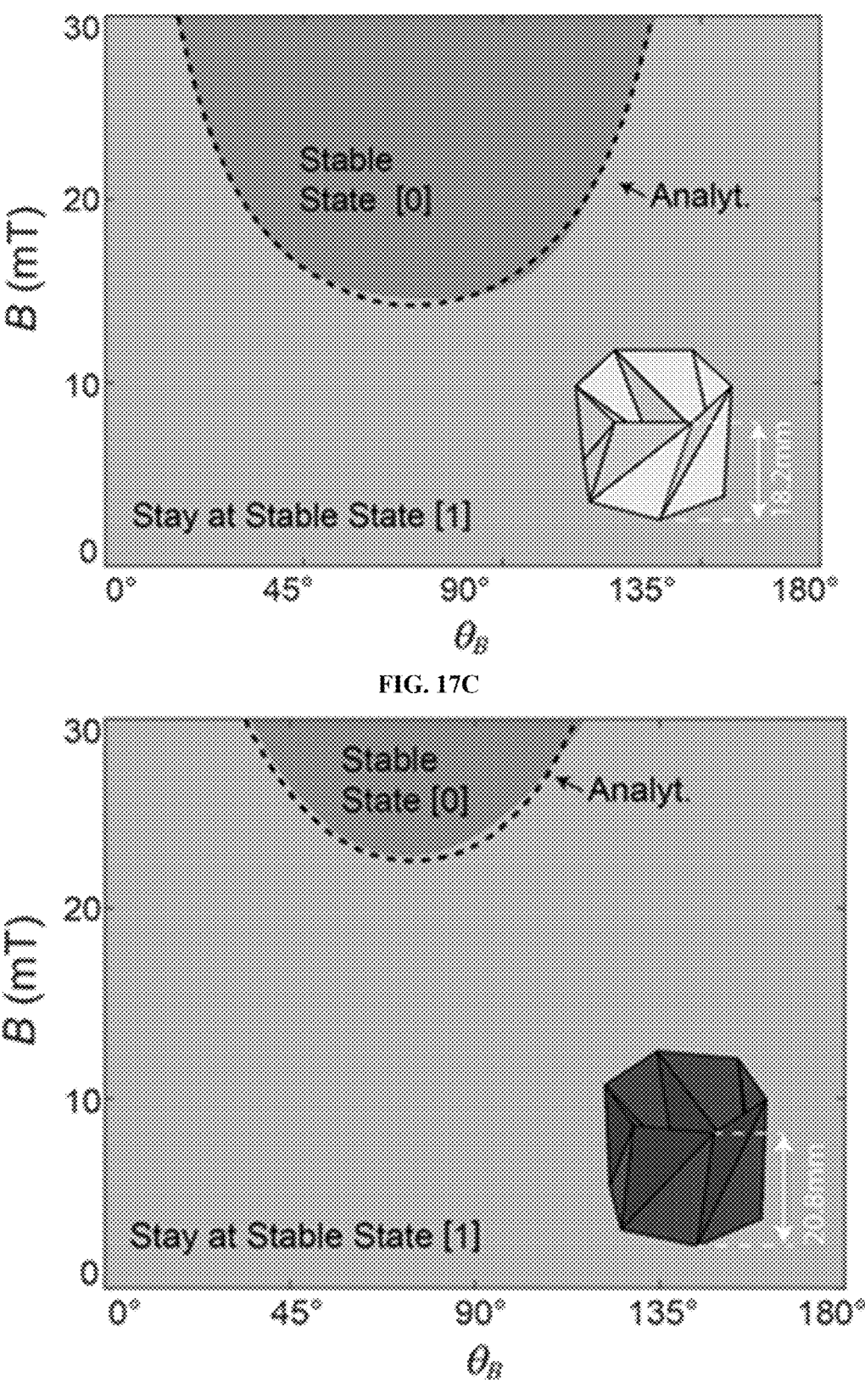

Geometry and Magnetic Actuation. The Kresling pattern is a non-rigid foldable origami, meaning deformation is not restricted only to folding hinges but also involves bending and stretching of both panels and hinges. This nonrigid behavior is what allows for unit cell bistability. Although, theoretically, geometrically designed Kresling unit cells present bistability, the material plays an important role in whether or not this behavior will be observed in the fabricated unit cell. Thus, to guarantee bistability, the design of the pattern parameters (panel angle $\alpha$, and lengths a and b in FIG. 1D) is guided by both geometric relations (28) and computational mechanics simulations (29) (Supplementary information, section 1 and Table 1). The Kresling unit cells are fabricated with cut-relieved hinges (30); that is, we replace diagonal mountain folds by cuts (Supplementary information, FIG. 5). In each unit cell, we add a magnetic-responsive plate with volume V and a programmed magnetization M, whose direction is always in the plane of the plate. In the presence of an external magnetic field B, a magnetic torque T=V (M B) is generated, which tends to align the plate magnetization direction $\theta_M$ with the magnetic field direction $\theta_B$. Note that the direction of the applied magnetic field is also in the plane of the plate, so that the induced magnetic torque causes a rotational motion of the plate around the longitudinal axis of the Kresling unit cell. This motion twists the unit cell by an angle $\delta\theta$. FIG. 1A shows a single unit cell that folds under a clockwise magnetic torque. Because the unit cell is bistable, an energy barrier has to be overcome for the switch from stable state [1](deployed) to state [0] (folded). We experimentally quantified this energy barrier (Supplementary information, sections 3 and 6) by obtaining the required torque to fold the unit cell (black curve in FIG. 1B). This means that the magnetic torque has to be both clockwise and larger than the required torque (Tr+) for the unit cell to fold. The magnetic torque T with clockwise as the positive direction is computed as T=BMV $\sin(\theta_M \theta_B)$, where B is the magnetic field intensity, M is the magnetization intensity of the magnetic plate (Supplementary information, section 7), and both directions $\theta_B$ and $\theta_M$ are defined with respect to the x axis. Taking the case with magnetization direction $\theta_M$=180° at the deployed state, as an example, the Kresling pattern folds when the provided magnetic torque is larger than the required torque during the entire folding process (red curve in FIG. 1B with B=20 mT and $\theta_B$=80°). Note that the magnetic torque varies during the rotation of the magnetic plate. If the applied magnetic torque is smaller than the required torque at any angle during the entire folding process (blue curve in FIG. 1B with B=20 mT and $\theta_B$=140°), the Kresling pattern will fail to achieve the folded state and will return to the deployed state when the magnetic field is removed. Because of the tunability of the magnetic field, the actuation speed can be controlled as quickly as a tenth of a second. FIG. 1C shows the required actuation condition (combination of B and $\theta_B$) to fold the Kres-ling from state [1] to [0] (Supplementary information, sections 4 and 8). For the deployment of the unit cell (switching from state [0] to [1]), a counterclockwise torque T<Tr throughout the rotation is required. Supplementary information, FIG. 15 shows the deployment process and required actuation condition.

Figure 1D:
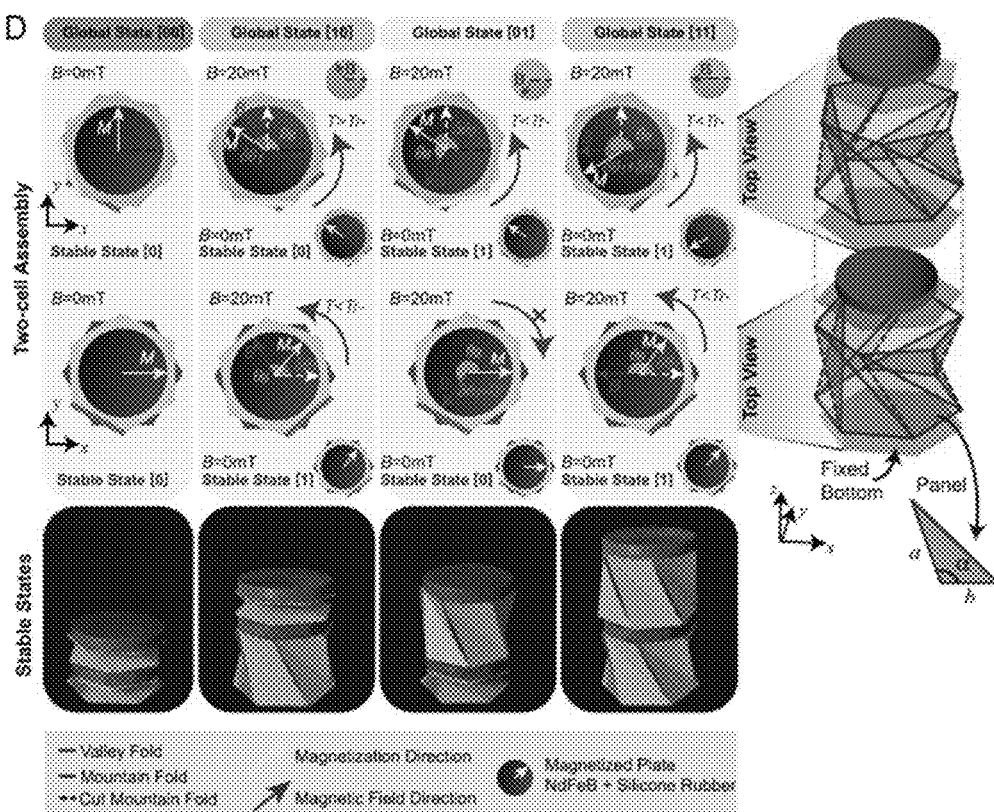
Figure 1E:
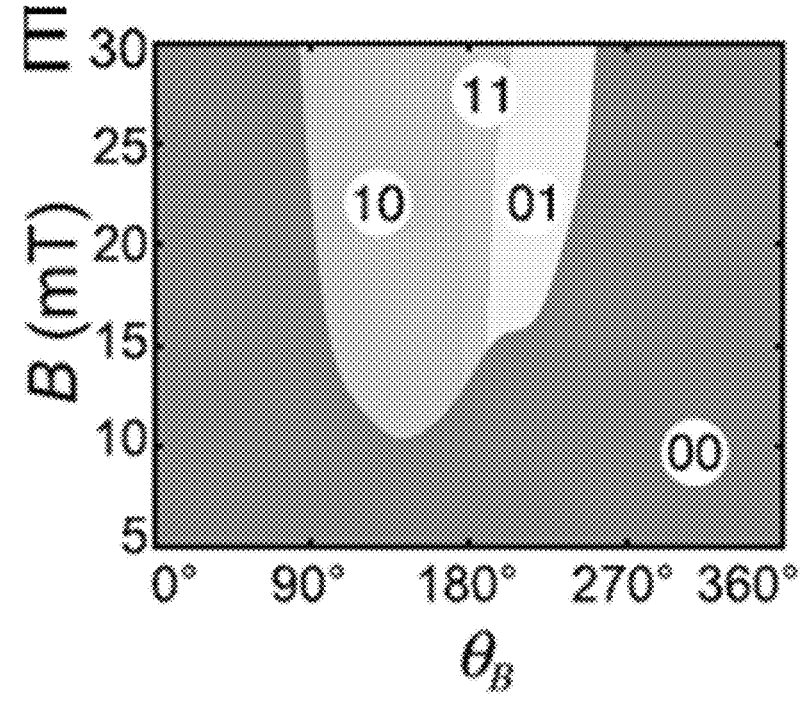

Distributed Actuation. Rationally designing the individual magnetization on each unit cell of the Kresling assembly allows a distributed torque to be introduced along the longitudinal axis of the assembly and under the applied magnetic field. To explain the concept, FIGS. 1D and 1E shows the actuation of a two-cell assembly with equivalent geometries (Supplementary information, section 5). The global states are defined by a binary code [ij], with i and j denoting the bottom and top unit cells, respectively. For example, global state [10] corresponds to the state in which the bottom unit cell is deployed and the top unit cell is folded. Each unit cell behaves differently due to the different magnetization directions of the attached magnetic plates (e.g., 0° and 90° at the folded state [00]). By tailoring the intensity and direction of the magnetic field, the two-cell assembly can be precisely actuated from, and to, any of the four stable states. In FIG. 1D, we provide the top view of the unit cells as the assembly switches from the stable state [00] to the other three stable states under a 20 mT magnetic field. Starting from the state [00], when a 20 mT magnetic field is applied at $\theta_B$=120°, the torque generated is enough to deploy the bottom unit cell, but not the top one, leading to a new stable state [10]. Note that the torque generated on the top unit cell is determined only by the top magnetic plate, while the torque acting on the bottom unit cell is the vector summation of the magnetic torques from both magnetic plates. Thus, only the bottom unit cell can change state, rotating by $\delta\theta_1$, making the top unit cell rotate with it by rigid body motion (i.e., $\delta\theta_2 = \delta\theta_1$). FIG. 1E shows the contour plot of the magnetic field direction and the intensity needed to keep the global state at [00] or to switch to any of the three other stable states [10], [11], and [01]. In Supplementary information, FIG. 16, we present the contour plots for the actuation starting from the stable states [10], [11], and [01], which provides guidance to achieve sequential deformations from a specific state to the others.

Based on the concept of distributed actuation, one could theoretically and ideally achieve $2^N$ stable states from a Kresling assembly with N unit cells. This multistable assembly therefore enables a large number of state shiftings, which can be further explored for multifunctional applications such as tunable physical properties and logic computing that will be discussed in the following sections.

Figure 2A:
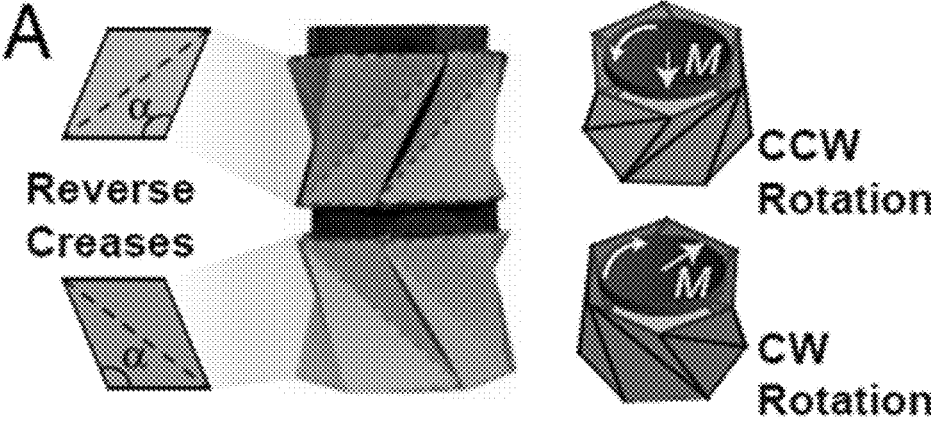
FIG. 2A-2D show magnetic actuation of generalized reverse creases Kresling assemblies with multiple cells. (2A) Two-cell Kresling assembly with reverse creases. (2B) Sequential magnetic actuation of unit cells with reverse creases. (2C) Magnetic actuation setup used to provide the 2D magnetic field. (2D) Magnetic actuation of multicell assembly with reversed creases leading to cyclic switch of states [11], [01], [00], [10], [11], . . . , etc. Each contour plot provides the set of actuation parameters (B and $\theta_B$) needed to switch the unit cell from one stable state to the other.
Figure 2B:
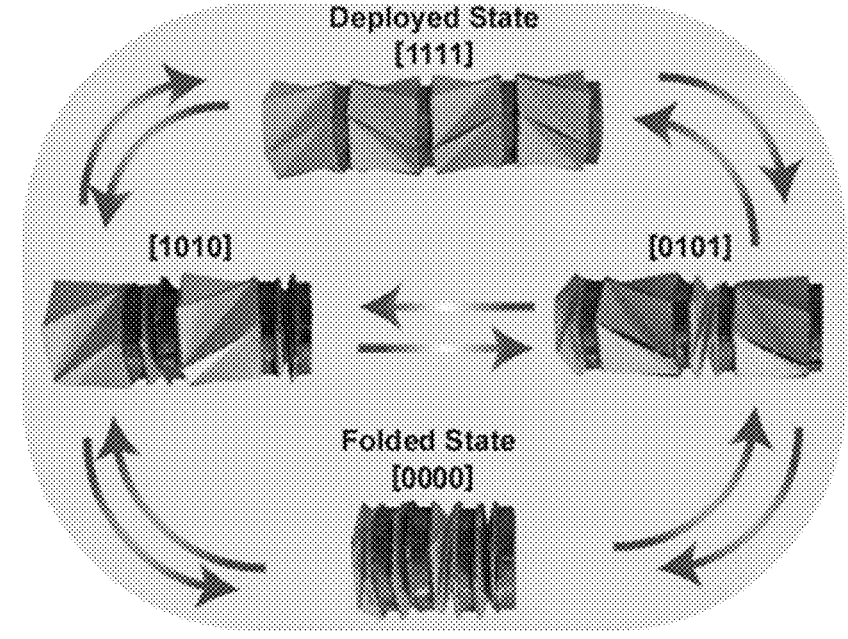
Figure 2C:
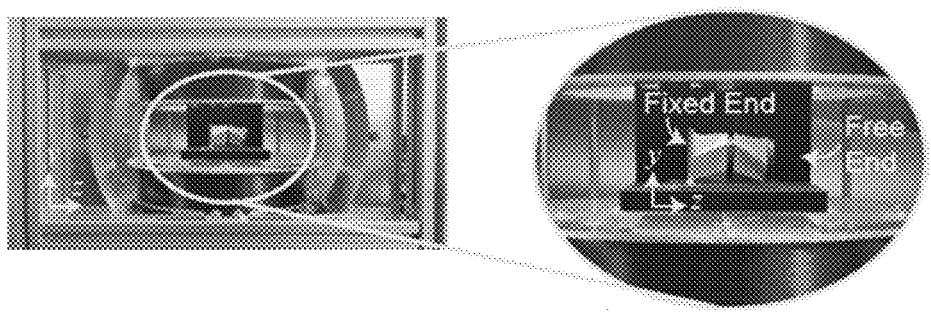
Figure 2D:
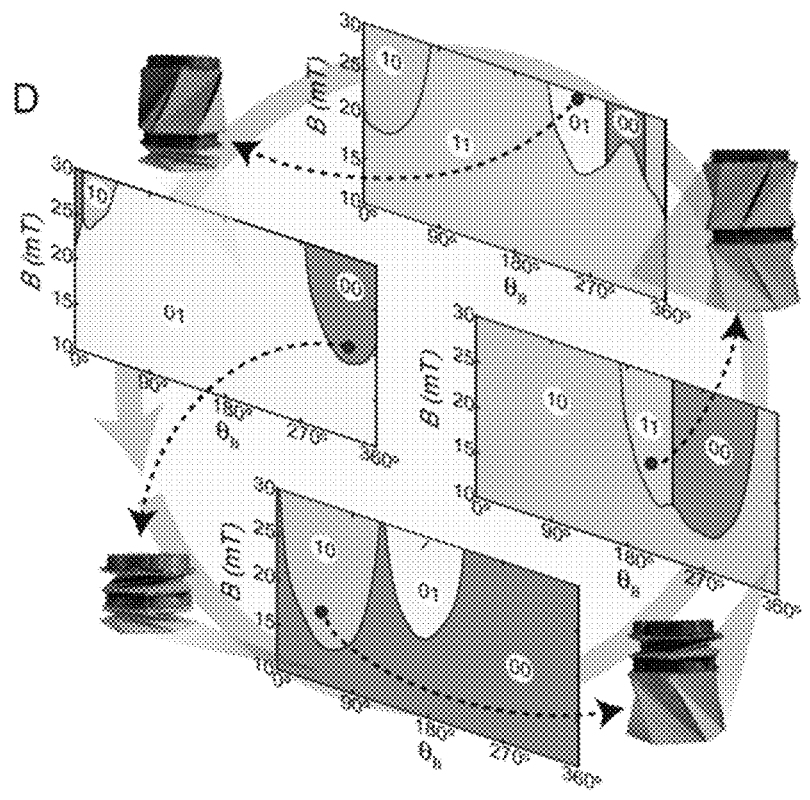

State Shifting of Kresling Assembly. Taking advantage of distributed actuation, we explore the state shifting behavior of the Kresling with enhanced programmability by assembling unit cells with reverse creases. As shown in FIG. 2A, the two assembled unit cells are chiral to each other and have opposite folding rotational direction. The orange unit cell folds under clockwise (CW) rotation, while the blue unit cell folds under counterclockwise (CCW) rotation. As an example, we show, in FIG. 2B, a four-cell Kresling assembly with chiral unit cells (blue-orange-blue-orange) in which we can program the actuation of the achiral groups (represented by same colors) to fold/deploy together. This strategy also allows for two global actuation modes: 1) purely rotational modes in which the change in global state occurs without axial displacement (represented by switching between states [1010] and [0101] in FIG. 2B) and 2) purely axial modes in which the change in global state occurs without the change in global rotation (for example, switching between states [1111] and [0000] in FIG. 2B). This occurs because the rotations of the pair of chiral unit cells cancel each other, leading to no rotation between the polygonal panels in the two extremities. The distributed actuation allows us to achieve the fully and selectively folded/deployed states even though we control the unit cells in groups. All of the reported actuation strategies are possible because of the local response of the magnetic plates, assembled directly on the unit cell under the two-dimensional (2D) magnetic field generated by the setup in FIG. 2C. The setup consists of two pairs of coils along the Cartesian x and y directions. Inside the coil assembly, the samples are attached to an acrylic base that kinematically restricts one of the ends, leaving the other end free for any type of displacement. In FIG. 2D, we show the contour plots with the measured actuation parameters (B and BB) needed to cyclically switch states [11], [01], [00], and [10]. Although some transformations cannot be attained directly, the actuation actually closes a loop, meaning that we can actuate the Kresling assembly to all of the possible global stable states via the ultrafast magnetic actuation method by controlling applied magnetic field intensity and direction.

Figure 3A:
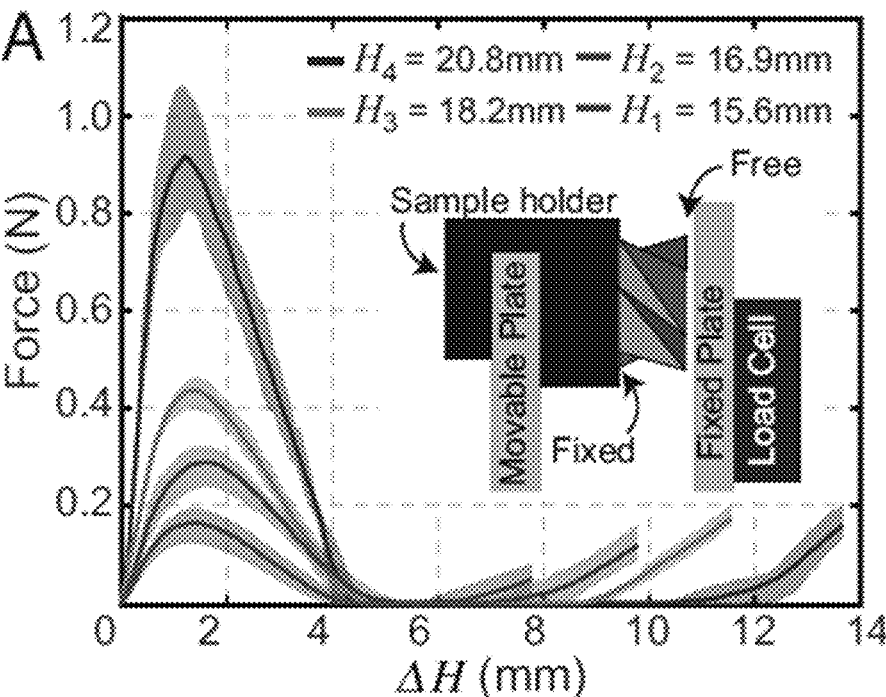
FIG. 3A-3E show tunable mechanical response of a multicell Kresling assembly. (3A) Measured force-displacement curves for unit cells with distinct heights. Solid lines represent the average responses, and shaded envelopes delimit maximum and minimum response ranges. Inset shows the schematic of the compression setup with fixed-free boundary conditions. (3B) Stored energy versus axial displacement, obtained from the averaged force-displacement curves prior to snapping. (3C) Contour plot with measured and analytical (dashed lines) conditions for the magnetic actuation depending on each unit cell geometry. (3D) Measured force-displacement curve for a four-cell Kresling assembly in the stable state [1111]. (3E) Tunable mechanical response of the four-cell Kresling assembly. From multiple consecutive testing cycles, we obtain the average (columns) and maximum/minimum (error bars) stiffness of the assembly. Theoretical values are approximated by a system of springs in series (Supplementary information, section 3).
Figures 3B, 3C:
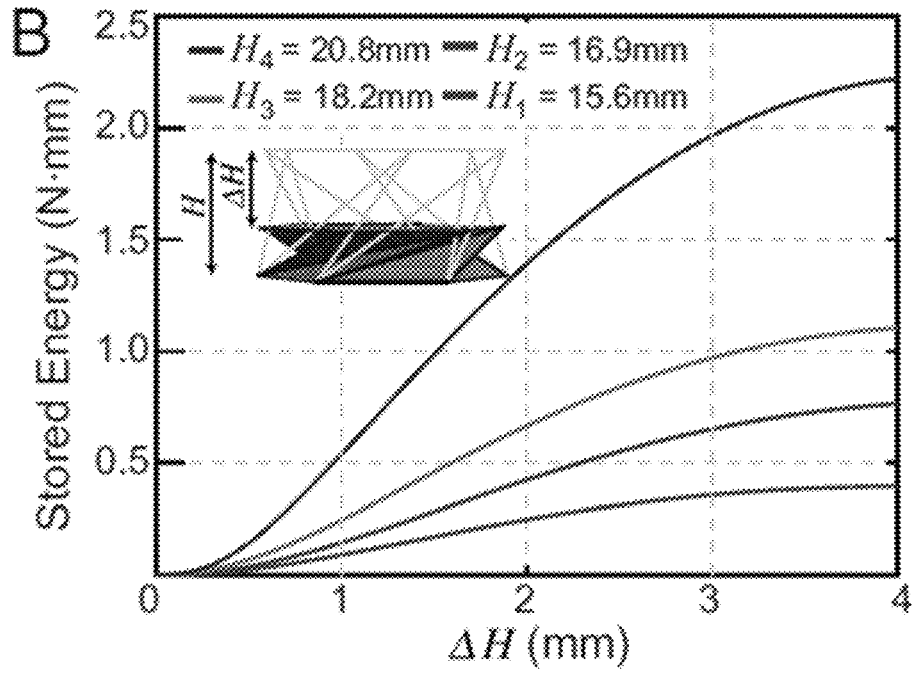

Distributed Actuation for Tunable Physical Property. The aforementioned discussion focuses on the Kresling assemblies with the same unit cell geometry (same required torque and energy barrier between stable states). Since their multicell assemblies are capable of shifting between states under the distributed actuation, we geometrically engineer the energy barriers needed to fold/deploy each unit cell to achieve tunable physical property. In our designs, the polygon size and type are fixed, and only the height of the unit cell in the deployed state is changed to effectively tune the required energy barrier. From those constraints, the crease pattern parameters are computed (Supplementary information, section 1). The increase in height relates to the increasing of the energy barrier between states, as shown in FIGS. 3A and 3B by the experimentally measured force-displacement curves and the computed stored energy of the unit cells under the axial compression load (Supplementary information, section 3). The samples are fixed at the bottom, which restricts both rotation and axial displacement, and are completely free at the top (FIG. 3A). Because of the specific test boundary conditions (fixed-free ends), we do not obtain (measure) negative forces. Instead, the null forces in FIG. 3A indicate that the unit cell snaps and loses contact with the load cell. Although the test gives no information about the unit cell during the snapping process, it provides the height change between the states of each unit cell and the stored energy prior to snapping (FIG. 3B). The initial slope of the force-displacement curve can be further used to calculate the stiffness of each unit cell. From the uniaxial compression, we obtain the required torque needed to actuate each unit cell design (Supplementary information, section 6 and FIG. 18), which guides the parameter design of the magnetic actuation. FIG. 3C shows the contour plots with the analytical and experimental values for the actuation parameters. It can be seen that actuation of the unit cells with higher energy barrier requires larger B, meaning that we can use distinct energy barriers for actuation, where the wide range of magnetic field intensity allows for the local control of assemblies with a larger number of unit cells (e.g., N>4).

Figure 3D:
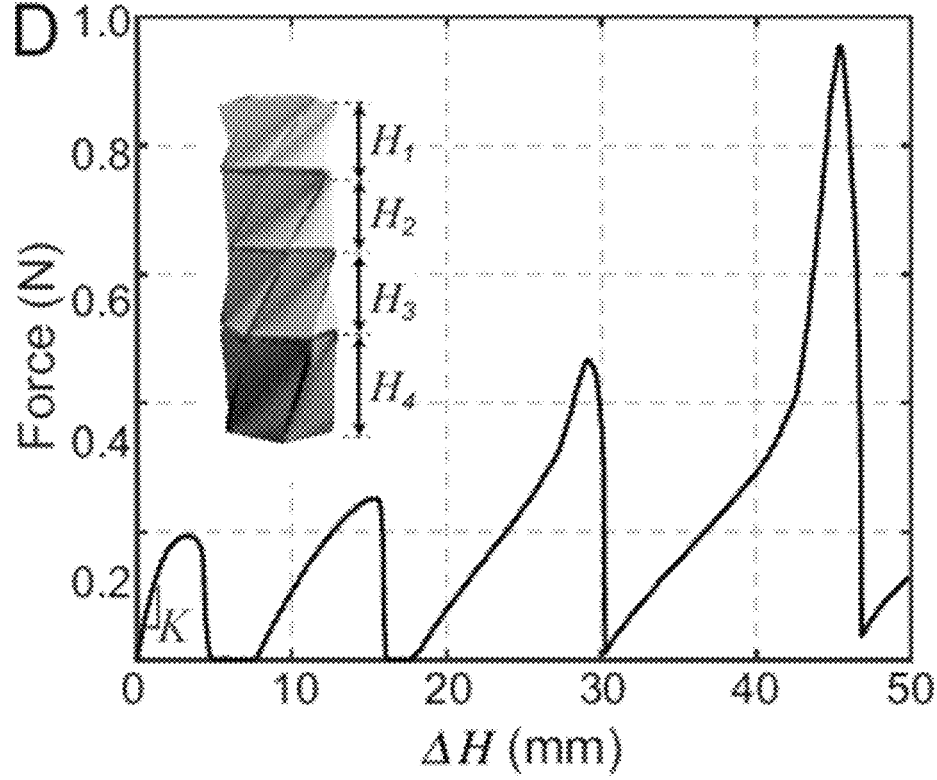

The assembly of geometrically different unit cells enables tunable mechanical properties under the distributed magnetic actuation. Because each unit cell presents a distinct stiffness, we can conceptualize the assembly as springs in series and compute the stiffness of the system in each one of the global states, where the Kresling units are selectively folded/deployed. FIG. 3D shows the experimental force-displacement curve for the four-cell assembly. In this plot, we observe a sequential compression of the unit cells. In the first linear region, we characterize the stiffness K at the all-deployed state [1111]. Similarly, we characterize the stiffness of the assembly at the other states and report it in FIG. 3E together with the theoretical values (Supplementary information, section 3). From this figure, we observe that, using the proposed distributed actuation, we can tune the stiffness of the assembly by switching between stable states.

Figure 4A:
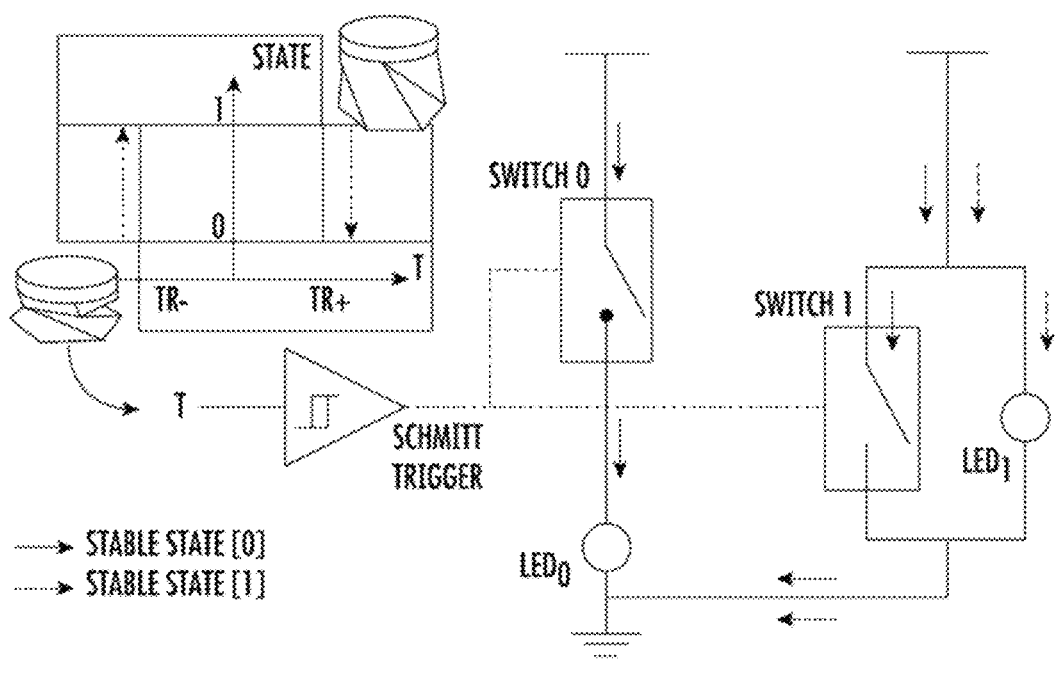
FIG. 4A-4D show origami logic circuit with LED. (4A) Schematics of the electric circuit of a single unit cell, where the arrows show the current direction depending on the state of the unit cell. If the unit cell is deployed, both switches are open, and the current follows the green arrows, turning on the green light. Otherwise, the switches are closed, and the blue light is on. (4B) Schematics showing the placement of the copper tape inside the crease pattern and folded unit cell. (4C) Schematic showing how the state of the unit cell controls whether both switches are open or closed. (4D) Demonstration of the logic circuit on a multicell pattern with unit cells with distinct energy barriers.
Figure 4B:
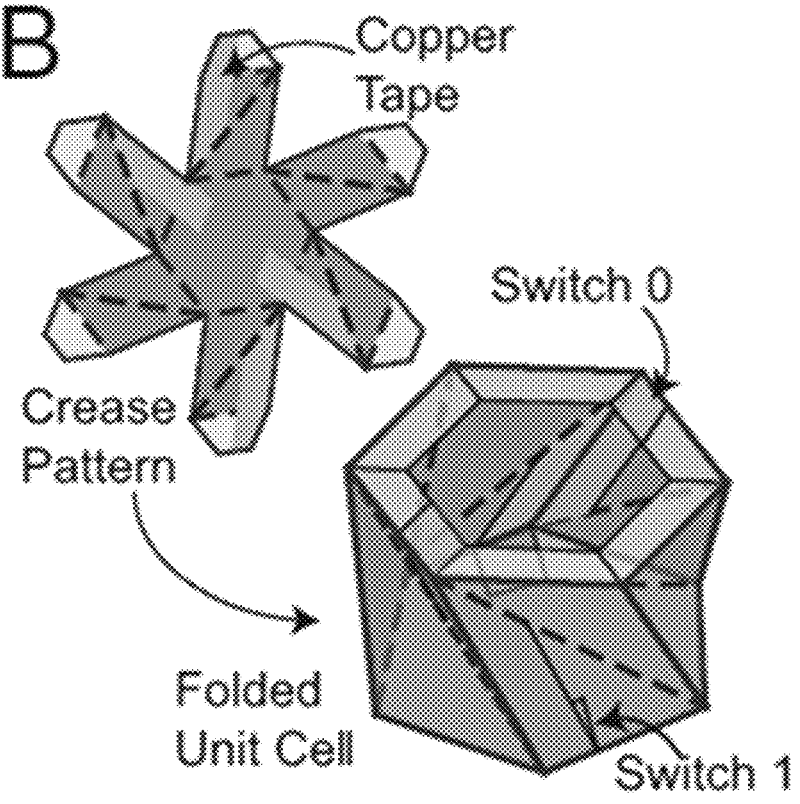
Figure 4C:
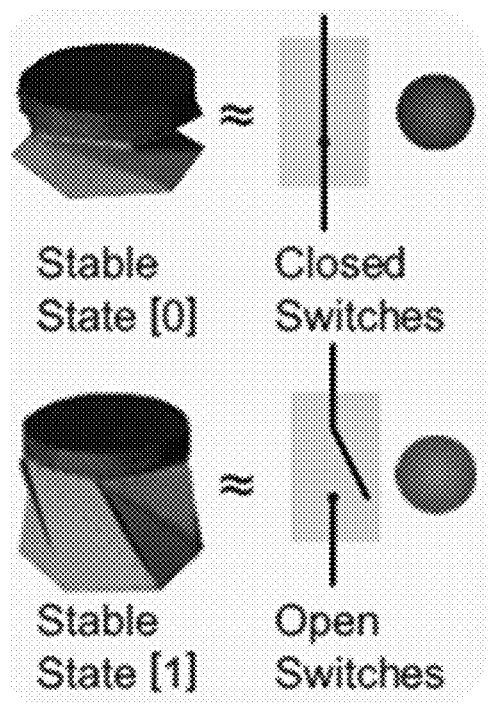
Figure 4D:
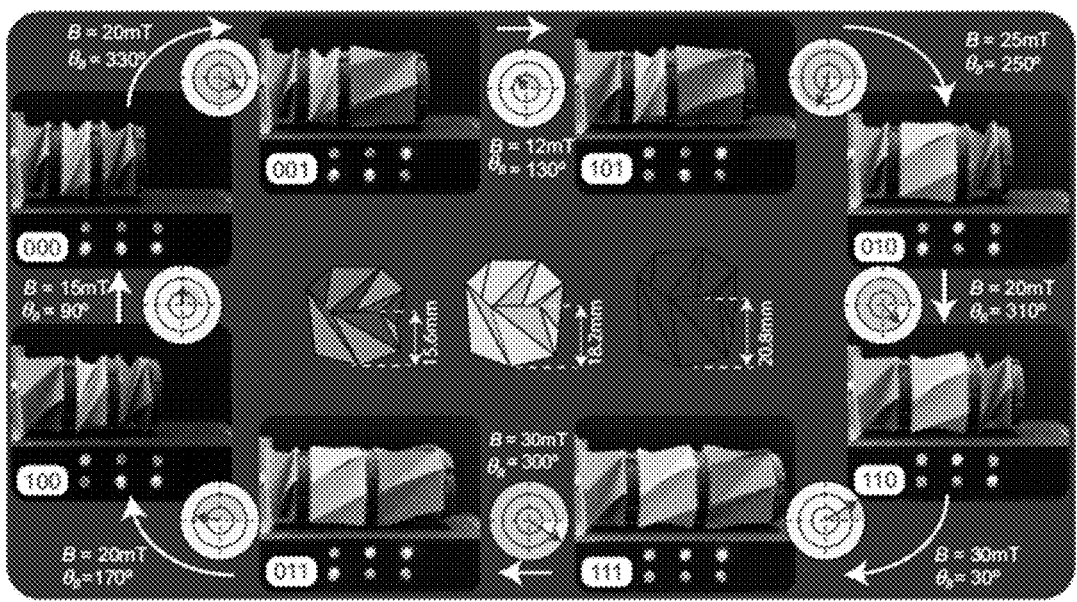

Multifunctional Origami for Digital Computing. Origami systems have recently been explored for digital computing because of the potential applications in intelligent autonomous soft robots, integrating the capabilities of actuation, sensing, and computing in the origami assemblies, acting as either basic logic gates (15) or integrated memory storage devices (22). The multifunctional origami can eliminate the requirement of conventional rigid electronic components and its stiffness mismatch with compliant origami bodies. The bistable nature of the Kresling pattern shows its potential in representing a binary system for digital computing, introducing multifunctionality into our Kresling system that goes beyond structural actuation. To develop a multifunctional Kresling assembly, we employ a magneto-mechano-electric device that incorporates actuation and computing capabilities, which could be further extended to sense external stimulation. The operation of the assembly is based on the distributed actuation of the Kresling unit cells with distinct, geometrically designed, energy barriers. By treating the applied magnetic torque as the input signal and digitizing the resultant mechanical states of the Kresling pattern as digital output [1] (deployed state) or [0] (folded state), it can be regarded as a Schmitt Trigger (FIG. 4A), a basic comparator circuit to convert analog input signal to a digital output signal. The higher and lower thresholds of the "Origami Schmitt Trigger" are the required torques (Tr+ and Tr) to change the stable state of the unit cell (Supplementary information, section 9). In FIG. 4A, blue and green LEDs are used to represent the folded and deployed stable states, respectively. To construct the circuit, copper tape is attached inside the unit cell to form two switches (FIG. 4B): Switch 0 is connected to the blue LED in series, and switch 1 is connected to the green LED in parallel (FIG. 4A). Starting from the deployed state, when T>Tr+, the unit cell changes to the folded state [0], and both switches are closed (blue paths in FIG. 4A). The green LED is short-circuited, and only the blue LED is turned on (FIG. 4C). Now, starting from the folded state, if we apply a T<Tr, the unit cell changes to the deployed state [1], both switches are open, and only the green LED is turned on (green path in FIG. 4A). If the applied magnetic torque is not enough to change the state of the Kresling pattern, the "Origami Schmitt Trigger" remains in its state and possesses memory. Thus, using the concept of the "Origami Schmitt Trigger," we design a device for three-bit information storage and display by a three-cell magneto-mechano-electric Kresling assembly that has three different energy barriers and controllable multimodal distributed actuation (FIG. 4D). Each unit cell is represented by two LEDs, with lighted blue denoting the folded state. The other colored LEDs are green, yellow, and red, whose lighted state denotes the deployed state of the unit cell with the same color. In this way, the state of the Kresling assembly is digitized as three-bit information with real-time display. FIG. 4D demonstrates the transition between the eight states in a loop by accurately controlling the intensity and direction of the magnetic field (B, $\theta_B$). The initial magnetization directions of the attached magnetic plates and the circuit of the Kresling assembly circuit are shown in Supplementary information, Table 2 and FIG. 22C, respectively. Note that, by designing the Kresling geometries and magnetic controlling parameters, this device can be extended to an N-layer assembly with the capabilities of N-bit information storage resulting from the $2^N$ distinct states. Additionally, because of the differently designed energy barriers in the assembly, the device can passively sense and actively respond to the external load, enabling an intelligent system with integrated actuation, sensing, and computing.

Concluding

This work closes the gap existing in most origami applications by providing an actuation solution that acts locally and remotely on complex origami assemblies. We propose a coupling between magnetic-responsive materials with a bistable origami pattern, eliminating the need for explicit shape-locking mechanisms, and allowing for a fast shape changing and instantaneous shape locking of those structures. In addition, we are capable of actuating complex assemblies (as opposed to single or dual unit cells) with local control. That is, each unit cell can fold and deploy independently, on demand. This approach is extendable to other origami materials, as the magnetic material is assembled to the unit cells. Thus, we envision a simple transition to other material systems, including 3D printing, previously used to fabricate origami structures.

Materials and Methods

Sample Fabrication. We fabricated each Kresling unit cell by perforating and cutting the pattern on Tant origami paper (0.1 mm thick). The Kresling pattern is modified to a flower-like shape (Supplementary information, FIG. 5) to accommodate the cuts along the mountain folds. After the pattern is folded, we attach the top and bottom polygons that are made of 160 g/m Canson Mi-Teintes paper (0.2 mm thick). To the top of the unit cell, we attach a 3-mm-thick magnetized plate that is made from a mix of Ecoflex 00-30 silicone rubber and NdFeB (neodymium-iron-boron) particles (30 vol %). The geometry of the unit cells and magnetization directions of the plates are provided in Supplementary information, Tables 1 and 2. More details are provided in Supplementary information, section 2.

REFERENCES

1. M. Schenk, S. D. Guest, Geometry of Miura-folded metamaterials. Proc. Natl. Acad. Sci. U.S.A. 110, 3276-3281 (2013).
2. J. L. Silverberg et al., Using origami design principles to fold reprogrammable mechanical metamaterials. Science 345, 647-650 (2014).
3. S. A. Nauroze, L. S. Novelino, M. M. Tentzeris, G. H. Paulino, Continuous-range tun-able multilayer frequency-selective surfaces using origami and inkjet printing. Proc. Natl. Acad. Sci. U.S.A. 115, 13210-13215 (2018).
4. E. T. Filipov, T. Tachi, G. H. Paulino, Origami tubes assembled into stiff, yet reconfig-urable structures and metamaterials. Proc. Natl. Acad. Sci. U.S.A. 112, 12321-12326 (2015).
5. S. A. Zirbel et al., Accommodating thickness in origami-based deployable arrays. J. Mech. Des. 135, 111005 (2013).
6. T. Chen, O. R. Bilal, R. Lang, C. Daraio, K. Shea, Autonomous deployment of a solar panel using elastic origami and distributed shape-memory-polymer actuators. Phys. Rev. Applied 11, 064069 (2019).
7. S. Li, D. M. Vogt, D. Rus, R. J. Wood, Fluid-driven origami-inspired artificial muscles. Proc. Natl. Acad. Sci. U.S.A. 114, 13132-13137 (2017).
8. P. Bhovad, J. Kaufmann, S. Li, Peristaltic locomotion without digital controllers: Exploiting multi-stability in origami to coordinate robotic motion. Extreme Mech. Lett. 32, 100552 (2019).
9. J. T. Overvelde et al., A three-dimensional actuated origami-inspired transformable metamaterial with multiple degrees of freedom. Nat. Commun. 7, 10929 (2016).
10. J. A. Faber, A. F. Arrieta, A. R. Studart, Bioinspired spring origami. Science 359, 1386-1391 (2018).
11. W. Kim et al., Bioinspired dual-morphing stretchable origami. Sci. Robot. 4, eaay3493 (2019).
12. Y. Tang et al., Leveraging elastic instabilities for amplified performance: Spine-inspired high-speed and high-force soft robots. Sci. Adv. 6, eaaz6912 (2020).
13. K. Liu, J. Wu, G. H. Paulino, H. J. Qi, Programmable deployment of tensegrity structures by stimulus-responsive polymers. Sci. Rep. 7, 1-8 (2017).
14. J. H. Na et al., Programming reversibly self-folding origami with micropatterned photo-crosslinkable polymer trilayers. Adv. Mater. 27, 79-85 (2015).
15. B. Treml, A. Gillman, P. Buskohl, R. Vaia, Origami mechanologic. Proc. Natl. Acad. Sci. U.S.A. 115, 6916-6921 (2018).
16. M. Z. Miskin et al., Graphene-based bimorphs for micron-sized, autonomous origami machines. Proc. Natl. Acad. Sci. U.S.A. 115, 466-470 (2018).
17. P. M. Reis, A perspective on the revival of structural (In)stability with novel opportunities for function: From buckliphobia to buckliphilia. J. Appl. Mech. 82, 111001 (2015).
18. A. Rafsanjani, Y. Zhang, B. Liu, S. M. Rubinstein, K. Bertoldi, Kirigami skins make a simple soft actuator crawl. Sci. Robotics 3, eaar7555 (2018).

19. Y. Zhang et al., A mechanically driven form of kirigami as a route to 3D mesostructures in micro/nanomembranes. Proc. Natl. Acad. Sci. U.S.A. 112, 11757-11764 (2015).

20. B. Kresling, "Folded tubes as compared to kikko ("Tortoise-Shell") bamboo" in Origami3: Proceedings of the Third International Meeting of Origami Science, Mathematics, and Education, T. C. Hull, Ed. (A.K. Peters, 2002), p. 197.

21. Z. Zhai, Y. Wang, H. Jiang, Origami-inspired, on-demand deployable and collapsible mechanical metamaterials with tunable stiffness. Proc. Natl. Acad. Sci. U.S.A. 115, 2032-2037 (2018).

22. H. Yasuda, T. Tachi, M. Lee, J. Yang, Origami-based tunable truss structures for non-volatile mechanical memory operation. Nat. Commun. 8, 1-7 (2017).

23. H. Yasuda et al., Origami-based impact mitigation via rarefaction solitary wave creation. Sci. Adv. 5, eaau2835 (2019).

24. J. Cui et al., Nanomagnetic encoding of shape-morphing micromachines. Nature 575, 164-168 (2019).

25. G. Z. Lum et al., Shape-programmable magnetic soft matter. Proc. Natl. Acad. Sci. U.S.A. 113, E6007-E6015 (2016).

26. S. Wu et al., Symmetry-breaking actuation mechanism for soft robotics and active metamaterials. ACS Appl. Mater. Interfaces 11, 41649-41658 (2019).

27. Q. Ze et al., Magnetic shape memory polymers with integrated multifunctional shape manipulation. Adv. Mater. 32, 1906657 (2020).

28. R. J. Lang, Twists, Tilings, and Tessellations: Mathematical Methods for Geometric Origami (CRC, 2017).

29. K. Liu, G. H. Paulino, Nonlinear mechanics of non-rigid origami: An efficient computational approach. Proc. Math. Phys. Eng. Sci. 473, 20170348 (2017).

30. N. Nayakanti, S. H. Tawfick, A. J. Hart, Twist-coupled kirigami cells and mechanisms. Extreme Mech. Lett. 21, 17-24 (2018).

SUPPLEMENTARY INFORMATION

1. Kresling Pattern Geometry and Design

A. Geometry. In this paper, we engineer the Kresling pattern (1, 2) to obtain desired mechanical properties and precise actuation. From a geometry perspective, the Kresling pattern is nonrigid origami and presents two stable states per unit cell. That means that each unit cell cannot transition between those two stable states through folding of the hinges alone. Each unit cell is tessellated with triangulated panels of equal geometry, that is, same panel angle $\alpha$ and lengths a and b (FIG. 5). In terms of geometrical assemblage, it is composed of multiple unit cells N, with the same or distinct geometries, that behave independently from each other. In fact, because each unit cell has two stable states, we can have 2N stable states.

The vertices of the triangles, when folded, all lie on the top and bottom polygon circumscribed circles. Those polygons twist in relation to each other, and the angle between them is the twisting angle ($\psi$). This angle varies from $\psi_1$ (deployed) to $\psi_2$ (folded) as the unit cell is folded, showing the coupling between rotation and axial displacement. The Kresling pattern is designed based on the height of the unit cell in the two stable states, number n of polygon edges, and corresponding edge lengths, b. From those parameters, we compute the design parameters of the crease pattern, that is panel length a and angle $\alpha$, as provided in (3)

$$\alpha = \cos^{-1}\left(\frac{x_2(x_2 - \cot(\pi/n))}{\sqrt{((x_2^2 + 1)(H_0^2(x_2^2 + 1) + x_2^2\csc(\pi/n)^2))}}\right) \quad [S1]$$

$$a = b\sqrt{H_0^2 + \frac{x_2^2\csc(\pi/n)^2}{(x_2^2 + 1)}} \quad [S2]$$

$$c = b\frac{\sqrt{(H_0^2(x_2^2 + 1)^2 + x_2^3\cot(\pi/n)(x_2\cot(\pi/n) + 2) + x_2^2)}}{(x_2^2 + 1)} \quad [S3]$$

where $H_0$ and H are the heights in the stable states [0] and [1], respectively, and $$x_1 = 2\sin(\pi/n)\frac{\left(\sin(\pi/n)\sqrt{(\cot(\pi/n)^2\csc(\pi/n)^2 - (H^2 - H_0^2)^2)} - \cos(\pi/n)\right)}{1 + H^2 - H_0^2 + (1 - H^2 + H_0^2)\cos(2\pi/n)} \quad [S4]$$

$$x_2 = 2\sin(\pi/n)\frac{\left(\sin(\pi/n)\sqrt{(\cot(\pi/n)^2\csc(\pi/n)^2 - (H^2 - H_0^2)^2)} - \cos(\pi/n)\right)}{1 - H^2 + H_0^2 + (1 + H^2 - H_0^2)\cos(2\pi/n)} \quad [S5]$$

The twisting angles in the two stable configurations are computed as $$\psi_1 = 2\tan^{-1}x_1, \psi_0 = 2\tan^{-1}x_0 \quad [S6]$$

When the twisting angle between bottom and top vertices of a valley fold is equal to 180°, that is $\psi_0 = \pi - 2\pi/n$, the valley folds meet at the center, making this a critical design. If $\psi_0 > \pi - 2\pi/n$, the pattern will experience contact among its panels and will not be able to reach the folded stable state. This angle restriction results in a design constraint on the choice of the height difference between stable states (3), $$|H^2| - H_0^2| \le \cot^2(\pi/n) \quad [S7]$$

In this paper, because we work with compact assemblies that have large changes in geometry, we opt for flat-foldable designs, that is, we design the unit cells to have zero height at the folded state (H0=0). In addition, all the designs are based on hexagons (n=6) with sides length b=13 mm, resulting on height restriction of Hcrit=22.52 mm. Respecting this design constraint, we investigate unit cells with H=15.6 mm, 16.9 mm, 18.2 mm, and 20.8 mm (see Table 1). For each unit cell, we define the folded and deployed stable states as state [0] and state [1], respectively (FIG. 5A).

TABLE 1

| Geometry of the Kresling Unit Cells | | | | | | |
|---|---|---|---|---|---|---|
| Design | H (mm) | a | c (mm) | a (mm) | $\psi_1$ | $\psi_2$ | $\Delta\psi$ |
| 1 | 15.6 | 107.72° | 16.66 | 17.34 | 35.44° | 84.56° | 49.12° |
| 2 | 16.9 | 105.40° | 17.60 | 18.26 | 30.80° | 89.20° | 58.40° |
| 3 | 18.2 | 102.77° | 18.61 | 19.08 | 25.54° | 94.46° | 68.92° |
| 4 | 20.8 | 96.18° | 20.87 | 20.99 | 12.35° | 107.65° | 95.30° |

Figure 6C:
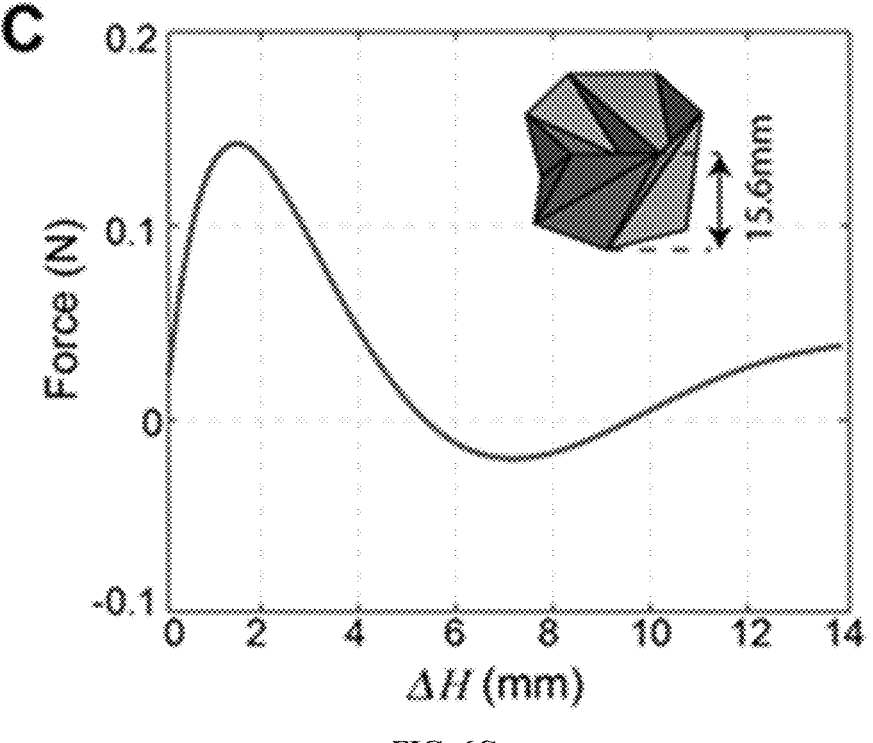
Figure 6D:
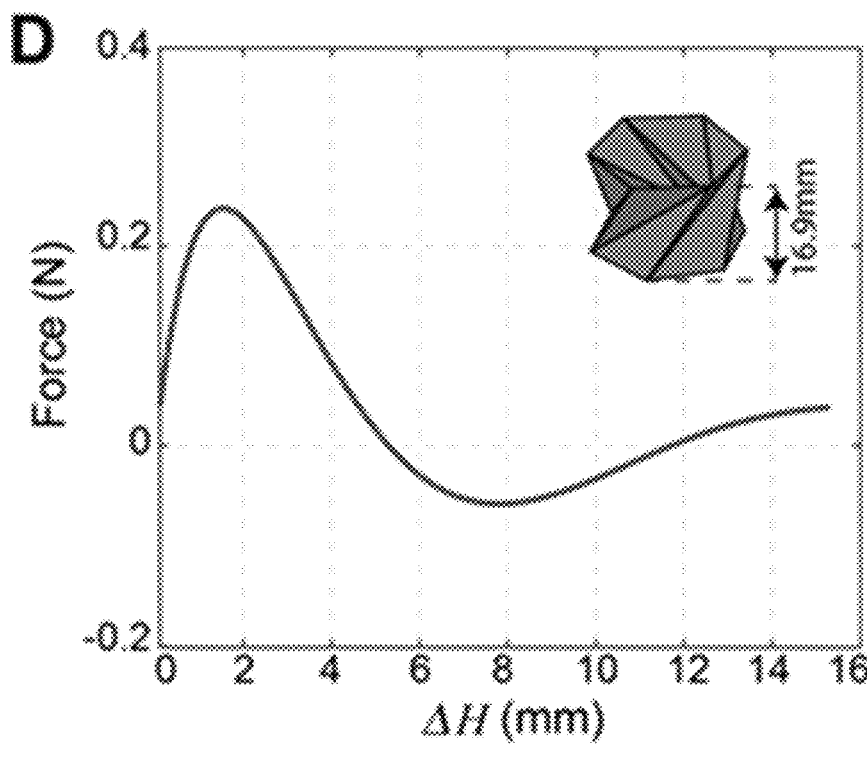
Figures 6E, 6F:
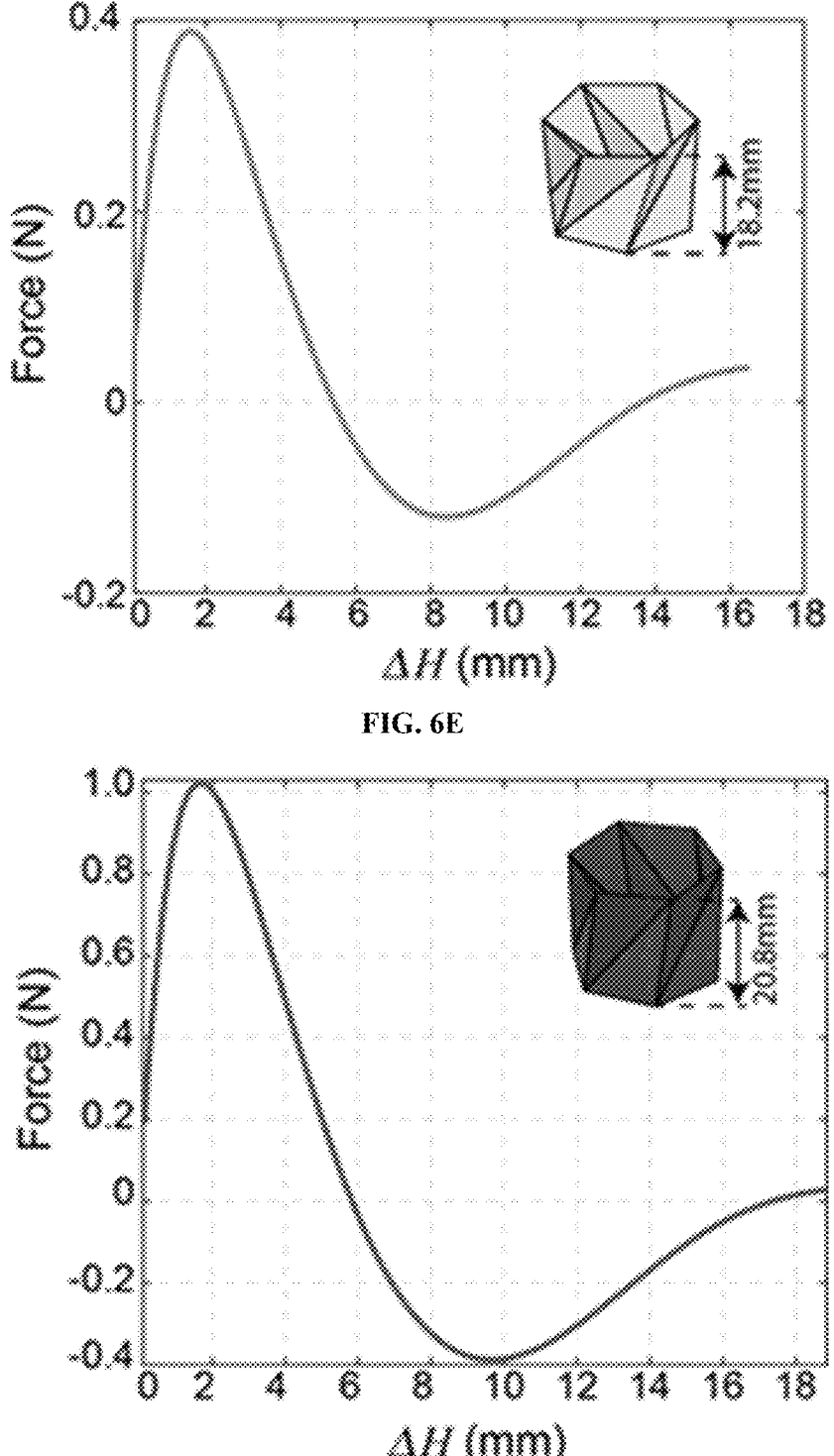

B. Mechanics. Geometrically, the Kresling pattern always presents bistability, with an energy barrier correlated to the height of the unit cell. However, this statement is only valid under the assumption of zero stiffness hinges. In reality, the crease lines store energy as we fold the pattern, making the existence of bistability dependent on the material properties of both hinges and panels. To guide our design, we simulate the unit cells with distinct heights (FIG. 6) using the MERLIN software (4). This software uses a nonlinear formulation combined with the modified generalized displacement control method (5), which allows tracking of the complete equilibrium path, even for structures displaying snap-type behavior, as is the case of the Kresling pattern. The MERLIN software uses a reduced order model (6, 7) that considers the crease lines as bars with rotational springs along them. For non-triangular (quadrilateral) panels, this model adds an extra bar along the panels' shortest diagonals to avoid mechanisms and to approximate the bending of the panels. However, because the Kresling pattern is already tessellated by triangles, the simulation will not consider any bending of the panels and consider that all the deformation occurs either by the folding of the hinges or stretching of the crease lines and panels. The reduced order model provides information on the global behavior of the unit cell and how the geometry is correlated with the energy barrier between stable states (4).

2. Samples Fabrication

We fabricate each unit cell of the Kresling pattern by perforating and cutting the pattern on Tant origami paper (0.1 mm thick) with the PLS4.75 laser cutting system (Universal laser systems). The Kresling pattern is modified to a flower-like shape (FIG. 5B) to accommodate the cuts along the mountain folds. Those cuts avoid kinks in the mountain folds, creating samples with similar response on multiple folding cycles (8). After the pattern is folded, we use 3M Scotch double sided tape to attach the top and bottom polygons (FIG. 5C). These polygons are made of 160 g/m Canson Mi-Teintes paper (0.2 mm thick), a thicker paper meant to provide stiffness and avoid bending of the polygons.

To the top of each unit cell, we attach the magnetized plate using Sil-Poxy silicone adhesive. We fabricate the magnetized plates by first mixing Ecoflex 00-30 silicone rubber and NdFeB particles into a homogeneous mixture with 30% NdFeB volume. This mixture is poured into a circular 3D-printed mold with 22 mm of diameter and 3 mm of depth and cured for one hour at 60° C. Next, we magnetize the plates using a magnetizer with an 1.5T impulse magnetic field. In Table 2, we provide the magnetization directions of the magnetic plates at the folded state with respect to the x axis and the geometries of the unit cells for the Kresling assembly presented in the main text.

TABLE 2

| Unit cells design and actuation | | |
| --- | --- | --- |
| Structure (Fixed to Free end) | Geometry | Magnetization direction Folded |
| Unit cell (FIG. 1A-C, FIG. S11) | Design 3 | $\theta_M = 129°$ |
| Two-cell assembly (FIG. 1D-E, FIG. S12) | Design 3 (bottom) | $\theta_M = 0°$ |
| | Design 3 (top) | $\theta_M = 90°$ |
| Reversed creases assembly (FIG. 2) | Design 3 (orange) | $\theta_M = 0°$ |
| | Design 3 (blue) | $\theta_M = -90°$ |
| LED assembly (FIG. 4) | Design 1 (green) | $\theta_M = 0°$ |
| | Design 3 (yellow) | $\theta_M = 90°$ |
| | Design 4 (red) | $\theta_M = 180°$ |

Figure 7:
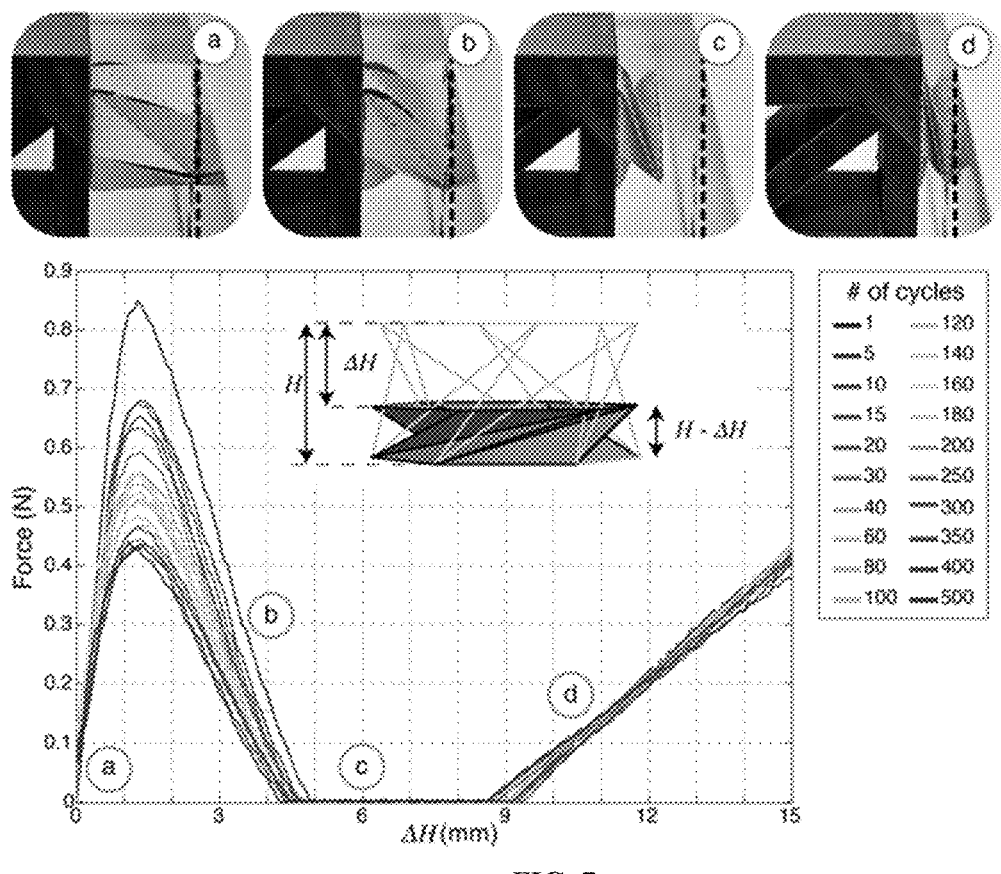
FIG. 7 show Kresling pattern (Design 3, H=18.2 mm) responses up to 500 compression cycles and snapshots of the experiment. Points a, b, and d are contact points, while point c is a non-contact point. Note that once the unit cell snaps, it loses contact with the load cell (e.g. point c), resulting on null forces until the contact is restored (e.g. point d).

We investigate the variability of the mechanical properties over multiple compression cycles. In FIG. 7, we show the force-displacement response of a design 3 unit cell (see Table 1) up to its 500th folding cycle. We observed that the mechanical response stabilizes around the cycle 300. Thus, for consistent results, all the samples were folded and deployed up to 300 times prior to performing the magnetic actuation and mechanical tests reported in this work.

3. Mechanical Test

We test the mechanical properties of the Kresling unit cells under compression using a customized testing bed (FIG. 8) that was previously reported in (9). The setup consists of a metallic frame that integrates two steel plates. One plate is fixed and is connected to a 50N capacity load cell (RSP1, Loadstar Sensors) with accuracy to 0.02% full scale. The other plate is movable and is controlled by a stepper motor (STP-MTR-23079, SureStep). The testing bed has a safety mechanism that limits the distance between the two plates to be no smaller than 15 mm, which is about the size of our samples. To overcome this size limitation, we add a 3D-printed sample holder to the setup.

From the experiments, we observe that the stable states of the samples differ from the geometric folded stable state. In reality, the folded stable state is not equivalent to the flat-foldable state (that is, H0>0). Similarly, the rotational angles δθ are also different from those geometrically computed Ayr and reported in Table 1. This difference comes from the fact that the fabricated samples have panels with thickness and hinges with stiffness, while the geometric model assumes panels with zero thickness and hinges with zero stiffness.

Figure 8A:
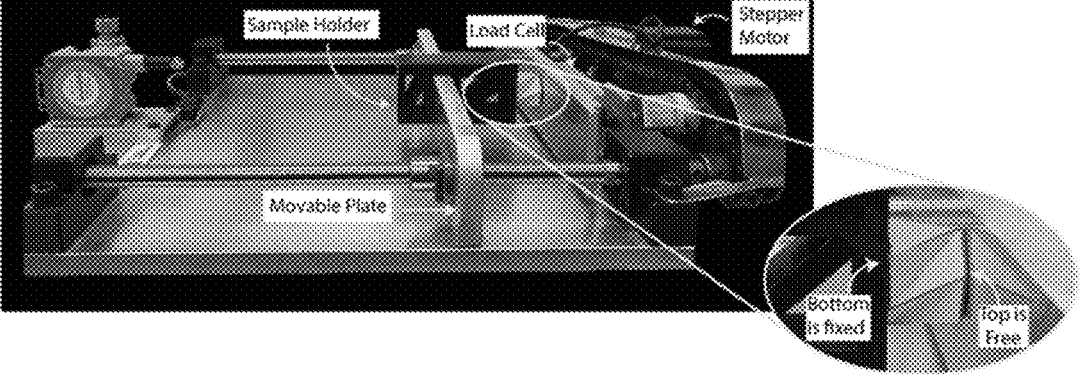
FIG. 8A-8B show compression test (setup #1). (8A) Compression test bed and (8B) Schematic of the test with fixed-free boundary conditions.
Figure 8B:
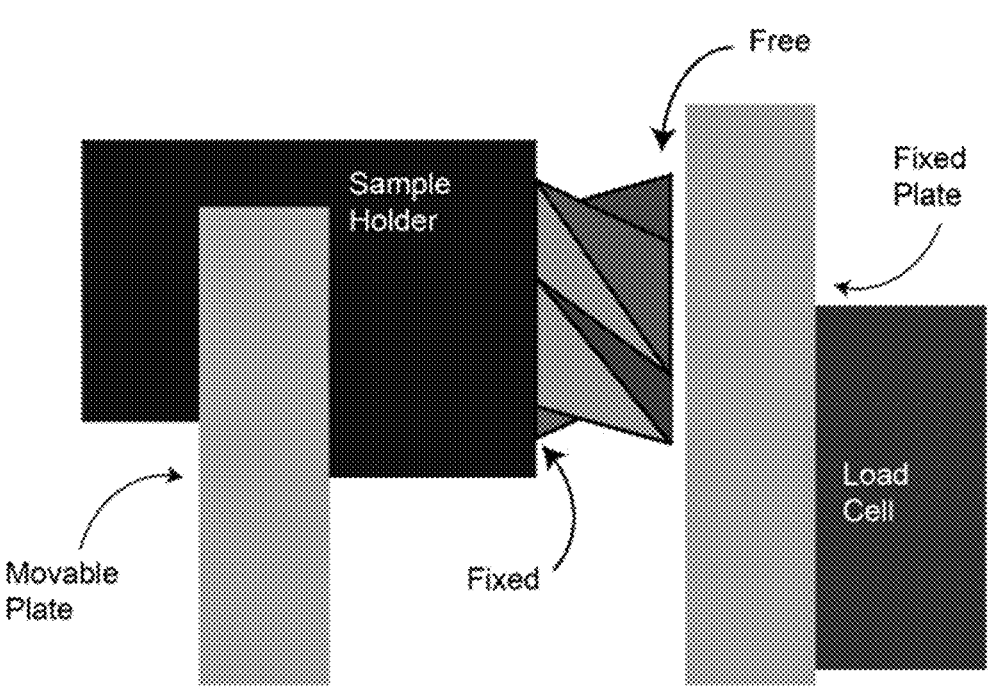

A. Setup #1: Folding of the Unit Cell. For each unit cell design in Table 1, we test five samples under compression. For the tests, we attach one end of the unit cell to the sample holder, while leaving the other end completely free (FIG. 8). The free end is compressed against the fixed plate. To reduce the friction between the sample and the fixed plate, we lubricate the fixed plate before each test. Note that because the sample has no physical connection to the fixed plate, once the sample snaps, the free end loses contact with the load cell (see snapshots in FIG. 7). This results in the region with zero load in the force-displacement curves. Once the free end reaches the load cell again, we see the load increasing (FIG. 3A).

Figure 9A:
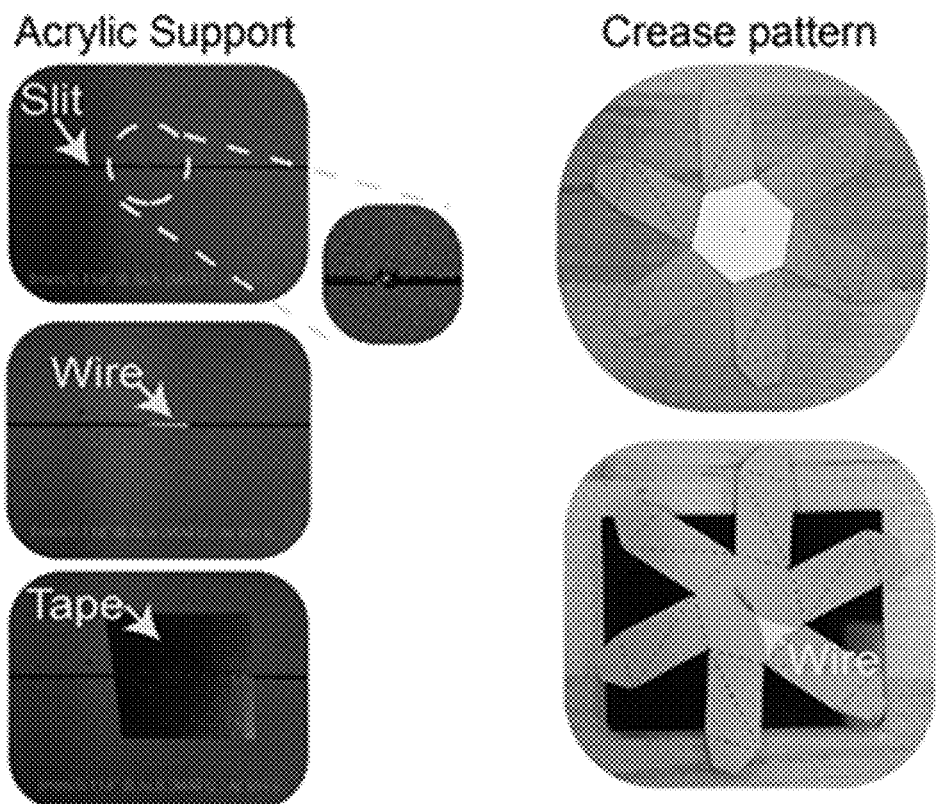
FIG. 9A-9C show compression and Tension test (setup #2). (9A) Modified sample with a wire connection to an acrylic plate. (9B) Sample assembled in the test bed. The sample is directly attached to the sample holder and the acrylic support to the fixed plate. (9C) Schematic of the test setup.
Figure 9B:
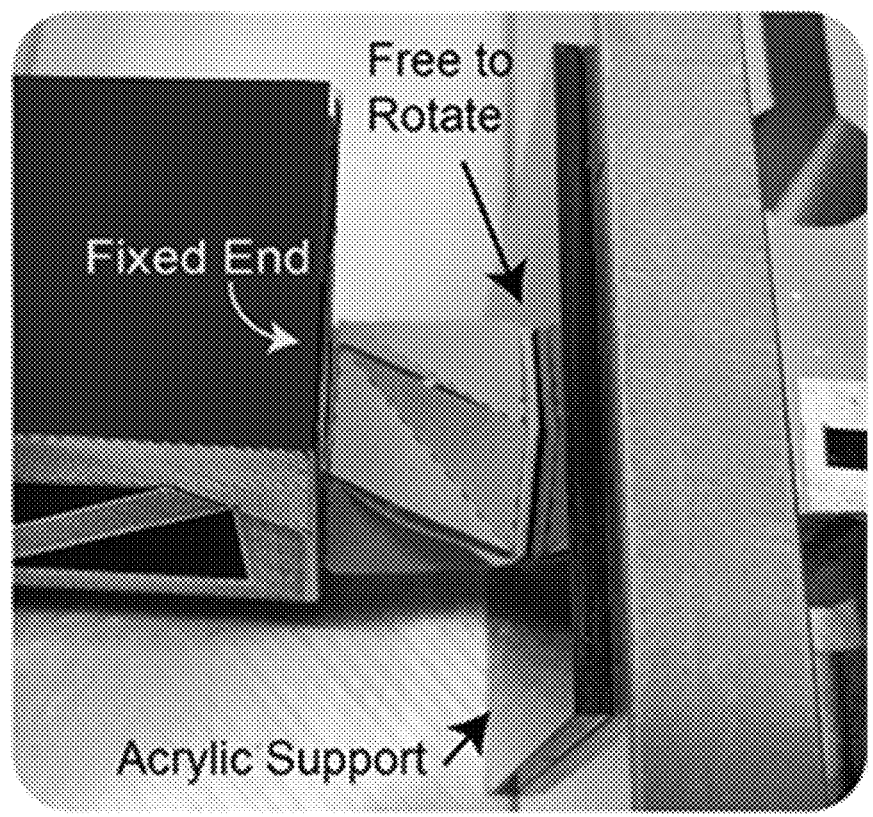
Figure 9C:
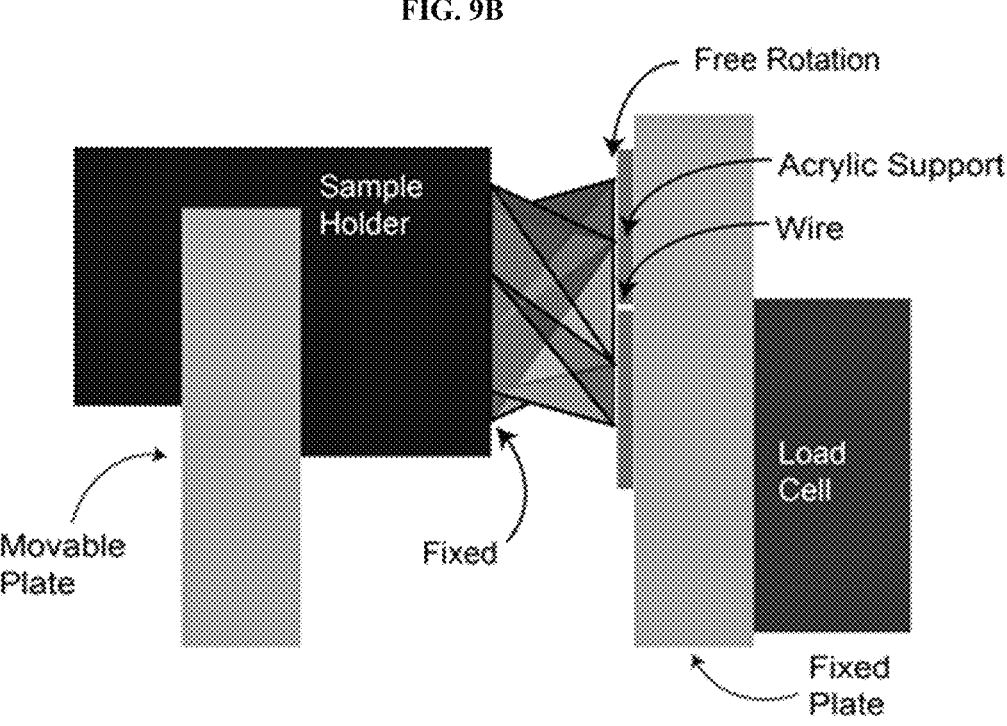
Figure 10A:
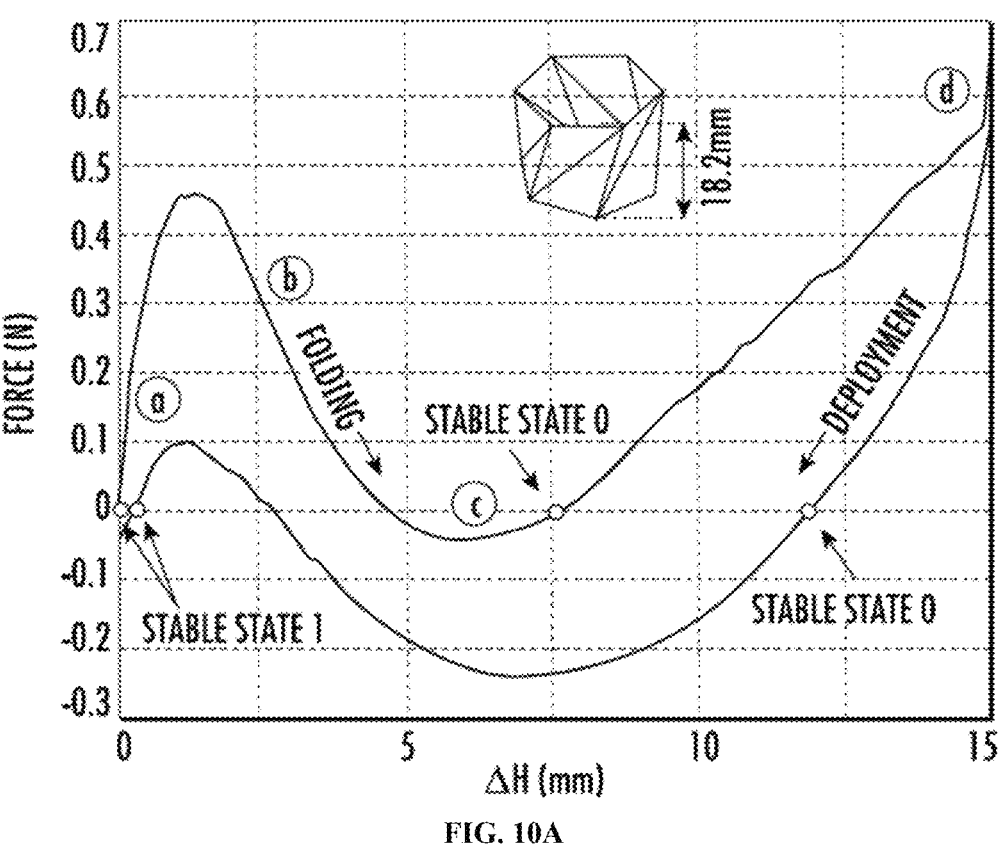
FIG. 10A-10C show (10A) Force-displacement curve obtained from the compression/tension test (setup #2) of the Design 3 unit cell. (10B) Torque-rotation curve obtained from the derivation of the stored energy. (10C) Snapshots of the experiment. Note that the left side of the sample is fixed to the sample holder and the right side uses a wire connection that constrains the unit cell while allowing for free rotation. The constraints at both ends permit the measurement of the entire equilibrium path. Contact at the right-hand-side of the setup is maintained at all times (points a, b, c, d).
Figure 10B:
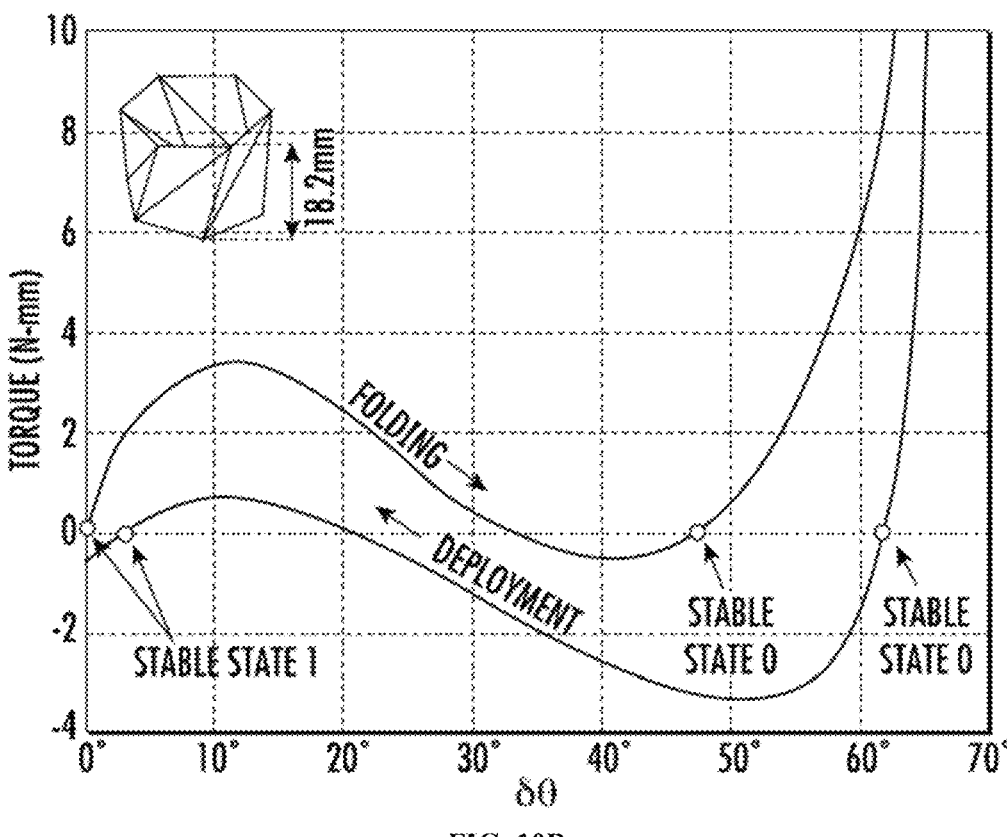
Figure 10C:
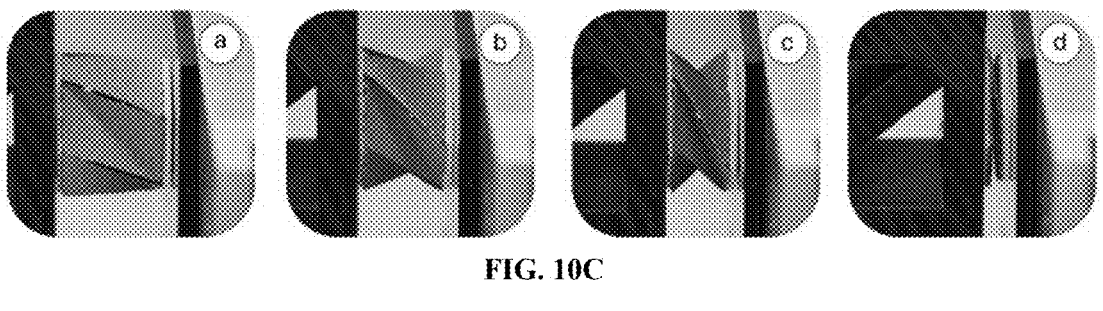

B. Setup #2: Folding and Deployment of the Unit Cell. Because we need to measure the required forces to both fold (compress) and deploy (pull) the unit cell, we modified the boundary conditions of the testing setup. For deployment, we need to constrain both ends of the unit cell, while allowing for rotation of the end in contact with the fixed plate. Thus, we use a wire to attach the crease pattern to a pre-lubricated acrylic plate (FIG. 9A). In the acrylic plate, we laser cut a hole and a slot, allowing for the wire to pass through the plate and to be folded into the slot. This wire connection is enough to constraint the unit cell to the plate, while allowing for it to freely rotate. Once the attachment is done, we fold the unit cell, as described previously (FIG. 5C). Next, we attach the acrylic plate to the testing bed fixed plate and attach the bottom of the unit cell to the sample holder (FIG. 9B,C). We first compress (fold) each unit cell from the deployed to the flat-folded state. Because both ends of the unit cell are constrained, the sample will not lose contact with the load cell. Thus, we obtain the entire equilibrium path between the stable states (FIG. 10) in which we observe a change in the direction of the axial load (from compression to tension). Once the unit cell reaches the stable state [0], the load changes direction again (from tension to compression) and the unit cell is compressed until it reaches the flat-folded state. After reaching the flat-folded state, we start the deployment of the unit cell. At first, the unit cell deploys without any force being applied (i.e., the unit cell experiences unloading). After a stable state is reached, the unit cell starts to experience tension. Similarly, to the folding process, we capture the entire equilibrium path and we observe a change in the direction of force (from tension to compression). Once the unit cell reaches another stable, further deployment is only possible under tension (FIG. 10).

Figure 11:
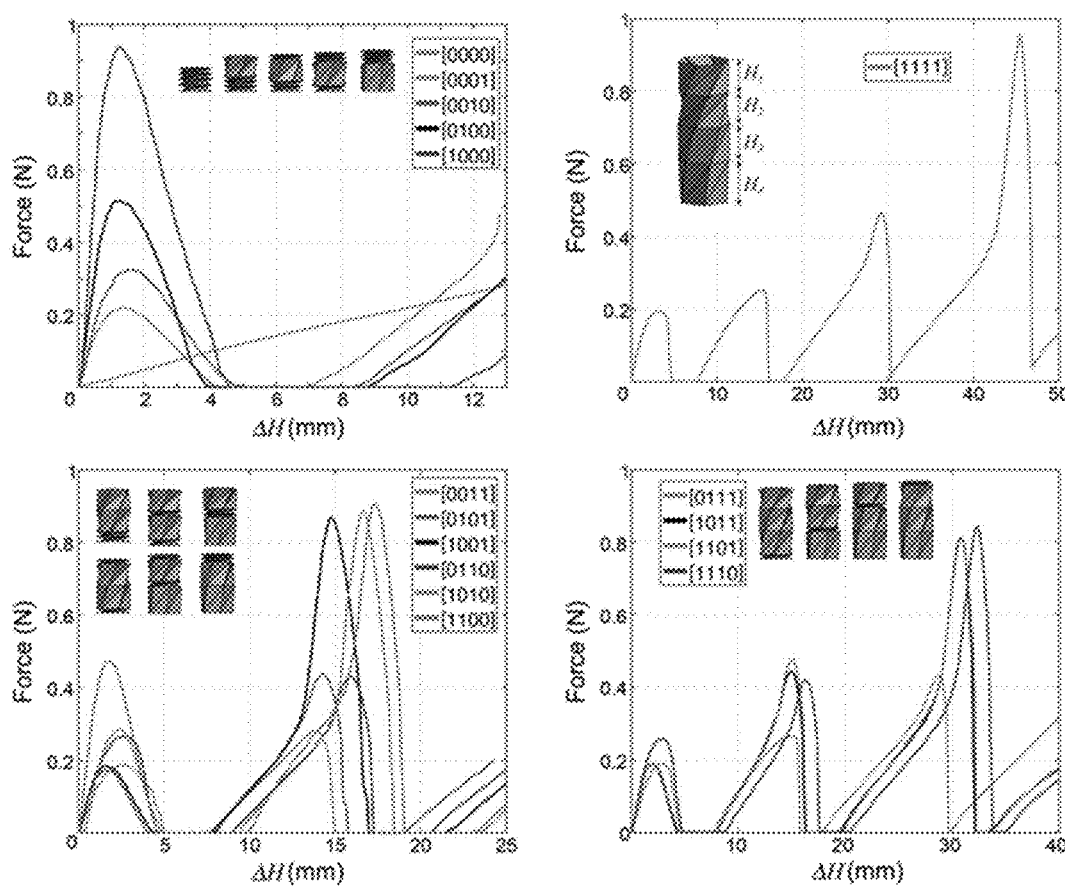
FIG. 11 show average force-displacement curves of the sixteen stable states of the four-cell Kresling assembly, where H1=15.6 mm, H2=16.9 mm, H3=18.2 mm, and H4.=20.8 mm. For this test, we use setup #1 (FIG. 8A-8B). Legend refers to the state of each unit cell (bottom to top).

C. Mechanical Properties of the Four-Cell Kresling Pattern. We investigate the mechanical tunability of the four-cell Kresling pattern (FIG. 3D,E) by axial compression of the assembly at all sixteen stable states. The assembly is composed of unit cells with designs 1 to 4 (top to bottom) presented in Table 1. However, because the folded unit cells (state [0]) are not completely flat-folded during the experiments, we decided to remove them for a better quantification of the stiffness of the assembly in each state. Thus, we test only the unit cells that are deployed. For example, the quantification of the stiffness of the stable state [1001] involves testing the assembly using only the unit cells with design 1 and 4. For each one of the sixteen stable states, we test the same assembly sample under compression three times using the experiment setup #1 described in SI Section 3A. That is, the assembly has one end attached to the sample holder, and the other end is free. The legend in FIG. 11 refers to the stable state of the unit cells (from bottom to top), and it is in this figure that we show the averaged force-displacement curves for all three tests in each of the stable states. By comparing those curves, we observe a dramatic change in the mechanical behavior between some of the stable states, showing that we can use our actuation method to tailor the mechanical properties of a Kresling metamaterial.

Figure 3E:
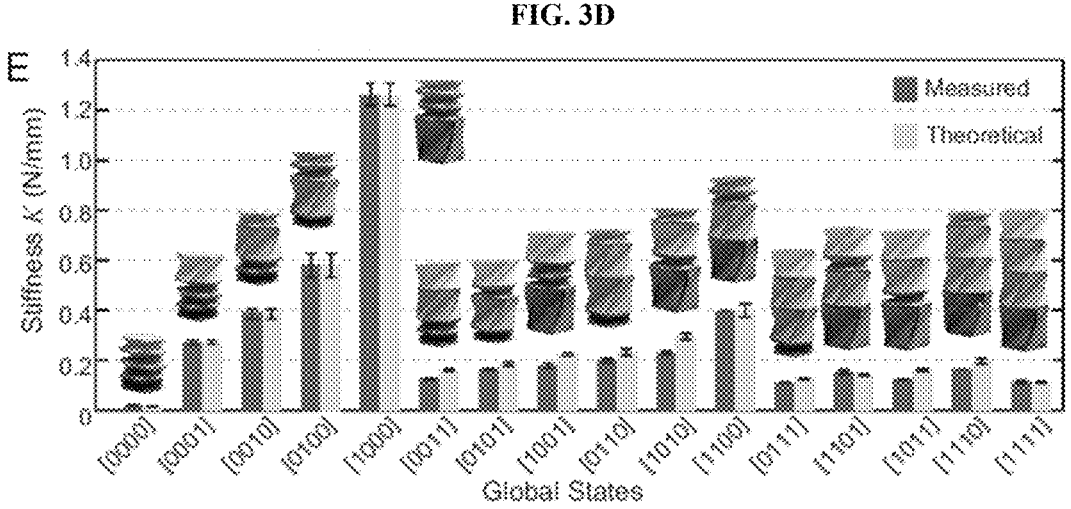

From the force-displacement curves, we obtain the stiffness K. This stiffness is defined as the slope of the first linear region of the force-displacement curves. In FIG. 3E, we compare theoretical values of the equivalent modulus for each state with the measured values. The theoretical values are obtained from the simplification of the four-cell assembly to a system of springs in series, where the stiffness of each spring corresponds to the stiffness of each unit cell that is obtained from the compression test. Thus, we compute the theoretical stiffness Keq as $$\frac{1}{K_{eq}} = \sum_{n=1}^{N} \frac{1}{K_i} \qquad [S8]$$

where $K_i$ is the stiffness of each spring (i.e., unit cell) i in the deployed state and N is the number of deployed unit cells.

Because the values of $K_i$ are obtained experimentally, in FIG. 3E, we provide the theoretical values computed with the averaged (columns), maximum and minimum (error bars) stiffness values. The averaged measured values for single unit cells are $K_1$=0.25 N/mm, $K_2$=0.39 N/mm, $K_3$=0.59 N/mm, and $K_4$=1.26 N/mm.

Figure 12:
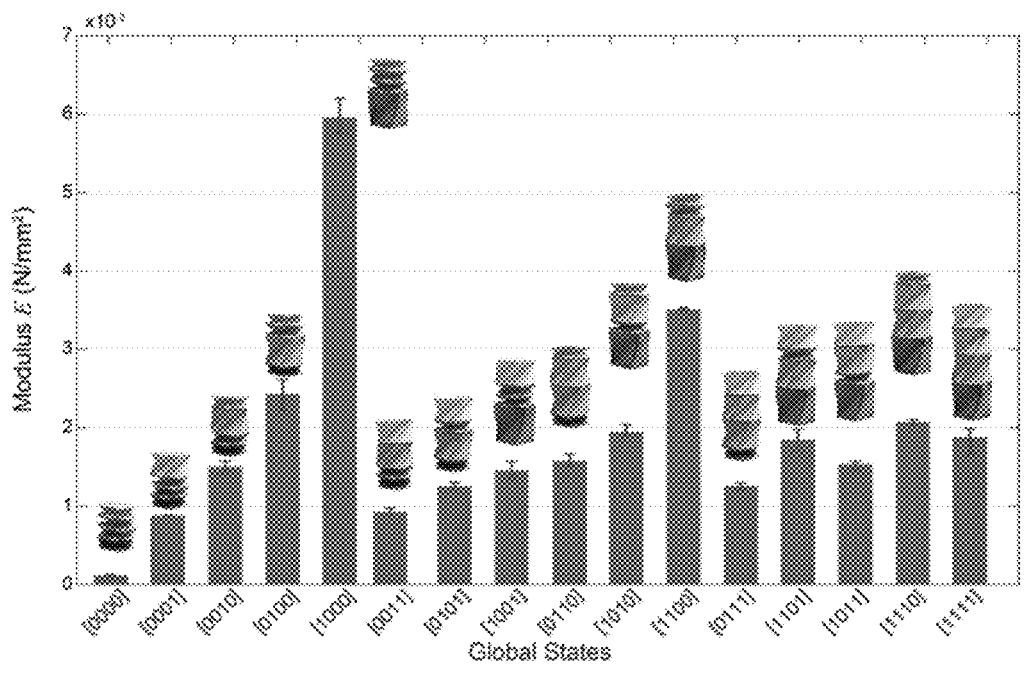
FIG. 12 show tunable mechanical response of the four-cell Kresling assembly. From multiple consecutive testing cycles, we obtain the average (columns) and maximum/minimum (error bars) values of the modulus E (Eq. S9).

In FIG. 12, we provide a comparison of the modulus E of each state, which is defined as the slope of the first linear region of the stress-strain (_–_) curves, being expressed as $$E = \frac{\sigma}{\epsilon} = \frac{F}{A} \frac{H}{\Delta H} \qquad [S9]$$

where F is the measured force, A is the area of the unit cell polygon, _H is the applied displacement, and H is the sum of the heights of the deployed unit cells. The averaged measured values for single unit cells are $E_1$=0.86×10–2 N/mm2, $E_2$=1.4×10–2 N/mm², $E_3$=2.4× 10–2 N/mm², and $E_4$=5.9×10–2 N/mm².

4. Magnetic Actuation Experiment

Figure 13:
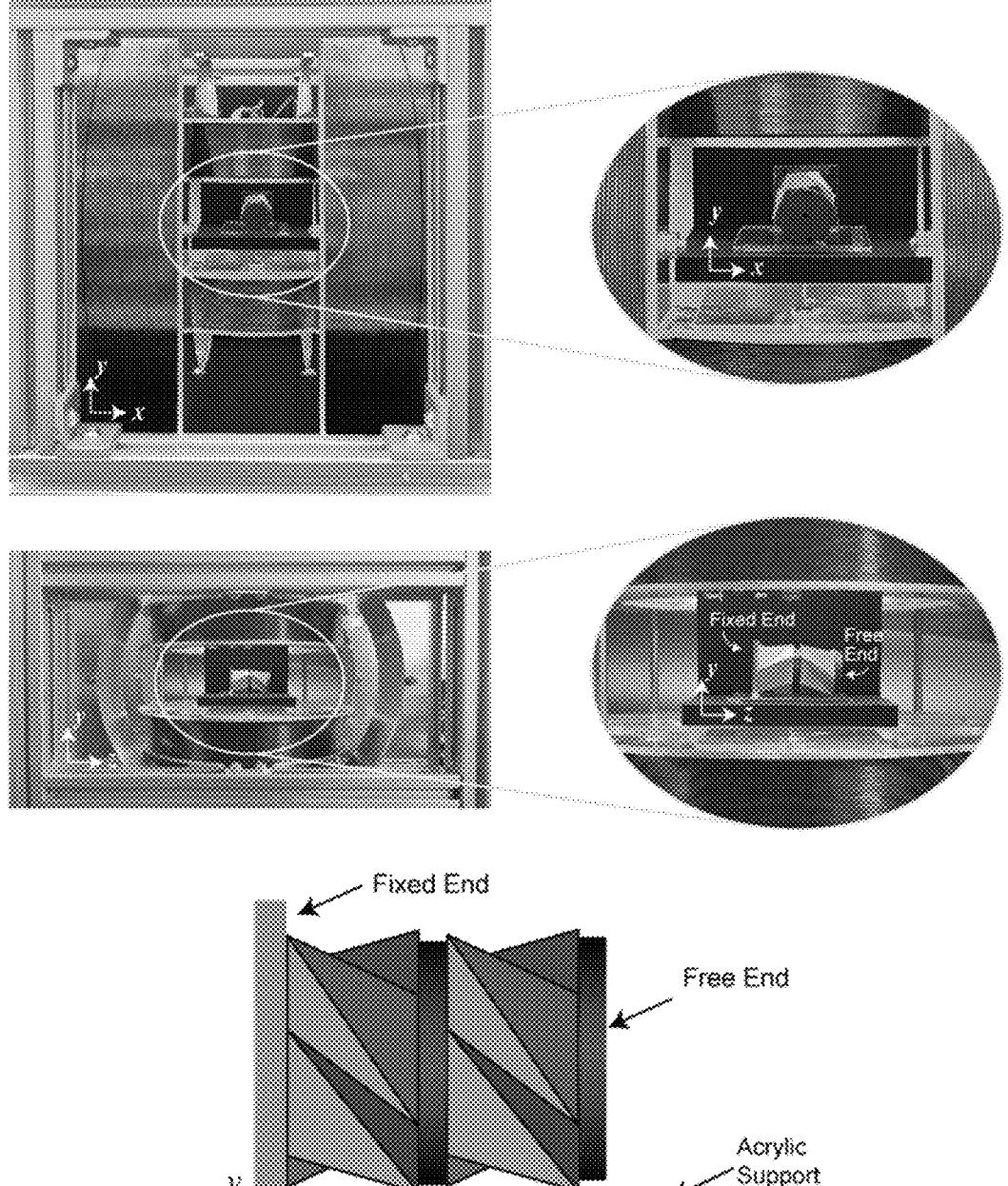
FIG. 13 show magnetic actuation setup with electromagnetic coils. Bottom schematic shows the boundary conditions of the sample inside the coils.

A. Electromagnetic Coil. The Kresling patterns with magnetic plates are actuated within a customized electromagnetic coil system, which can generate a two-dimensional (2D) uniform magnetic field (FIG. 13). Two sets of standard Helmholtz coils are configured perpendicularly to each other in the xy-plane. The in-plane magnetic field direction and intensity can be accurately controlled by the current in the coils. The coils can generate 2.7 mT/A and 3.3 mT/A uniform magnetic fields with 60 mm and 80 mm spacing for the x and y axes, respectively.

B. Uniformity of Magnetic Field.

In order to quantitatively study the magnetic field distribution, finite element analysis is performed to show that the magnetic field generated by the two pairs of Helmholtz coils are sufficiently uniform in both axial direction and perpendicular direction. The 2D Helmholtz coil used for magnetic actuation is shown in FIG. 13. Defining the central point in the 2D coils as the origin of the xyz coordinate system, the simulation results of the magnetic field distribution with 10 A current in the coils are shown in FIG. 14. Here we define the uniformity of the magnetic field in any axis as 1–($B_{max}$– $B_{min}$)/$B_{center}$, where $B_{max}$, $B_{min}$, and $B_{center}$ are the maximum, minimum, and central fields within the defined range, respectively.

The magnetic field used to actuate the origami is in the xy plane. The distances between two coils in the x and y axes are 80 mm and 60 mm, respectively. The field in x direction is denoted by $B_x$, which is generated by a pair of coils along the x axis. The field in y direction is denoted by $B_y$, which is generated by a pair of coils along the y axis. The uniformities of $B_x$ along the x axis and z-axis are 98.8% and 99.9%, respectively, for the working space between –40 mm and 40 mm. The uniformities of By along the y-axis and z axis are 99.0% and 99.8%, respectively, for the working space between –30 mm and 30 mm. The simulation results indicate that the magnetic field generated by the two pairs of Helmholtz coils are sufficiently uniform in all directions.

The origami assemblies in this paper are more sensitive to the uniformity of the magnetic field along the z axis, especially when the number of the unit cells is large. The maximum height of the origami assembly in this paper is about 85 mm as shown in FIG. 2 and FIG. 14. For this height, the uniformity of the magnetic field can be larger than 98.5% in both xy plane and z axis. Even when the height increases to 120 mm, the uniformity can still reach 93.2%, which is sufficiently high for this application.

C. Magnetic Actuation.

All Kresling unit cells and multicell assemblies are tested in the 2D electromagnetic coils. The Kresling samples are attached to an acrylic support (FIG. 13), so that only the bottom polygon is constrained against any type of displacement, and the other end is completely free. All magnetic plates are placed parallel with the xy plane of the coils. The induced magnetic torque can fold and deploy the patterns along the z axis. Then, a specific direction of the magnetic field is set, and the amplitude increases from 0 mT to 30 mT at a rate of 1 mT/s. When the Kresling patterns change states, the corresponding magnetic field is recorded. This is the minimum required magnetic field to actuate the Kresling pattern in this specific direction. Then, we change the magnetic field direction and repeat the same procedure. A step of 5° is used to scan the xy-plane from 0° to 360°. We fit the recorded magnetic field direction and amplitude data using the Fourier series and plot the corresponding experimental contours of magnetic actuation (FIGS. 1C and E, FIG. 2D, FIG. 3C, FIG. 15C, FIG. 16, and FIG. 17).

5. Distributed Actuation

A. Unit cell Actuation. Each Kresling pattern can be locally actuated (i.e., folded and deployed) under a magnetic field B. In FIG. 1A-C and FIG. 15, we show the actuation process and required actuation parameters ($\theta_B$ and B) for the folding and deployment a design 3 (Table 1) unit cell, respectively. We define Tr+ and Tr as the required torques to fold and deploy, respectively, the unit cells. Because of rotation and displacement coupling of the Kresling pattern (SI Section 6), the required torques are obtained from the uniaxial test with displacement control described in SI Section 3B.

B. Assembly Actuation. From the individual actuation allowed by the attached magnetic plates, a local torque can be induced in each unit cell. In FIG. 16, we show the contour plots with the required actuation parameters (B and $\theta_B$) for the two-cell Kresling assembly (FIG. 1D) from, and to, any stable state. Following, we discuss the actuation from the [00] to the states [01], [10], and [11] for the assembly shown in FIG. 1D:

From Global State [00] to [10]: The change of state occurs under a magnetic field with intensity B=20 mT and direction $\theta_B$=120%. The magnetic field induces a counterclockwise magnetic torque, which is enough to deploy the bottom unit cell, but not the top unit. Thus, only the bottom unit cell deploys, rotating by $\delta\theta1$. The top unit cell remains in the folded configuration, rotating by $\delta\theta1$ as a rigid body with the bottom unit cell.

From Global State [00] to [01]: The change of state occurs under a magnetic field with intensity B=20 mT and direction $\theta_B$=240%. In the bottom unit cell, the magnetic field induces a clockwise magnetic torque that is opposite to the rotation direction for deployment, preventing the state change ($\delta\theta_1$=0). While, in the top unit cell, the magnetic field induces a counterclockwise torque larger than the required torque (i.e., T<Tr), leading to the unit cell deployment with a rotation 302.

From Global State [00] to [11]: The change of state occurs under a magnetic field with intensity B=20 mT and direction $\theta_B$=180%. In both bottom and top unit cells, the magnetic field induces a counterclockwise torque larger than the required torque (i.e., T<Tr-). Thus, the bottom unit cell rotates by $\delta\theta_1$ and the top unit cell rotates by $\delta\theta_1+\delta\theta_2$.

6. Rotation and Displacement Coupling

Figure 18A:
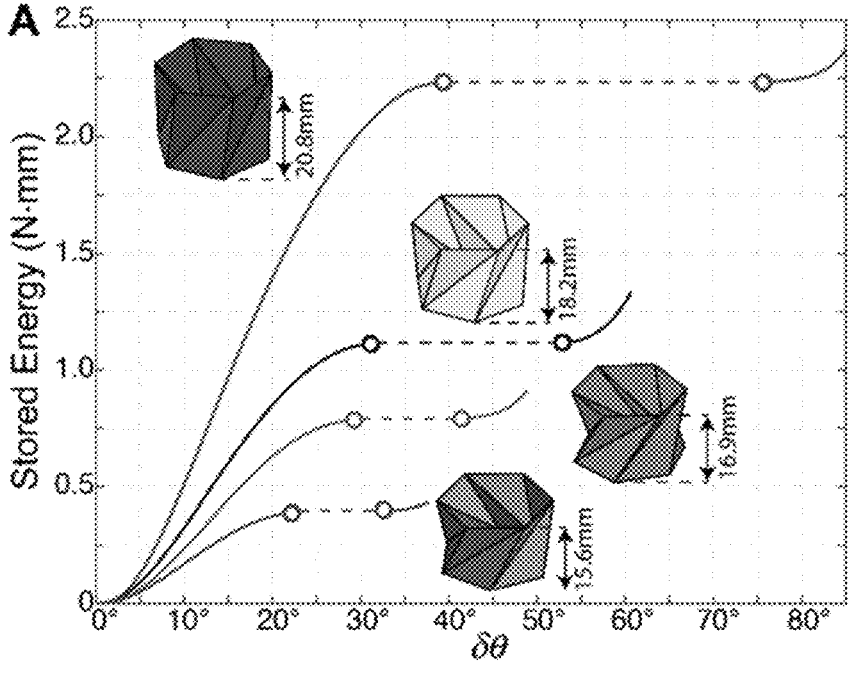
FIG. 18A-18B show mechanical response obtained from the average of the force-displacement curves (FIG. 3A) of the unit cells tested with fixed-free boundary condition, i.e., setup #1 (FIG. 8). (18A) Stored energy and (18B) Torque required to fold each designed unit cell, where δθ is the rotation angle. Dashed lines represent the region in which the unit cell loses contact with the load cell.
Figure 18B:
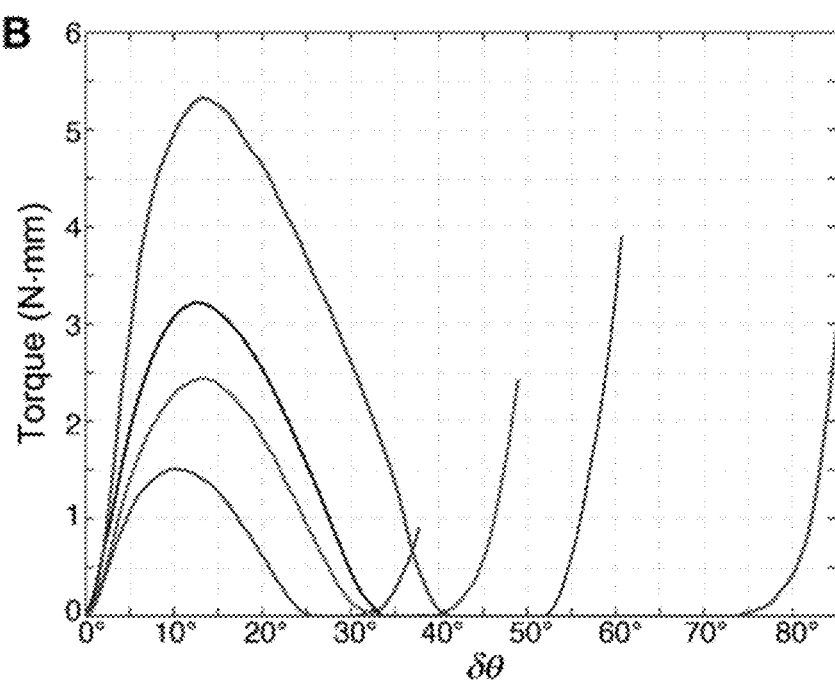

Because the Kresling pattern displays a coupling between compression and torsion, we can obtain the required torque to fold the unit cells from the uniaxial compression test. Thus, we use a compression test setup to measure the force needed to transition between the two stable states of the pattern (FIG. 3A). From the measured results, we obtain the stored energy. The derivative of the stored energy with respect to the rotation angle variation $\delta\theta$ results on the torque (Tr+) required to fold the unit cells. Thus, we express the stored energy as a function of $\delta\theta$, instead of $\Delta H$ (FIG. 18). With the torque, we compute the parameters (B and BB) needed to actuate each one of the unit cell designs (Table 1), which are provided in FIG. 17.

Although the Kresling pattern has a coupling between rotation and axial displacement, the relationship between the two is not available from kinematic equations. Because the Kresling pattern is a nonrigid origami, we only have a geometrical relationship between height and rotation angle $\delta\theta$ at the stable states. Thus, we approximate this relationship from the simulation of each unit cell under axial load using the MERLIN software (4). From the displacement history of the nodal coordinates, we obtain both the axial and rotational displacements of the unit cell. We approximate this data by a polynomial function and use this function to plot the stored energy as a function of the rotation angle.

7. Material Characterization

A. Mechanical Properties. To measure the stiffness of the hinges, we test samples with a primary hinge manufactured with the same process as the valley folds of the Kresling unit cell samples. That is, the hinge is cut with a dashed line pattern and is folded and deployed for 300 cycles. Parallel to the primary hinge, we add secondary hinges that are made weaker than the primary one, making the stiffness at those hinges close to zero.

Figure 19A:
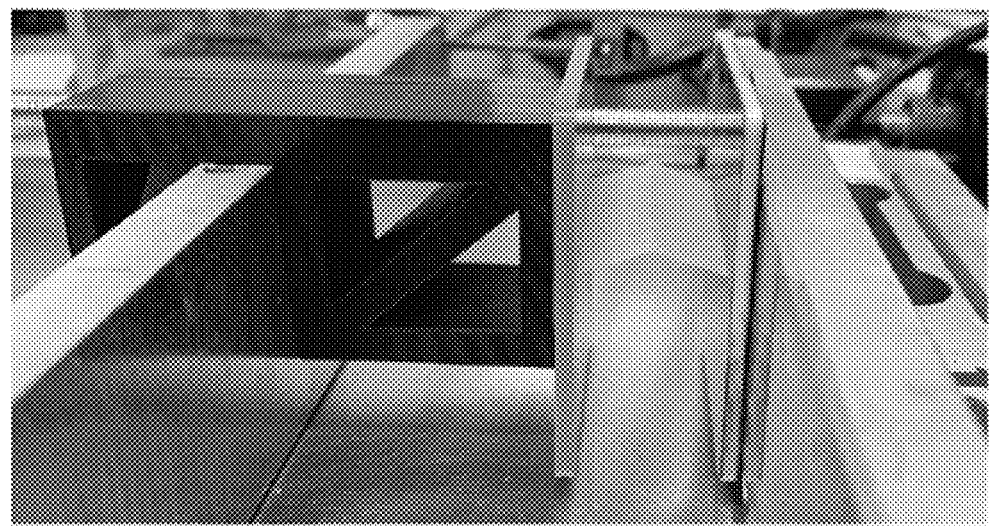
FIG. 19A-19D show characterization of the rotational stiffness of the hinges. (19A) Testing setup and (19B) schematics. (19C) Tested sample, where b=13 mm. (19D) Measured bending moment vs. rotation at the primary hinge, with each curve corresponding to one tested sample. From those curves, we obtain an average rotational stiffness $k_f = 2.4 \times 10^{-3}$ N·mm(rad·mm)−1.
Figure 19B:
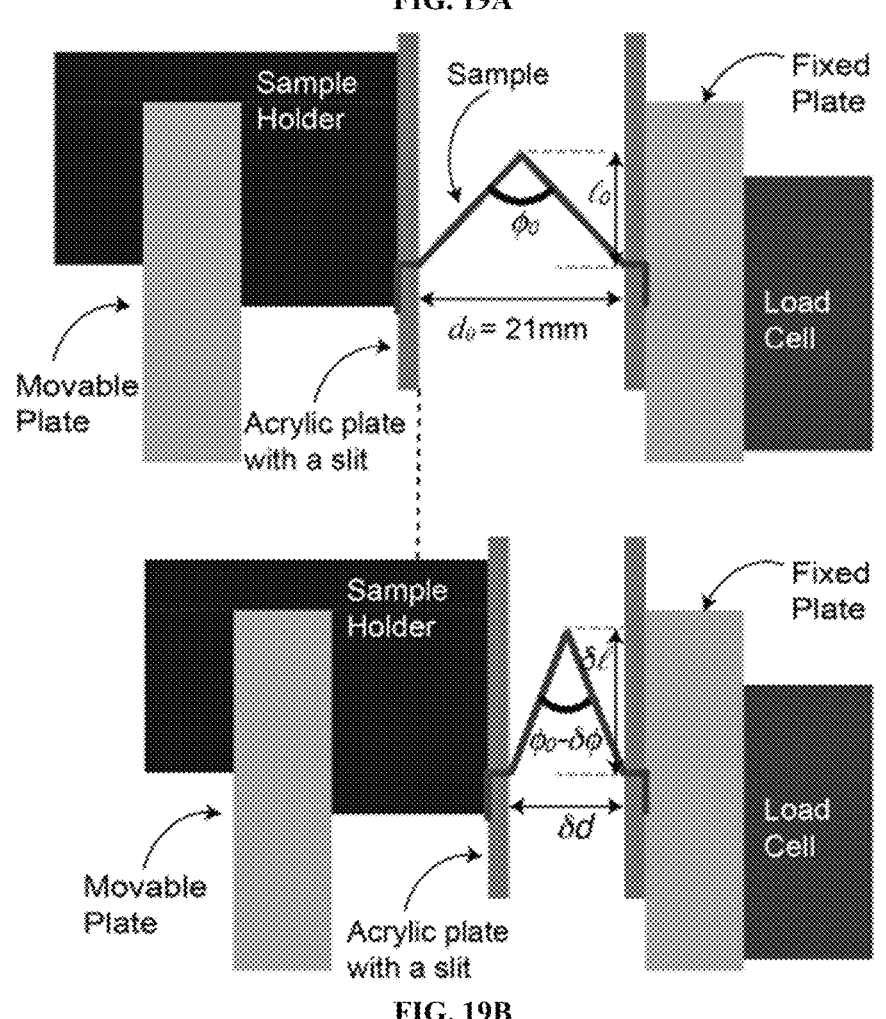
Figures 19C, 19D:
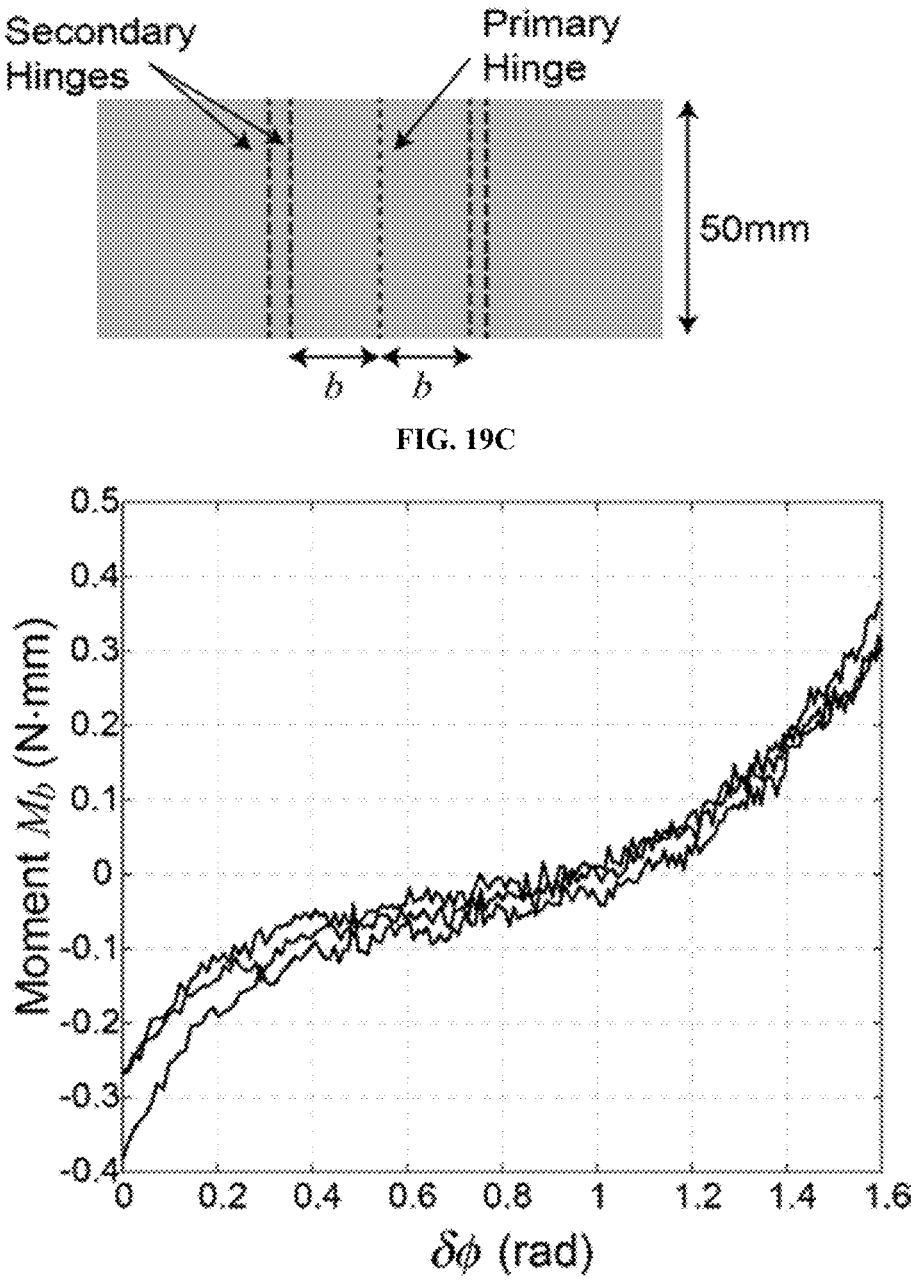

Each end of the sample is attached to an acrylic plate. Those plates have a slit cut, allowing for the edges of the sample to pass through it and be folded and taped on the other side. The acrylic plates are assembled to the test bed shown in FIG. 8, such that one plate is attached to the sample holder and the other to the fixed plate (FIG. 19). From the experiment, we measure the displacement d and force F, and with this information, we calculate the bending moment $M_b$ and the change in folding angle $\delta\varphi$ as $$M_b=F\delta l, \delta\varphi>=2\sin^{-1}(d_0/2b)-2\sin^{-1}(\delta d/2b) \quad [S10]$$

where $\delta l$ is the vertical distance between the edges and the hinge, b=13 mm is the panel size, $d_0$=21 mm is the initial opening of the hinge, and $\delta d=d_0-d$ (FIG. 19B). From the slope of the bending moment versus folding angle curves, we obtain the rotational stiffness of the hinges. This value is divided by the length of the hinge, that is 50 mm, resulting on an average stiffness of $k_f$=2.4×10–3 N·mn (rad·mm)–1.

Figure 20:
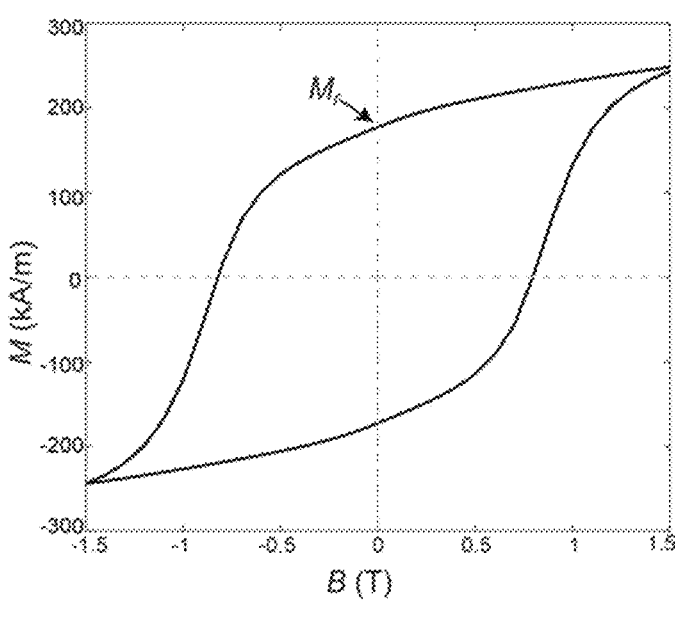
FIG. 20 show the M-B curve of the magnetic material

B. Magnetic Properties. The magnetic properties of the magnetic material for the plates are measured on a Vibrating Sample Magnetometer (VSM, 7400A series, Lake Shore Ciyotronics, Inc., Chicago, IL, USA). The magnetic moments of the material under external magnetic field (B) from –1.5 T to 1.5 T are scanned and recorded. The corresponding magnetic moment densities (M) are calculated from the magnetic moments by dividing by the sample volume. From the measured M-B curve in FIG. 20, the remanent magnetic moment density ($M_r$) is 177.39 kA/m and will be used as the magnetization intensity M for analyzing the magnetic actuation performance in the next section.

8. Analytical Calculation for Magnetic Actuation

Under a uniform magnetic field, the magnetic torque (T) will be induced to align the magnetization direction of the magnetic material to the external magnetic field and is calculated as $$T=BMV\sin(\theta_M-\theta_B) \quad [S11]$$

where V is the volume of the magnetic plate, B is the magnetic field intensity, $\theta_M$ and $\theta_B$ are the directions of the magnetization and the external magnetic field, respectively. With the folding process of a Kresling pattern as an example in FIG. 1A, the Kresling pattern will rotate clockwise. The angles of $\delta\theta_s$ and $\delta\theta$ are defined as the angle difference between two stable states and the real-time rotation angle during the actuation process, respectively. The Kresling pattern can be changed to state [0] (folded) when the magnetic torque (T) is larger than the required torque (Tr+) at any angle $\delta\theta$ (FIG. 1B). In the analytical calculations, 0.1° is chosen as the angle step.

Figure 21:
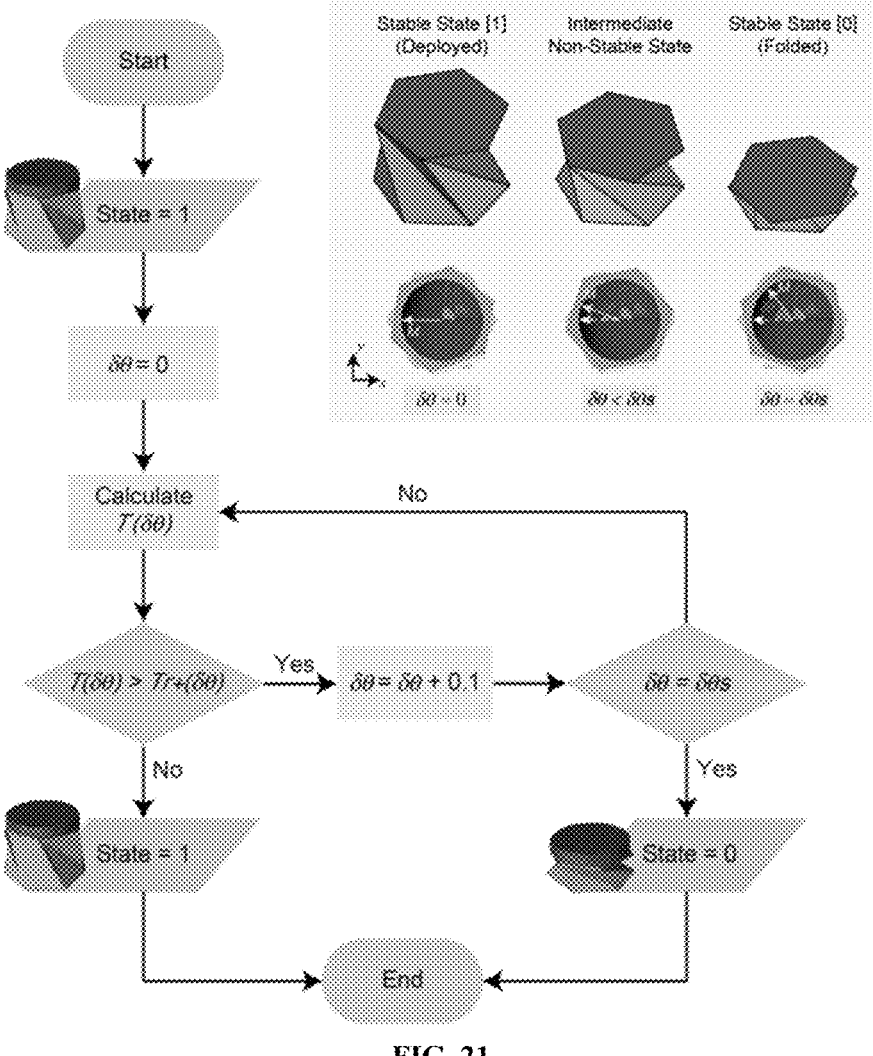
FIG. 21 show flowchart of the analytical calculation algorithm for the magnetic actuation of single unit cell with initial state [1]. Inset shows three different stages of the Kresling Pattern.

The state of the Kresling pattern under a specific magnetic field direction and amplitude will be determined as in the flowchart shown in FIG. 21, and the states of the Kresling patterns under different magnetic field directions can be predicted numerically with the same flow. The analytical results shown in FIG. 1C, FIG. 15C, and FIG. 17 display good agreement with the experimental results.

9. LED Circuit

A. Fabrication. In the modified crease pattern (FIG. 4B), we glue a layer of foam to the unit cell, followed by a layer of copper tape (0.1 mm thick). Next, we connect the copper tape to a copper wire and finally fold and assembly the unit cells and magnetized plates.

Figure 22A:
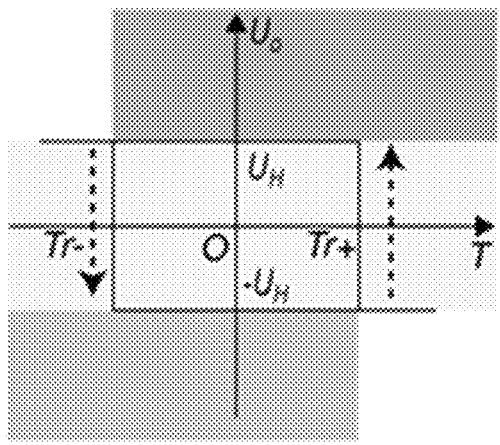
FIG. 22A-22C show (22A) Hysteresis loop and (22B) schematic of the Origami Schmitt Trigger for a Kresling unit cell. (22C) Schematic of the LED demonstration for Kresling pattern assembly FIG. 23 show controlled origami actuation.
Figure 22B:
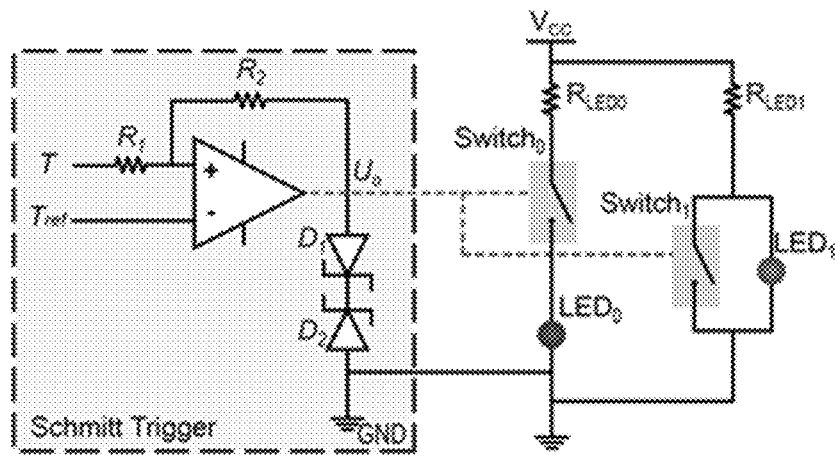

B. Schmitt trigger circuit. Schmitt trigger is a frequently used analog-to-digital converter circuit, which exhibits the same bistable characteristic as the designed Kresling patterns. The applied magnetic torque can be used to change the states of the Kresling pattern between state [0] and state [1]. In correspondence, the input voltage of the Schmitt trigger can be used to change its output between UH and UH, which are regulated by reverse connected Zener diodes. Therefore, the applied magnetic torque can be considered as the input of the "origami Schmitt trigger". FIG. 22A shows the typical hysteresis loop of the "origami Schmitt trigger". To show the similar characterization between Schmitt trigger and a Kresling pattern unit cell, a demonstration of two LEDs with different colors showing the different states is designed and its comprehensive circuit is shown in FIG. 22B. When the applied magnetic torque is larger than the positive required torque of the specific Kresling pattern, the output voltage is UH, which can be used to drive controllable switches. The green LED is short-circuited by Switch 1 and the blue LED is turned on to indicate the state [0] of the unit cell. In contrast, when the applied magnetic torque is smaller than the negative required torque, the output voltage will snap to UH. In this case, the controllable switch will be opened. The green LED is turned on to indicate state [1] of the unit cell. The Zener diodes D1 and D2 with Zener voltage of UH are used to regulate the output voltage U0. The reference input Tref and resistances R1, R2 are used to reflect the mechanical properties of the Kresling pattern. As we have already measured the positive and negative required torque of the specific Kresling pattern, Tref and the ratio between R1 and R2 can be calculated as $$T_{ref} = \frac{U_H(Tr_+ + Tr_-)}{2U_H + Tr_+ - Tr_-}, \frac{R_1}{R_2} = \frac{Tr_+ - Tr_-}{2U_H} \qquad [S12]$$

Figure 22C:
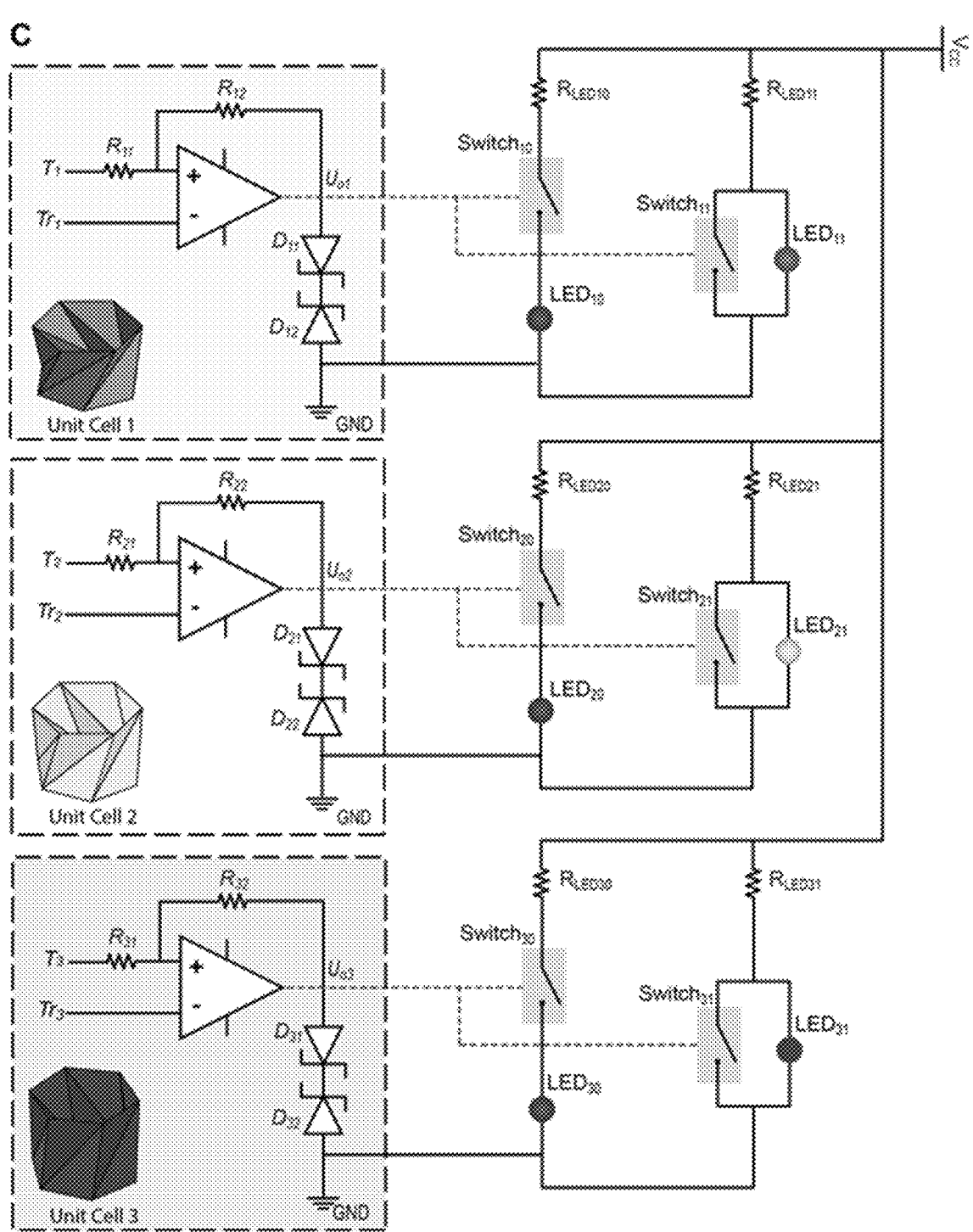
Figure 23:
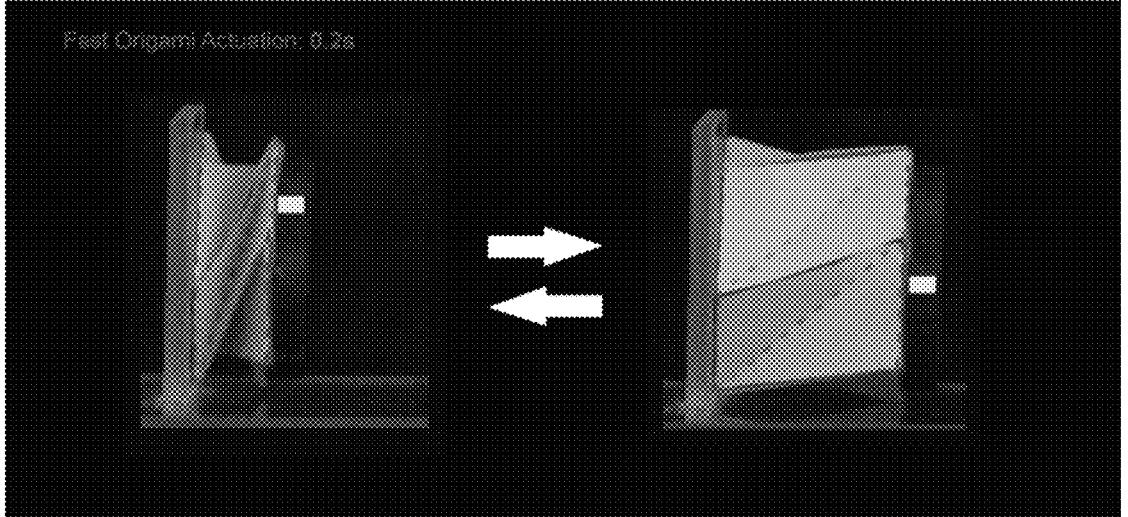
Figure 24:
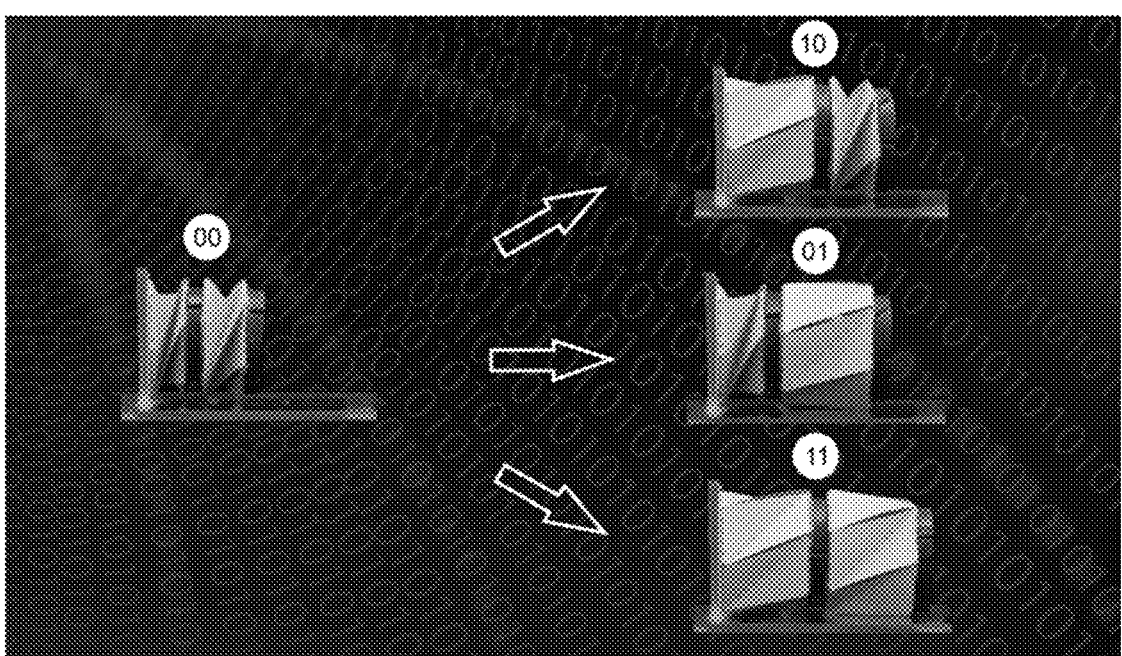
FIG. 24 show distributed actuation of a two-cell Kresling assembly.
Figure 25:
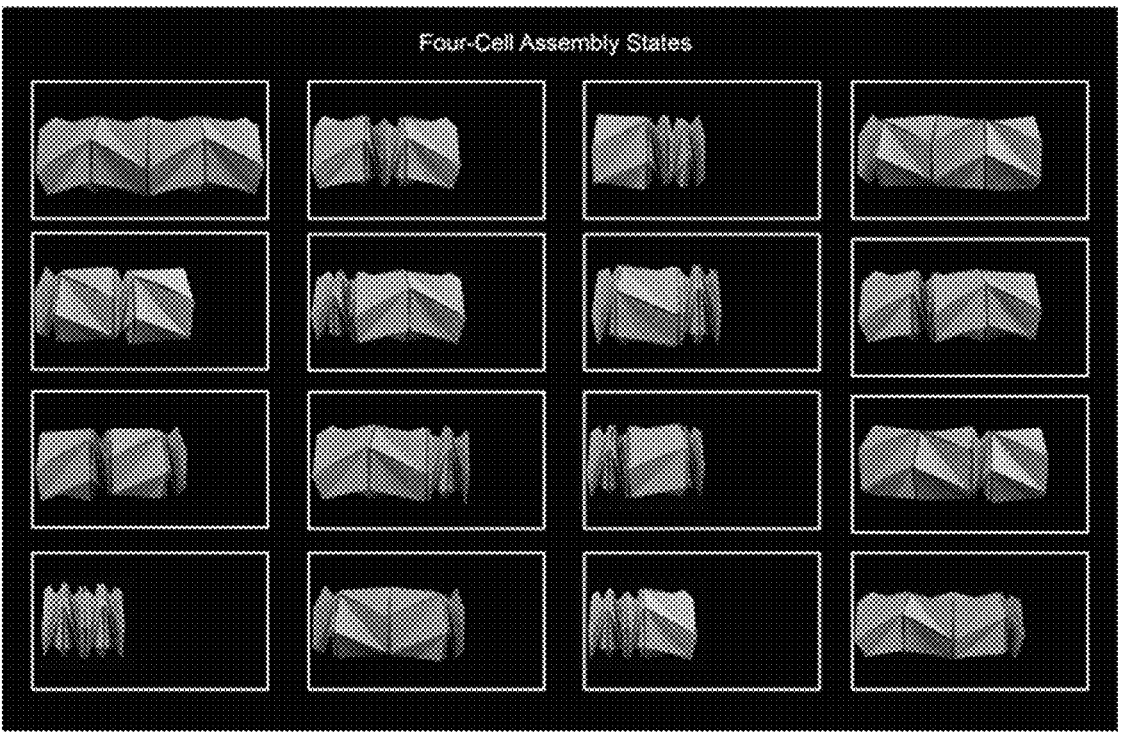
FIG. 25 show distributed actuation of Kresling assemblies with reverse creases.
Figure 26:
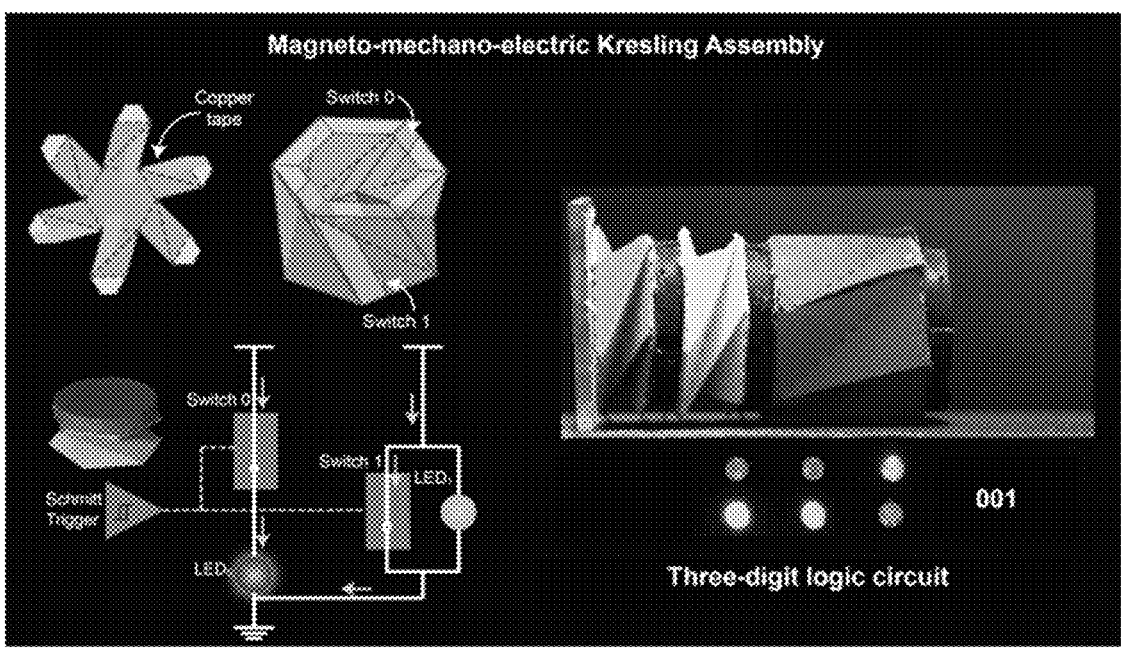
FIG. 26 show multifunctional Kresling assembly for digital computing.

C. LED demonstration for Kresling pattern assembly. For the LED circuit in FIG. 4, we use designs 1,3 and 4 (green, yellow and red unit cells, respectively) to create the logic circuit. FIG. 22(C) shows the schematic of the LED demonstration for Kresling assembly. As the three unit cells have different mechanical properties, the corresponding "Origami Schmitt trigger" has different input references and resistance ratios. And their input torques can be calculated as $$T_1 = T_{M1} + T_{M2} + T_{M3}, T_2 = T_{M2} + T_{M3}, T_3 = T_{M3} \qquad [S13]$$

where $T_{M1}$, $T_{M2}$, and $T_{M3}$ are the applied magnetic torques of each unit cell.

REFERENCES

1. B Kresling, Natural twist buckling in shells: from the hawkmoth's bellows to the deployable kresling-pattern and cylindrical Miura-ori in Proceedings of the 6th International Conference on Computation of Shell and Spatial Structures, eds. J F Abel, J R Cooke. pp. 1-4 (2008).

2. B Kresling, Folded tubes as compared to kikko ("Tortoise-Shell") bamboo. Origami3: Proc. Third Int. Meet. Origami Sci. Math. Educ., 197 (2002).

3. R J Lang, Twists, tilings, and tessellations: Mathematical methods for geometric origami. (CRC Press), (2017).

4. K Liu, G H Paulino, Nonlinear mechanics of non-rigid origami: an efficient computational approach. Proc. Royal Soc. A: Math. Phys. Eng. Sci. 473, 20170348 (2017).

5. S E Leon, E N Lages, C N De Araajo, G H Paulino, On the effect of constraint parameters on the generalized displacement control method. Mech. Res. Commun. 56, 123-129 (2014).

6. M Schenk, S D Guest, Geometry of Miura-folded meta-materials. Proc. Natl. Acad. Sci. 110, 3276-3281 (2013).

7. E Filipov, K Liu, T Tachi, M Schenk, G Paulino, Bar and hinge models for scalable analysis of origami. Int. J. Solids Struct. 124, 26-45 (2017).

8. N Nayakanti, S H Tawfick, A J Hart, Twist-coupled kirigami cells and mechanisms. Extrem. Mech. Lett. 21, 17-24 (2018).

9. K Liu, L S Novelino, P Gardoni, G H Paulino, Big influence of small random imperfections in origami-based metamaterials. Proc. Royal Soc. A: Math. Phys. Eng. Sci. (2020).

Example 2: Stretchable Origami Robotic Arm with Omnidirectional Bending and Twisting Inspired by the embodied intelligence observed in the octopus arms, we introduce magnetically controlled origami robotic arms based on Kresling patterns for multimodal deformations including stretching, folding, omnidirectional bending, and twisting. The highly integrated motion of the robotic arms is attributed to the inherent features of the reconfigurable Kresling unit, whose controllable bistable deploying/folding and omnidirectional bending can be achieved through precise magnetic actuation. We investigate single and multiple unit robotic systems, the latter exhibiting higher biomimetic resemblance to actual octopus' arms. We start from the single Kresling unit to delineate the working mechanism of the magnetic actuation for deploying and bending from the folded unit. The two-unit Kresling assembly demonstrates the basic integrated motion that combines omnidirectional bending with deployment. The four-unit Kresling assembly constitutes a robotic arm with a larger omnidirectional bending angle and stretchability induced from the deployable unit. With the foundation of the basic integrated motion, scalability of Kresling assemblies is demonstrated through distributed magnetic actuation of double-digit number of units, which enables robotic arms with sophisticated motions such as continuous stretching and contracting, reconfigurable bending, and multi-axis twisting. Such complex motions allow for functions mimicking octopus arms that grasp and lift objects. The Kresling robotic arm with non-contact actuation provides a distinctive mechanism for applications that require synergistic robotic motions for navigation, sensing, and interaction with objects in environments with limited or constrained access. Based on the small-scale Kresling robotic arms, medical devices such as tubes and catheters can be developed in conjunction with endoscopy, intubation, and catheterization procedures using the functionalities of object manipulation and motion under remote magnetic control.

Introduction

The octopus quickly reconfigures its arms to perform highly integrated tasks such as swimming, walking, and preying. Inspired by such soft-bodied cephalopod biosystem, we engineer compliant origami robotic arms to achieve multimodal deformations that integrate stretching, folding, omnidirectional bending, and twisting for functions such as grasping and lifting objects by means of precise magnetic actuation. The remote magnetic field control allows distributed actuation of the multiple degree-of-freedom robotic system for complex motions to achieve the aforementioned shape-changing capabilities and functionalities. The origami robotic arms with untethered control are applicable to biomedical devices and morphing mechanisms in environments with limited access.

Compared to traditional robotic arms where rigid links are connected by joints to provide rotational and translational degrees of freedom (DOF), the soft counterparts in cephalopods, for example octopus arms, exhibit intriguing features such as large and continuous deformations, adjustable compliance, and agile motions for moving and preying (1). Inspired by such biosystems, compliant mechanisms such as foldable origami has been explored. Origami is a paper-folding technique that reshapes planar materials or structures into intricate three-dimensional (3D) architectures in various scales for robotic motions (2, 3) that can be applied to engineering fields including morphing structures (4-7), biomedical devices (8, 9), aerospace (10, 11), and electronics (12-14). Different origami mechanisms for robotic arms have been studied to achieve motions such as contraction (15, 16), deployment (17-19), bending (20, 21), and twisting (22, 23). These motions are demonstrated for various functions such as object grasping and biopsy (24-28). However, most existing origami robotic arms' motions are hindered by limited DOFs such as contraction/deployment-only (29), single-directional bending (30), and bidirectional bending (31). Although some systems are developed to have limited integrated motions with multiple DOF, they generally rely on multiple bulky actuators and/or wired driving force such as motors (22, 23, 32) and pneumatic pumps (33), which significantly limit the operation flexibility and versatility of the robotic arm in harsh environments with limited human and machine access. Motivated by these existing problems, a remotely actuated origami mechanism that can provide agile multi-DOF deformation for integrated large contraction/deployment, omnidirectional bending, and twisting is highly desired.

Figure 27A:
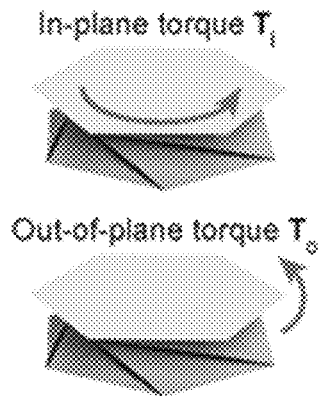
FIG. 27A-27I show actuation mechanisms of magnetic Kresling unit for folding/deploying, bidirectional bending, and omnidirectional bending. (27A) Folding/deploying and bending deformation modes of Kresling origami induced by in-plane and out-of-plane torques, respectively. (27B) Mechanical characterization of the folding and deploying processes. Images show the folded unit (stable state [0]) and deployed unit (stable state [1]). (27C) Mechanical characterization of the bending behavior. Dots are from experimental measurements, fitted by a polynomial function. Insets are images of a unit with different bending angles. (27D) Magnetic Kresling with programmed inclined magnetization (60°) for both folding/deploying and omnidirectional bending. (27E) Actuation mechanism of folding/deploying induced by the in-plane magnetization $M_i$ and in-plane magnetic field B. (27F) Phase diagram showing the magnetic field conditions for switching the Kresling unit from the folded state (stable state [0]) to the deployed state (stable state [1]). Dots are from experimental measurements, fitted by a polynomial function. (27G) Actuation mechanism of bidirectional bending induced by the in-plane magnetization $M_i$ and out-of-plane magnetic field B. (27H) Actuation mechanism of omnidirectional bending induced by the out-of-plane magnetization $M_o$ and in-plane magnetic field B. (27I) Polar plot and experimental images showing the bending angles in all directions. The applied magnetic field is perpendicular to the axial direction of the undeformed unit. The grey area denotes the conditions when the folded unit deploys.
Figure 27B:
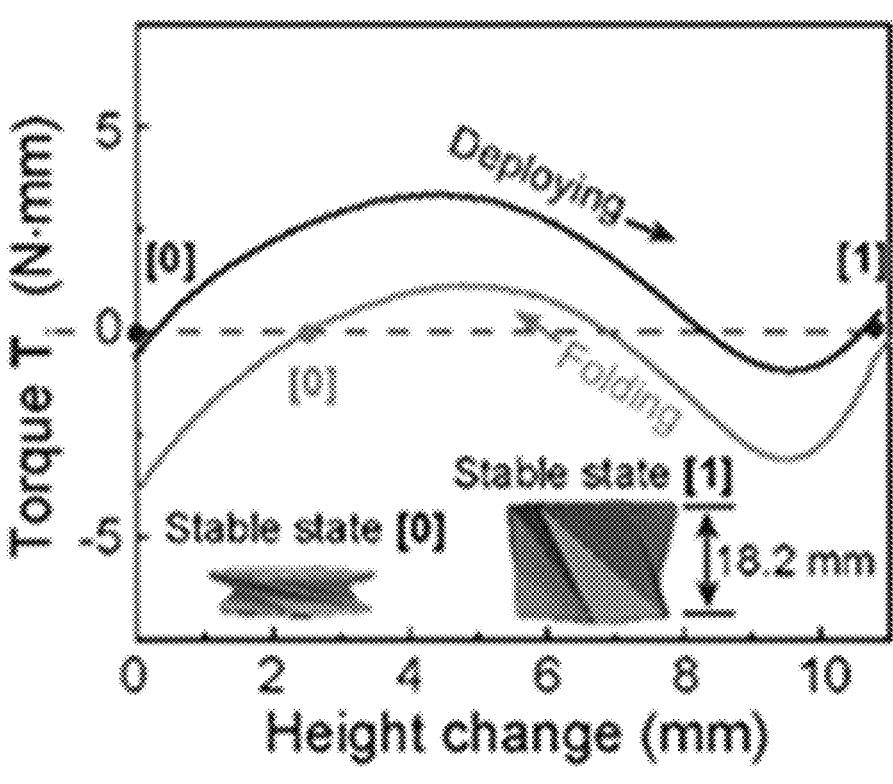
Figure 27C:
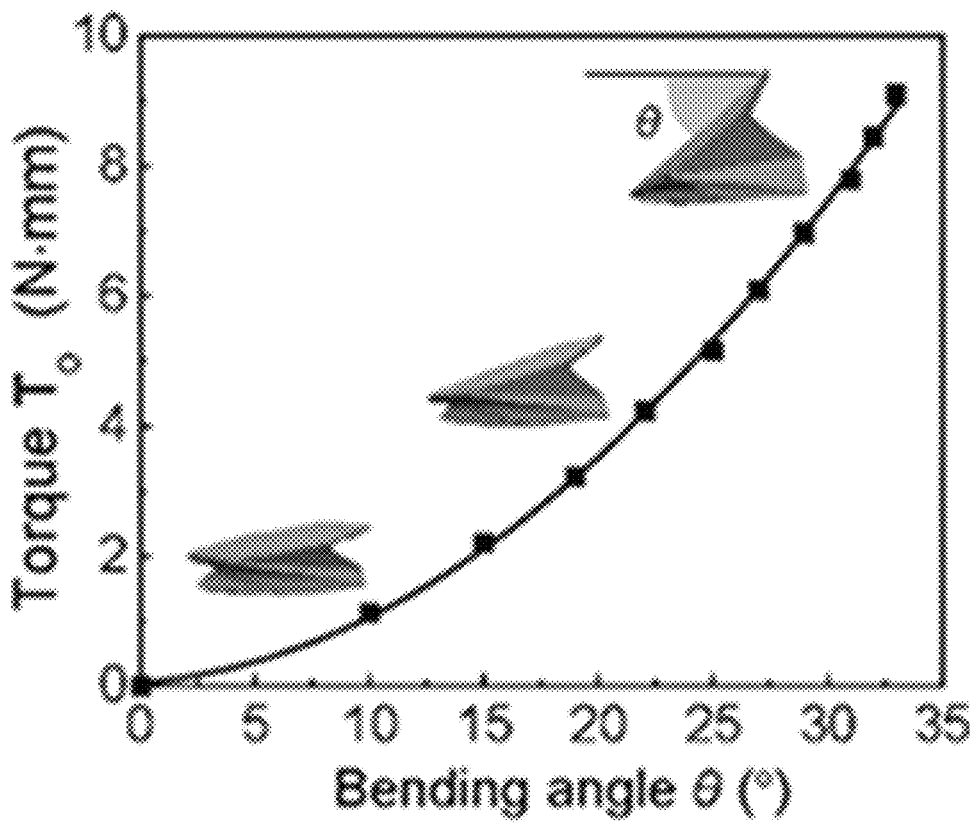

Kresling origami, created from buckling of thin shell cylinders (34, 35), is an ideal building block for the origami robotic arm due to its inherent capability of multimodal deformation that provides deploying/folding and bending. As shown in FIG. 1A, the folding/deploying is induced by an in-plane torque $T_i$ and the bending is induced by an out-of-plane torque $T_o$. In this paper, in-plane and out-of-plane are defined with respect to the plane of the bottom hexagonal plane, where the Kresling unit is fixed. The bistable Kresling origami with the stable folded state [0] and the stable deployed state [1] is achieved by the geometrical design (36) (FIG. 32). Under application of a positive in-plane torque (counterclockwise direction), the folded unit (stable state [0]) gradually deploys with the increased torque and snaps to the stable state [1] after it overcomes the energy barrier (FIG. 27B). Similarly, the deployed unit can fold back to the stable state [0] under a negative torque (FIG. 33). When an out-of-plane torque is applied to the top hexagon of the Kresling unit, it bends with an angle of 6, defined as the angle between the horizontal direction and the top hexagon (FIG. 27C and FIG. 34). The bending increases with the applied out-of-plane torque and has a maximum value due to the geometric limit. As discussed above, the direction and plane of the applied torque together determine the Kresling origami's deformation mode: folding/deploying or bending. To realize fast-switchable deformation modes, we introduce the magnetic actuation (37-40) to effectively and remotely control the instantaneous shift of the torque direction and torque plane for highly integrated complex motions, which haven't been achieved by conventional actuation strategies (31, 32). With delicate designs of the magnetic Kresling structures and precise controls of the applied magnetic field, origami robotic arms with integrated multimodal deformations for large contraction/deployment, omnidirectional bending, and twisting are demonstrated in the following sections. Meanwhile, magnetic actuation enables small-scale robotic arms with the capability of flexible omnidirectional bending and integrated motions, allowing for the development of medical devices in confined biomedical environments such as stomach, intestine, trachea, and bronchi.

Multimodal Deformation of Kresling Unit Under Magnetic Actuation

Figure 27D:
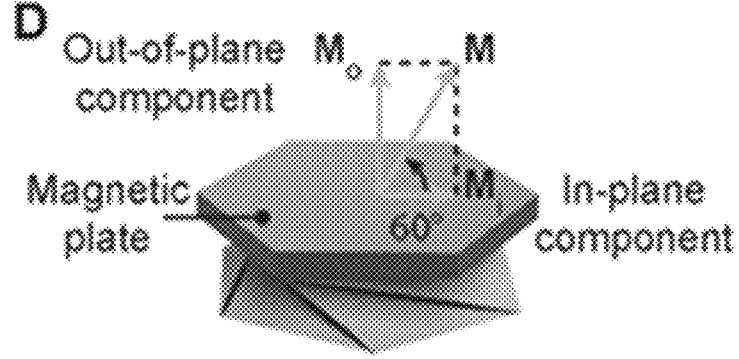
Figure 27E:
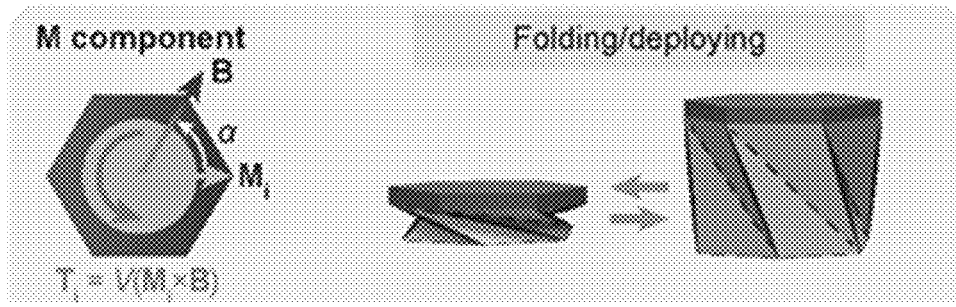
Figure 27F:
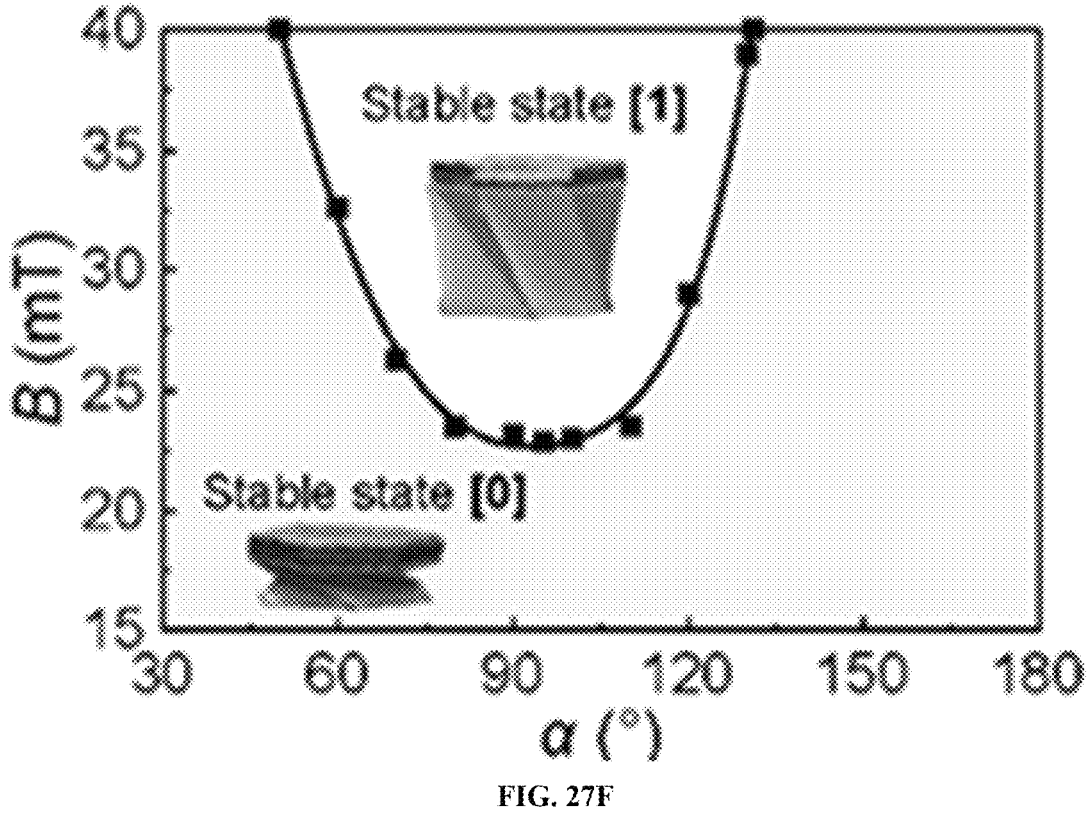
Figure 27G:
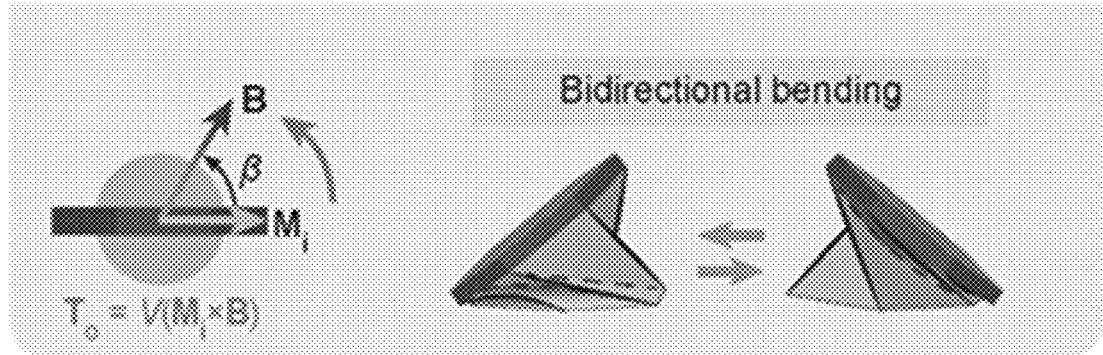
Figure 27H:
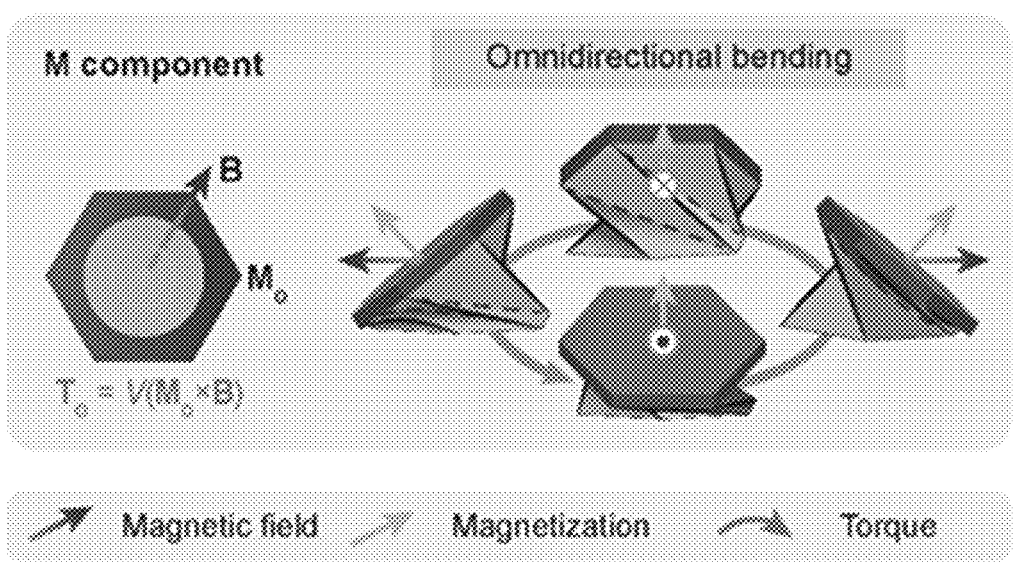
Figure 27I:
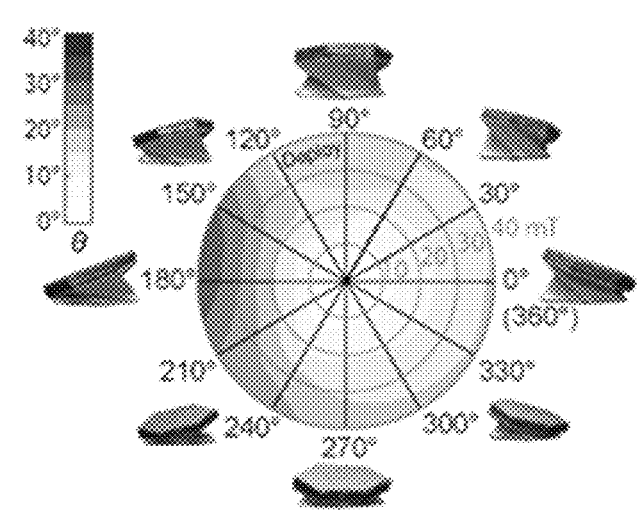
Figure 36:
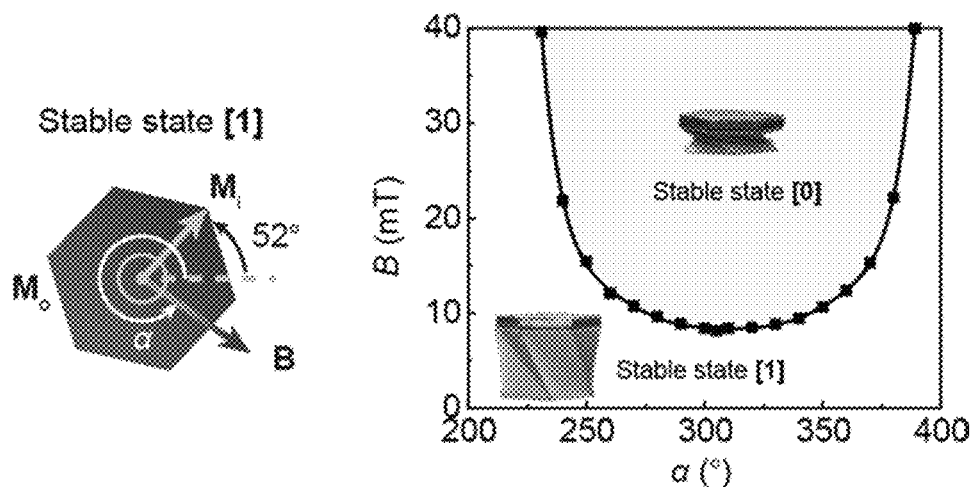

Here, we use the magnetic actuation to provide the torques for both folding/deploying and omnidirectional bending of the Kresling unit by simply attaching a magnetic plate to its top plane and actuating it under well-controlled 3D magnetic fields (36) (FIG. 35). A magnetic torque is generated when the magnetization of the magnetic plate tries to align itself with the applied magnetic field. Once the magnetization is set, the direction and intensity of the resultant torque can be controlled by tuning the direction and intensity of the applied magnetic field. FIG. 27D shows an example of the magnetic Kresling unit with an inclined magnetization that is 60° with respect to the Kresling unit's top plane. In this case, the Kresling unit can provide both folding/deploying and omnidirectional bending under different designed magnetic fields B as the magnetization M has both in-plane magnetization component $M_i$ and out-of-plane magnetization component $M_o$. FIG. 27E illustrates the mechanism of folding/deploying behavior of the Kresling unit which is attributed to the in-plane magnetization $M_i$ under an in-plane magnetic field B, with the initial angle between $M_i$ and B to be $\alpha$. It results in an in-plane torque $T_i=V$ ($M_i \times B$) to fold or deploy the unit (Movie S1), where V is the volume of the magnetic plate. The phase diagram in FIG. 27F dictates the experimental conditions for the Kresling unit to deploy from the stable state [0] (orange region) to the stable state [1] (white region), where B is the intensity of B. Additionally, the magnetic field conditions for the Kresling unit to fold from the stable state [1] to the stable state [0] are shown in FIG. 36. The in-plane magnetization $M_i$ can also provide bidirectional bending under an out-of-plane magnetic field B, as shown in FIG. 27G. When B is applied with an initial angle of $\beta$ to $M_i$, the out-of-plane torque $T_o=V$ ($M_i \times B$) leads to bidirectional bending of the Kresling unit (FIG. 27G). The omnidirectional bending deformation relies on an out-of-plane magnetization component $M_o$ as shown in FIG. 27H. Since out-of-plane magnetic torques $T_o=V$ ($M_o \times B$) can be generated by B in any directions that are not aligned with M., the bending direction of the Kresling unit is determined by the field direction, which is omnidirectional (Movie S1). It should be noted that if the magnetic plate only possesses the out-of-plane magnetization, the bending angle is homogeneous under the applied in-plane sweeping magnetic field. With the 60° inclined magnetization (coupled in-plane and out-of-plane magnetizations), the omnidirectional bending angle of the Kresling unit is shown in FIG. 27I. Note that the in-plane magnetization component $M_i$ could affect the bending angle when the in-plane B sweeps with a constant intensity (10 mT to 40 mT with a step of 10 mT). With an increasing magnetic field intensity, $\theta$ increases in all directions but the bending towards 1800 is higher due to the influence of $M_i$. When the applied magnetic field further increases and the in-plane magnetic torque reaches a critical value, the unit may deploy under certain magnetic field conditions denoted by the grey region in FIG. 27I. The inhomogeneous bending angle can be compensated by applying a varying magnetic field accordingly. Additionally, the bending angle can be enlarged by adjusting the angle between $M_o$ and B (FIG. 37).

Integrated Motion of Omnidirectional Bending and Deploying

Figure 28A:
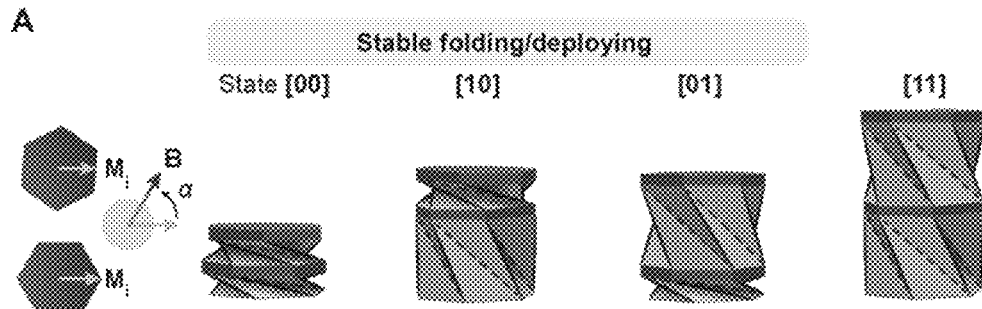
FIGS. 28A-28J show integrated motion of two-unit magnetic Kresling assemblies. (28A) State shifting of a two-unit Kresling assembly with in-plane magnetizations $M_i$ and in-plane magnetic field B. A binary code is used to represent the state of the assembly, with the first and second digits corresponding to the bottom and top units, respectively. (28B) Phase diagram showing the magnetic field conditions for the structure to switch from state [00] to states [10], [01], and [11]. Dots are from experimental measurements, fitted by a polynomial function. (28C) Bidirectional bending of the two-unit Kresling assembly with in-plane magnetizations $M_i$ and out-of-plane magnetic field B. (28D) Experimental measurements of the bidirectional bending angle. Dots are from experimental measurements, fitted by sinusoidal functions. (28E) Omnidirectional bending of a two-unit Kresling assembly with out-of-plane magnetizations $M_o$ and in-plane magnetic field B, and (28F) polar plot of the experimental bending angle measurement. (28G-28J) Multimodal deformation of a two-unit Kresling assembly with both in-plane and out-of-plane magnetizations and in-plane magnetic field B, showing (28G) omnidirectional bending at state [00] and (28I) omnidirectional bending at state [01]. (28H-28J) Experimental measurements of the bending angle (28H) polar plot at state [00] and (28J) polar plot at state [01]. The grey region in (28J) denotes the conditions when the top unit folds.
Figures 28B, 28C:
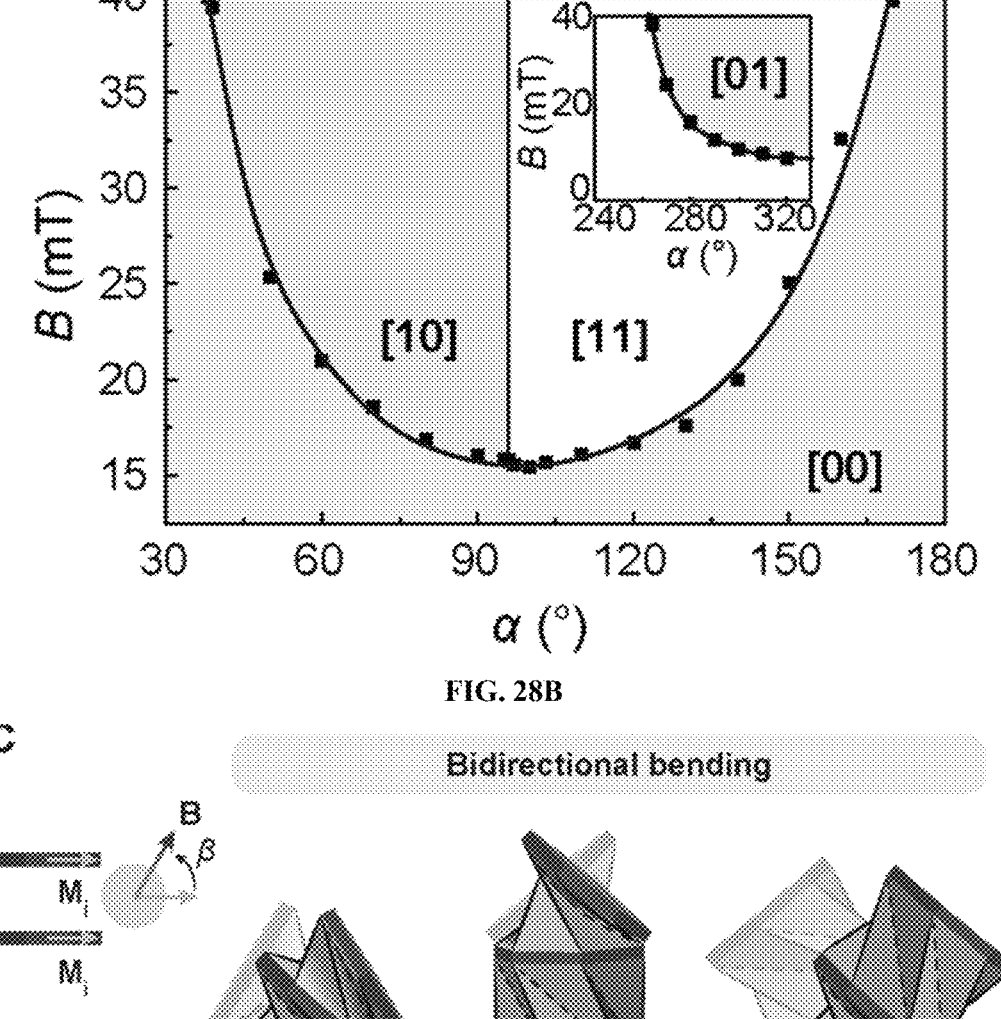
Figure 28D:
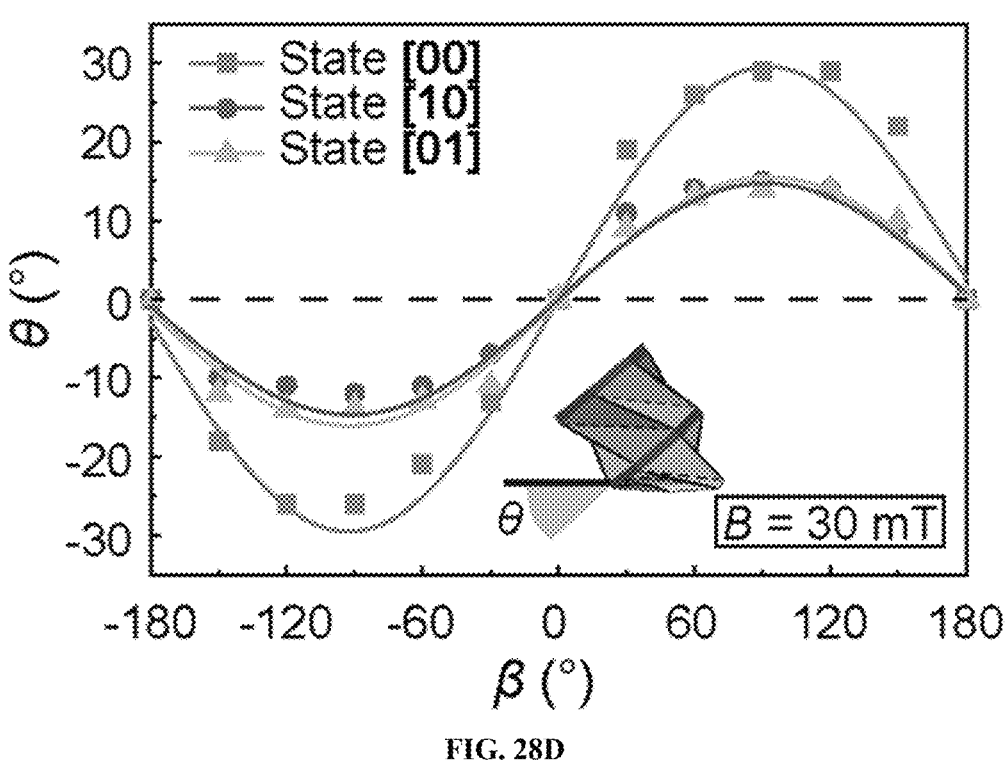
Figure 28E:
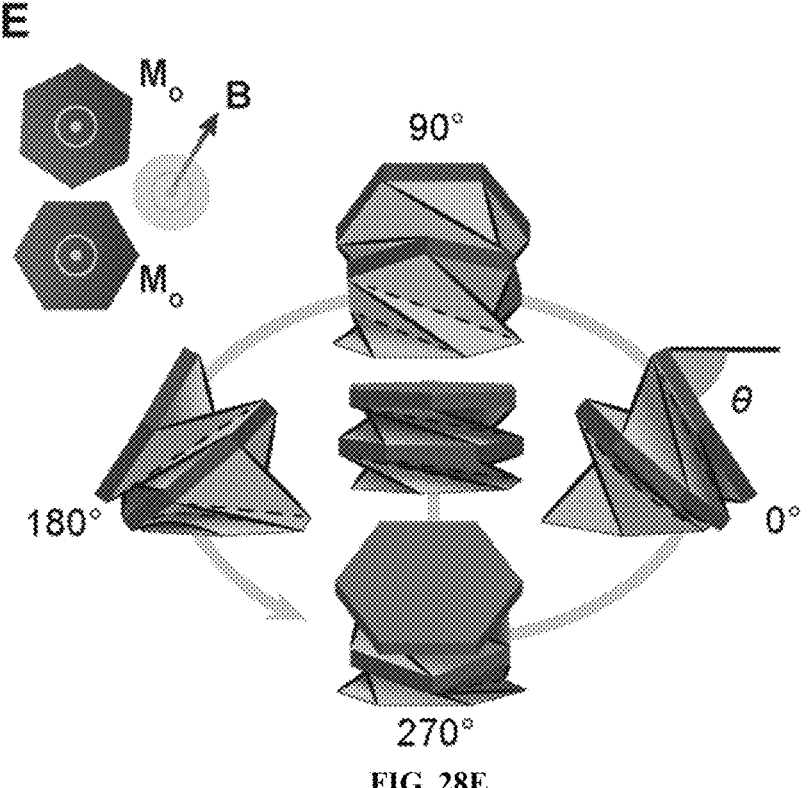
Figure 28F:
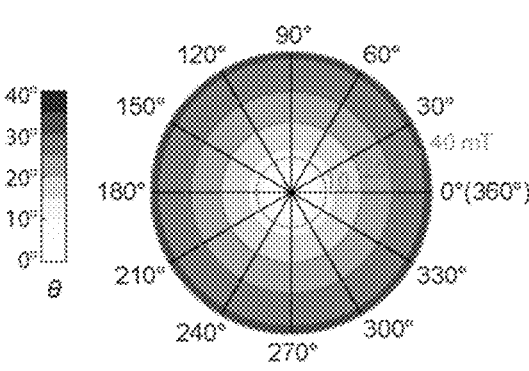

Although the folded Kresling unit can effectively achieve either deploying or bending, it cannot deploy and bend at the same time. Here, we use two-unit Kresling assemblies to show the basic concept of integrated motion that combines Kresling bending with deployment, implemented by the distributed actuation of the magnetic field. In FIG. 28, three two-unit Kresling assemblies with different magnetization combinations are demonstrated by attaching two magnetic plates to the top of two Kresling units. FIG. 28A shows the first magnetization combination, where both magnetic plates are programmed with in-plane magnetizations $M_i$ along the same rightward direction at the all-folded state [00]. Note that the binary code represents the state of the assembly, with the first and second digits corresponding to the bottom and top units, respectively. When an in-plane magnetic field B is applied with an angle of $\alpha$ to the rightward direction ($M_i$ direction at state [00]), in-plane magnetic torques are generated on both magnetic plates, driving the assembly to transform between four stable states via stable folding and deploying (FIG. 38). From the phase diagram in FIG. 28B, starting from stable state [00], stable states [10] and [11] can be directly reached when designing magnetic field intensity B and direction $\alpha$. The stable state [01] can be achieved following stable state [11] (FIG. 39). Bidirectional bending of states [00], [10], and [01] under an out-of-plane magnetic field with an angle of $\beta$ to the horizontal direction is shown in FIG. 28C, with [10] and [01] revealing integrated bending and deploying deformations (Movie S2). Note that the deployed unit cannot bend under the applied magnetic field. FIG. 28D shows the experimental measurements of the bending angles (states [00], [10], and [01]) under a 30 mT magnetic field with the varying directions ($\beta$ ranging from $-180°$ to $180°$). The bending angle $\theta$ is defined as the angle between the horizontal direction and the folded unit's top plane, showing a sinusoidal relation with respect to $\beta$. States [01] and [10] exhibit the similar bending behavior with a maximum angle about 15°, as only one folded unit contributes to the overall bending, and state [00] shows larger bending with a maximum bending angle about 30° as the bending is accumulated from two folded units.

Figure 28G:
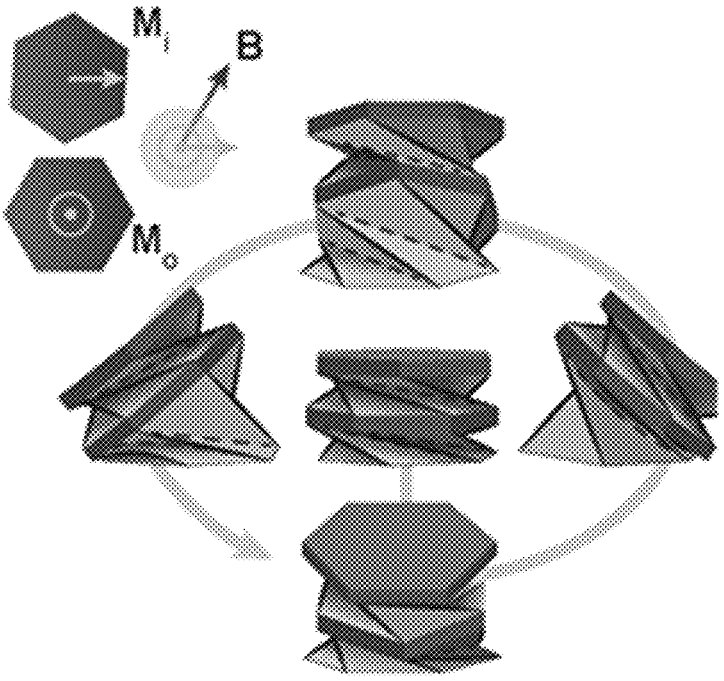
Figure 28H:
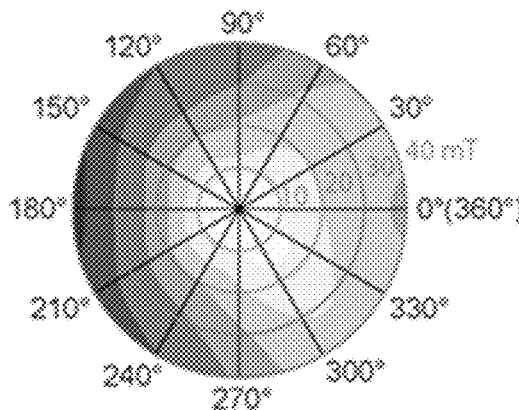
Figure 28I:
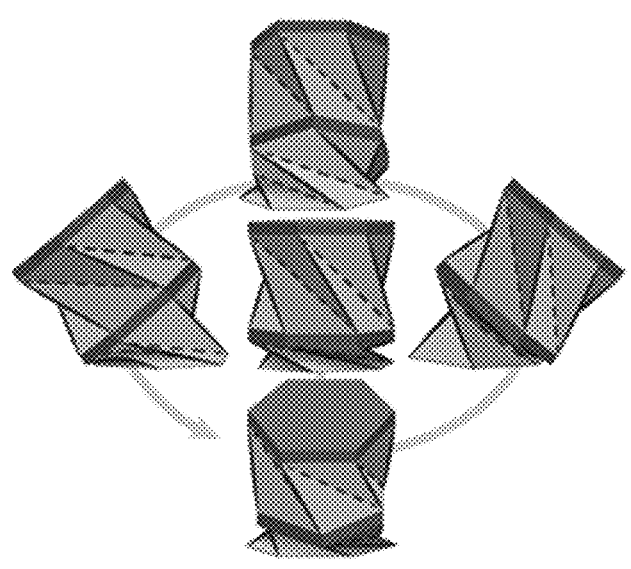
Figure 28J:
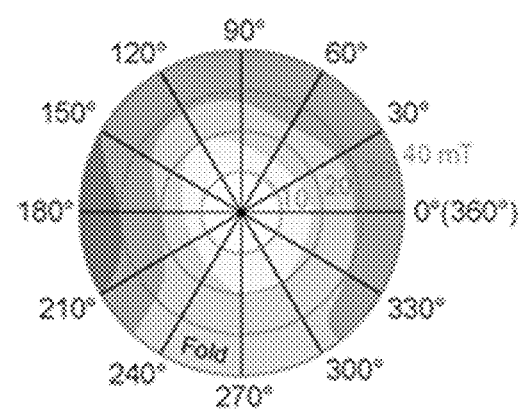

The second magnetization combination of the two-unit Kresling assembly has both magnetic plates programmed with out-of-plane magnetizations $M_o$ (FIG. 28E) for omnidirectional bending. Under the applied magnetic field that sweeps in-plane, a homogeneous bending is demonstrated in all directions with a maximum bending angle of 31° as shown by the polar plot in FIG. 28F. The bending angle can be enlarged by increasing magnetic field intensity B or adjusting the angle between $M_o$ and B (FIG. 40). To integrate omnidirectional bending with folding/deploying deformation in the two-unit Kresling assembly, the third magnetization combination is shown in FIG. 28G, with the bottom Kresling unit possessing an out-of-plane magnetization $M_o$ for omnidirectional bending and the top Kresling unit possessing an in-plane magnetization $M_i$ for folding/deploying (FIG. 41). The omnidirectional bending angles of state [00] in FIG. 28G and state [01] in FIG. 28I under in-plane sweeping magnetic fields are characterized in FIG. 28H and FIG. 28J, respectively. Maximum bending angles of 37° (state [00]) and 28° (state [01]) towards the 180° direction are obtained. In both cases the bending is not homogeneous due to the influence of $M_i$, which can be compensated by applying a varying magnetic field. Increasing the magnetic field can lead to larger bending angles but may also cause folding of the top unit at state [01] denoted by the grey region in FIG. 28J.

Omnidirectional Bending and Deploying of a Four-Unit Kresling Robotic Arm

Figure 29A:
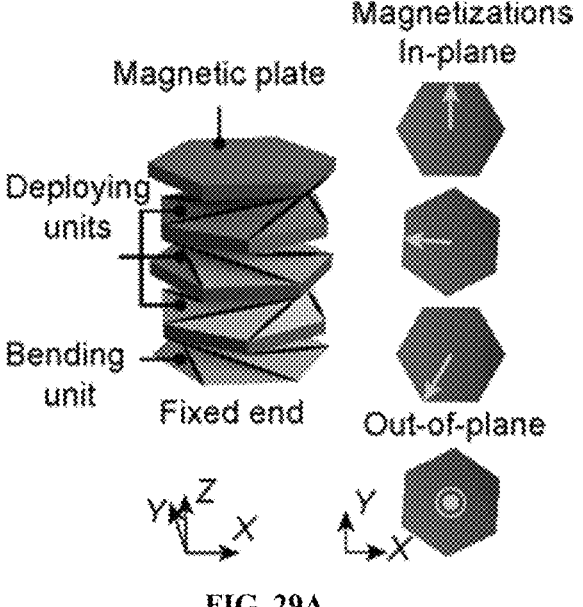
FIGS. 29A-29E show omnidirectional bending and deploying of a four-unit Kresling robotic arm with large bending angles. (29A) Schematic design and magnetization distribution of the four-unit robotic arm. The top three units are used for deploying in all directions, and the bottom unit is used for omnidirectional bending. (29B) An example magnetic field profile of the robotic arm for bending towards 0° direction and then deploying its top red unit. The insets show the experimental results of the four-unit robotic arm at folded state (bending only) and deployed state (bending with deploying). (29C) Experimental bending angle characterization of the robotic arm towards 0° direction without deployed unit and with deployed red unit. (29D) Experimental results from top view of the robotic arm omnidirectional bending with one deployed unit. Colored contour boxes represent yellow, blue, and red units deployed in the eight directions. A binary code is used to represent the state of the entire robotic arm from the bottom to the top units. (29E) Experimental results from front view of the undeformed arm and bending and stretching toward 0° and 180°. Scale bars: 10 mm.
Figure 29B:
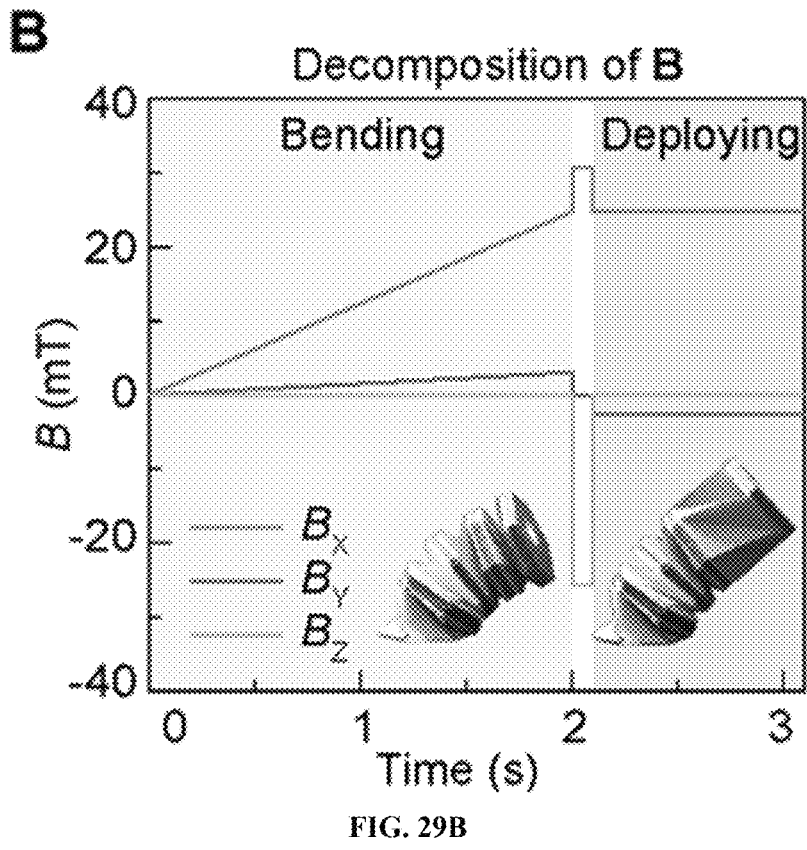
Figure 29C:
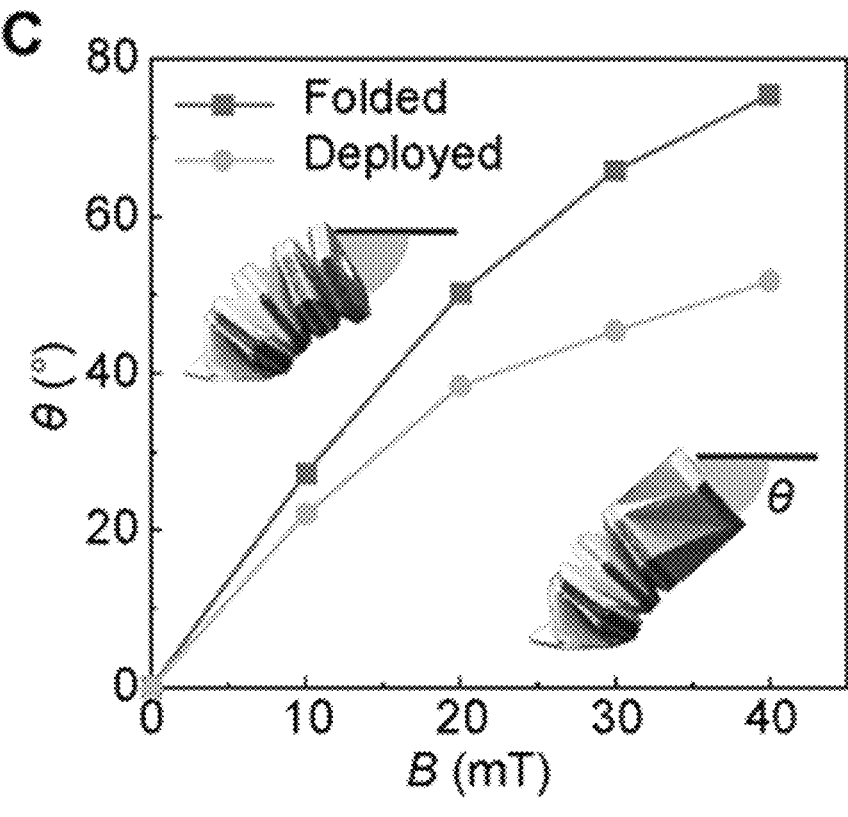
Figure 29D:
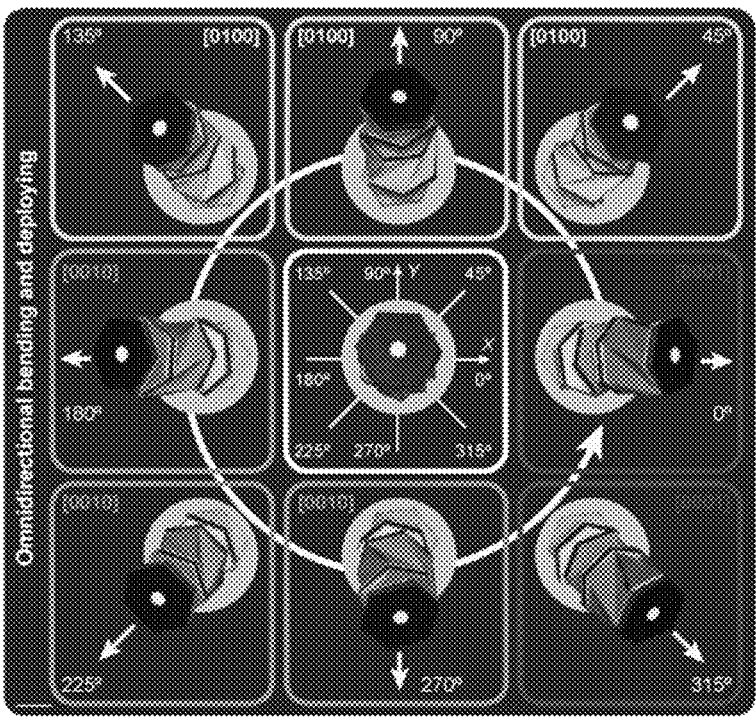
Figure 29E:
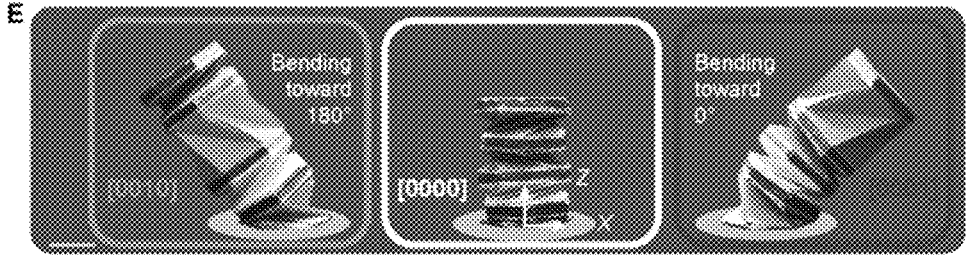

Based on the concept of integrated deformation with combined omnidirectional bending and deployment of the Kresling units, we next design a Kresling robotic arm consisting of four Kresling units as shown in FIG. 29A to achieve much larger bending angles with deployability. The green unit with a fixed bottom and an out-of-plane magnetization allows the omnidirectional bending capability, and it is called the bending unit (Movie S3). Then, three units (yellow, blue, and red units) with alternating crease directions are added to the axial direction of the robotic arm to provide deployability for the "stretching" behavior of the arm, and they are regarded as the deploying units. Here, the yellow unit and the red unit can be deployed with clockwise torque, and the blue unit can be deployed with counterclockwise torque. The deploying units have in-plane magnetization directions to trigger selective deployment under different magnetic fields (Movie S3). Due to the accumulated deformation from multiple units, the four-unit robotic arm shows large onmidirectional bending and stretching. FIG. 29B shows an example magnetic field profile to bend and stretch the structure toward 0° direction (X-direction). A 25 mT magnetic field in XY-plane is first applied to bend the arm toward 0° direction. The white marker on the top of the robotic arm illustrates a precisely controlled bending direction toward 0°. Then an impulse magnetic field (40 mT) parallel to the top magnetic plate is applied to quickly deploy the red unit (See Supplementary information, Coordinate Transformation). To keep the bending direction after stretching, another 25 mT magnetic field that is different from the bending magnetic field is applied as the plate's magnetization direction changes during the deployment (FIG. 29B). FIG. 29C characterizes the 0°-direction bending angle 9, defined as the angle between the deformed top plane and the horizontal direction at the robotic arm's all-folded state (bending only) and deployed state (bending with deploying). With increased magnetic field intensity, the robotic arm shows large bending angles for both states with maximum values of 75° (Bending only) and 52° (bending with deploying). The same bending and stretching of the robotic arm are omnidirectional based on rationally designed magnetic field profiles (FIG. 29D). B is a vector field that can be decomposed into three Cartesian directions ($B_X$, $B_Y$, $B_Z$). With the designed deploying units' crease directions and magnetizations, a specific deploying unit (denoted by the colored contour box) can be deployed when the arm bends to different directions (FIG. 29E). Detailed magnetic field profiles to bend and stretch the robotic arms to eight different directions are shown in FIG. 42, and the omnidirectional bending angles at the all-folded state and deployed state are characterized by the polar plots in FIG. 43.

Octopus-Like Robotic Arms for Stretching, Bending, and Twisting Motions

Figure 30A:
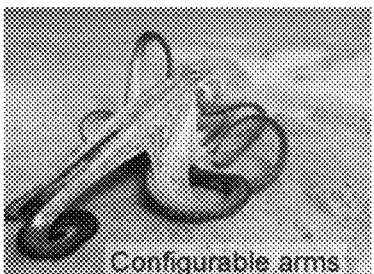
Figure 30B:
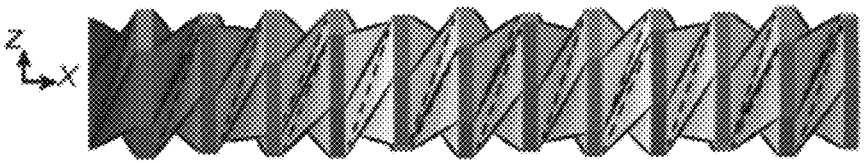
Figure 30E:
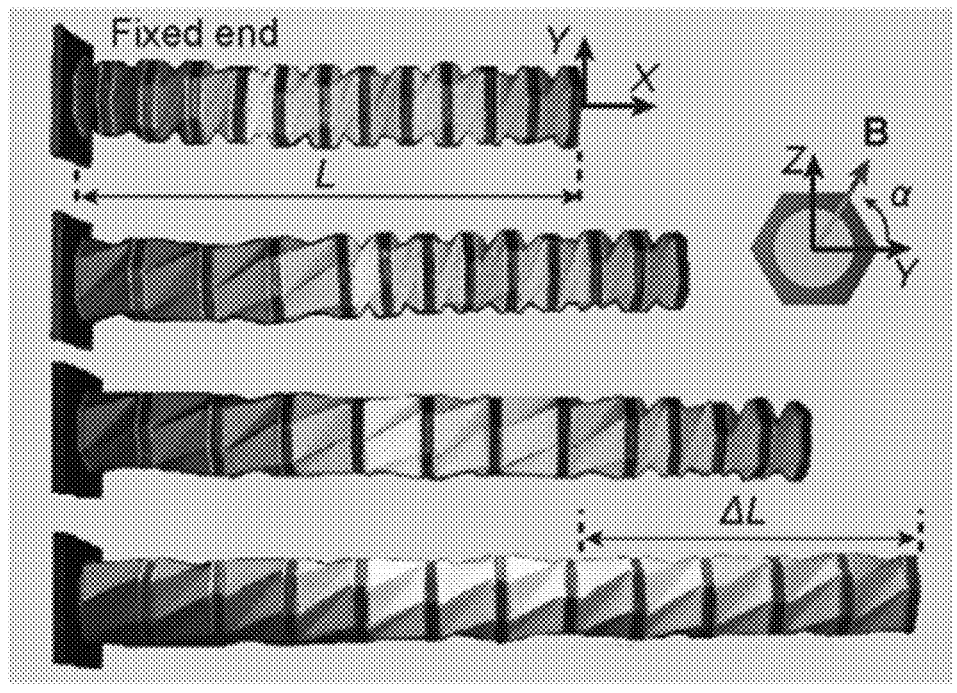

The octopus arms' configurability to stretch, contract, bend, and twist permits multifunctional motions such as walking, swimming, and preying (FIG. 30A). Inspired by this biosystem, we engineer a twelve-unit Kresling robotic arm with all in-plane magnetizations as shown in FIG. 30B. The magnetizations of the magnetic plates are programmed to be in the same negative Z-direction at the all-folded state under compression (FIG. 44). Due to structural resistance of Kresling units and the repulsive forces between the magnetic plates, each unit expands slightly from the flat-folded state, leading to distributed magnetizations as shown by the side view in FIG. 30C. One fascinating feature of octopus arms is the controllable stretching and bending which allows for a tunable bending point to reach and interact with the prey as shown in FIG. 30D (41). Our twelve-unit robotic arm can achieve controllable deployment with integrated bending to mimic the motion of the octopus arm. FIG. 30E illustrates reversible stretching and contracting (Movie S5). During the stretching motion, the units can be deployed sequentially from left to right under a counterclockwise rotating magnetic field parallel to the fixed end (YZ-plane). The magnetic field direction is defined by a relative angle $\alpha$ to the Y-direction in the YZ-plane. FIG. 30F illustrates that the stretching ratio $\Delta L/L$ has a linear relationship with the rotation of the magnetic field with a maximum value of 66.7%, where L is the initial length of the robotic arm and $\Delta L$ is the length change. The robotic arm can contract back to the folded state under a clockwise rotating magnetic field. Due to the unevenly distributed magnetizations at the deployed state (FIG. 45), the contraction process of the units is not sequential. However, the arm's total length can still linearly decrease with respect to time and the rotational magnetic field. Its contracting speed is approximately the same as the stretching speed (FIG. 46).

Figure 30G:
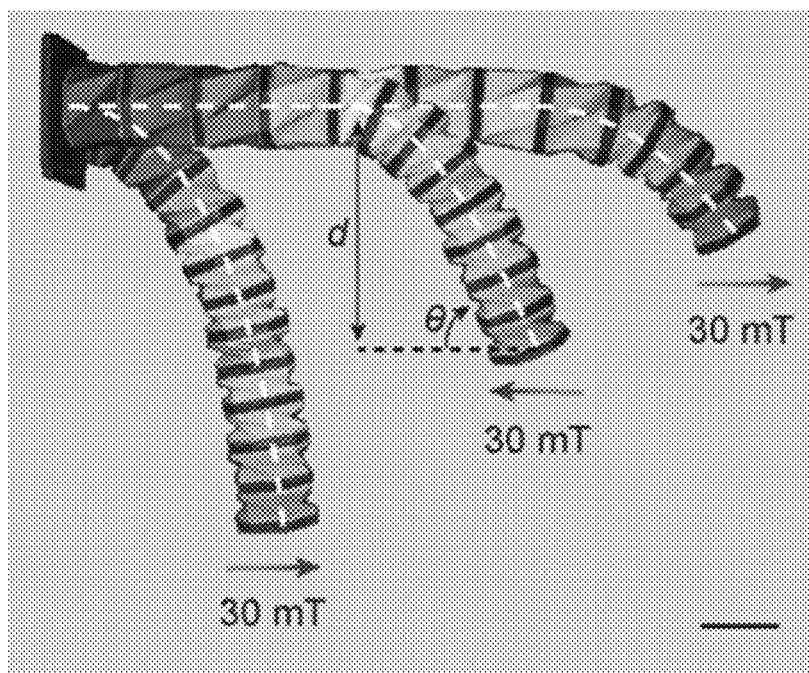
Figures 30F, 30H:
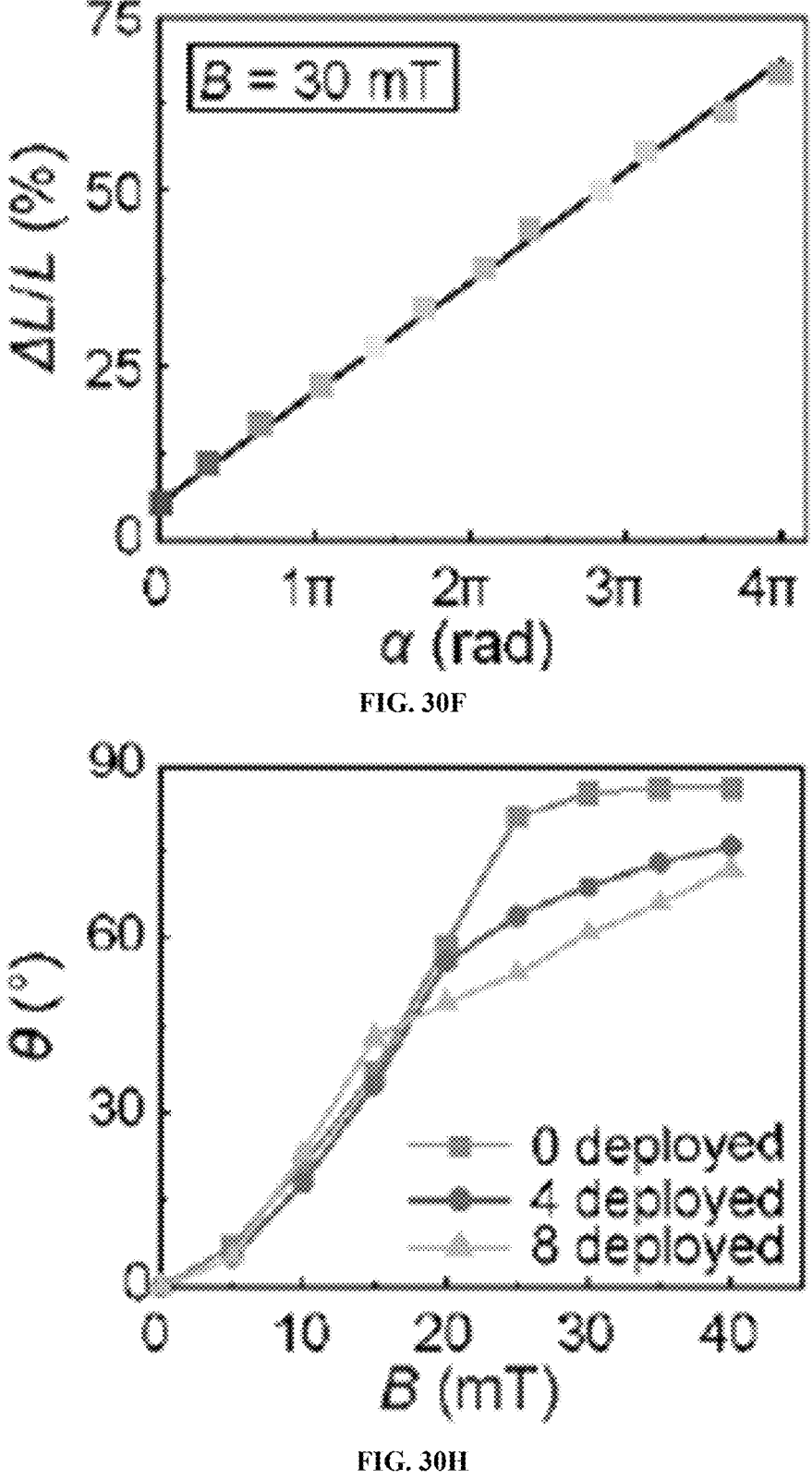

The robotic arm can also induce bending deformation under a different magnetic field as shown in FIG. 30G. The bending behavior of the robotic arm can be easily coupled with a selective number of deployed units (0 unit, 4 units, and 8 units in FIG. 30G and Movie S5), which resembles the bending and stretching behaviors of the octopus arm (FIG. 30D). In this way, the overall length and stiffness of the bent arm is tunable. FIGS. 30H and 30I characterize the bending angle $\theta$ and normalized deflection (d/L) of the controllable bending with stretching. The bending angle $\theta$ is defined as the angle between the neutral axis at the free-end and horizontal direction, and the deflection d is defined as the vertical distance between the arm's two ends. As shown in FIG. 30H, with the increasing magnetic field to B=40 mT, $\theta$ increases and then reaches 72°, 76°, and 86° for three cases with 8, 4, 0 deployed units, respectively. Similarly, the number of the deployed unit notably influences the robotic arm's normalized deflection with a maximum value of 39.8%, 57.1%, and 79.4% for three cases with 8, 4, 0 deployed units as shown in FIG. 30I.

Figures 30K, 31A, 31B, 31C, 31D:
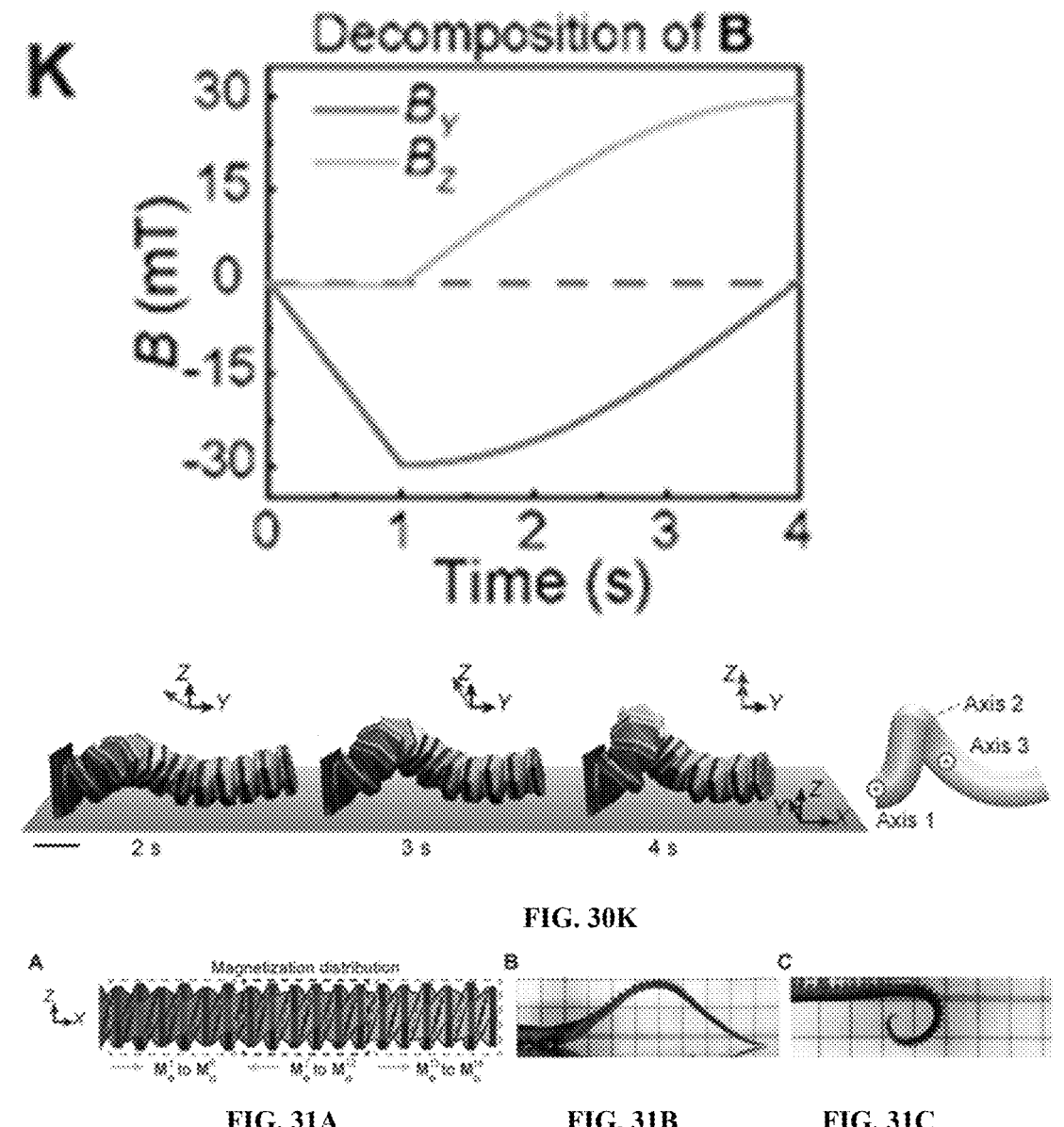

More interestingly, 3D out-of-plane shape reconfiguration of the robotic arm can be achieved through integrated bending and twisting motion under programmed magnetic fields. When applying a counterclockwise rotating magnetic field in XY-plane starting along the negative X-direction, the arm first bends in XY-plane and then twists out of plane while interacting with the ground (FIG. 30J). This bending-twisting is approximately divided into two segments with two different bending axes as denoted by blue and yellow in the 3D schematic in FIG. 30J. By changing the magnetic field to a clockwise rotating magnetic field in YZ-plane starting along the negative Y-direction, the arm first slightly contracts and then buckles out of the XY-plane with three bending axes as shown in FIG. 30K, leading to a different bending-twisting deformation with three segments (blue, yellow, and green in the 3D schematic). The morphology of twisting can be determined by the time-dependent B field.

Kresling robotic arms have demonstrated the capability of realizing multimodal deformation under magnetic control. By designing the magnetization distribution of the multi-unit robotic arm, more interesting highly integrated motions can be achieved. FIG. 31 shows an eighteen-unit octopus arm-like robotic arm that can induce omnidirectional bending to interact with objects. The eighteen out-of-plane magnetizations are programmed with alternating directions for every six units as illustrated in FIG. 31A. An octopus wiggles its arms to different curled shapes to circumvent obstacles, reach and get the prey (FIGS. 31B and 31C). To mimic the wavy motion in FIG. 31B by the robotic arm, a 35 mT magnetic field along the Y-direction (1 s) is first applied, and the arm morphs into a curled shape in XY-plane (FIG. 31D). Following by rotating the magnetic field in YZ-plane, the eighteen-unit arm realizes a dynamic omnidirectional bending (Movie S6). The curled octopus arm configuration in FIG. 31C can be realized and further explored for functions such as grasping and lifting objects. As demonstrated in FIG. 31E, a rotating magnetic field in the XY-plane is applied to curl the arm tip and grasp an object in 4s. Then the applied magnetic field is programmed to rotate about X-axis to lift the object in another 4s.

CONCLUDING

We have engineered multifunctional origami robotic arms for biomimetic multimodal deformations and motions with untethered actuation using magnetic fields. By means of synergistically designed Kresling origami assemblies and magnetic controls, several robotic arm designs are demonstrated with integrated deformations of folding, stretching, omnidirectional bending, and twisting. With control of robotic arm's agile motions, functional operations such as object grasping and lifting become feasible. The magnetic actuation allows untethered and ultrafast control of the robotic arm, and in the meantime makes small-scale devices possible (FIG. 47). The omnidirectional bending and integrated motions of demonstrated small-scale robotic arms (FIG. 48 and FIG. 49) can be used to develop medical devices for endoscopy, intubation, and catheterization with the functionalities of object manipulation and motion in 3D space. The Kresling robotic arm's integrated motions, together with the untethered and distributed magnetic actuation, provide an innovative strategy for functional operations such as navigating, sensing and interacting with objects in environments with limited access.

REFERENCES

1. Sumbre G, Gutfreund Y, Fiorito G, Flash T, & Hochner B (2001) Control of octopus arm extension by a peripheral motor program. *Science* 293(5536):1845-1848.
2. Rus D & Tolley M T (2018) Design, fabrication and control of origami robots. *Nature Reviews Materials* 3(6):101-112.
3. Kotikian A, et al. (2019) Untethered soft robotic matter with passive control of shape morphing and propulsion. *Science Robotics* 4(33).
4. Zhao Z, et al. (2017) Origami by frontal photopolymerization. *Science advances* 3(4):e1602326.
5. Zhao Z, et al. (2018) 3D printing of complex origami assemblages for reconfigurable structures. *Soft Matter* 14(39):8051-8059.

6. Zhang Y, et al. (2015) A mechanically driven form of Kirigami as a route to 3D mesostructures in micro/nanomembranes. *Proceedings of the National Academy of Sciences* 112(38):11757-11764.

7. Yan Z, et al. (2016) Controlled mechanical buckling for origami-inspired construction of 3D microstructures in advanced materials. *Advanced functional materials* 26(16):2629-2639.

8. Ahmed A R, Gauntlett O C, & Camci-Unal G (2020) Origami-Inspired Approaches for Biomedical Applications. *ACS Omega* 6(1):46-54.

9. Leong T G, et al. (2009) Tetherless thermobiochemically actuated microgrippers. *Proceedings of the National Academy of Sciences* 106(3):703-708.

10. Zirbel S A, et al. (2013) Accommodating thickness in origami-based deployable arrays. *Journal of Mechanical Design* 135(11).

11. Chen T, Bilal O R, Lang R, Daraio C, & Shea K (2019) Autonomous deployment of a solar panel using elastic origami and distributed shape-memory-polymer actuators. *Physical Review* Applied 11(6):064069.

12. Nauroze S A, Novelino L S, Tentzeris M M, & Paulino G H (2018) Continuous-range tunable multilayer frequency-selective surfaces using origami and inkjet printing. *Proceedings of the National Academy of Sciences* 115(52):13210-13215.

13. Cheng Q, et al. (2013) Folding paper-based lithium-ion batteries for higher areal energy densities. *Nano letters* 13(10):4969-4974.

14. Jape S, et al. (2020) Self-foldable origami reflector antenna enabled by shape memory polymer actuation. *Smart Materials and Structures* 29(11):115011.

15. Li S, Vogt D M, Rus D, & Wood R J (2017) Fluid-driven origami-inspired artificial muscles. *Proceedings of the National academy of Sciences* 114(50):13132-13137.

16. Yasuda H, Tachi T, Lee M, & Yang J (2017) Origami-based tunable truss structures for non-volatile mechanical memory operation. *Nature communications* 8(1):1-7.

17. Kim S-J, Lee D-Y, Jung G-P, & Cho K-J (2018) An origami-inspired, self-locking robotic arm that can be folded flat. *Science Robotics* 3(16):eaar2915.

18. Filipov E T, Tachi T, & Paulino G H (2015) Origami tubes assembled into stiff, yet reconfigurable structures and metamaterials. *Proceedings of the National Academy of Sciences* 112(40):12321-12326.

19. Melancon D, Gorissen B, Garcia-Mora C J, Hoberman C, & Bertoldi K (2021) Multistable inflatable origami structures at the metre scale. *Nature* 592(7855):545-550.

20. Martinez R V, Fish C R, Chen X, & Whitesides G M (2012) Elastomeric origami: programmable paper-elastomer composites as pneumatic actuators. *Advanced functional materials* 22(7):1376-1384.

21. Paez L, Agarwal G, & Paik J (2016) Design and analysis of a soft pneumatic actuator with origami shell reinforcement. *Soft Robotics* 3(3):109-119.

22. Liu T, Wang Y, & Lee K (2017) Three-dimensional printable origami twisted tower: Design, fabrication, and robot embodiment. *IEEE Robotics and Automation Letters* 3(1):116-123.

23. Santoso J & Onal C D (2020) An Origami Continuum Robot Capable of Precise Motion Through Torsionally Stiff Body and Smooth Inverse Kinematics. *Soft Robotics*.

24. Boyvat M, Koh J-S, & Wood R J (2017) Addressable wireless actuation for multijoint folding robots and devices. *Science Robotics* 2(8).

25. Li S, et al. (2019) A vacuum-driven origami "magic-ball" soft gripper. 2019 *International Conference on Robotics and Automation (ICRA)*, (IEEB), pp 7401-7408.

26. Salerno M, Zhang K, Menciassi A, & Dai J S (2016) A novel 4-DOF origami grasper with an SMA-actuation system for minimally invasive surgery. *IEEE Transactions on Robotics* 32(3):484-498.

27. Yim S, Gultepe E, Gracias D H, & Sitti M (2013) Biopsy using a magnetic capsule endoscope carrying, releasing, and retrieving untethered microgrippers. *IEEE Transactions on Biomedical Engineering* 61(2):513-521.

28. Faber J A, Arrieta A F, & Studart A R (2018) Bioinspired spring origami. *Science* 359(6382):1386-1391.

29. Hu F, Wang W, Cheng J, & Bao Y (2020) Origami spring-inspired metamaterials and robots: An attempt at fully programmable robotics. *Science Progress* 103(3): 0036850420946162.

30. Kim W, et al. (2019) Bioinspired dual-morphing stretchable origami. *Science Robotics* 4(36).

31. Pagano A, Yan T, Chien B, Wissa A, & Tawfick S (2017) A crawling robot driven by multi-stable origami. *Smart Materials and Structures* 26(9):094007.

32. Kaufmann J, Bhovad P, & Li S (2021) Harnessing the Multistability of Kresling Origami for Reconfigurable Articulation in Soft Robotic Arms. *Soft Robotics*.

33. Overvelde J T, et al. (2016) A three-dimensional actuated origami-inspired transformable metamaterial with multiple degrees of freedom. *Nature communications* 7(1):1-8.

34. Kidambi N & Wang K (2020) Dynamics of Kresling origami deployment. *Physical Review E* 101(6):063003.

35. Nayakanti N, Tawfick S H, & Hart A J (2018) Twist-coupled kirigami cells and mechanisms. *Extreme Mechanics Letters* 21:17-24.

36. Novelino L S, Ze Q, Wu S, Paulino G H, & Zhao R (2020) Untethered control of functional origami micro-robots with distributed actuation. *Proceedings of the National Academy of Sciences* 117(39):24096-24101.

37. Ze Q, et al. (2020) Magnetic Shape Memory Polymers with Integrated Multifunctional Shape Manipulation. *Advanced Materials* 32(4):1906657.

38. Miyashita S, Guitron S, Ludersdorfer M, Sung C R, & Rus D (2015) An untethered miniature origami robot that self-folds, walks, swims, and degrades. 2015 *IEEE International Conference on Robotics and Automation (ICRA)*, (IEEB), pp 1490-1496.

39. Wu S, et al. (2019) Symmetry-breaking Actuation Mechanism for Soft Robotics and Active Metamaterials. *ACS Applied Materials & Interfaces* 11(44):41649-41658.

40. Xu T, Zhang J, Salehizadeh M, Onaizah O, & Diller E (2019) Millimeter-scale flexible robots with programmable three-dimensional magnetization and motions. *Science Robotics* 4(29).

41. Yekutieli Y, Sumbre G, Flash T, & Hochner B (2002) How to move with no rigid skeleton? *Biologist* 49(6): 250-254.

42. Grubich J (2011) Octopus Arm and Sucker Kinematics.

SUPPLEMENTARY INFORMATION

Materials and Methods

1. Sample Fabrication

A. Kresling Pattern. The Kresling units used in the main text have the same geometry but two different sizes as shown in FIG. 32A and FIG. 32B. For the demonstrations of 12-unit and 18-unit robotic arms used in FIG. 30 and FIG. 31, the unit size is 75% of the units used in FIGS. 27-29. Both units are fabricated using Tant origami paper (0.14 mm thick) with an 80 W $CO_2$ laser cutter (Orion Motor Tech, China). The small-scale robotic arms use a different Kresling geometry (FIG. 32C) with a comparable cross-section dimension to an endotracheal intubation tube (FIG. 47). The small-scale units are fabricated using polypropylene film (0.08 mm thick) with a mechanical cutter (Cricut Maker, Cricut, Inc., USA). After the patterns are folded, 3M Scotch double-sided tape is used to attach the stiff top and bottom hexagons. Canson Mi-Teintes paper hexagons (0.2 mm thick) are used for the units in the main text and Mylar hexagons (0.13 mm thick) are used for the small-scale units. All fabricated units exhibit bistable properties, and we define the folded state and deployed state as state [0] and state [1], respectively.

B. Magnetic Plates. The magnetic plates are molded by mixing Ecoflex-0030 (Smooth-On, Inc., USA) silicone rubber precursor and magnetic microparticles (NdFeB) (Magnequench, Singapore) with an average size of 100 μm and loadings of 20 vol % or 40 vol %. Hexagonal magnetic plates with a thickness of 2 mm and an edge length of 13 mm or 9.8 mm are used for the units in the main text. Hexagonal magnetic plates with a thickness of 1.0 mm and an edge length of 4.9 mm are used for the small-scale units. After curing at 80° C. for 0.5 h, the magnetic plates are taken out from the molds and magnetized using a homemade magnetizer with a 1.5 T impulse magnetic field. The Kresling units and magnetic plates are assembled using Sil-poxy adhesive (Smooth-On, Inc., USA.) for different demonstrations.

2. Magnetic Properties of Magnetic Plates

The magnetic properties of the magnetic materials are measured using a 7400A vibrating sample magnetometer (Lake Shore Cryotronics, Inc., USA). The magnetic moments of 4 mm×4 mm×1 mm samples are measured. Corresponding remanent magnetic moment densities (Mr) are calculated by dividing the magnetic moment by the sample volume. The Mr of the 20 vol % and the 40 vol % magnetic materials are 112.1 kA $m^{-1}$ and 227.5 kA $m^{-1}$, respectively.

3. Mechanical Characterizations of the Kresling Unit

A. Folding and Deploying Behaviors. The force-displacement curves of the Kresling unit's folding and deploying processes are measured using a universal testing machine (3344, Instron, Inc., USA). The experimental setup is shown in FIGS. 33A and 33B. Cyclic tension-compression tests are performed to characterize the mechanical properties of fabricated Kresling units as shown in FIG. 33C. The mechanical performance is stable after around 300 cycles. The exhibited hysteresis in the folding-deploying plot comes from energy dissipation, due to the contact and friction between Kresling panels during deploying and folding (1). All fabricated Kresling units are cyclically loaded 300 times for a stable behavior before being used in magnetic actuation in this work. The torque-displacement curve at stable state is derived from the force-displacement curve and displacement-rotation angle relation. See (2) for more details about the measurement and derivation.

B. Bending Behavior. The torque-bending angle curve of the Kresling unit in FIG. 27C is derived from its magnetic bending actuation. As shown in FIG. 34A, a magnetic plate (thickness of 2 mm, edge length of 13 mm, 40 vol % of magnetic particles) with an out-of-plane magnetization $M_o$ is attached to a Kresling unit. A magnetic field B is applied in the horizontal direction, perpendicular to the magnetization of the undeformed magnetic Kresling. The magnetic field's intensity ranges from 0 mT to 40 mT with a 5 mTinterval. The bending angle θ with respect to the magnetic field intensity B is measured, as shown in FIG. 34B. The out-of-plane torque $T_o$ to bend the unit is derived based on magnetic torque as $T_o=V$ ($M_o$×B) with a magnitude of:

$$T_o = BM_rV \sin \theta_{B,} = BM_rV \sin(90-\theta),$$

where Mr is the remanent magnetic moment density 227.5 kA $m^{-1}$, V is the volume of the magnetic plate 0.88 $cm^3$, θBM is the angle between magnetic field and the magnetization direction, θ is the unit's bending angle.

4. Magnetic Actuation Setup

All demonstrations are performed using a 3D Helmholtz coil system shown in FIG. 35. Three pairs of standard Helmholtz coils are configured orthogonally to each other. The coils can generate 2.96 mT $A^{-1}$, 2.97 mT $A^{-1}$, and 2.90 mT $A^{-1}$ uniform magnetic fields within a space of 160 mm by 120 mm by 80 mm (X-axis, Y-axis, and Z-axis), respectively. The magnetic field direction and intensity can be manipulated by controlling the currents in the three pairs of coils.

5. Coordinate Transformations

For the magnetic actuation of the four-unit robotic arm, both global and local coordinate systems are used to realize bending and deploying. The global XYZ coordinate system is based on the 3D coils and the local xyz coordinate system is fixed at the top unit. To generate the magnetic field with specific direction and intensity in the 3D space, the magnetic field vector B can be decomposed to three axes of the global coordinate system and expressed as:

$$B = B_XX + B_YY + B_ZZ,$$

where $B_X$, $B_Y$, and $B_Z$ are the magnetic fields generated by the pair of coils in the X-axis, Y-axis, and Z-axis, respectively. B can also be decomposed to three axes of the local coordinate system and expressed as:

$$B = B_xx + B_yy + B_zz,$$

where Bx, By, and Bz are the magnetic fields in the x-axis, y-axis, and z-axis of the local xyz coordinate system, respectively. Considering the magnetic field in 3D space is uniform, the transformation between the global XYZ and local xyz coordinate systems requires only rotation and can thus be expressed as:

$$\begin{bmatrix} B_X \\ B_Y \\ B_Z \end{bmatrix} = Q \begin{bmatrix} B_x \\ B_y \\ B_z \end{bmatrix},$$

where Q is the transformation matrix between two coordinate systems. The designed four-unit robotic arm can bend toward any direction (denoted by γ) in the XY-plane with a bending angle of θ (FIG. 42). The transformation matrix Q can be expressed as:

$$Q = \begin{bmatrix} \cos\theta\cos^2\gamma + \sin^2\gamma & \cos\theta\cos\gamma\sin\gamma - \cos\gamma\sin\gamma & \sin\theta\cos\gamma \\ \cos\theta\cos\gamma\sin\gamma - \cos\gamma\sin\gamma & \cos\theta\sin^2\gamma + \cos^2\gamma & \sin\theta\sin\gamma \\ -\sin\theta\cos\gamma & -\sin\theta\sin\gamma & \cos\theta \end{bmatrix}$$

To realize stretching after the robotic arm's bending deformation, a magnetic field in the xy-plane of the local coordinate system should be applied to induce deployment. Then $B_X$, $B_Y$, and $B_Z$ can be calculated from the bending deformation (y and θ) of the robotic arm and the required deploying magnetic field Bx, By, and Bz. The reference currents are calculated and sent to the controller of the 3D Helmholtz coils.

6. Magnetic Actuation Experiments

A. Single-Unit Kresling Experiments.

The bottom plate of the magnetic Kresling unit is fixed and the top plate is free. A magnetic plate (40 vol % of magnetic particles) with an inclined magnetization (60° to the plate) is attached to the unit. The deploying/folding experiments are conducted by applying a magnetic field in the plane of the fixed end. The direction of the in-plane magnetization component at folded state is defined as the reference direction (α=0°). The intensity of the magnetic field at the direction α increases from 0 mT to 40 mT at 1 mT s−1. The corresponding magnetic fields are recorded when the Kresling unit changes its state from the stable state [0] to the stable state [1] (FIG. 27F) and from the stable state [1] to the stable state [0] (FIG. 36).

The omnidirectional bending behavior is attributed to the out-of-plane magnetization component that can generate out-of-plane torque under the designed magnetic field. To quantitatively evaluate the bending performance, a magnetic field in the plane of the fixed bottom plate is applied with its intensity ranging from 0 mT to 40 mT with 10 mT interval and the direction ranging from 0° to 360° with 30° interval. The relationships between bending angle, magnetic field direction, and magnetic field intensity are illustrated in the polar plot in FIG. 27I.

Experimental actuations of magnetic Kresling units with only in-plane magnetization/out-of-plane magnetization are used to illustrate the actuation mechanisms as shown in FIG. 37. As shown in FIG. 37A, a magnetic plate (40 vol % of magnetic particles) programmed with in-plane magnetization is attached to a blue Kresling unit, which can lead to folding/deploying and bidirectional bending under in-plane and out-of-plane torques, respectively. As shown in FIG. 37B, a magnetic plate (40 vol % of magnetic particles) programmed with out-of-plane magnetization is attached to a green Kresling unit, which enables omnidirectional bending induced by the out-of-plane torques in all directions.

B. Two-unit Kresling Experiments. In FIG. 28, three two-unit Kresling assemblies with different magnetization distributions are explored to demonstrate the deformations including stable folding/deploying and bidirectional bending (blue-blue assembly), omnidirectional bending (green-green assembly), and multimodal deformation (green-blue assembly). For all demonstrations, the bottom of the Kresling assembly is fixed and the top is free.

For the demonstration of stable folding/deploying and bidirectional bending (blue-blue assembly), two magnetic plates with 20 vol % of magnetic particles and the same in-plane magnetization are attached to the Kresling units as shown in FIG. 38A. The magnetization direction at state [00] is defined as the reference direction (α=0°). The measured phase diagrams of state shifting from states [00], [10], [11], and [01] to other states are shown in FIG. 39. The bidirectional bending deformations of the two-unit Kresling assembly at three states [00], [10], and [01] are demonstrated by applying out-of-plane magnetic fields as shown in FIG. 38B. The characterizations of the bending behaviors at three states are measured by applying a 30 mT magnetic field with an angle of β relative to the magnetization direction at the undeformed state.

For the demonstration of omnidirectional bending (green-green assembly), two magnetic plates (20 vol % of magnetic particles) with out-of-plane magnetizations are attached to the assembly as shown in FIG. 40A. A magnetic field in the plane of the fixed end is applied with its intensity ranging from 0 mT to 40 mT with 10 mT interval and the direction ranging from 0° to 360° with 30° interval. The characterization of bending angle with respect to magnetic field directions and intensities are shown by the polar plot in FIG. 40B.

Figures 41B, 41D, 42A, 42B:
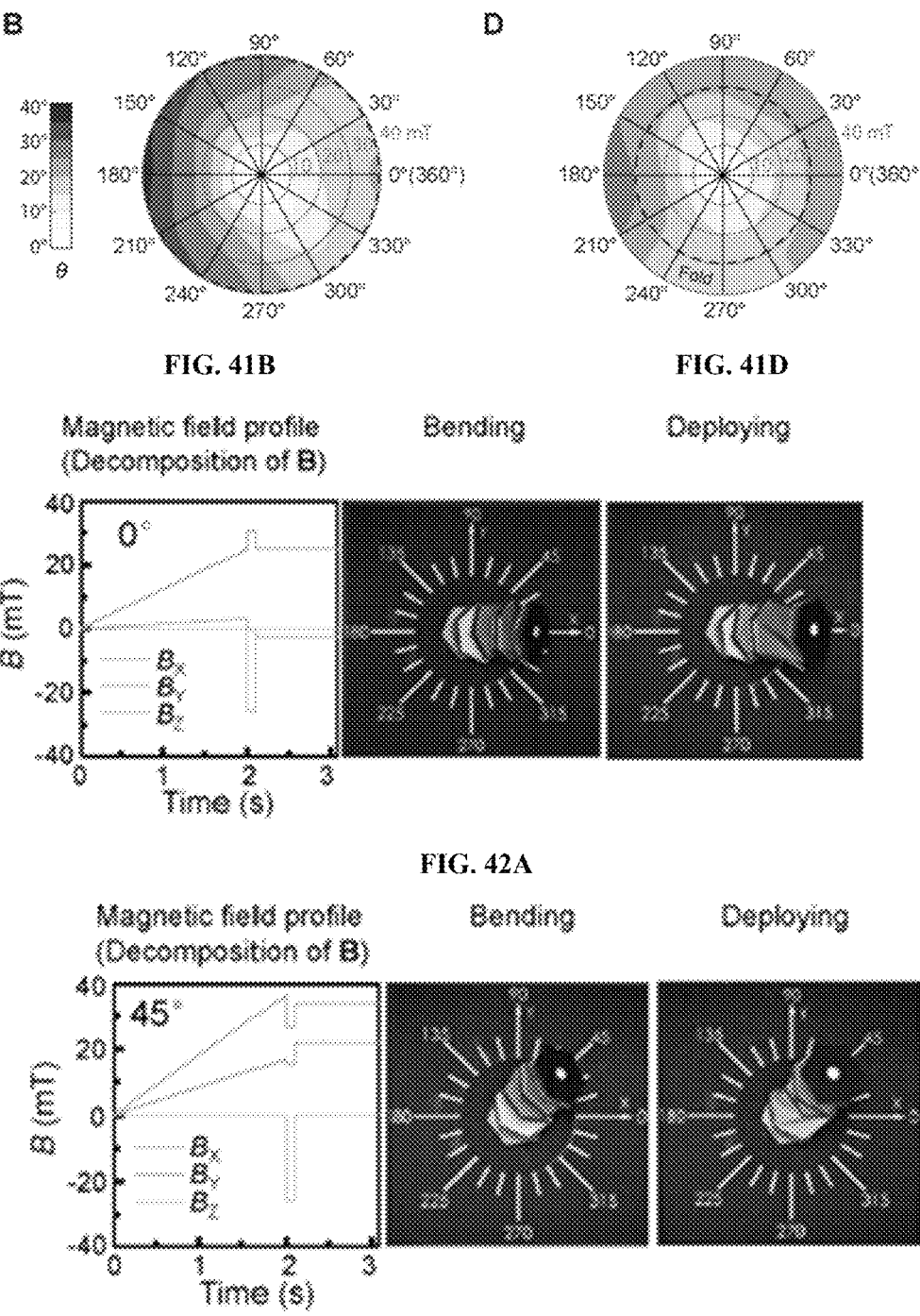
Figure 42F:
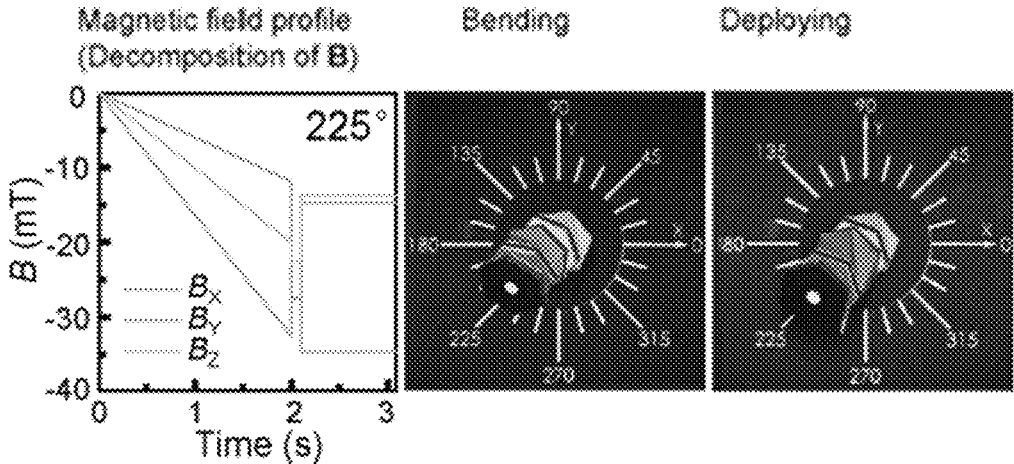
Figure 42G:
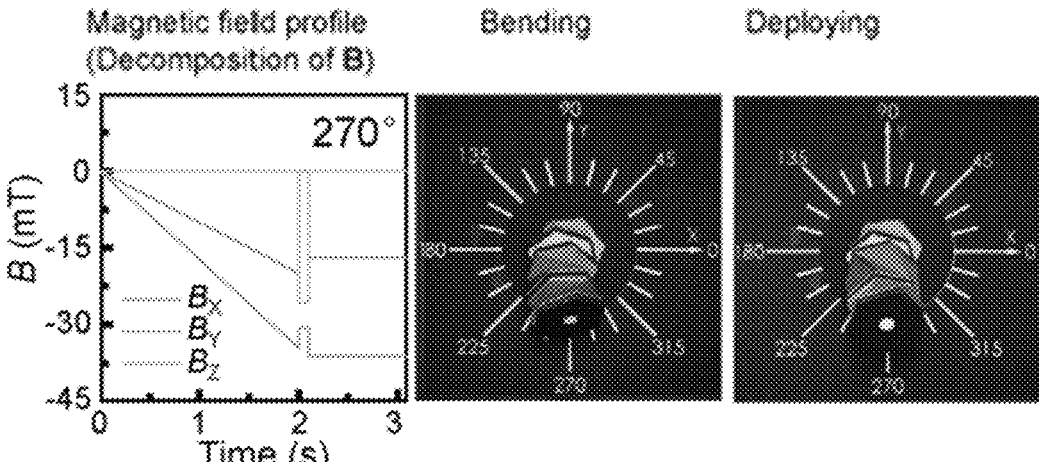
Figure 42H:
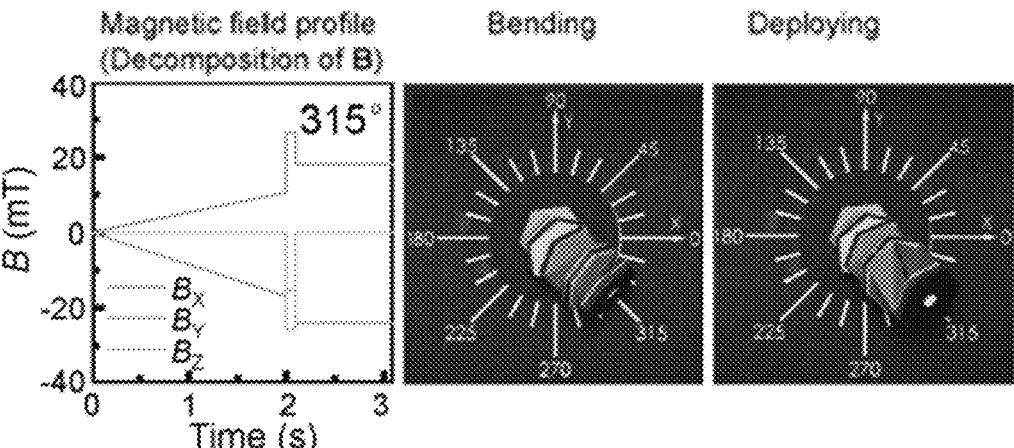

For the demonstration of multimodal deformation in FIGS. 41A and 41C (green-blue assembly), a magnetic plate (40 vol % of magnetic particles) with an out-of-plane magnetization is attached to the green unit to provide omnidirectional bending, and a magnetic plate (20 vol % of magnetic particles) with an in-plane magnetization is attached to the blue unit to provide state shifting. The same in-plane magnetic fields are applied for the characterizations of bending behaviors at state [00] and state [01] (FIGS. 41B and 41D).

C. Four-unit Kresling Robotic Arm. The actuation of the four-unit Kresling robotic arm has a bending phase and a deploying phase as shown in FIG. 42. The white marker on the top plate is used to indicate the bending direction of the robotic arm (0° to 360° with 45° interval) and to evaluate whether it follows the desired actuation direction.

The bending angles of the four-unit Kresling robotic arm at 8 different directions (0° to 360° with 45° interval) are measured. At each direction, the magnetic field is applied with an intensity ranging from 0 mT to 40 mT with 10 mT interval. The experimental results are illustrated by the polar plots in FIG. 43.

Figures 46A, 46B, 46C, 46D:
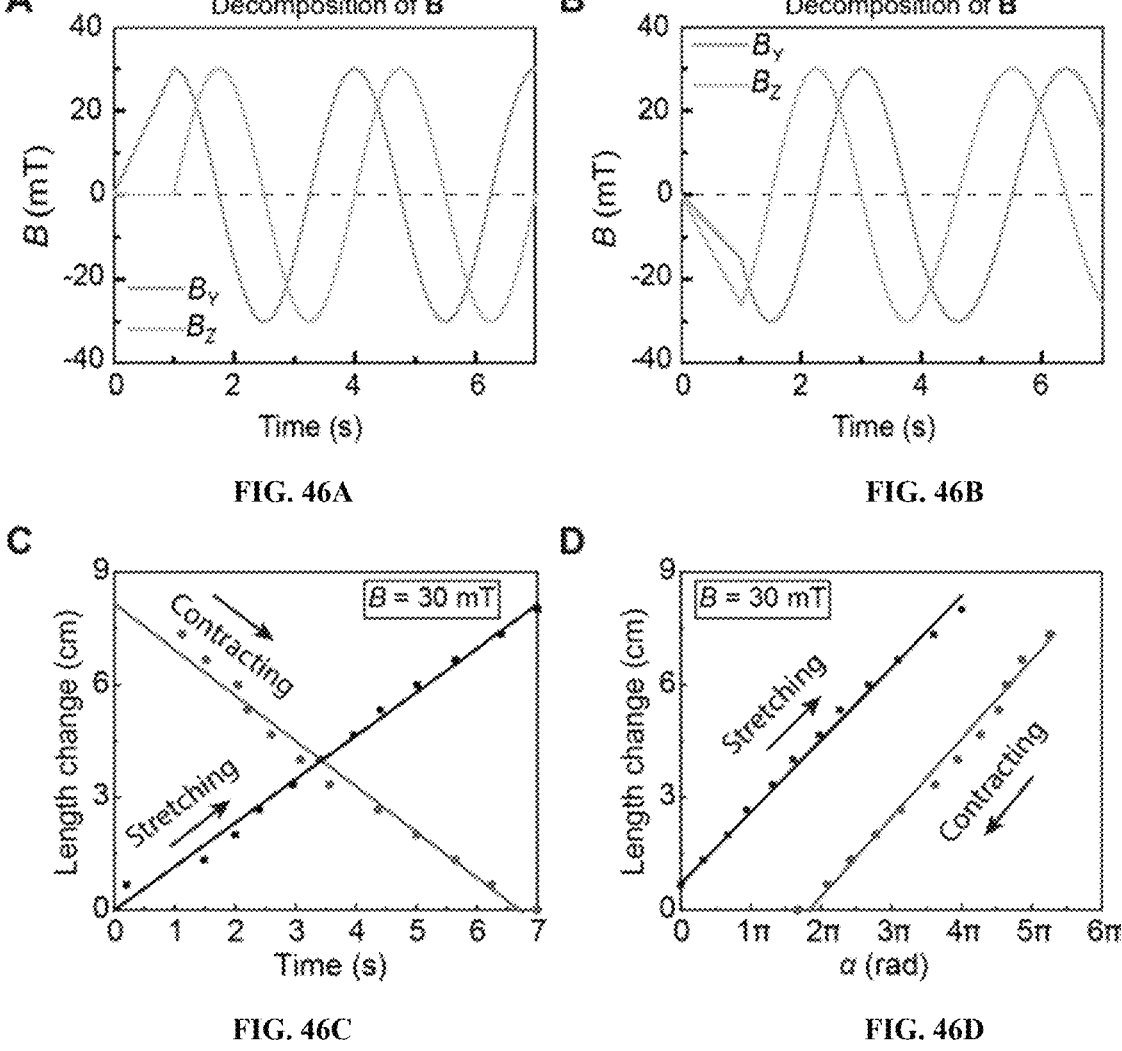

D. 12-unit Kresling Robotic Arm. In the experiment, the left-end of the 12-unit Kresling robotic arm is fixed, and the rest of the robotic arm is free to generate stretching/contracting, bending, and twisting motions under rationally designed magnetic fields. All the magnetic plates (20 vol % of magnetic particles) are programmed to be in the same negative Z-direction at the all-folded state as shown in FIG. 44. By applying a rotating magnetic field in the YZ-plane as shown in FIG. 46A, all 12 units can be deployed one-by-one from the folded state. By applying a rotating magnetic field in the YZ-plane as shown in FIG. 46B, the arm can gradually decrease its length and return to all folded state.

E. 18-unit Kresling Robotic Arm. The left-end of the 18-unit Kresling robotic arm is fixed, and the rest of the robotic arm is free to generate omnidirectional bending and object grasping motions with rationally designed magnetic fields. All magnetic plates (20 vol % of magnetic particles) in the 18-unit Kresling robotic arm are programmed with out-of-plane magnetizations. The magnetization distribution is shown in FIG. 31A.

F. Small-scale Kresling Robotic Arms. The eight-unit and four-unit small-scale Kresling robotic arms are hanging straight down with the top-end fixed. Both arms provide versatile motion including bending, folding and weight manipulating under programmable magnetic fields. For the eight-unit arm, all magnetic plates (20 vol % of magnetic particles) are programmed with out-of-plane magnetizations, demonstrating bend-lifting and three-dimensional motion of a 1 g weight (FIG. 48). For the four-unit small-scale robotic arm, all magnetic plates (40 vol % of magnetic particles) are programmed with in-plane magnetizations, demonstrating both fold-lifting and bend-lifting of a 1 g weight (FIG. 49)

TABLE 3

| | Weights on the robotic arms | | |
|---|---|---|---|
| Robotic arm design | Particle loading of magnetic plate | Weight of single unit | Total weight of the arm |
| Four-unit arm (FIG. 29) | Bending unit (40 vol %) | ~4.8 g | 13.4 g |
| | Deploying unit (20 vol %) | ~2.7 g | |
| 12-unit arm (FIG. 30) | 20 vol % | ~1.5 g | 18.7 g |
| 18-unit arm (FIG. 31) | 20 vol % | ~1.5 g | 28.6 g |
| Eight-unit small-scale arm (FIG. 48) | 20 vol % | ~0.18 g | 1.8 g |
| Four-unit small-scale arm (FIG. 49) | 40 vol % | ~0.33 g | 1.5 g |

REFERENCE

1. Nayakanti, N., Tawfick, S. H., & Hart, A. J. (2018). Twist-coupled kirigami cells and mechanisms. *Extreme Mechanics Letters,* 21, 17-24.
2. Novelino, L. S., Ze, Q., Wu, S., Paulino, G. H., & Zhao, R. (2020). Untethered control of functional origami microrobots with distributed actuation. *Proceedings of the National Academy of Sciences,* 117(39), 24096-24101.
3. Walrath, B. D., Harper, S., Barnard, E., Tobin, J. M., Drew, B., Cunningham, C., . . . & Martin, M. (2018). Airway management for trauma patients. *Military medicine,* 183(suppl_2), 29-31.
4. Ochiai, Y., Kato, M., Kiguchi, Y., Akimoto, T., Nakayama, A., Sasaki, M., . . . & Yahagi, N. (2019). Current status and challenges of endoscopic treatments for duodenal tumors. *Digestion,* 99(1), 21-26.
5. Forsberg, A., & Engström, A. (2018). Critical care nurses' experiences of performing successful peripheral intravenous catheterization in difficult situations. *Journal of Vascular Nursing,* 36(2), 64-70.

Example 3: Soft Robotic Origami Crawler

Abstract

Biomimetic soft robotic crawlers have attracted extensive attention in various engineering fields, owing to their adaptivity to different terrains. Earthworm-like crawlers realize locomotion through in-plane contraction, while inchworm-like crawlers exhibit out-of-plane bending-based motions. Although in-plane contraction crawlers demonstrate effective motion in confined spaces, miniaturization is challenging due to limited actuation methods and complex structures. Here, we report a magnetically actuated small-scale origami crawler with in-plane contraction. The contraction mechanism is achieved through a four-unit Kresling origami assembly consisting of two Kresling dipoles with two-level symmetry. Magnetic actuation is utilized to provide appropriate torque distribution, enabling a small-scale and untethered robot with both crawling and steering capabilities. The crawler can overcome large resistances from severely confined spaces by its anisotropic and magnetically tunable structural stiffness. The multifunctionality of the crawler is explored by utilizing the internal cavity of the crawler for drug storage and release. The magnetic origami crawler can potentially serve as a minimally invasive device for biomedical applications.

Introduction

Crawling motion is a navigation strategy that is commonly observed in animals, especially in worms. In such animals, body contraction paired with inhomogeneous friction between the surfaces of contact enables forward motion. Worm-based crawling motion shows high adaptivity to complicated terrains (1-3), owing to the soft deformable body. By engineering effective crawling, robotic crawlers on various scales have attracted extensive efforts for applications, including planetary subsurface exploration (4, 5), in-pipe inspection (6, 7), and gastrointestinal endoscopy (8, 9), where the operating space is limited or confined.

Based on observed crawling mechanisms, earthworm-like crawlers have been designed to realize locomotion through in-plane contraction (10, 11), while inchworm-like crawlers are designed to exhibit out-of-plane bending-based motions (12, 13). In confined spaces where out-of-plane motion is constrained, the in-plane contraction crawling mechanism surpasses the bending-based counterpart. The contraction of in-plane crawlers is usually achieved through contractile structures (14-16) or soft materials (17-19). Most of the crawlers based on contractive mechanisms only demonstrate straight motion by actuating either the whole body with a single actuator (20, 21) or several individual segments synergistically with multiple actuators (22, 23). On the other hand, the steering function requires additional mechanisms with added actuators (24). These actuators, including motors and pneumatic pumps, commonly lead to bulky systems with extensive wires or tubes. The complicated structures and control systems pose challenges for small-scale applications such as those in the biomedical field. To this effect, an alternative is crawlers made of stimuli-responsive soft materials that generate contraction via large deformation of the soft crawler body (25, 26), which usually has a relatively simple structure that permits small-scale design. Some recent crawlers with a millimeter-sized beam structure have demonstrated the capabilities of effective locomotion and cargo transportation for open biomedical environments, such as the stomach (27, 28). Although soft materials allow easy deformation for contraction, their low material stiffness makes it challenging for the crawler to overcome the large environmental resistance introduced by confined spaces, such as those in the gastrointestinal tract and abdomen, where contacts between tissues or organs are common. To navigate in such environments, systems that allow effective contraction for crawling while having the capability to overcome external load in the lateral direction are desirable.

Origami provides a seamless and effective way of generating contraction by means of structural folding and thus has been adopted to engineer robotic crawlers (29-31). Origami structures demonstrate anisotropic structural stiffness along folding directions and lateral directions, which is beneficial for effective crawling in confined spaces (32, 33). The inherently low stiffness in the foldable direction allows for easy contraction, while the significantly higher stiffness in the lateral direction makes the crawler more immune to unexpected disturbances from working environments. The Kresling pattern (34-36) is a specific type of origami that generates axial contraction under either torque or compressive force. Its contraction is coupled with a twist from the relative rotation between the two ends of the unit (FIG. 1A). When utilizing the Kresling unit for crawler contraction, the twist induces undesired lateral movement, which prohibits the straight motion of the crawler and limits its application to specific environments, such as in a tube (37). Although some works adopt two parallel Kresling assemblies with reverse crease directions to cancel out twists in the system (38, 39), the clumpy structure and multiple wired actuators hinder the miniaturization of the robotic crawler for applications in environments with limited access.

In this work, we report a magnetically actuated small-scale origami crawler for effective in-plane crawling motion. The crawler is made of a four-unit Kresling assembly with a rationally designed structure to avoid the relative rotation between the two ends of the assembly and to cancel out internal twists for efficient straight motion. The required torque distribution on the crawler is theoretically derived and verified by finite element analysis (FEA) to obtain simultaneous contraction of all four Kresling units for the crawling motion. The torques are then realized by distributed magnetic actuation. By controlling the magnitude and direction of the external magnetic field, the Kresling crawler can achieve contraction for forward motion and instantaneous steering. The untethered magnetic actuation eliminates the need for bulky and wired actuators, enabling a small-scale and neat robotic system. The measured anisotropic and magnetically tunable structural stiffness along the axial and lateral directions of the Kresling crawler helps the crawler achieve effective locomotion in severely confined spaces. In addition, drug storage and release capabilities are demonstrated to illustrate the multifunctionality of the crawler.

Results

The Kresling unit shows a coupled twist-contraction motion (blue and green circles in FIG. 50A) under either a pair of torques or compressive forces. The twisting direction is either clockwise (CW) or counterclockwise (CCW) based on the crease direction of the Kresling unit (FIG. 56). To have a purely translational crawling motion, the Kresling-based crawler design needs to avoid the lateral movement that can be caused by the relative rotation between the two ends of a Kresling unit. To address this, the Kresling dipole is introduced to eliminate the overall twist during contraction. As illustrated in FIG. 50B, the Kresling dipole is composed of two Kresling units with the same geometry and reverse crease directions, showing mirror symmetry. Note that the crease direction only decides the twisting direction without influencing the magnitude of force/torque required to fold the unit. The two units with reverse crease directions can achieve equal amounts of contraction when compressing the two ends of the Kresling dipole (FIG. 50B). Due to the same relative rotation angles with reverse directions of two Kresling units, the two ends of the Kresling dipole are free of relative rotation, as indicated by green circles, while its middle interface shows a rotation, as indicated by blue circles. In this way, the Kresling dipole serves as a robust alternative to build crawlers by providing effective in-plane contraction for translational motion while maintaining contacts of two end-points with the ground for stick-slip motion, which is usually necessary for crawling motion (28, 40, 41).

Figure 50C:
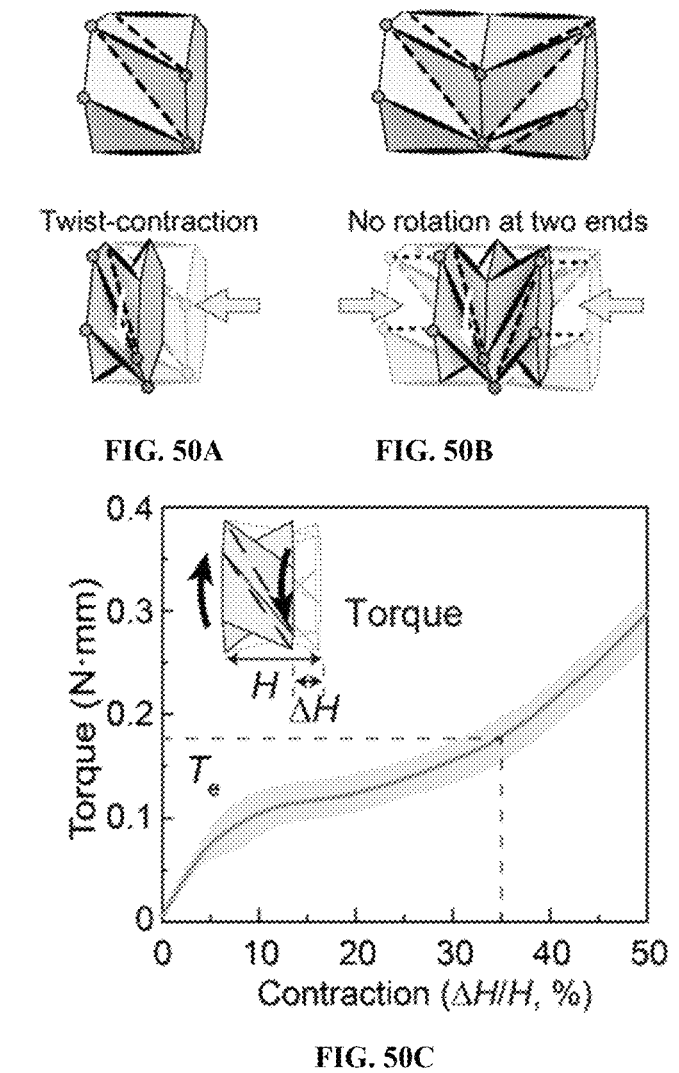

The Kresling unit can be designed to be monostable or bistable (35, 42). For the in-plane crawling motion with contraction phase and recovery phase, the Kresling assembly is designed to be monostable for smooth and continuous deformation. Meanwhile, monostability allows automatic recovery to the stress-free initial state of the crawler after releasing the applied loading. By choosing appropriate geometric design (FIG. 56) and material (FIG. 57), a fabricated Kresling unit shows monostable behavior from the measured force-contraction curve (FIGS. 58 & 59A) and torque-contraction curve (FIG. 50C). Under a pair of reasonably small torques of $T_e$=0.18 N-mm, the fabricated unit can generate a 35% contraction for effective crawling motion (FIG. 50C).

To further cancel out the contraction-induced rotational motion at the middle interface of the Kresling dipole (white arrow in FIG. 50B), a crawler made of two Kresling dipoles aligned in the axial direction is designed, as shown in FIG. 50D. Here, we define directions perpendicular and parallel to hexagonal planes as the axial and lateral directions of the Kresling assembly, respectively. The structure possesses two levels of symmetry, including central symmetry of the whole structure and mirror symmetry of each Kresling dipole. With this configuration, the $2^{nd}$ and $4^{th}$ hexagonal planes of the crawler from left to right have the same degree of rotation in reverse directions (white arrows in FIG. 50D) when the four units contract simultaneously. The Kresling crawler shows no rotation at both the center ($3^{rd}$ hexagonal plane) and two ends ($1^{st}$ and $5^{th}$ hexagonal planes) during contraction.

To achieve such deformations for effective in-plane crawling motion, a well-designed torque distribution (FIG. 50E) is needed to ensure simultaneous contraction of the four units based on three requirements.

1) A purely translational crawling motion requires torque balance of the whole system, which can be expressed as:

$$T_1+T_3=T_2+T_4, \tag{1}$$

where $T_1$, $T_2$, $T_3$, and $T_4$ are the magnitudes of applied torques at $1^{st}$, $2^{nd}$, $4^{th}$, and $5^{th}$ hexagonal planes of the crawler from left to right.

2) The simultaneous and equal contraction of all four Kresling units requires the torque exerted to each individual Kresling unit to be the same, which can be expressed as:

$$T_{U1}=T_{U2}=T_{U3}=T_{U4}, \tag{2}$$

where $T_{U1}$, $T_{U2}$, $T_{U3}$, and $T_{U4}$ are torque magnitudes on units U1, U2, U3, and U4, respectively. Based on the structural symmetry and the torque balance analysis from free body diagrams (See supplementary information section and FIG. 60 for more details), we have:

$$T_2=2T_1, T_3=T_2=T_4=T_1. \tag{3}$$

3) The torque on each Kresling unit needs to reach a sufficient value to generate effective contraction, and we define this torque as $T_e$, which comes from the mechanical characterization of the Kresling unit (FIG. 50C). Note that $T_e$ for the yellow and blue units have the same magnitude but opposite directions. Upon fulfilling the three aforementioned requirements, the crawler can generate contraction by folding the four units simultaneously while the two ends remain free of relative rotation.

Figure 61C:
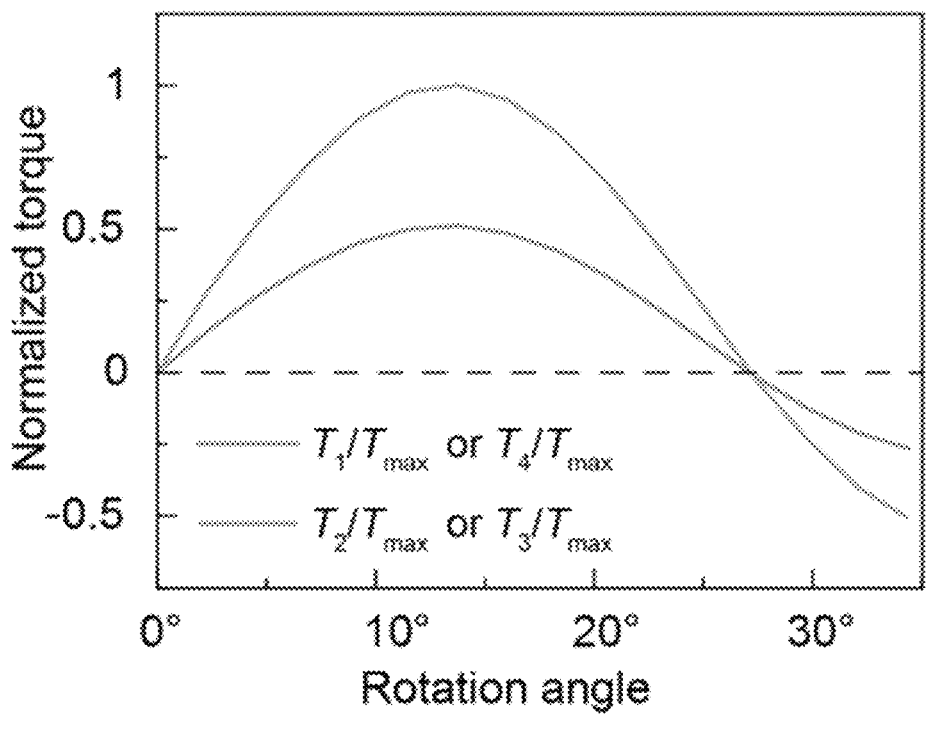
Figure 61D:
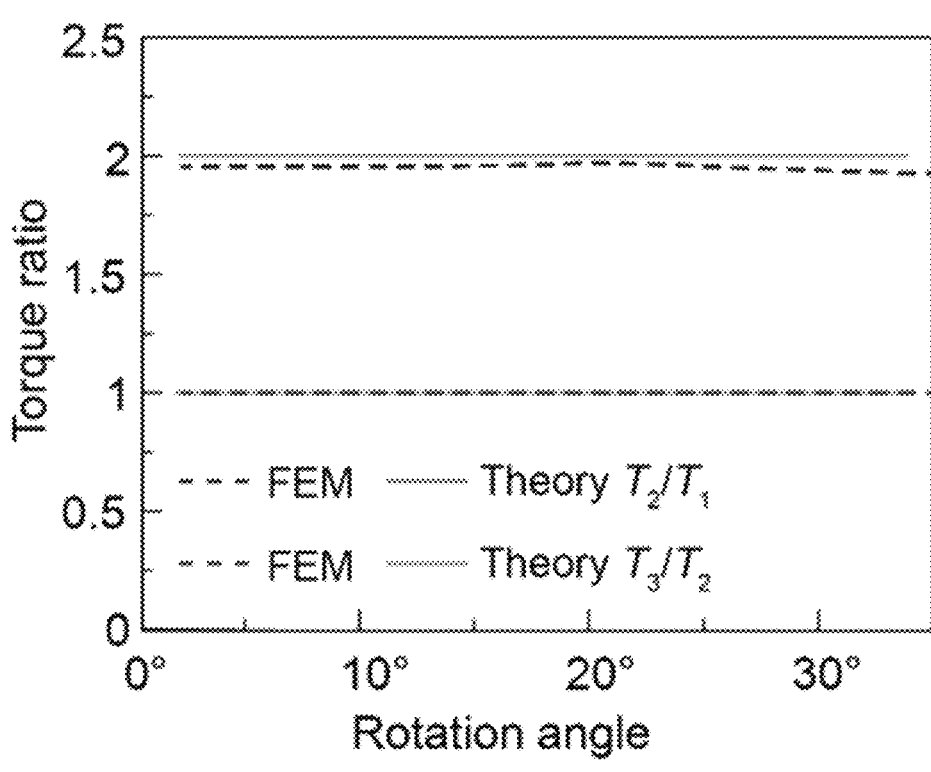

To verify the derived torque distribution, contraction of the Kresling crawler is simulated via FEA, as shown in FIG. 50F (See FIG. 61 for the comparison between FEA results and analytical derivation). Based on the relative rotation angle-contraction curve of the Kresling unit (FIG. 59C), a 32° relative rotation between the two ends of the Kresling unit corresponds to 35% contraction for effective crawling motion. Rotation angles of 0°, 32°, −32°, and 0° are then enforced to the $1^{st}$, $2^{nd}$, $4^{th}$, and $5^{th}$ hexagonal planes of the crawler from left to right in the FEA, with all hexagonal planes free to move along the axial direction. In the simulation, we record the corresponding reaction torques $T_1$, $T_2$, $T_3$, and $T_4$ at the $1^{st}$, $2^{nd}$, $4^{th}$, and $5^{th}$ hexagonal planes of the crawler from left to right and compare their relations with the theoretical derivation. Under the applied boundary conditions, the four units of the crawler contract simultaneously and show no rotation at the center plane (the $3^{rd}$ hexagonal plane) and the two ends of the crawler (Movie S1). The simulated reaction torque relations ($T_2/T_1$ and $T_3/T_2$) shown in FIG. 61D follow Eq. 3 during the entire contraction process, which verifies the analytically derived torque distribution. By applying the distributed loadings cyclically, the monostable Kresling crawler can provide repeatable contraction for continuous crawling motion.

An appropriate actuation method is necessary to provide the torque distribution for the crawler to achieve desired simultaneous contraction. Compared to other actuation methods, such as motor (33, 38) and pneumatic actuation (11, 19), magnetic actuation is an ideal option, as outlined next. First, magnetic actuation permits untethered and fast response, allowing real-time manipulation of the crawler in an environment with limited access. Second, magnetic actuation isolates the power and controlling system from the crawler, making miniaturization of the crawler feasible for applications in small and confined spaces (27). FIG. 51A shows an image of the fabricated Kresling crawler on a fingertip, illustrating the miniaturized robot for potential applications in environments with limited access, such as drug delivery in the intestines and stomach. Third, magnetic control has recently demonstrated distributed actuation for selective or sequential actuation of functional deformable units of origami assembly (34, 43). This further provides the possibility of utilizing the magnetic field to program the torque distribution on the Kresling crawler to have simultaneous contraction of all Kresling units for effective crawling motion.

As shown in FIG. 51A, four magnetic plates are attached to the $1^{st}$, $2^{nd}$, $4^{th}$, and $5^{th}$ hexagonal planes of the crawler from left to right, where distributed torques are needed according to the theoretical derivation. Each magnetic plate is made of silicone embedded with hard-magnetic particles so that the magnetization density is tunable by adjusting the volume fraction of the magnetic particles. The magnetic plate possesses a pre-determined magnetization M with a specific direction. Under a uniform magnetic field B, the magnetic plate generates a torque T=V(M×B), which tends to align its M with the applied B by rigid body rotation of the magnetic plate. V is the volume of the magnetic plate. Both the direction and magnitude of the torque can be programmed by specially designing the magnetic plate magnetization and manipulating the applied magnetic field. Here, the four magnetic plates have the same magnetization density but different magnetization directions (FIG. 51A) to provide local and distributed torques that satisfy the derived torque relations in Eq. 3.

To better describe the magnetic actuation and relative rotation of the magnetic plates, we define a local right-handed coordinate system whose origin sits at the center of the rightmost magnetic plate of the crawler. The y-axis and the z-axis are parallel and perpendicular to the top edge of the rightmost magnetic plate, respectively, as shown in FIG. 51A. The x-axis is along the axial direction of the crawler and faces outward. The magnetization directions of the four magnetic plates are all in the yz-plane of the local coordinate system with relative angles of $\theta_1$, $\theta_2$, $\theta_3$, $\theta_4$ to the y-axis. Under a uniform magnetic field along the y-axis, the generated distributed torques of the four magnetic plates have magnitudes of $$T_i^m = |T_i^m| = V|M_i \times B| = BM_i V \sin \theta_i (i=1,2,3,4), \quad (4)$$

where $M_i$ is the magnetization of each magnetic plate, B is the applied magnetic field with a magnitude of B, $M_r$ and V are the measured remanent magnetization and volume of each magnetic plate, respectively. The magnetization directions of the $1^{st}$ and $4^{th}$ ($2^{nd}$ and $3^{rd}$) plates indicate mirror symmetry about the y-axis to assure that $T_i^m$ and $T_4^m$, or $T_2^m$ and $T_3^m$ have the same torque magnitude but reverse directions under the uniform magnetic field applied along the y-axis. Note that the crawler always aligns its net magnetization Me (y-axis) with the applied magnetic field, and the corresponding torque distribution would then provide simultaneous contraction of all four Kresling units. By substituting Eq. 4 into Eq. 3, we have:

$$\sin \theta_1 = \tfrac{1}{2} \sin \theta_2 = \tfrac{1}{2} \sin \theta_3 = \sin \theta_4 \quad (5)$$

However, the magnetization directions $\theta_2$ and $\theta_3$ change during the continuous contraction of the crawler, as shown in FIG. 51B. Thus, in practice, the torque distribution would deviate from the ideal torque relations. Taking the left Kresling dipole of the crawler as an example, we derive the torques on unit 1 and unit 2 as:

$$\begin{cases} T_{U1}^m = T_1^m = BM_t V \sin\theta_1 \\ T_{U2}^m = T_2^m - T_1^m = BM_t V \sin\theta_2 - BM_t V \sin\theta_1 \end{cases} \quad (6)$$

where $T_{U1}^m$ and $T_{U2}^m$ are torque magnitudes on units U1 and U2 under magnetic actuation, respectively. Assuming that the four units of the Kresling crawler still contract simultaneously and its two ends do not rotate during this dynamic process, $\theta_2$ gradually decreases while $\theta_1$ remains unchanged. To ensure that the torque $T_{U2}^m$ follows $T_{U1}^m$ as much as possible, the change of $\sin \theta_2$ should be minimized to limit the torque fluctuation during the crawler contraction. In this way, $T_{U1}^m$ and $T_{U2}^2$ are close enough to guarantee nearly simultaneous and equal contraction. This is possible when $\theta_2$ swings around 90°, as the change rate of $\sin \theta_2$ reaches zero at this point and stays very small within a moderate angle variation. The corresponding $\theta_1$ is obtained to be 30°. Therefore, the ideal angles of the magnetizations are:

$$\theta_1 = \theta_4 = 30° \quad \theta_2 = \theta_3 = 90°. \quad (7)$$

Since $\theta_2$ and $\theta_3$ are changing during contraction, the idealized 90° is set to be the angle at the half-way contraction of the unit. Then the angle swing during the whole contraction process is expressed as:

$$\theta_2^i = 90° + \theta_{r/2}, \theta_2^c = 90° - \theta_r/2, \quad (8)$$

where $\theta_2^i$ is the angle of $\theta_2$ at the initial state of the Kresling crawler, $\theta_2^c$ is the angle of $\theta_2$ at the contracted state of the Kresling crawler, and $\theta_r$ is the total rotation angle of $\theta_2$ during contraction.

Figure 59A:
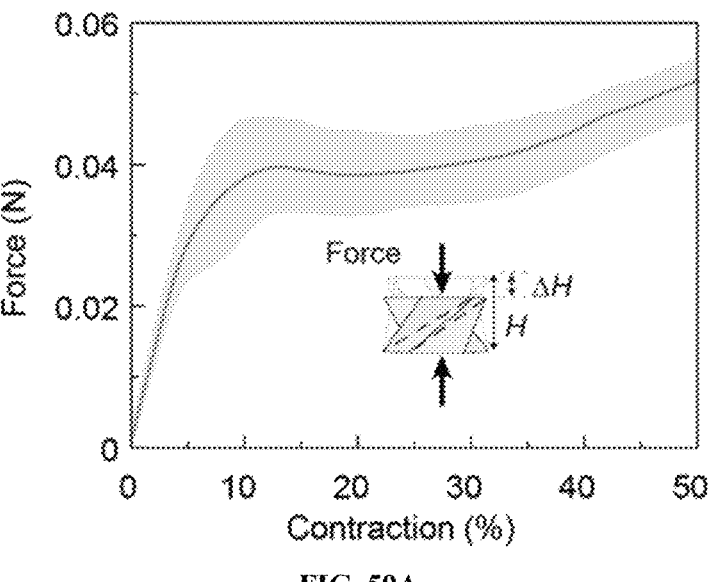
Figures 59B, 59C:
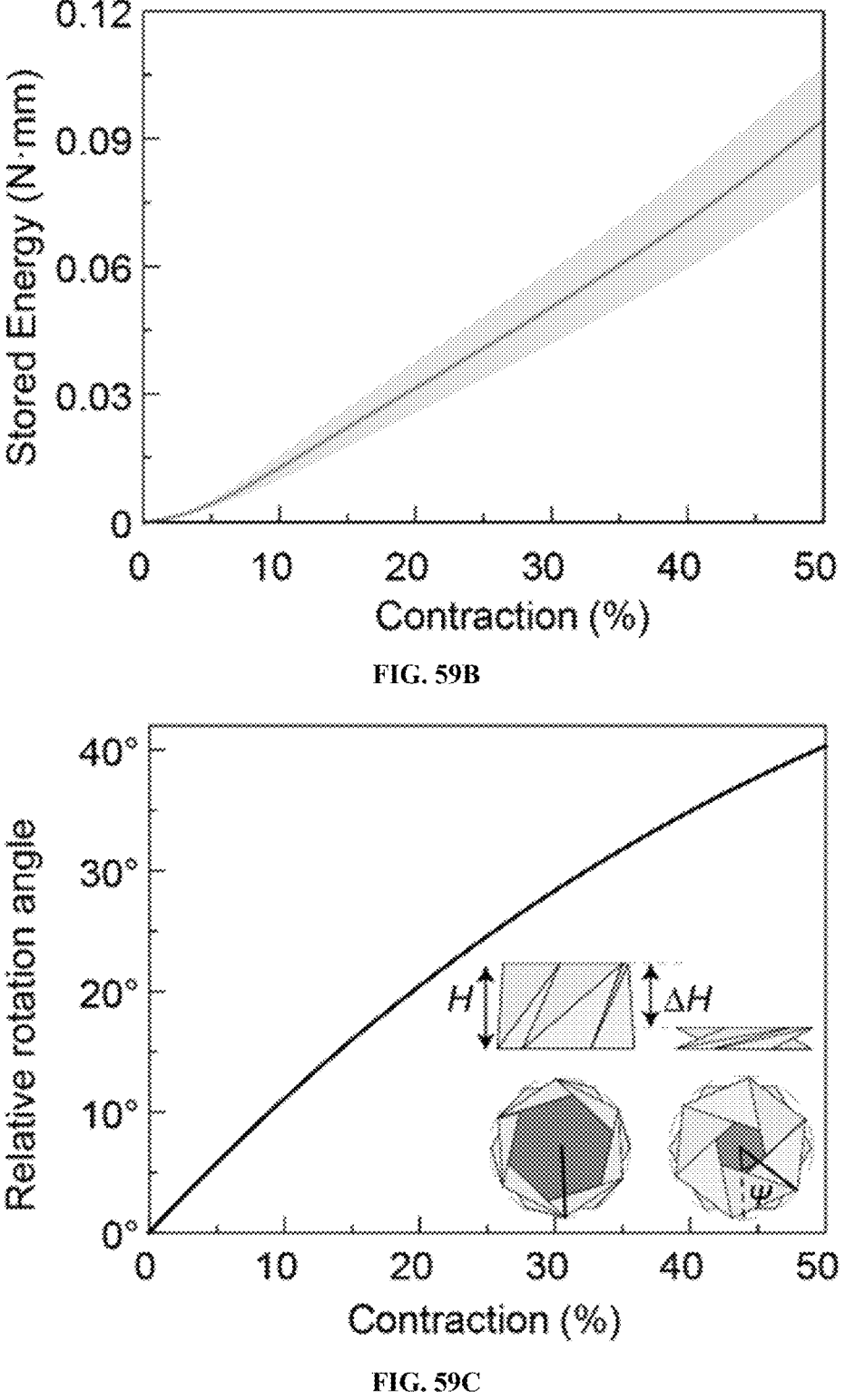

For the Kresling crawler, a 35% contraction of each unit could provide effective crawling motion under a reasonably small torque, which corresponds to a rotation angle $\theta_r$ of 32° from the relative rotation angle-contraction curve of the Kresling unit in FIG. 59C. For $\theta_2$ and $\theta_3$ swinging from 106° (90°+16°) to 74° (90°−16°), $\sin \theta_2$ and $\sin \theta_3$ ranges within 0.96 to 1, and $\sin \theta_1 = \sin \theta_4 = 0.5$. This follows the magnetization angle requirement in Eq. 5 with a small deviation. In this case, the ratio $T_{U2}^m/T_{U1}^m$ ($T_{U3}^m/T_{U4}^m$) ranges from 0.92 to 1 during crawler contraction, as shown in FIG. 51C, exhibiting an acceptable torque fluctuation. Therefore, we finalize the magnetization directions for magnetic plates as:

$$\theta_1 = \theta_4 = 30°, \theta_2 = \theta_3 = 106°. \quad (9)$$

The derived crawler contraction is then experimentally verified by magnetic actuation (See FIG. 62 for experimental setup of magnetic actuation). Upon applying the magnetic field in the y-axis, the four units of the crawler start to contract simultaneously. For the sake of illustration, FIG. 51D displays the initial and contracted states of the crawler under a 40 mT magnetic field. It can be seen that the four units of the crawler have roughly the same magnitude of contraction, and the magnetic plates on the two sides remain rotation-free (green marks) while the middle planes of the two Kresling dipoles rotate in reverse directions (blue marks). The magnetically actuated contraction of the crawler is characterized as shown in FIG. 51E. Here, the contraction of the crawler is defined as 1−l/L, where L and f are the lengths of the crawler at the initial state and contracted state, respectively. The magnitude of contraction increases with the increasing magnetic field. The crawler can achieve a contraction of about 30% under the 40 mT magnetic field.

The magnetic actuation permits a well-regulated torque distribution that enables effective in-plane contraction of the Kresling crawler. To utilize the friction with the ground for forward motion, we design two feet with anisotropic friction to the front and rear of the crawler. The foot design has a high friction portion and a low friction portion, which are made by PDMS and acetate tape, respectively (see SI for more details). Their friction coefficients are measured and shown in FIG. 63. The directional friction converts the contraction/recovery deformations of the crawler into translational motion, as shown in FIG. 52A. During the contraction phase, the rear foot moves forward while the front foot stays stationary, as low friction and high friction portions of the rear and front feet contact the substrate, respectively. During the recovery phase, the rear foot has larger friction, and the only front foot moves forward (Movie S2). After one cycle of contraction and recovery, the crawler can move forward along the x-axis with a distance, which is defined as the stride length. Continuous crawling motion can be obtained by cyclically applying and removing the magnetic field, which is realized by repeating the magnetic field profile shown in FIG. 64. The crawling speed can be easily tuned by changing applied magnetic field magnitude and frequency.

The strides and speeds of the crawler are characterized under magnetic fields with different magnitudes and frequencies, as shown in FIGS. 52B & 52C, respectively. The magnetic field magnitudes range from 0 to 40 mT with a 5 mT interval, and the frequencies are set as 1.67 Hz, 2.5 Hz, or 5 Hz. As shown in FIG. 52B, there is no locomotion when the magnetic field magnitude is smaller than 15 mT because the magnetic field is insufficient to overcome the friction between feet and substrate. Then, the stride length increases with a stronger magnetic field and achieves a maximum value of 3 mm under a 40 mT magnetic field.

Increasing the magnetic field frequency while keeping the same magnitude does not influence the stride length much. However, the crawling speed can be enhanced by increasing either magnitude or frequency of the applied magnetic field, as evidenced in FIG. 52C. The crawling speed reaches 13.2 mm s$^{-1}$ when the magnitude and frequency of the magnetic field are 40 mT and 5 Hz, respectively. Notice that the crawling speed can be further enhanced by increasing the magnitude and frequency of the magnetic field. A comparison between the Kresling crawler in this paper and some existing crawlers in terms of their actuation mechanisms, size, weight, and crawling speed can be found in Table S1.

In addition to the locomotion along a straight line, the steering capability is crucial for robots to navigate in complex environments. Compared to some crawlers with other actuation methods (3, 16, 38), the magnetically actuated Kresling crawler in this paper shows advantages in navigation with multiple degrees of freedom, which do not require extra mechanism design or actuators (44-46). As shown in FIG. 53A, the crawler possesses a net magnetization $M_{net}$ along the local y-axis of the crawler due to the specially designed magnetization distribution. Since the net magnetization always tends to align with the applied magnetic field, the crawler can instantaneously steer by rigid body rotation upon the change of external magnetic field direction in the global XY-plane. In FIG. 53A, the crawler is initially positioned with its local coordinate coinciding with the global coordinate. When we change the angle between the magnetic field and the Y-axis CCW to 60°, 120°, 180°, 240°, and 300° in sequence, the crawler can immediately rotate to the corresponding directions to align its net magnetization direction with the external magnetic field direction (Movie S3). Here, a 10 mT magnetic field is enough for the rigid body rotation of the crawler.

FIG. 53B demonstrates the crawler navigation with a "Z" path, consisting of three discrete straight segments (Movie S3). Segments 1 and 3 are along the X-axis. Segment 2 is 130° C. W from the X-axis. In each segment, the magnetic field of 40 mT is cyclically applied and removed along the net magnetization direction of the crawler for it to crawl along the local x-axis. The transition from segment 1 to segment 2 or from segment 2 to segment 3 requires the crawler to pause and then steer to the new crawling direction by applying a 10 mT magnetic field along the desired direction, which is 1300 CW or CCW from the current net magnetization direction, respectively.

The crawler can also change moving direction during crawling. For instance, FIG. 53C demonstrates the navigation of the crawler about an "O" crawling path by continuously changing the angle between the magnetic field direction and the Y-axis from 0° to 3600 CW over time (Movie S3). Since the net magnetization direction of the crawler always tends to align with the external magnetic field direction, the crawler can keep changing its crawling direction to follow the desired circular path. The magnitude of the magnetic field for crawling in this demonstration is 40 mT. These two paths show the precise maneuverability and omnidirectional locomotion capability of the Kresling crawler.

Figures 54B, 54C:
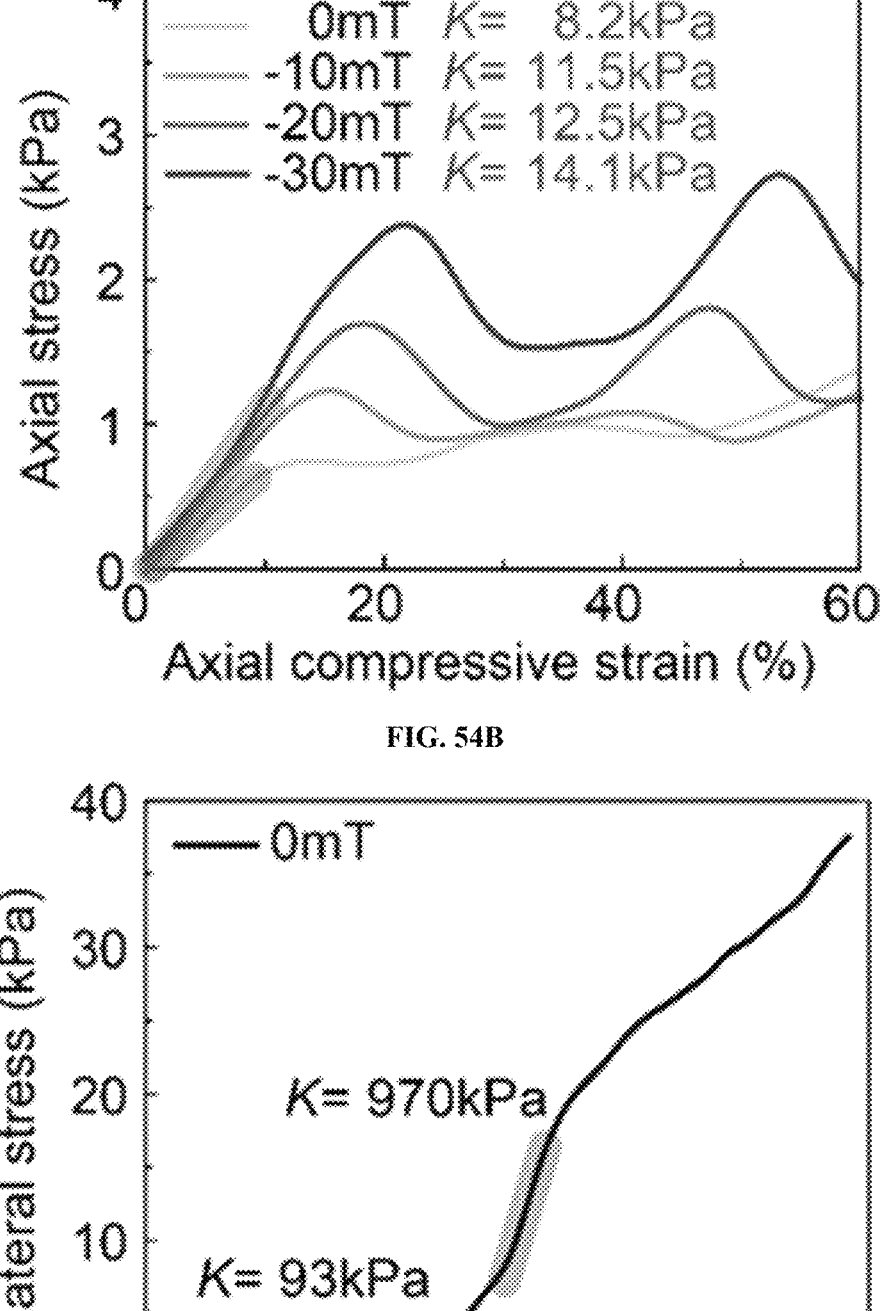

In biomedical environments, the large resistance from the contact between tissues and organs can hinder the motion and function of soft machines due to their low material and structure stiffness (47, 48). The Kresling crawler possesses a unique anisotropic stiffness that is important to promote crawling motion and maintain the integrity and function of the crawler in confined spaces. In addition, the magnetic field can tune the crawler structure stiffness along its axial direction for enhanced crawling performance. When we compress the crawler along its axial and lateral direction, as shown in FIG. 54A (see FIG. 65 for experimental setup), a significant stiffness difference is observed, regardless of whether a magnetic field is applied or not. FIG. 54B and FIG. 54C show the stress-strain curves from the axial and lateral compression tests, respectively. When no magnetic field is applied, the low axial stiffness of 8.2 kPa (Measured at 10% strain from the lightest blue curve in FIG. 54B) enables easy contraction under relatively small magnetic fields for effective locomotion. On the contrary, the stiffness in the lateral direction is as high as 93 kPa, even at a small strain of 5% (FIG. 54C). Once reaching complete contact under increasing compression (from 6% strain), its lateral stiffness increases significantly to 970 kPa, preventing potential structural damage from the high lateral resistance. Furthermore, the mechanical behavior of the crawler in its axial direction is tunable when applying a magnetic field opposite to the net magnetization direction of the crawler, stretching and stiffening the structure from its initial stress-free configuration. The stiffness (measured at 10% strain) can be reinforced to 11.5 kPa, 12.5 kPa, and 14.1 kPa under −10 mT, −20 mT, and −30 mT magnetic fields, respectively. These results demonstrate the tunable structure stiffness to help the crawler overcome the resistance from the axial direction during the crawling motion. We remark that the lateral stiffness of the crawler is also tunable by the magnetic field, as shown in FIG. 66. When the negative magnetic field is applied, the crawler is stretched, and its lateral stiffness is almost unchanged. When the positive magnetic field is applied, the crawler contracts and its lateral stiffness is enhanced with an increasing magnetic field.

Figure 54D:
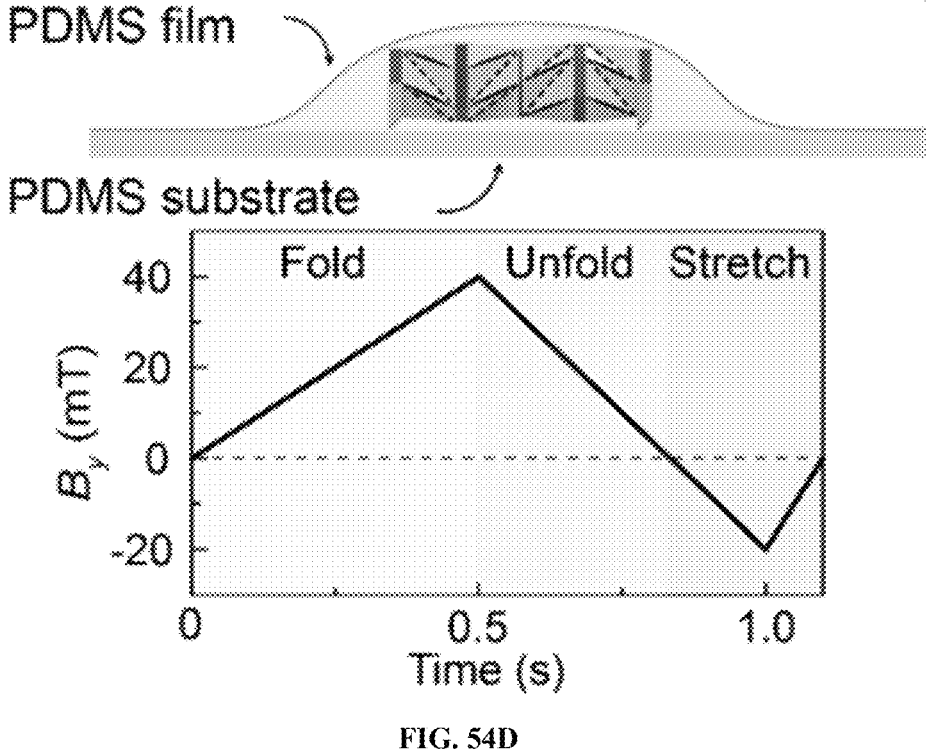
Figure 54E:
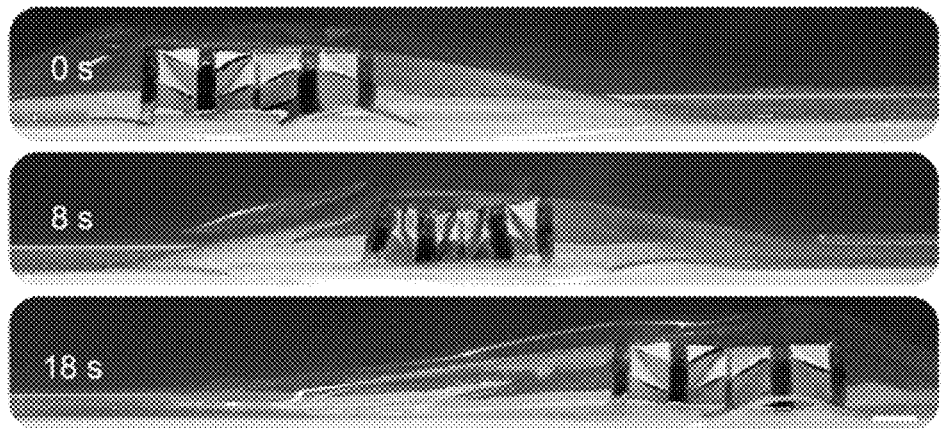

The crawler is sandwiched between a PDMS substrate and a PDMS film to demonstrate that the anisotropic stiffness and magnetically assisted reinforcement of the crawler allow it to move in severely confined spaces (FIG. 54D). For the magnetic field profile in FIG. 54D, the positive 40 mT magnetic field is for the crawler contraction, and the negative 20 mT field is for the reinforced axial stiffness to help stretch the crawler. During the crawling motion, as shown in FIG. 54E, the crawler moves forward by effectively cracking open the contact area at the interface of the substrate and film. Meanwhile, its deployment under the negative magnetic field generates a large pushing force, which is essential to open and extend the crack front at the substrate-film interface. The stride length in FIG. 54E is comparable to that of crawling motion in open spaces (~3 mm in FIG. 52B), indicating the capability of the crawler to move in confined spaces.

With the capability to agilely crawl and steer under precise magnetic control and move in confined spaces, the miniaturized Kresling crawler could potentially be used for biomedical applications like endoscopy, biopsy, or on-demand drug release. Components such as mini cameras, forceps, or drug pills can be integrated into the system to enable such functions. Note that the Kresling unit is a thin shell structure whose inner cavity permits the loading of functional components without increasing the overall dimension of the system, which is especially favored for environments with limited space. In FIG. 55, we demonstrate the drug storage and release of the Kresling crawler. As shown in FIG. 55A, to utilize the Kresling origami inner cavity as storage, the crawler is modified with a through hole in its axial direction by assembling Kresling units and magnetic plates with holes. Then, a cylinder-shaped pill is inserted into the crawler for drug storage. Here, the pill has a length equal to the total thickness of two magnetic plates and one Kresling unit, illustrated by the cross-section view of the right two units (FIG. 55B, corresponding to the blue dashed box in FIG. 55A). The pill is fixed to the rightmost magnetic plate, having a diameter slightly smaller than the diameter of the through hole. When the crawler contracts, the pill can be pushed into the adjacent unit without influencing the crawling motion, as illustrated in FIG. 55B. Although the internal space of the Kresling unit shrinks during the contracting process, the triangular panels do not interfere with the central cylindrical pill. To illustrate the on-demand drug release capability of the crawler, the pill is fabricated by encapsulating blue dye inside the cylindrical water-soluble paper. Once the crawler reaches the target position, water is poured to surround the crawler. Then, the pill gradually dissolves in the water environment, as indicated by the intensity of the blue dye for four minutes (FIG. 55C). Based on various applications, alternative drug release mechanisms are also available such as using pH-responsive or protein-sensitive materials in further works.

Discussion

In this work, we have demonstrated a magnetically actuated small-scale Kresling crawler for effective in-plane crawling motion in confined spaces. The Kresling dipole is introduced as the building block of the crawler, canceling out the relative rotation between the two ends of the crawler for contraction-only motion. Rationally designed torque distribution for simultaneous contraction of the Kresling units is implemented by magnetic actuation for crawling. Magnetic actuation also provides the capability of steering by driving the rigid body rotation of the crawler. In addition, the anisotropic and magnetically tunable structure stiffness helps the crawler effectively overcome the large resistance from severely confined spaces during crawling. Finally, we demonstrate the drug storage and release capabilities of the crawler by utilizing the inherent internal cavity of the Kresling unit. To expand the work, advanced fabrication methods, such as small-scale 3D printing (49), stress-controlled folding (50), and mechanically guided assembly (51), can further downsize the origami crawler, bringing forth potential applications in more narrow and confined environments. Highly autonomous biomedical robots based on the presented design are promising for future disease diagnoses and treatment by integrating the functionalities of sensing, vision, computing, and drug storage into the Kresling origami internal cavity.

Materials and Methods

Fabrication of the Kresling crawler. The four-unit Kresling crawler is fabricated by assembling Kresling units, magnetic plates, and feet with anisotropic friction. The Kresling unit is folded from the designed Kresling pattern (FIG. 56) using polyethylene film (0.05 mm thick). Hexagonal Mylar plates (0.127 mm thick) are attached to the top and bottom planes of the unit to provide high stiffness. Hexagonal magnetic plate (edge length of 3.9 mm and thickness of 1.4 mm) is made of Ecoflex-0030 silicone (Smooth-On, Inc., USA) embedded with 40 vol % hard-magnetic particles (NdFeB, average size of 100 m, Magnequench, Singapore). The feet are molded by PDMS (Sylgard 184, Dow Corning, USA, base to curing agent in a ratio of 5:1) with dimensions shown in FIG. 63A. Acetate tape is attached to the inclined surface of the feet to provide lower friction than PDMS.

Finite element analysis. The commercial software ABAQUS 2020 (Dassault Systemes, France) is utilized for the finite element analysis (FEA) of the Kresling crawler contraction. Linear-elastic material models are used for hexagonal bases, triangular panels, and hinges connecting the panels with the C3D8 element for the whole model discretization.

More details about sample fabrication, FEA, material characterization, and experimental setup are provided in the Supplementary Materials.

REFERENCES

1. N. Saga, T. Nakamura, Development of a peristaltic crawling robot using magnetic fluid on the basis of the locomotion mechanism of the earthworm. *Smart Materials and Structures* 13, 566 (2004).

2. S. Chen, Y. Cao, M. Sarparast, H. Yuan, L. Dong, X. Tan, C. Cao, Soft crawling robots: design, actuation, and locomotion. *Advanced Materials Technologies* 5, 1900837 (2020).

3. G. Gu, J. Zou, R. Zhao, X. Zhao, X. Zhu, Soft wall-climbing robots. *Science Robotics* 3, (2018).

4. H. Omori, T. Murakami, H. Nagai, T. Nakamura, T. Kubota, Development of a novel bio-inspired planetary subsurface explorer: initial experimental study by prototype excavator with propulsion and excavation units. *IEEE/ASME Transactions on Mechatronics* 18, 459-470 (2012).

5. M. M. Coad, L. H. Blumenschein, S. Cutler, J. A. R. Zepeda, N. D. Naclerio, H. El-Hussieny, U. Mehmood, J.-H. Ryu, E. W. Hawkes, A. M. Okamura, Vine robots: Design, teleoperation, and deployment for navigation and exploration. *IEEE Robotics & Automation Magazine* 27, 120-132 (2019).

6. M. Kamata, S. Yamazaki, Y. Tanise, Y. Yamada, T. Nakamura, Morphological change in peristaltic crawling motion of a narrow pipe inspection robot inspired by earthworm's locomotion. *Advanced Robotics* 32, 386-397 (2018). C.-Y. Yeh, C.-Y. Chen, J.-Y. Juang, Soft hopping and crawling robot for in-pipe traveling. *Extreme Mechanics Letters* 39, 100854 (2020).

8. T. Nakamura, Y. Hidaka, M. Yokojima, K. Adachi, Development of peristaltic crawling robot with artificial rubber muscles attached to large intestine endoscope. *Advanced Robotics* 26, 1161-1182 (2012).

9. M. Runciman, A. Darzi, G. P. Mylonas, Soft robotics in minimally invasive surgery. *Soft Robotics* 6, 423-443 (2019).

10. S. Seok, C. D. Onal, K.-J. Cho, R. J. Wood, D. Rus, S. Kim, Meshworm: a peristaltic soft robot with antagonistic nickel titanium coil actuators. *IEEE/ASME Transactions on mechatronics* 18, 1485-1497 (2012).

11. A. Rafsanjani, Y. Zhang, B. Liu, S. M. Rubinstein, K. Bertoldi, Kirigami skins make a simple soft actuator crawl. *Science Robotics* 3, (2018).

12. S. Wu, Q. Ze, R. Zhang, N. Hu, Y. Cheng, F. Yang, R. Zhao, Symmetry-breaking actuation mechanism for soft robotics and active metamaterials. *ACS Applied Materials & Interfaces* 11, 41649-41658 (2019).

13. S. Wu, C. M. Hamel, Q. Ze, F. Yang, H. J. Qi, R. Zhao, Evolutionary Algorithm-Guided Voxel-Encoding Printing of Functional Hard-Magnetic Soft Active Materials. *Advanced Intelligent Systems* 2, 2000060 (2020).

14. M. Calisti, G. Picardi, C. Laschi, Fundamentals of soft robot locomotion. *Journal of The Royal Society Interface* 14, 20170101 (2017).

15. M. S. Verma, A. Ainla, D. Yang, D. Harburg, G. M. Whitesides, A soft tube-climbing robot. *Soft Robotics* 5, 133-137 (2018).

16. J.-S. Koh, K.-J. Cho, Omega-shaped inchworm-inspired crawling robot with large-index-and-pitch (LIP) SMA spring actuators. *IEEE/ASME Transactions On Mechatronics* 18, 419-429 (2012).

17. M. Rogóż, H. Zeng, C. Xuan, D. S. Wiersma, P. Wasylczyk, Light-driven soft robot mimics caterpillar locomotion in natural scale. *Advanced Optical Materials* 4, 1689-1694 (2016).

18. X. Qian, Q. Chen, Y. Yang, Y. Xu, Z. Li, Z. Wang, Y. Wu, Y. Wei, Y. Ji, Untethered recyclable tubular actuators with versatile locomotion for soft continuum robots. *Advanced Materials* 30, 1801103 (2018).

19. R. F. Shepherd, F. Ilievski, W. Choi, S. A. Morin, A. A. Stokes, A. D. Mazzeo, X. Chen, M. Wang, G. M. Whitesides, Multigait soft robot. *Proceedings of the national academy of sciences* 108, 20400-20403 (2011).

20. P. Rothemund, A. Ainla, L. Belding, D. J. Preston, S. Kurihara, Z. Suo, G. M. Whitesides, A soft, bistable valve for autonomous control of soft actuators. *Science Robotics* 3, (2018).

21. Z. G. Joey, A. A. Calderón, L. Chang, N. O. Pérez-Arancibia, An earthworm-inspired friction-controlled soft robot capable of bidirectional locomotion. *Bioinspiration & Biomimetics* 14, 036004 (2019).

22. J. E. Bernth, A. Arezzo, H. Liu, A novel robotic mesh-worm with segment-bending anchoring for colonoscopy. *IEEE Robotics and Automation Letters* 2, 1718-1724 (2017).

23. A. Kandhari, Y. Wang, H. J. Chiel, R. D. Quinn, K. A. Daltorio, An analysis of peristaltic locomotion for maximizing velocity or minimizing cost of transport of earthworm-like robots. *Soft Robotics*, (2020).

24. J. Zou, Y. Lin, C. Ji, H. Yang, A reconfigurable omni-directional soft robot based on caterpillar locomotion. *Soft Robotics* 5, 164-174 (2018).

25. Y. Y. Xiao, Z. C. Jiang, X. Tong, Y. Zhao, Biomimetic locomotion of electrically powered "Janus" soft robots using a liquid crystal polymer. *Advanced Materials* 31, 1903452 (2019).

Y. Wu, J. K. Yim, J. Liang, Z. Shao, M. Qi, J. Zhong, Z. Luo, X. Yan, M. Zhang, X. Wang, Insect-scale fast moving and ultrarobust soft robot. *Science Robotics* 4, (2019).

27. W. Hu, G. Z. Lum, M. Mastrangeli, M. Sitti, Small-scale soft-bodied robot with multimodal locomotion. *Nature* 554, 81-85 (2018).

28. H. Lu, M. Zhang, Y. Yang, Q. Huang, T. Fukuda, Z. Wang, Y. Shen, A bioinspired multilegged soft millirobot that functions in both dry and wet conditions. *Nature Communications* 9, 1-7 (2018).

29. C. D. Onal, R. J. Wood, D. Rus, An origami-inspired approach to worm robots. *IEEE/ASME Transactions on Mechatronics* 18, 430-438 (2012).

30. H. Banerjee, N. Pusalkar, H. Ren, Single-motor controlled tendon-driven peristaltic soft origami robot. *Journal of Mechanisms and Robotics* 10, (2018).

31. W. Kim, J. Byun, J.-K. Kim, W.-Y. Choi, K. Jakobsen, J. Jakobsen, D.-Y. Lee, K.-J. Cho, Bioinspired dual-morphing stretchable origami. *Science Robotics* 4, (2019).

32. E. T. Filipov, T. Tachi, G. H. Paulino, Origami tubes assembled into stiff, yet reconfigurable structures and metamaterials. *Proceedings of the National Academy of Sciences* 112, 12321-12326 (2015).

33. H. Fang, Y. Zhang, K. Wang, Origami-based earthworm-like locomotion robots. *Bioinspiration & Biomimetics* 12, 065003 (2017).

34. L. S. Novelino, Q. Ze, S. Wu, G. H. Paulino, R. Zhao, Untethered control of functional origami microrobots with distributed actuation. *Proceedings of the National Academy of Sciences* 117, 24096-24101 (2020).

35. Z. Li, N. Kidambi, L. Wang, K.-W. Wang, Uncovering rotational multifunctionalities of coupled Kresling modular structures. *Extreme Mechanics Letters* 39, 100795 (2020).

36. J. Kaufmann, P. Bhovad, S. Li, Harnessing the Multistability of Kresling Origami for Reconfigurable Articulation in Soft Robotic Arms. *Soft Robotics*, (2021).

37. P. Bhovad, J. Kaufmann, S. Li, Peristaltic locomotion without digital controllers: Exploiting multi-stability in origami to coordinate robotic motion. *Extreme Mechanics Letters* 32, 100552 (2019).

38. A. Pagano, T. Yan, B. Chien, A. Wissa, S. Tawfick, A crawling robot driven by multi-stable origami. *Smart Materials and Structures* 26, 094007 (2017).

39. K. Gustafson, O. Angatkina, A. Wissa, Model-based design of a multistable origami-enabled crawling robot. *Smart Materials and Structures* 29, 015013 (2019).

40. L. Qin, X. Liang, H. Huang, C. K. Chui, R. C.-H. Yeow, J. Zhu, A versatile soft crawling robot with rapid locomotion. *Soft Robotics* 6, 455-467 (2019).

41. T. Li, Z. Zou, G. Mao, X. Yang, Y. Liang, C. Li, S. Qu, Z. Suo, W. Yang, Agile and resilient insect-scale robot. *Soft Robotics* 6, 133-141 (2019).

42. N. Nayakanti, S. H. Tawfick, A. J. Hart, Twist-coupled kirigami cells and mechanisms. *Extreme Mechanics Letters* 21, 17-24 (2018).

43. S. Wu, Q. Ze, J. Dai, N. Udipi, G. H. Paulino, R. Zhao, Stretchable origami robotic arm with omnidirectional bending and twisting. *Proceedings of the National Academy of Sciences* 118, (2021).

44. E. B. Joyee, Y. Pan, A fully three-dimensional printed inchworm-inspired soft robot with magnetic actuation. *Soft Robotics* 6, 333-345 (2019).

45. J. Zhang, E. Diller, Untethered miniature soft robots: Modeling and design of a millimeter-scale swimming magnetic sheet. *Soft Robotics* 5, 761-776 (2018).

46. X. Kuang, S. Wu, Q. Ze, L. Yue, Y. Jin, S. M. Montgomery, F. Yang, H. J. Qi, R. Zhao, Magnetic Dynamic Polymers for Modular Assembling and Reconfigurable Morphing Architectures. *Advanced Materials* 33, 2102113 (2021).

M. Sitti, H. Ceylan, W. Hu, J. Giltinan, M. Turan, S. Yim, E. Diller, Biomedical applications of untethered mobile milli/microrobots. *Proceedings of the IEEE* 103, 205-224 (2015).

48. E. W. Hawkes, L. H. Blumenschein, J. D. Greer, A. M. Okamura, A soft robot that navigates its environment through growth. *Science Robotics* 2, (2017).

49. Z. Lin, L. S. Novelino, H. Wei, N. A. Alderete, G. H. Paulino, H. D. Espinosa, S. Krishnaswamy, Folding at the Microscale: Enabling Multifunctional 3D Origami-Architected Metamaterials. *Small* 16, 2002229 (2020).

50. J. H. Na, A. A. Evans, J. Bae, M. C. Chiappelli, C. D. Santangelo, R. J. Lang, T. C. Hull, R. C. Hayward, Programming reversibly self-folding origami with micropatterned photo-crosslinkable polymer trilayers. *Advanced Materials* 27, 79-85 (2015).

51. S. Xu, Z. Yan, K.-I. Jang, W. Huang, H. Fu, J. Kim, Z. Wei, M. Flavin, J. McCracken, R. Wang, Assembly of micro/nanomaterials into complex, three-dimensional architectures by compressive buckling. *Science* 347, 154-159 (2015).

SUPPLEMENTARY INFORMATION

1. Sample Fabrication

Kresling origami. Two kinds of Kresling units with the same geometry and reverse creases are used to fabricate the two-unit Kresling dipole and four-unit crawler in this work. As shown in FIG. 56, both units have the same dimensions with a=5.33 mm, b=3.9 mm, c=5.1 mm, and α=106.89°. The units are fabricated from polyethylene film (0.05 mm thick), which is cut into a flower-shaped pattern using a mechanical cutter (Cricut Maker, Cricut, Inc., USA). The pattern is then folded, and Mylar hexagons (0.127 mm thick) are attached to the top and bottom sides of the unit to provide high stiffness.

Magnetic plate. Hard-magnetic microparticles (NdFeB, average size 100 μm, Magnequench, Singapore) are mixed homogeneously into Ecoflex-0030 precursor (Smooth-On, Inc., USA) with a volume fraction of 40%. To fabricate magnetic plates, the mixture is poured into hexagon-shaped acrylic molds (edge length of 3.9 mm and thickness of 1.4 mm) and cured at 80° C. for 0.5 h. The magnetic plates are magnetized by a home-made magnetizer with a 1.5 T impulse magnetic field before being attached to the Kresling units using Sil-poxy adhesive (Smooth-On, Inc., USA).

2. Material Characterization

Magnetic material. The magnetic properties of the magnetic plates are measured using a vibrating sample magnetometer (7400A, Lake Shore Cryotronics, Inc., USA). The magnetic moments along the magnetization direction are measured using 4 mm by 4 mm by 1 mm samples. The corresponding remanent magnetization ($M_r$) is calculated from the magnetic moment by dividing the sample volume. The $M_r$ of the sample with 40 vol % of magnetic particles is measured to be 227.50 kA m$^{-1}$.

Polyethylene film. The polyethylene film is characterized by uniaxial tensile tests using a universal testing machine (3344, Instron, Inc., USA). A 100 N load cell is used. Thin-film samples (gauge zone 15 mm by 5 mm by 0.05 mm) are stretched to 5% strain at a strain rate of 0.01 s$^{-1}$, as shown in FIG. 57. Its Young's modulus is calculated to be 207.9 MPa by the secant modulus at 0.5% strain.

3. Mechanical Characterization of the Kresling Unit

Figure 59D:
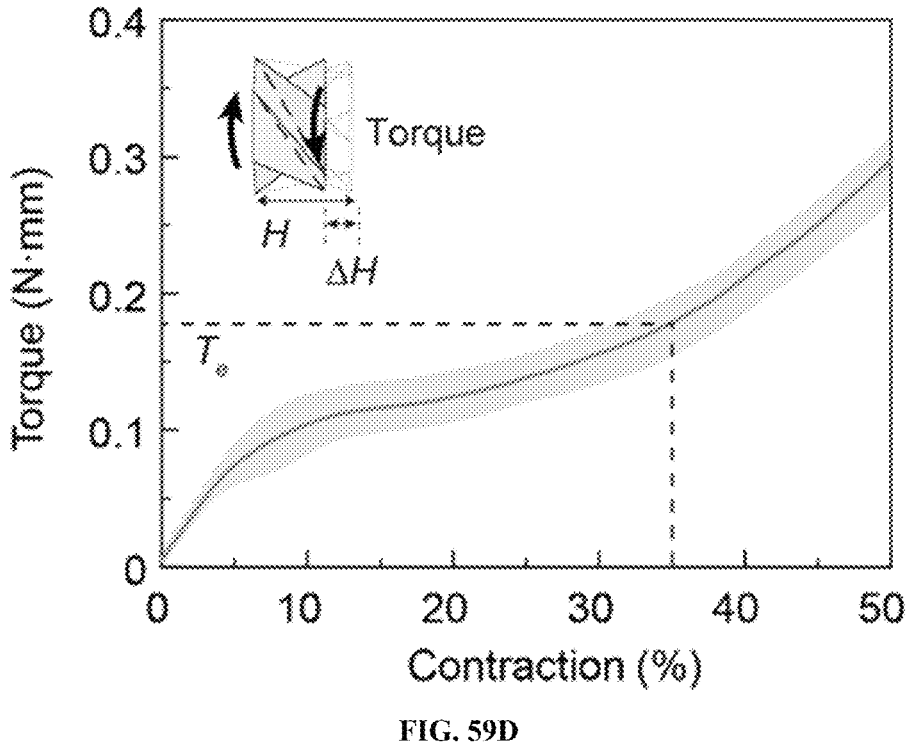

To characterize the mechanical behavior of fabricated Kresling units, we perform axial compression tests using a universal testing machine, as shown in FIG. 58A. From the cyclic compression test results of the Kresling unit in FIGS. 58B, we observe that the mechanical response stabilizes after 400 cycles approximately. To obtain consistent results, all fabricated Kresling units are manually compressed 400 times prior to performing other mechanical tests and magnetic actuation. Then, three samples are compressed with 50% strain at a strain rate of 0.01 s$^{-1}$ FIG. 59A shows the measured force-contraction (ΔH/H) curve of fabricated units, where H is the initial unit height and ΔH is the height change during compression. Stored energy is obtained by integrating the experimentally measured force-displacement results (FIG. 59B). The Kresling unit shows coupled contraction and rotation behaviors, which means that it can be folded under either a compressive force or a pair of torques. To derive the torque-rotation angle relationship from the force-contraction curve, the geometrical contraction-rotation angle (ψ) relation is needed, which is obtained by simulating the Kresling unit contraction using FEA and is shown in FIG. 59C. By deriving the stored energy with respect to y, we can obtain the torque needed to fold the Kresling unit (FIG. 59D).

4. Free Body Diagram of the Kresling Crawler

The introduced Kresling dipole with mirror symmetry demonstrates contraction while free of relative rotation between the two ends. Here we design a crawler composed of two Kresling dipoles with central symmetry arrangement as shown in FIG. 60. $T_1$, $T_2$, $T_3$, and $T_4$ are magnitudes of applied torques at the 1$^{st}$, 2$^{nd}$, 4$^{th}$, and 5$^{th}$ hexagonal planes of the crawler from left to right. To realize simultaneous contraction of all units, it is required that the torque distribution fulfill three conditions.

1) Balance of torque for the pure translational motion:

$$T_1+T_3=T_2+T_4, \tag{S1}$$

2) Same torque magnitude on all units for simultaneous contraction:

$$T_{U1}=T_{U2}=T_{U3}=T_{U4}, \tag{S2}$$

where $T_{U1}$, $T_{U2}$, $T_{U3}$, and $T_{U4}$ are the torque magnitudes on units U1, U2, U3, and U4, respectively.

3) Sufficient torque magnitude on each unit for effective contraction. We define this torque as $T_e$ with the value of 0.18 N-mm, which is a reasonably small torque permitting 35% contraction of units used in this work (FIG. 59D).

Based on the free body diagrams in FIG. 60, we have:

$$T_{U1}=T_1, T_{U2}=T_2-T_1. \tag{S3}$$

Due to the symmetry of the structure and loadings, we have:

$$T_{U3}=T_3-T_4, T_{U4}=T_4. \tag{S4}$$

Combining Eqs. S1-4, we have:

$$T_2=2T_1, T_3=T_2, T_4=T_1, \tag{S5}$$

Notice that $T_1$ and $T_4$ are in reverse directions, and similarly, $T_2$ and $T_3$ are in reverse directions.

5. Finite Element Analysis

The commercial software ABAQUS 2020 (Dassault Systemes, France) is utilized for the Kresling crawler contraction finite element analysis (FEA). The model of each Kresling unit consists of three sections: hexagonal bases, triangular panels, and hinges connecting the panels and bases (FIG. 61A). Linear-elastic material models are used for all three sections. Normalized Young's moduli of 10, 40, and 1 (consistent units) are used for the bases, panels, and hinges, respectively, with the same Poisson's ratio of 0.4. The mesh of the crawler model is shown in FIG. 61B. Five elements are assigned through the thickness direction of bases, hinges, and panels. The pre-defined element C3D8 is used for the whole model.

To numerically verify the derived torque relations in Eq. S5, the boundary conditions applied to the crawler in FEA follow two requirements: 1) No rotation at two ends of the Kresling crawler ($1^{st}$ and $5^{th}$ hexagonal planes from left to right). 2) Reverse rotations with the same rotation angles at the $2^{nd}$ and $4^{th}$ hexagonal planes of the crawler from left to right. Here, we define the local xyz coordinate on the crawler with the x-axis along the axial direction of the crawler (FIG. 61B). The $3^{rd}$ hexagonal plane of the crawler is constrained along the x-axis, and central nodes of all hexagonal planes are constrained in the y-axis and z-axis. Rotation angles of $0°$, $32°$, $-32°$, and $0°$ around the x-axis are then enforced to the $1^{st}$, $2^{nd}$, $4^{th}$, and $5^{th}$ hexagonal planes of the crawler from left to right (positive rotation direction follows the right-handed rule).

Reaction torques $T_1$, $T_2$, $T_3$, and $T_4$ at the $1^{st}$, $2^{nd}$, $4^{th}$, and $5^{th}$ hexagonal planes of the crawler from left to right are exported, and normalized torque-rotation angle curves are shown in FIG. 61C. The torque relation from FEA (FIG. 61D) verifies the theoretically derived torque distribution in Eq. S5 for simultaneous contraction of four units.

6. Magnetic Actuation Setup

The crawler is actuated under a three-dimensional (3D) magnetic field, which is generated by customized 3D Helmholtz coils shown in FIG. 62. Three pairs of standard Helmholtz coils are configured orthogonally to each other. The magnetic field direction and magnitude can be manipulated by controlling the currents in three pairs of coils. The coils can generate 2.96 mT $A^{-1}$, 2.97 mT $A^{-1}$, and 2.90 mT $A^{-1}$ uniform magnetic fields within a space of 160 mm by 120 mm by 80 mm (X-axis, Y-axis, and Z-axis), respectively.

7. Experimental Details of the Kresling Crawler

Contraction test. The magnetic field along the local y-axis is applied to the Kresling crawler, and its magnitude ranges from 0 to 40 mT with a 5 mT interval. In FIG. 51E, contractions are calculated as $1-l/L$, where L and l are the lengths of the crawler at the initial state and after contraction, respectively. We test three samples, and each sample is tested three times to obtain average values and the range of responses.

Feet design. The locomotion of the crawler relies on anisotropic friction of the feet during the contraction phase and expansion phase in FIG. 52A. The feet are molded by PDMS (Sylgard 184, Dow Corning, USA, base to curing agent in a ratio of 5:1) with dimensions shown in FIG. 63A. Acetate tape is attached to the inclined surface. By design, the PDMS portion provides high friction, and the tape portion provides low friction.

Friction coefficient measurement. Locomotion of the crawler is conducted on two substrates, paper and PDMS (base to curing agent in a ratio of 5:1) with lubricant oil. We measure friction coefficients of PDMS (high friction) and tape (low friction) for the feet of the crawler on both substrates using the setup shown in FIG. 63B. The pulley and wire transmit the pulling force from the universal testing machine to a cubic sample (dimension: 15 mm×15 mm×10 mm). Cubes with and without tape attached to the bottom surface are tested. For each cube, three tests are conducted at a pulling speed of 40 mm $min^{-1}$, 80 mm $min^{-1}$, and 160 mm $min^{-1}$. The friction coefficient can be calculated by dividing the average measured force by the weight of the cube sample. FIG. 63C shows that the measured friction coefficient of PDMS is higher than that of tape on both substrates, indicating the effective design of the high friction and low friction portions for the feet of the crawler.

Characterization of crawling motion. A triangular wave in FIG. 64A is first used to demonstrate the robotic crawling mechanism, as shown in FIG. 52A. To characterize the influence of the magnetic field profile on the crawling performance, triangular wave profiles (FIG. 64B) with different frequencies (1.67 Hz, 2.5 Hz, and 5 Hz) and magnitudes (10 mT to 40 mT with a step of 5 mT) are applied. The measured stride distance and crawling speed are shown in FIGS. 52B and 52C, respectively. Multiple tests are conducted to obtain average values and range of responses.

"Z" crawling path. The Z-shaped path (FIG. 53B) consists of three straight segments. Segments 1 and 3 are along the X-axis. Segment 2 has an angle of $-130°$ with respect to the X-axis. The frequency of the magnetic field profile for the crawler is 1.67 Hz. The magnetic field applied for actuation is always along the local y-axis of the crawler.

"O" crawling path. The crawling along the O-shaped path (FIG. 53C) is achieved by continuously changing the relative angle between the global and local coordinate systems from $0°$ to $360°$ over time. It takes 118 cycles to complete the path. The frequency of the magnetic field profile for the crawler is 1.67 Hz. The magnetic field applied for actuation is always along the local y-axis of the crawler.

Anisotropic structure stiffness measurement. Compression tests along both axial and lateral directions of the crawler body are carried out using a universal testing machine, as shown in FIG. 65. For the axial compression, a modified setup is used, as shown in FIG. 65A. The pulley and wire transmit the force from the universal testing machine to a slider in the electromagnetic coils to axially compress the Kresling crawler under a magnetic field (see detail in FIG. 65B). The force-displacement curves are exported with a total compressive displacement of 13 mm at a strain rate of 0.01 s$^{-1}$. To obtain the effective structure stiffness, we divide the displacement by the initial length of the sample (~28 mm) to obtain axial compressive strain and divide the force by the hexagon area (39.5 mm$^2$) to obtain the axial compressive stress as shown in FIG. 54B. A compression mode of the universal testing machine is used for the lateral compression without magnetic field, as shown in FIG. 65C. In this case, a total displacement of 1 mm is applied at a strain rate of 0.01 s$^{-1}$. We divide the displacement by the initial height of the sample (6.8 mm) to get lateral compressive strain and divide the force by the contacted area (109.2 mm$^2$) to get the lateral compressive stress as shown in FIG. 54C. To study the effect of the magnetic field on the lateral stiffness of the crawler, we perform the lateral compression tests under magnetic field in a modified setup based on the universal testing machine, as shown in FIG. 66A. The compression mode of the universal testing machine is used, and a total displacement of 1 mm is applied at a strain rate of 0.01 s$^{-1}$. The lateral compressive strain is film (0.15 mm thickness) is spin-coated by the same material at 200 rpm for 30 s. The magnetic field profile shown in FIG. 54D is applied to actuate the crawler. Due to the large lateral structure stiffness of the crawler, it can effectively overcome the lateral resistance from the confined environment by cracking open the contacted areas and moving forward. It should be noted that a reverse magnetic field is applied at the end of each crawling cycle to further stretch the crawler and provide an enhanced stiffness along the axial direction. This high axial stiffness helps the crawler overcome the resistance from the axial direction during movement in confined spaces. The crawler exhibits axial stiffnesses of 8.2 kPa and 12.5 kPa, when no magnetic field and a negative 20 mT magnetic field are applied, respectively.

Drug storage and release. The mechanism of drug storage of the crawler is shown in FIG. 55A. All units and magnetic plates have holes with a diameter of 2.5 mm. The concentrated gel-based teal dye (Wilton Brands LLC, USA) is sealed inside the water-soluble container (SmartSolve Industries, USA) to make a pill with a length of 7.6 mm and a diameter of 2 mm. The pill is then inserted into the internal cavity of the rightmost Kresling unit. The right end of the pill is fixed to the magnetic plate using Sil-poxy adhesive.

TABLE 4

Comparison between Kresling origami crawler and other crawling robots reviewed.

| Mechanism | Actuation | Robot design | Wireless control | Steering | Body length (BL, mm) | Weight (g) | Speed (BL/s) |
|---|---|---|---|---|---|---|---|
| Contractile structure | Magnetic | Four-unit origami assembly with two-level symmetry | Y | Y | 28 | 0.95 | 0.47 |
| | Motor | Two chiral origami towers | N | Y | 150 | 136 | 0.025 |
| | | Six origami ball structure | N | N | 603 | 220 | 0.02 |
| | Pneumatic | Quadrupedal structure | N | N | 150 | — | 0.05 |
| | | Elastomeric tube body with kirigami-enabled anisotropic frictional skin | Y | N | 164 | 65 | 0.05 |
| | Thermal | Two four-bar mechanisms | N | Y | 150 | 1.2 | 0.06 |
| | | Tubular body with multiple origami segments | N | N | 100 | 4.2 | 0.003 |
| Stimuli-responsive materials | Magnetic | Four-cell structure with alternating magnetization and asymmetric joints | Y | N | 60 | 2.4 | 0.56 |
| | | Beam structure with multiple tapered feet | Y | Y | 17 | 0.04 | 1.68 |
| | Thermal | Uniaxially oriented strip | N | N | 35 | 0.08 | 0.03 |
| | | Strip with spatially modulated alignment pattern | Y | N | 14.8 | 0.03 | 0.02 |
| | Electrical | Prestretched dielectric elastomer membrane with a flexible frame | N | Y | 85 | — | 1.04 |
| | | Curved unimorph piezoelectric structure | N | N | 10 | 0.024 | 20 | also calculated by dividing the displacement by the initial height of the sample (6.8 mm). To calculate the lateral compressive stress, it should be noted that the contacted area changes with the applied magnetic field. When we apply the negative magnetic fields, the crawler expands, and its configuration is almost unchanged. In contrast, when we apply the positive magnetic fields, the crawler contracts, and the contact area under compression changes. The measured stress-strain curves and calculated lateral stiffnesses at 10% strain under negative and positive magnetic fields are shown in FIGS. 66B and 66C, respectively.

Crawling motion in confined spaces. To demonstrate the crawling motion in confined spaces, the Kresling crawler is sandwiched between a soft substrate and a soft film with lubricant oil added in between. The substrate is molded by PDMS (base to curing agent in a ratio of 5:1), and the top Example 4: Magnetic Origami Robots for Targeted Drug Delivery Miniature robots have attracted extensive attention for their various possible applications in biomedical engineering, such as wireless capsule endoscopy, targeted drug delivery, and minimally invasive surgery. Magnetic robots, which are actuated by the magnetic field, are of particular interest due to the advantages of untethered actuation, fast and precise controllability, and high penetration depth, etc. From the perspective of structure, magnetic robots in biomedical field can be classified into two categories, namely rigid and soft magnetic robots. Rigid magnetic robots have been investigated for decades. However, for the application of targeted drug delivery, the single robot can only deliver low doses of drugs due to the limit surface area. Although this issue can be improved by using swarming robots, the difficulty of precise control is significantly increased, and the collective motion is more sensitive to the environment disturbance. In past several years, the concerns on the adaptability to complex biological tissues gradually bring the research interests from rigid robots to soft robot. Soft magnetic robots achieve the capability of locomotion and manipulation via the elastic deformation of soft body. With pre-programmed shape changes, the soft magnetic robots can successfully realize multimodal locomotion and implement various tasks in complex environments. However, the low structure stiffness of the body cause the robots hard to overcome the resistance from the tissues and highly viscous liquid. At the same time, the locomotion relied on out-of-plane deformation limit the applications in confined spaces. Besides, the capability of effective targeted drug delivery has not been well demonstrated.

Origami robots, inspired by nature and the ancient art of paper folding, can achieve shape change, locomotion, and manipulation by folding or/and deploying. The rigid body and inherent compliance from the crease structure make the origami robots integrate the advantages of conventional rigid and soft robots[1]. These characters help origami robots become potential candidates for medical device applications, which usually require small-scale size and multifunctionality. Specifically, magnetic origami robots have been demonstrated for drug release or treating gastric ulcer. However, most existing works only use magnetic actuation for locomotion. The treatments arise from the deformation of origami structure need other mechanisms, which are either irreversible or passive. Taking full advantage of magnetic actuation and origami structure for multifunctional origami robots remains a challenge.

In this paper, we introduce two multifunctional origami robots based on Kresling pattern for both of locomotion and drug delivery. The Kresling pattern as shown in FIG. 67A is a foldable cylinder shell. Geometrically, Kresling pattern has two stable states, namely deployed state and folded state. For the same structure but different material properties, the Kresling pattern can also be monostable[2], which is utilized in our robot designs. The two states can be switched by applying and removing the torsion loading. Regardless of whether the cylinder shell structure is in the deployed state or folded state, the inherent internal cavity in the folded state will not be interfered by deformation of the structure, which provides an ideal space for storing large doses of drug. At the same time, the comparable size between the medical capsule and the Kresling unit cells used in this paper (FIG. 67B) allows the potential applications for gastrointestinal drug delivery. FIG. 67C shows the mechanical properties of the two unit cells, which have scaled geometries and are used for crawling robot and swimming robot.

Figure 67D:
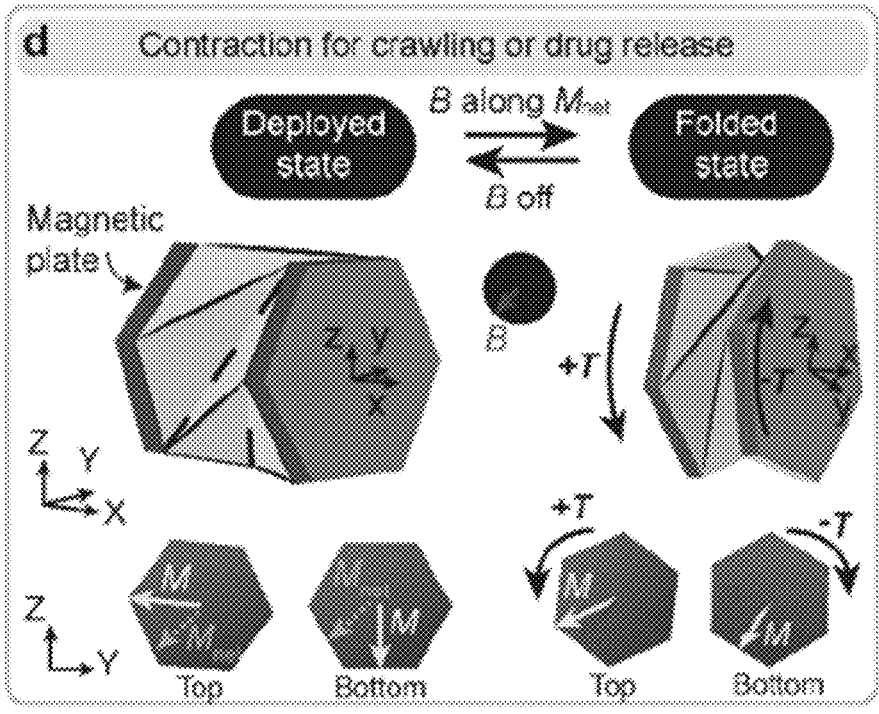
Figure 67E:
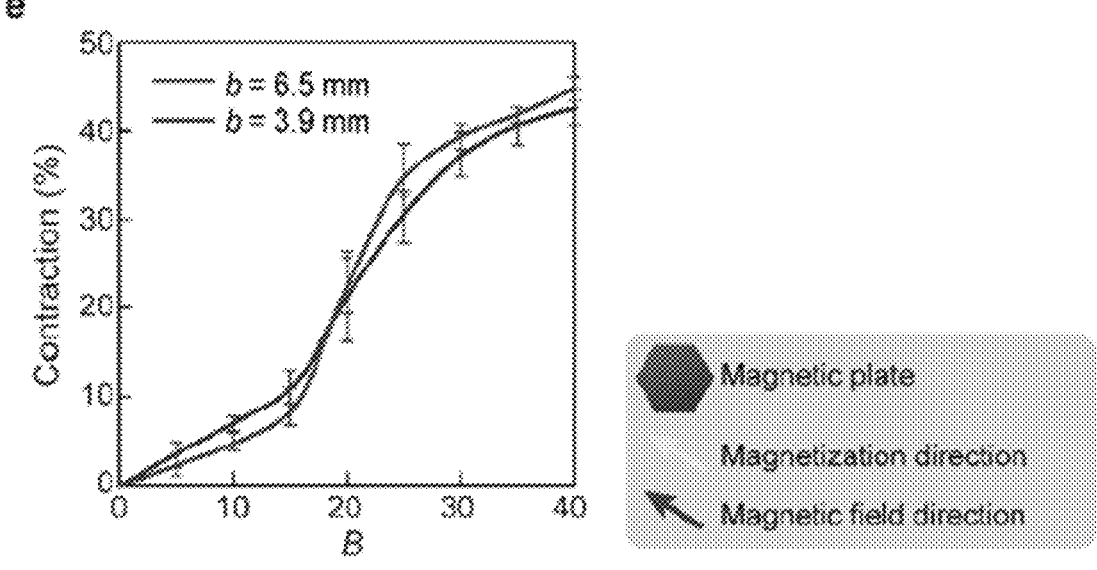

To achieve the remotely controllable behaviors of folding and deploying, two magnetically-responsive plates with the same volume V and distinct magnetization directions (M1 and M2) are attached to the hexagons on both sides of the Kresling unit cell (FIG. 67D). The overall unit cell thus has a net magnetization Mnet along the vector sum of M1 and M2. When an external magnetic field B with the same direction of Mnet is applied, the magnetic torques T1 and T2 regulated by Tn=V (Mn×B) are generated to rotate the magnetic plate, trying to overcome the internal resistance of unit cell to align M1, M2 with B, where n=1 or 2. As the intensity of the magnetic field increases, the contraction lengths of the unit cells gradually increase. The contraction deformation can be used for the mechanisms of either locomotion or drug release, which will be detailed in the subsequent robot designs. Here, we define the global XYZ coordinate system and local xyz coordination system for the ease of analysis and magnetic field control. Among them, the local xyz coordinate system located at the unit cell will rotate or displace with the deformation or locomotion of the unit cell. FIG. 67E shows the magnetic actuation results for two unit cells with scaled geometries and the same angle of 90° between M1 and M2. The contractions of two unit cells for crawling robot and swimming robot are close when the thickness of them are set as 1.4 mm and 1 mm, respectively. If only one magnetic plate is attached to the Kresling unit cell, only rigid-body rotation can be achieved. In this case, assuming the unit cell is working in a free space without external resistance, the unit cell can immediately rotate to align M and B when the external magnetic field is applied. We can obtain two different locomotion modes by changing the manner of the applied magnetic field. As shown in FIG. 67F, the magnetization M is along the y-axis and the two coordinate systems coincide in the initial state. If the magnetic field is in the xy-plane, for example along the x-axis, the magnetic torque will reorient the unit cell around its radial axis (z-axis) to align M and B, which can be used for robot turning. And if the applied magnetic field rotates in the yz-plane, the unit cell can spin round the x-axis to make M follow the rotation of B. This scenario can be used for the propulsion of swimming robot. These two locomotion modes of the Kresling unit cell with one magnetic plate can also be achieved when two magnetic plates are attached. If the external magnetic field B is not align with Mnet, the magnetic torque generated by Mnet will rotate and fold the unit cell simultaneously.

The motion of the Kresling crawling robot arises from the contraction of the unit cells. A four-cell Kresling assembly forms the body of the robot as shown in FIG. 68A. The middle two unit cells (in blue) and end two unit cells (in yellow) have opposite crease directions, but the same geometric parameters. Four magnetic discs with carefully designed magnetization directions as shown in FIG. 68B are attached to specific positions for achieving the similar deformation of each unit cell. By defining the local xyz coordinate system, the net magnetization of the robot body is along the y-axis. When the fabricated sample shown in FIG. 68C are folded simultaneously along the x-axis, the rotations of the unit cells with opposite crease directions cancel each other. The orientations of two magnetic plates at two ends remain unchanged, while the two magnetic plates in the middle rotate in opposite directions (FIG. 68D and When an increasing magnetic field is applied along the y-axis, the crawling robot gradually contracts its body from initial length L to length l. The contraction of the body governed by the magnetic field intensity is defined as L–l and characterized as shown in FIG. 68E.

Current soft crawling robots in biomedical application are mostly based on the out-of-plane deformation of the soft body. However, the organs and tissues are crowded in human body, which applies large resistance to the medical robots. Therefore, a certain structure stiffness is necessary to guarantee the effective locomotion inside the human body, which is not compatible to existing soft crawling robots. Taking advantage of the structure anisotropy of the Kresling pattern, the designed crawling robot has anisotropic stiffness in the axial and lateral directions, providing a potential solution to this issue. The compression tests along the axial and lateral directions of the crawling robot are conducted to quantify the stiffness difference. The results shown in FIG. 68F indicate that the maximum stiffness in the lateral direction is three orders of magnitude greater than that in the axial direction. In this way, the low stiffness in the axial direction enables the easy contraction for locomotion and the high stiffness in the lateral direction helps the robot crack open a space between the contacted tissues, guiding a way for the crawling motion.

A pair of feet with different models is designed and assembled to magnetic plates at two ends. The high friction portion and low friction portion of each foot provide asymmetric frictions in the contraction phase and expansion phase to enable the overall in-plane locomotion of the crawling robot. The locomotion speed depends on the applied magnetic field intensity and frequency. In order to mimic the behavior of cracking open between contacted tissues, such as inside the stomach (FIG. 68G), the crawling robot is sandwiched between two layers of film, whose distance is lower than the height of the robot. By applying a periodic magnetic field with the maximum amplitude of 30 mT and the frequency of 1 Hz (FIG. S5B), the crawling robot gradually open the forehead space between films and moves forward to the targeted position. The drug wrapped in the water-soluble paper is stored in the inner cavity of the foremost unit cell (FIG. S6) and gradually released by hydration. The contraction of the crawling robot can accelerate the drug release process.

The net magnetization direction of the crawling robot is along the y-axis. By utilizing the mechanism of robot turning shown in FIG. 67F, the crawling robot can changing its moving directions by applying magnetic field in the XY-plane. The net magnetization direction is always align with the external magnetic field direction. For example, in FIG. 68H, the applied magnetic field is along the direction, which has an angle of 60° with the initial y-axis. The crawling robot immediately rotates to the new moving direction counterclockwise. Since the amplitude of the magnetic field is only 10 mT, no contraction is observed. This turning mechanism can be used for complex navigation of the crawling robot. FIGS. 68I and 68J demonstrate the "Z" path and "O" path, respectively (Video S2). The "Z" path is consist of three straight paths. The turning duration between these straight paths can be less than 0.1s. The "O" path has constant curvature. The circle is divided into 118 steps in total and the moving direction of the crawling robot keeps changing during the whole process. These two paths show the excellent maneuverability of the crawling robot and the capability of omnidirectional locomotion in the XY-plane. Combined with aforementioned stiffness anisotropy of the structure and capability of targeted drug delivery, the multifunctional crawling robot can be suggested as a potential alternative in gastrointestinal drug delivery.

Figure 69A:
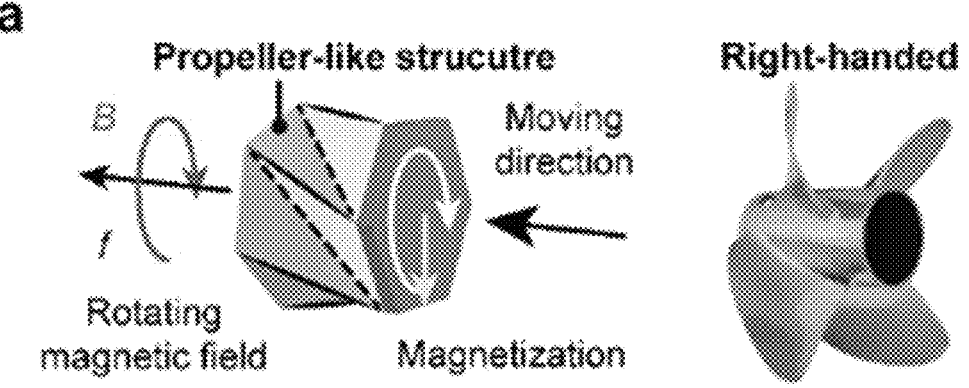
Figure 69B:
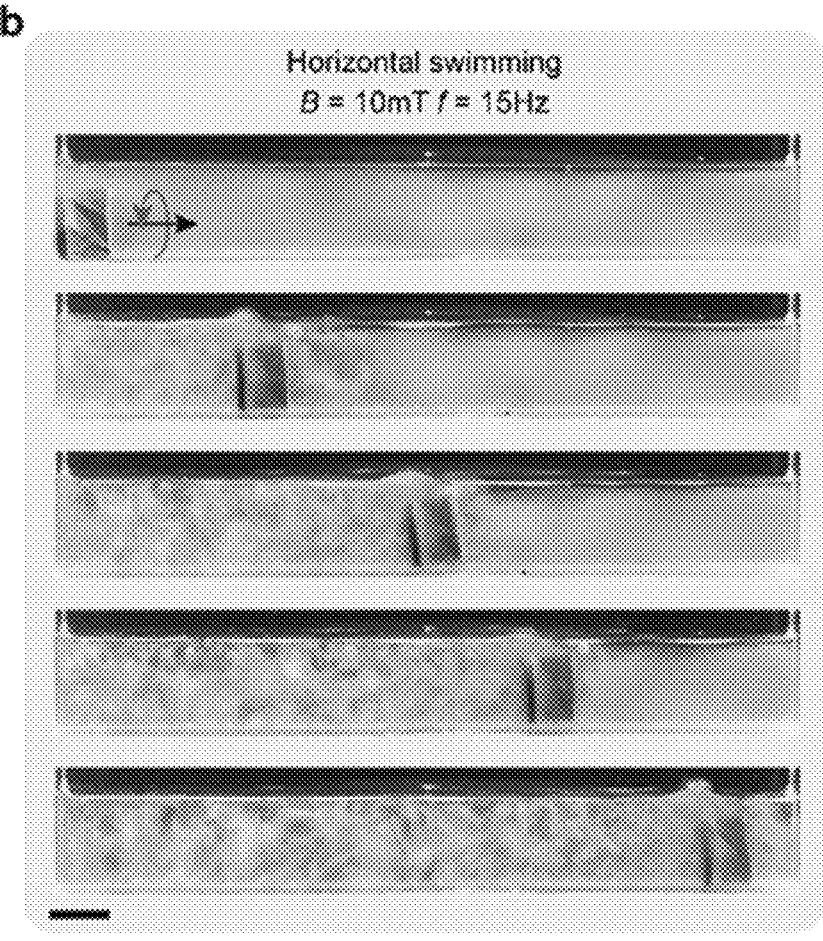
Figures 69C, 69D:
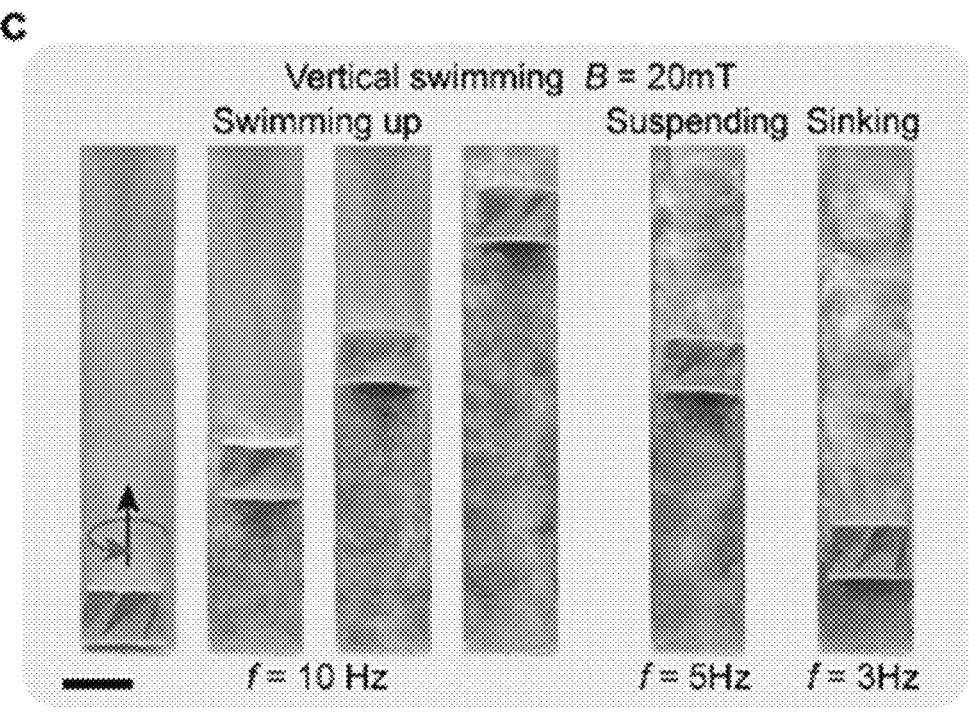

While utilizing the naturally coupled axial contraction and rotation of the Kresling origami, the four-cell magnetic robot realizes a contraction-based crawling motion. The in-plane motion and programmed locomotion further enable a potential targeted drug release in confined spaces such as the stomach or in-between organs. After taking a close look at the geometrical shape of the Kresling pattern, a fascinating feature, the naturally tilted panels, can be further utilized for robotic swimming motions for potential biomedical applications in the liquid environment[3,4]. For the Kresling unit cell shown in FIG. 69A, each blue panel possesses a normal direction with a component pointing to the magnetic disc direction (back of the swimming robot), resembling a propeller blade (FIG. 69A). With a programmed magnetization along the radial direction, the attached magnetic plate provides a magnetic torque to spin the unit cell under a rotating magnetic field B (with a frequency off). When spinning along the clockwise direction (view from the disc side), the blue panels exert force on the surrounding fluids, providing a forward pressure. First, a one-plate (40 vol % of NdFeB particles) Kresling robot is demonstrated to swim horizontally in a water tank with rheoscopic fluid added, as illustrated in FIG. 69B.Under a rotating magnetic field with B=10 mT and f=15 Hz, the robot achieves forward swimming with a speed of 18 mm s$^{-1}$. During the horizontal swimming, a clear water level levitation can be observed at the back of the robot, indicating a pressure head that drives the Kresling robot to swim forward. Also, by controlling the spinning direction, the swimming robot can swim both to the left and right directions on-demand. Apart from horizontal swimming, the robot is also capable of a vertical swimming motion, as illustrated in FIG. 69C. While applying a rotating magnetic field with constant magnitude (20 mT), multiple controllable dynamic locomotion modes, including upward swimming, suspending, and sinking, are achieved by manipulating the frequency as 10 Hz, 5 Hz, and 3 Hz, respectively.

The horizontal and vertical swimming speeds of the robot are measured with controlled rotating magnetic field magnitude and frequency to quantitatively characterize the dynamic motion performance. For horizontal swimming in FIG. 69D, the speed increase with both increased magnetic field magnitude and frequency with a maximum speed up to 25 mm s$^{-1}$. For vertical swimming in FIG. 69E, the 5 mT magnetic field is not large enough for the robot to overcome constrain from the tank wall. Also, a minimum frequency (~5 Hz) is required for the robot to overcome the gravity and swim up. With the increased frequency, the speed increases until reaching the peak value because the actual spinning cannot follow the rotation speed of the field. It should be noted that with a larger field, a higher speed is obtained with higher frequency for the vertical swimming motion. A maximum swimming speed 14 mm s$^{-1}$ can be reached with B=20 mT and f=12 Hz. While the Kresling robot's propeller-like geometry helps achieve effective swimming via rigid body motion under a rotating magnetic field, the configurable and modifiable origami structure provides further possibilities in designing multifunctional robots. For instance, the internal cavity and the folding capability of the Kresling robot can be utilized for drug storage and on-demand drug release. As shown in FIG. 70A, a needle and a dye container are attached to the inner two ends of the swimming robot with an intermediate space. To achieve a magnetic folding actuation, two magnetic plates with separated magnetization directions are essential as discussed above. Here, we set a relative angle of 90° between the two magnetization directions denoted by the yellow arrows, with a net magnetization Mnet along the blue arrow direction. When applying a magnetic field B along the Mnet, the magnetic torques on the two plates tend to fold the Kresling unit cell, letting the needle puncture the dye container to release food colors (mimicking a drug release process in the following demonstrations). Note that when the applied B is not aligned with $M_{net}$, the swimming robot will self-adjust before the folding process. As illustrated by the images in FIG. 70B, when applying a 50 mT magnetic field along Z direction, the swimming robot folds to puncture the drug container. Meanwhile, the Kresling's internal cavity volume shrinks and pushes the drug out of the swimming robot, increasing the releasing rate. By further applying a rotating magnetic field (B=10 mT, f=3 Hz), the dynamic spinning motion realizes a relatively homogeneous mixing of the released drug as shown in FIG. 70B. By manipulating the applied magnetic field, the swimming robot's controllable motion and on-demand drug release capabilities show excellent potential in the biomedical and surgical fields. Moreover, both the position and amount of the drug to release can be well-regulated. As shown in FIG. 70C, two target positions for drug-releasing are denoted by the light blue and dark blue dashed boxes, respectively. Under a rotating magnetic field (B=10 mT, f=3 Hz), the swimming robot spins $M_{net}$ along the applied magnetic field, gaining forward propulsion. Once reaching the target position 1, the Kresling swimming robot carries out three consecutive foldings and releases a relatively low dose of the drug. With a spinning motion, the robot further mixes the released drug homogenously and swims forward. It should be noted that there is no obvious leakage during swimming motion unless the swimming robot folds to push the drug out. After reaching target position 2, the robot folds eight times at the designated position, leading to a higher dose of drug-releasing denoted by the darker blue color.

A robot that is capable of controllable navigation in restricted and tortuous space is highly desirable in biomedical applications. While the above demonstrations focus on a dynamic swimming motion along straight paths (horizontal and vertical ones), a controllable steering and navigation can be well-controlled by manipulating the magnitude, frequency, and rotating direction of the robot.

In conclusion, we have demonstrated two multifunctional origami robots based on Kresling pattern for both of locomotion and drug delivery.

REFERENCES

1 Rus, D. & Tolley, M. T. Design, fabrication and control of origami robots. *Nature Reviews Materials* 3, 101-112 (2018).

2 Yasuda, H., Tachi, T., Lee, M. & Yang, J. Origami-based tunable truss structures for non-volatile mechanical memory operation. *Nature communications* 8, 1-7 (2017).

3 Liu, B., Breuer, K. S. & Powers, T. R. Propulsion by a helical flagellum in a capillary tube. *Physics of Fluids* 26, 011701 (2014).

4 Spagnolie, S. E., Liu, B. & Powers, T. R. Locomotion of helical bodies in viscoelastic fluids: enhanced swimming at large helical amplitudes. *Physical review letters* 111, 068101 (2013).

The compositions and methods of the appended claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative compositions and method steps disclosed herein are specifically described, other combinations of the compositions and method steps also are intended to fall within the scope of the appended claims, even if not specifically recited. Thus, a combination of steps, elements, components, or constituents may be explicitly mentioned herein; however, other combinations of steps, elements, components, and constituents are included, even though not explicitly stated.

What is claimed is:

1. A device comprising a plurality of unit cells joined in series, wherein each unit cell comprises:
   a base plate;
   a top plate; and
   a lumen extending longitudinally from the base plate to the top plate, the lumen defined by a side wall formed from a plurality of cojoined panels extending between a bottom surface of the top plate and a top surface of the base plate;
   wherein the unit cell is magnetically actuatable, such that the unit cell can be reversibly transitioned between a contracted configuration, an extended configuration, or a combination thereof using an applied magnetic field.

2. The unit cell of claim 1, wherein a transition between a contracted configuration, an extended configuration, or a combination thereof comprises reorientation of the plurality of conjoined panels forming the side wall.

3. The unit cell of claim 2, wherein reorientation comprises folding of one or more of the conjoined panels, unfolding of one or more of the conjoined panels, or any combination thereof.

4. Then unit cell of claim 1, wherein the side wall has an extended configuration height and a contracted configuration height, wherein the extended configuration height is at least 2 times the contracted configuration height.

5. The unit cell of claim 1, wherein the unit cell has a cross sectional dimension of from 2 mm to 10 mm.

6. The unit cell of claim 1, wherein the extended configuration height of the side wall is of from 2 mm to 30 mm.

7. The unit cell of claim 1, wherein the contracted configuration height of the side wall is of from 1 mm to 10 mm.

8. The unit cell of claim 1, wherein the extended configuration, contracted configuration, or a combination thereof have the same cross-sectional dimension.

9. The unit cell of claim 1, wherein the base plate, the top plate, or any combination thereof comprises a magnetic responsive plate.

10. The unit cell of claim 1, wherein the applied magnetic field generates a magnetic torque on the unit cell.

11. The unit cell of claim 1, wherein the magnetic field has a magnetic field strength of from 0 mT to 300 mT.

12. The unit cell of claim 1, wherein the panels are formed from a polymeric material, a paper material, or any combination thereof.

13. The unit cell of claim 1, further comprising an active agent in the lumen of the unit cell.

14. The unit cell of claim 13, wherein when the unit cell is actuated the active agent releases from the unit cell.

15. A method of actuating the unit cell of claim 1, comprising:
   providing the unit cell, wherein the unit cell is capable of being programmed to transition between a contracted configuration, an extended configuration, or a combination thereof; and actuating the unit cell under an applied magnetic field.

16. A method of actuating a device to perform an activity on a subject, comprising:
   positioning a unit cell of claim 1 in a first position with regard to the subject, wherein the unit cell is capable of being programmed to transition between a contracted configuration, an extended configuration, or a combination thereof; and
   actuating the device under an applied magnetic field.

17. The method of claim 16, wherein the device can be actuated to translocate from a first position to another position.

18. The method of claim 16, wherein the device can be actuated to release an active agent.

19. A method of drug delivery comprising:

administering to a subject in need thereof a unit cell of claim 1, wherein the unit cell is capable of being programmed to transition between a contracted configuration, an extended configuration, or a combination thereof; and actuating the device using an applied magnetic field.

\* \* \* \* \*

82